(12) United States Patent
Nishitani et al.

(10) Patent No.: US 8,933,012 B2
(45) Date of Patent: *Jan. 13, 2015

(54) GLYCOPEPTIDE ANTIBIOTIC DERIVATIVE

(75) Inventors: Yasuhiro Nishitani, Osaka (JP); Osamu Yoshida, Osaka (JP); Tsutomu Iwaki, Osaka (JP); Issei Kato, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 1241 days.

This patent is subject to a terminal disclaimer.

(21) Appl. No.: 12/224,443

(22) PCT Filed: May 25, 2007

(86) PCT No.: PCT/JP2007/060673
§ 371 (c)(1),
(2), (4) Date: Aug. 27, 2008

(87) PCT Pub. No.: WO2007/138999
PCT Pub. Date: Dec. 6, 2007

(65) Prior Publication Data
US 2009/0286717 A1  Nov. 19, 2009

(30) Foreign Application Priority Data
May 26, 2006  (JP) ................. 2006-147008

(51) Int. Cl.
A61K 38/00 (2006.01)
A61P 31/04 (2006.01)
A01N 43/40 (2006.01)
A61K 31/445 (2006.01)
C07K 9/00 (2006.01)
A61K 38/04 (2006.01)

(52) U.S. Cl.
CPC ................. C07K 9/008 (2013.01); A61K 38/04 (2013.01); A61K 38/00 (2013.01)
USPC ............... 514/1.1; 514/3.2; 514/322

(58) Field of Classification Search
CPC ......... A61K 38/04; A61K 38/00; C07K 9/008
USPC .......................................... 514/1.1, 3.2, 322
See application file for complete search history.

(56) References Cited

U.S. PATENT DOCUMENTS 6,455,669 B1 * 9/2002 Judice et al. ............. 530/317
6,498,238 B1 * 12/2002 Kim et al. ................ 536/16.8

(Continued)

FOREIGN PATENT DOCUMENTS

| EP | 0 201 251 | 12/1986 |
| EP | 0 273 727 | 7/1988 |

(Continued)

OTHER PUBLICATIONS

Vippagunta, S.R., Brittain, H.G., Grant, D.J.W. (2001) Crystalline solids. Advanced Drug Delivery Reviews, vol. 48, pp. 3-26.*

(Continued)

*Primary Examiner* — Scarlett Goon
(74) *Attorney, Agent, or Firm* — Wenderoth, Lind & Ponack, L.L.P.

(57) ABSTRACT

The present invention provides a novel glycopeptide antibiotic derivative.

These derivatives are represented by the formula (I)

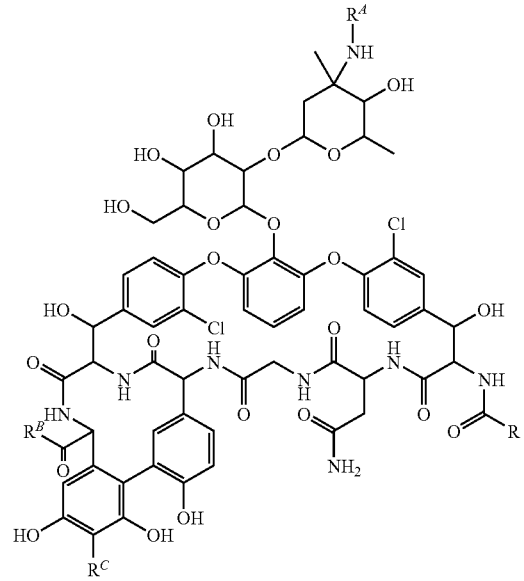

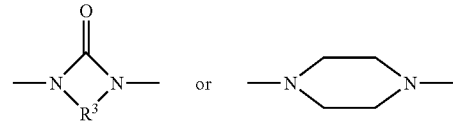

or a pharmaceutically acceptable salt or solvate thereof, wherein
$R^A$ is
$-X^1-Ar^1-X^2-Y-X^3-Ar^2$
wherein
$X^1$, $X^2$ and $X^3$ are single bond; heteroatom-containing group selected from the group consisting of $-N=$, $=N-$, $-NR^1-$ ($R^1$ is hydrogen or lower alkyl), $-O-$, $-S-$, $-SO-$ and $-SO_2-$, or a linkage thereof; or alkylene or alkenylene optionally substituted and optionally interrupted by one or more of said heteroatom-containing group;
Y is $-NR^2CO-$, $-CONR^2-$ ($R^2$ is hydrogen or lower alkyl), or a group of the formula (II) wherein $R^3$ is alkylene;
$Ar^1$ and $Ar^2$ are a carbocycle or a heterocycle which is optionally substituted and may have an unsaturated bond;
$R^B$ is
$-NHNR^XR^Y$ or $-NR^ZOR^W$
wherein
$R^X$ is hydrogen or lower alkyl;
$R^Y$ is hydrogen, optionally substituted lower alkyl, $C(=NH)NH_2$, $CSNH_2$, $COCONH_2$, $CN$, optionally substituted heterocyclic group, and optionally substituted carbamoyl;
$R^Z$ is hydrogen or lower alkyl;
$R^W$ is hydrogen, optionally substituted lower alkyl, optionally substituted lower alkenyl, optionally substituted heterocyclic group, optionally substituted heterocyclic carbonyl or optionally substituted carbamoyl;
$R^C$ is hydrogen or optionally substituted alkyl, wherein said alkyl may be interrupted by a heteroatom-containing group selected from N=, =N-, $-NR^1-$ ($R^1$ is hydrogen or lower alkyl), $-O-$, $-S-$, $-SO-$ and $-SO_2-$; and
R is optionally substituted alkyl.

12 Claims, No Drawings

(56) References Cited

U.S. PATENT DOCUMENTS

| | | | |
|---|---|---|---|
| 6,699,836 | B2 | 3/2004 | Kahne et al. |
| 2003/0068669 | A1 | 4/2003 | Thorson |
| 2004/0259228 | A1 | 12/2004 | Thorson |
| 2005/0239689 | A1 | 10/2005 | Thorson |
| 2005/0266523 | A1 | 12/2005 | Thorson |
| 2008/0097078 | A1* | 4/2008 | Arimoto et al. ............... 530/317 |

FOREIGN PATENT DOCUMENTS

| | | | |
|---|---|---|---|
| EP | 0 301 785 | 2/1989 | |
| EP | 0 435 503 | 12/1990 | |
| EP | 0 667 353 | 8/1995 | |
| EP | 1 016 670 | 7/2000 | |
| EP | 1 031 576 | 8/2000 | |
| EP | 1 818 340 | 8/2007 | |
| JP | 01-240196 | 9/1989 | |
| JP | 04-108800 | 4/1992 | |
| JP | 2000-302687 | 10/2000 | |
| JP | 2001-163898 | 6/2001 | |
| JP | 2003-026725 | 1/2003 | |
| JP | 2006-503015 | 1/2006 | |
| WO | 93/03060 | 2/1993 | |
| WO | 96/30401 | 10/1996 | |
| WO | 00/04044 | 1/2000 | |
| WO | 00/39156 | 7/2000 | |
| WO | 00/42067 | 7/2000 | |
| WO | 00/59528 | 10/2000 | |
| WO | 00/69893 | 11/2000 | |
| WO | 01/81372 | 11/2001 | |
| WO | 01/81373 | 11/2001 | |
| WO | 03/018608 | 3/2003 | |
| WO | 2004/019970 | 3/2004 | |
| WO | 2004/044222 | 5/2004 | |
| WO | 2005/018743 | 3/2005 | |
| WO | 2005/034856 | 4/2005 | |
| WO | 2006/003456 | 1/2006 | |
| WO | 2006/057288 | 6/2006 | |
| WO | WO 2006/057303 | * 6/2006 | ............... C07K 5/12 |
| WO | 2006/093933 | 9/2006 | |
| WO | 2006/094082 | 9/2006 | |

OTHER PUBLICATIONS

Morissette, S.L., Almarsson, Ö., Peterson, M.L., Remenar, J.F., Read, M.J., Lemmo, A.V., Ellis, S., Cima, M.J., Gardner, C.R. (2004) High-throughput crystallization: polymorphs, salts, co-crystals and solvates of pharmaceutical solids. Advanced Drug Delivery Reviews, vol. 56, pp. 275-300.*
Parenti, F., Cavalleri, B. (1990) Novel Glycopeptide Antibiotics of the Dalbaheptide Group. Drugs of the Future, vol. 15, No. 1, p. 57-72.*
Trani, A., Malabarba, A., Ferrari, P., Pallanza, Berti, M., Ciabatti, R. (1990) Carboxyhydrazides of the Aglycone of Teicoplanin Synthesis and Antibacterial Activity. The Journal of Antibiotics, vol. XLIII, No. 11, p. 1471-1481.*
M. N. Preobrazhenskaya et al.,"Patents on Glycopeptides of the Vancomycin Family and Their Derivatives as Antimicrobials: Jan. 1999-Jun. 2003", Expert Opin. Ther. Patents, vol. 14, No. 2, pp. 141-173, 2004.
J. F. Barrett, "Recent Developments in Glycopeptide Antibacterials", Current Opinion in Investigational Drugs, vol. 6, No. 8, pp. 781-790, 2005.
Reyes et al., "Efficacy of Televancin (TD-6424), A Rapidly Bactericidal Lipoglycopeptide with Multiple Mechanisms of Action, in a Murine Model of Pneumonia Induced by Methicillin-Resistant *Staphylococcus aureus*", Antimicrobial Agents and Chemotherapy, vol. 49, No. 10, pp. 4344-4346, Oct. 2005.
J. L. Pace et al., "Glycopeptides: Update on an Old Successful Antibiotic Class", Biochemical Pharmacology, vol. 71, No. 7, pp. 968-980, Mar. 2006.
O. Yoshida et al., "Novel Semi-Synthetic Glycopeptide Antibiotics Active Against Methicillin-Resistant *Staphylococcus aureus* (MRSA) and Vancomycin-Resistant Enterococci (VRE): Doubly-Modified Water-Soluble Derivatives of Chloroorienticin B", Bioorganic & Medicial Chemistry Letters, vol. 12, pp. 3027-3031, 2002.
J. K. Judice et al., "Semi-Synthetic Glycopeptide Antibacterials", Bioorganic & Medicinal Chemistry Letters, vol. 13, pp. 4165-4168, 2003.
Griffith et al.; "'Sweetening' Natural Products via Glycorandomization"; Current Opinion in Biotechnology; c. 2005; vol. 16; p. 622-30.
Lu et al.; "Characterization of a Regiospecific Epivancosaminyl Transferase GtfA and Enzymatic Reconstitution of the Antibiotic Chloroeremomycin"; Proceedings of the National Academy of Sciences; c. Mar. 2004; vol. 101, No. 13; p. 4390-4395.
Oberthür et al.; "A systematic Investigation of the Synthetic Utility of Glycopeptide Glycosyltransferases"; Journal of the American Chemical Society; c. 2005; vol. 127; p. 10747-10752.
Mulichak et al.; "Structure of the UDP—Glucosyltransferase GtfB that Modifies the Heptapeptide Aglycone in the Biosynthesis of Vancomycin Group Antibiotics"; Structure; c. Jul. 2001; vol. 9; p. 547-557.
Cooper et al.; "Reductive Alkylation of Glycopeptide Antibiotics: Synthesis and Antibacterial Activity"; The Journal of Antibiotics; c. 1996; vol. 49, No. 6; p. 575-581.
Shi et al.; "Catalysis of Carbamate Hydrolysis by Vancomycin and Semisynthetic Derivatives"; Journal of the American Chemical Society; c. 1993; vol. 115; p. 6482-6486.
Sundram et al.; "General and Efficient Method for the Solution- and Solid-Phase Synthesis of Vancomycin Carboxamide Derivatives"; Journal of Organic Chemistry; c. 1995; vol. 60; p. 1102-1103.
Pavlov et al.; "A New Type of Chemical Modification of Glycopeptides, Antibiotics, Aminomethylated Derivatives of Eremomycin and Their Antibacterial Activity"; The Journal of Antibiotics; c. 1997; vol. 50, No. 6; p. 509-513.
Malabarba et al.; "Structural Modifications of Glycopeptide Antibiotics"; Medicinal Research Reviews; c. 1997; vol. 17, No. 1; p. 69-137.
Allen et al.; "The Role of Hydrophobic Side Chains as Determinants of Antibacterial Activity of Semisynthetic Glycopeptide Antibiotics"; The Journal of Antibiotics; c. 1997; vol. 50; No. 8; p. 677-684.
Rodriguez et al.; "Novel Glycopeptide Antibiotics: *N*-Alkylated Derivatives Active Against Vancomycin-Resistant Enterococci"; The Journal of Antibiotics; c. Jun. 1998; vol. 51, No. 6; p. 560-569.
Fu et al.; "Antibiotic Optimization Via in vitro Glycorandomization"; Nature Biotechnology; c. Dec. 2003; vol. 21, No. 12; p. 1467-1469.
Melançon, III et al.; "Glyco-Stripping and Glyco-Swapping"; Acs Chemical Biology; c. Sep. 2006; vol. 1, No. 8; p. 499-504.
Balzarini et al.; "Inhibition of Feline (FIPV) and Human (SARS) Coronavirus by Semisynthetic Derivatives of Glycopeptide Antibiotics"; Antiviral Research; c. 2006; vol. 72; p. 20-33.
Maffioli et al.; "Synthesis and Antibacterial Activity of Alkyl Derivatives of the Glycopeptide Antibiotic A40926 and Their Amides"; Bioorganic & Medicinal Chemistry Letters; c. 2005; vol. 15; p. 3801-3805.
Fu et al.; "Diversifying Vancomycin via Chemoenzymatic Strategies"; Organic Letters; c. 2005; vol. 7, No. 8; p. 1513-1515.
Kruger et al.; "Tailoring of Glycopeptide Scaffolds by the Acyltransferases from the Teicoplanin and A-40,926 Biosynthetic Operons"; Chemistry & Biology; c. Jan. 2005; vol. 12, p. 131-140.
Ritter et al.; "A Programmable One-Pot Oligosaccharide Synthesis for Diversifying the Sugar Domains of Natural Products: A Case Study of Vancomycin"; Angewandte Chemie Int. Ed.; c. 2003; vol. 42; p. 4657-4660.
Balzarini et al.; "Antiretroviral Activity of Semisynthetic Derivatives of Glycopeptide Antibiotics"; The Journal of Medicinal Chemistry; c. 2003; vol. 46; p. 2755-2764.
Chen et al.; "Structural Requirements for VanA Activity of Vancomycin Analogues"; Tetrahedron; c. 2002; vol. 58; p. 6585-6594.
Blizzard et al.; "Antibacterial Activity of G6-Quaternary Ammonium Derivatives of a Lipophilic Vancomycin Analogue"; Bioorganic & Medicinal Chemistry Letters; c. 2002; vol. 12; p. 849-852.

(56) References Cited

OTHER PUBLICATIONS

Nicolaou et al.; "Solid- and Solution-Phase Synthesis of Vancomycin and Vancomycin Analogues with Activity Against Vancomycin-Resistant Bacteria"; Chemistry-A European Journal; c. 2001; vol. 7, No. 17; p. 3798-3823.

Kerns et al.; "The Role of Hydrophobic Substituents in the Biological Activity of Glycopeptide Antibiotics"; The Journal of the American Chemical Society; c. 2000; vol. 122; p. 12608-12609.

Pavlov et al.; "Synthesis and Antibacterial Activity of Derivatives of the Glycopeptide Antibiotic A-40926 N-alkylated at the Aminoglucuronyl Moiety"; The Journal of Antibiotics; c. 1998; vol. 51, No. 5; p. 525-527.

Nagarajan; "Structure-Activity Relationships of Vancomycin-Type Glycopeptide Antibiotics"; The Journal of Antibiotics; c. 1993, vol. 46, No. 8; p. 1181-1195.

Hubbard et al.; "Vancomycin Assembly: Nature's Way"; Angewandte Chemie; c. 2003; vol. 42, No. 7; p. 730-765.

Parenti et al.; "Proposal to Name the Vancomycin-Ristocetin Like Glycopeptides as Dalbaheptides"; The Journal of Antibiotics; c. Dec. 1989; vol. 42, No. 12, p. 1882-1883.

Rao et al.; "Studies Directed Toward the Synthesis of Vancomycin and Related Cyclic Peptides"; Chemical Review; c. 1995; vol. 95; p. 2135-2167.

Nicolaou et al.; "Chemistry, Biology, and Medicine of the Glycopeptide Antibiotics"; Angewandte Chemie; c. 1999; vol. 38; p. 2096-2152.

Van Bambeke et al.; "Glycopeptide Antibiotics from Conventional Molecules to New Derivatives"; Drugs; c. 2004; vol. 64, No. 9; p. 913-936.

Kahne et al.; "Glycopeptide and Lipoglycopeptide Antibiotics"; Chemical Review; c. 2005; vol. 105; p. 425-448.

Gerhard et al.; "The Role of the Sugar and Chlorine Substituents in the Dimerization of Vancomycin Antibiotics"; The Journal of the American Chemical Society; c. 1993; vol. 115; p. 232-237.

Ward et al.; "Oritavancin—an Investigational Glycopeptide Antibiotic"; Expert Opinion Investigating Drugs; c. 2006; vol. 15, No. 4; p. 417-429.

Williams et al.; "The Vancomycin Group of Antibiotics and the Fight Against Resistant Bacteria"; Angewandte Chemie; c. 1999; vol. 38; p. 1172-1193.

Malabarba et al.; "Glycopeptide Resistance in Multiple Antibiotic-Resistant Gram-Positive Bacteria: A Current Challenge for Novel Semi-Synthetic Glycopeptide Derivatives"; European Journal of Medicinal Chemistry; c. 1997; vol. 62; p. 459-478.

Nagarajan et al.; "The Structural Relationships of A82846B and Its Hydrolysis Products with Chloroorienticins A, B and C"; The Journal of Antibiotics; c. Sep. 1989; vol. 42, No. 9; p. 1438-1440.

Salas et al.; "Engineering the Glycosylation of Natural Products in Actinomycetes"; Trends in Microbiology; c. 2007; vol. 15, No. 5; p. 219-232.

Thayer et al.; "Vancomycin Analogues Containing Monosaccharides Exhibit Improved Antibiotic Activity: A Combined One-Pot Enzymatic Glycosylation and Chemical Diversification Strategy"; Chemistry—An Asian Journal; c. 2006; vol. 1; p. 445-452.

Supplementary European Search Report dated Dec. 28, 2011 in corresponding European Application No. 07 74 4107.

\* cited by examiner

GLYCOPEPTIDE ANTIBIOTIC DERIVATIVE

This application is a U.S. national stage of International Application No. PCT/JP2007/060673 filed May 25, 2007.

TECHNICAL FIELD

The invention relates to a glycopeptide antibiotic derivative and a pharmaceutical formulation comprising such derivative.

The claimed invention was made by or on behalf of the parties to a joint research agreement, within the meaning of 35 U.S.C. § 100(h) and 37 C.F.R § 1.9(e), which was in effect on or before the date the claimed invention was made, and the claimed invention was made as a result of activities undertaken within the scope of the joint research agreement. The parties of the joint research agreement are (1) "National University Corporation Nagoya University" of Aichi, Japan, and (2) "Shionogi & Co., Ltd." of Osaka, Japan.

BACKGROUND OF THE INVENTION

Glycopeptide antibiotics, which have a complex polycyclic peptide structure, are produced in various microorganism and effective to most gram-positive bacteria as an antimicrobial. In recent years, there are emergences of drug-resistant strains such as penicillin-resistant, cephalosporin-resistant, and serious problems of infections with multidrug resistant and methicillin-resistant Staphylococcus aureus (MRSA) has been raised in clinical practice. Glycopeptide antibiotics, such as vancomycin, are effective typically to these resistant strains, and vancomycin has been a drug as an ultimate tool for infections with MRSA and other resistant strains.

In certain strains, however, there is growing concern of emergence of resistance to vancomycin, such as vancomycin-resistant enterococci (VRE). VRE has a different mechanism and degree of resistance, depending on the gene type of a resistance-related gene such as Van A, B, C, D, E, G. For example, teicoplanin, which is a glycopeptide antibiotic as with vancomycin, is effective to Van B type VRE. On the other hand, effective glycopeptide antibiotic has not been released for Van A type VRE, while clinical measures to fight such resistant strain is especially needed. Furthermore, Staphylococcus aureus that has acquired the resistance of VRE (VRSA) has been discovered recently. Therefore, need for development of glycopeptide derivative having improved activity and/or selectivity exists. Many vancomycins and other glycopeptide derivatives have been known in the art. See, e.g., references as follows.
(1) Japanese Patent Publication 61-251699
(2) Japanese Patent Publication 7-258289
(3) WO96/30401
(4) WO00/39156
(5) Japanese Patent Publication 2000-302687
(6) WO2004/44222
(7) WO2001/81372
(8) WO2006/057303

DISCLOSURE OF INVENTION

Problems to be Resolved by the Invention

The invention relates to a novel glycopeptide antibiotic derivative that has an increased and improved property compared with that of conventional glycopeptide antibiotics. Certain glycopeptide derivatives of the invention, particularly vancomycin derivatives, show an increased antimicrobial activity compared with vancomycin itself.

Means of Solving the Problems

The invention provides:
(1) A compound of the formula:

[Chemical Formula 1]

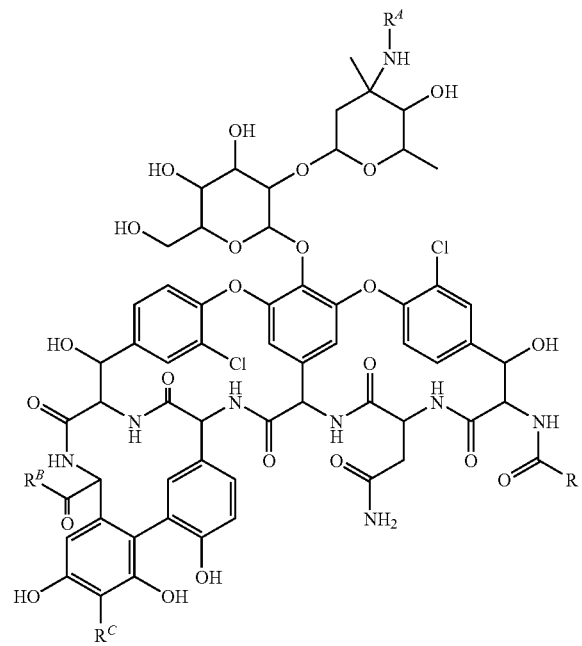

or a pharmaceutically acceptable salt or solvate thereof, wherein
$R^A$ is presented by the formula:

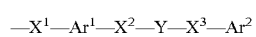

wherein $X^1$, $X^2$ and $X^3$ are independently
  a) single bond;
  b) heteroatom-containing group selected from the group consisting of —N=, =N—, —NR$^1$— (wherein R$^1$ is hydrogen or lower alkyl), —O—, —S—, —SO— and —SO$_2$—, or a linkage thereof; or
  c) optionally substituted alkylene or alkenylene optionally interrupted by one or more of the same or different heteroatom-containing group of (b);
Y is —NR$^2$CO— or —CONR$^2$— wherein R$^2$ is hydrogen or lower alkyl, or a group of the formula:

[Chemical Formula 2]

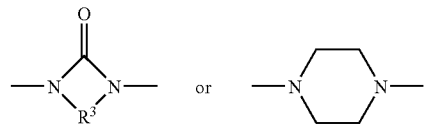

wherein R$^3$ is alkylene; and
  Ar$^1$ and Ar$^2$ are independently a carbocycle or heterocycle, each is optionally substituted and may have an unsaturated bond;

$R^B$ is

—NHNR$^X$R$^Y$ wherein

R$^X$ is hydrogen or lower alkyl;

R$^Y$ is selected from the group consisting of hydrogen, optionally substituted lower alkyl, C(=NH)NH$_2$, CSNH$_2$, COCONH$_2$, CN, optionally substituted heterocyclic group, lower alkylcarbonyl and optionally substituted carbamoyl; or

—NR$^Z$OR$^W$ wherein

R$^Z$ is hydrogen or lower alkyl;

R$^W$ is hydrogen, optionally substituted lower alkyl, optionally substituted lower alkenyl, optionally substituted heterocyclic group, optionally substituted heterocyclic carbonyl or optionally substituted carbamoyl;

R$^C$ is hydrogen or optionally substituted alkyl, wherein said alkyl may be interrupted by a heteroatom-containing group selected from the group consisting of N=, =N—, —NR$^1$— (wherein R$^1$ is hydrogen or lower alkyl), —O—, —S—, —SO— and —SO$_2$—; and R is optionally substituted alkyl;

with the proviso that the compound is not the following compounds:

[Chemical Formula 3]

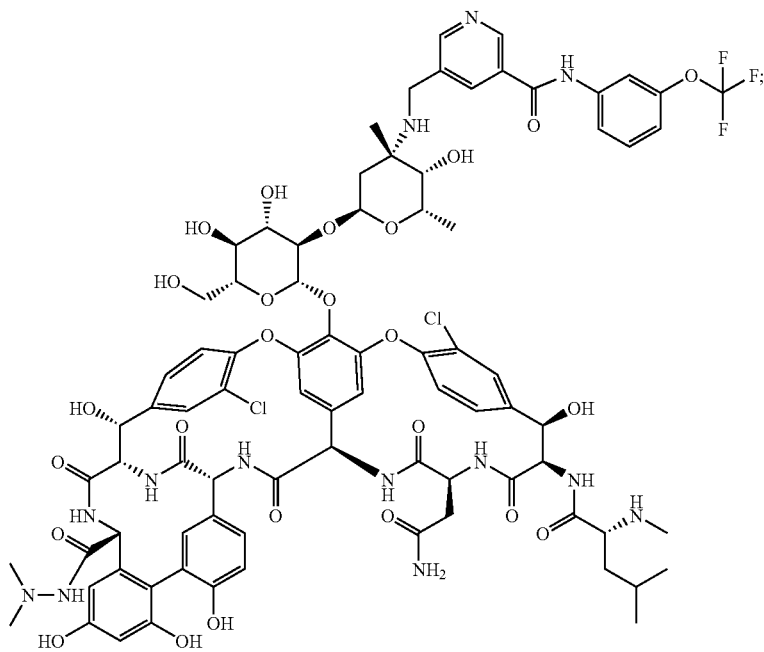

[Chemical Formula 4]

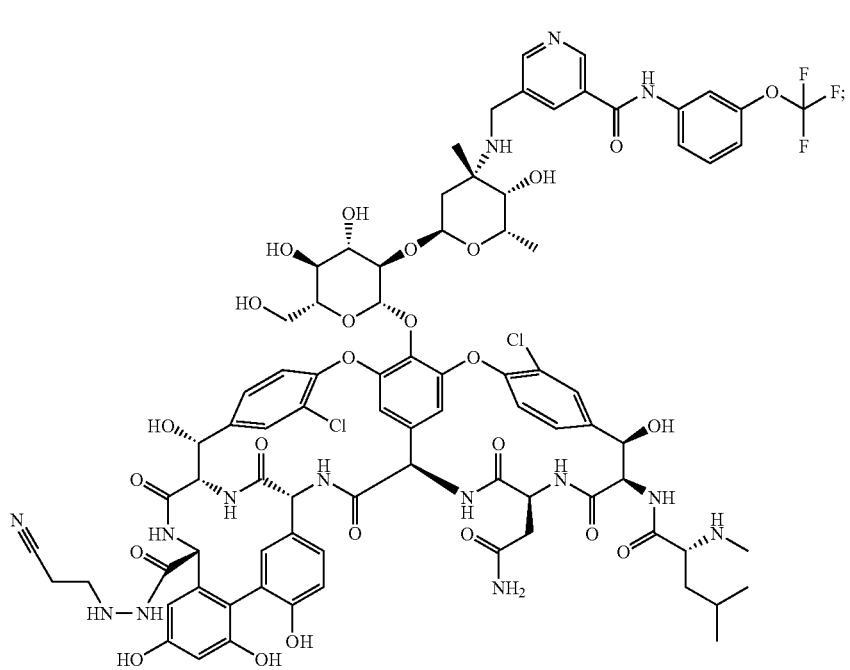

[Chemical Formula 5]
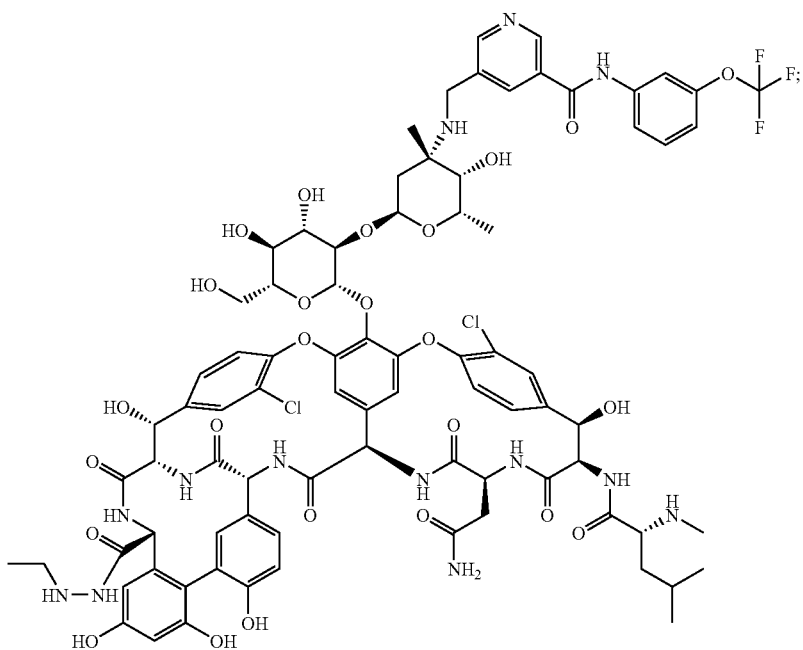
[Chemical Formula 6]
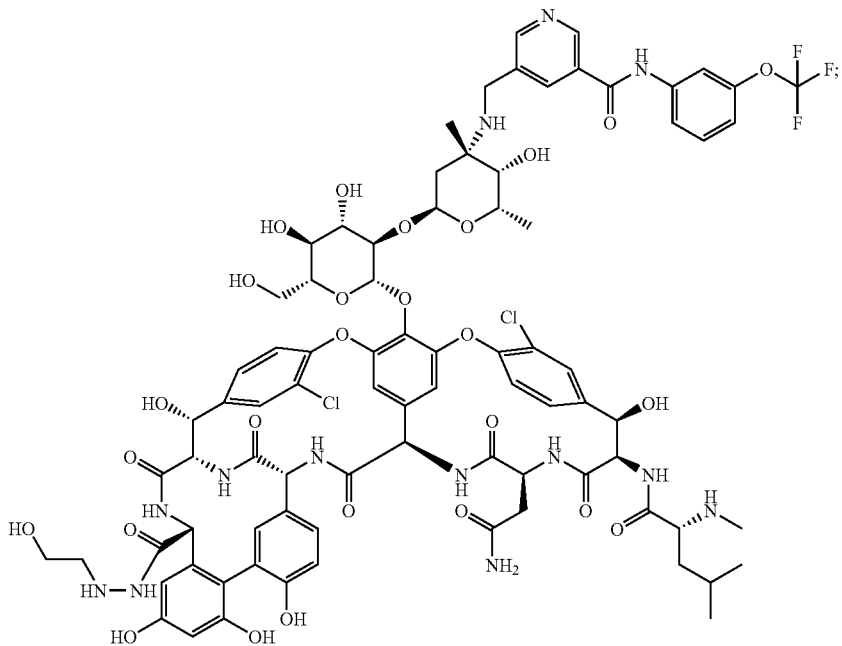

[Chemical Formula 7]
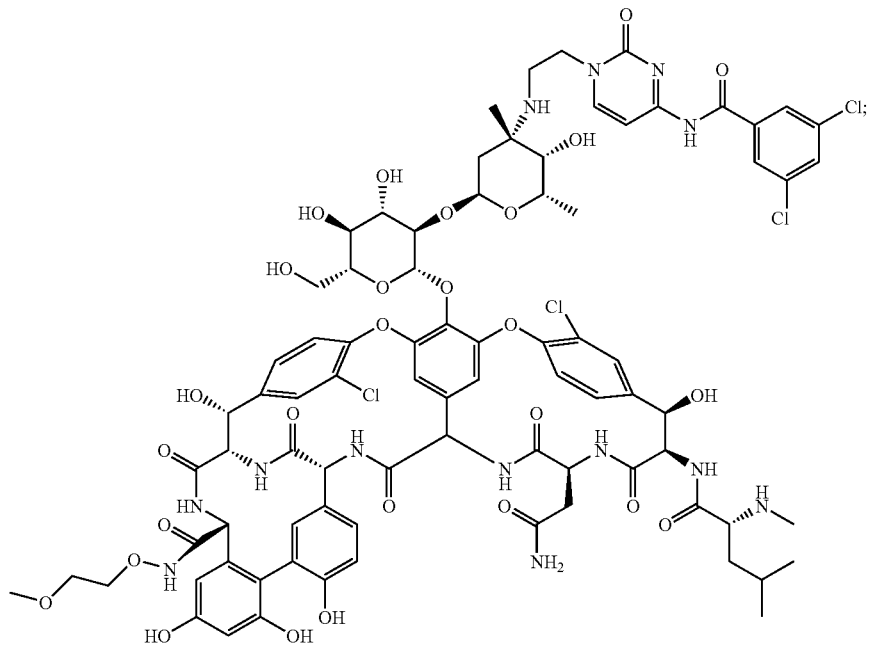
[Chemical Formula 8]
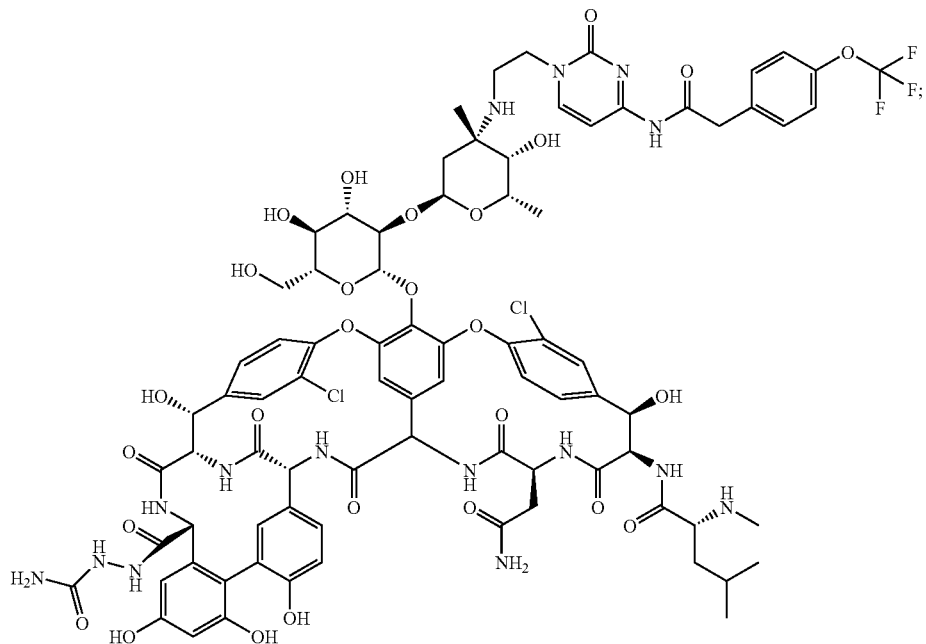

-continued
[Chemical Formula 9]
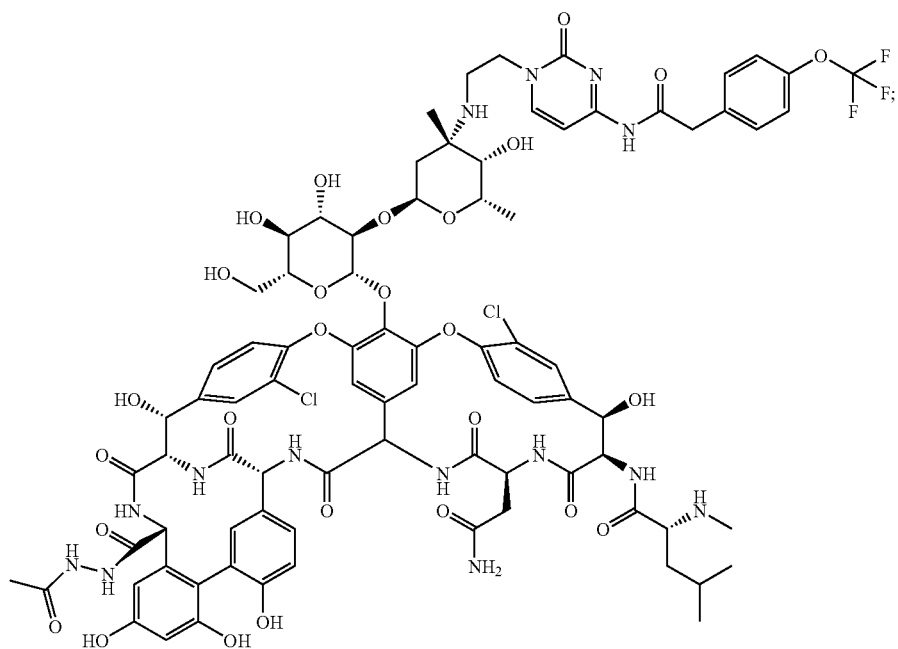
[Chemical Formula 10]
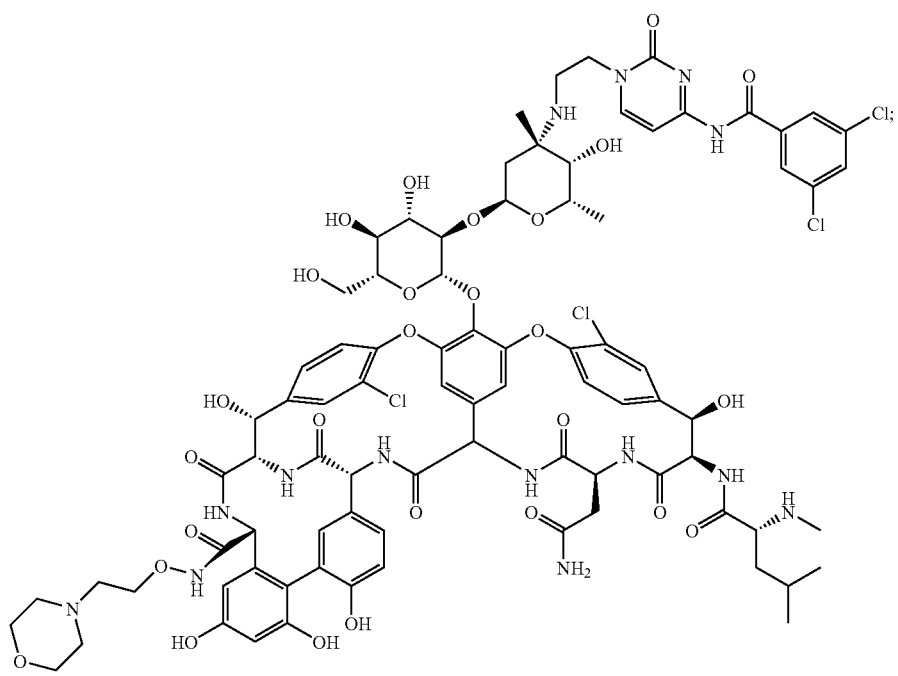

-continued

[Chemical Formula 11]

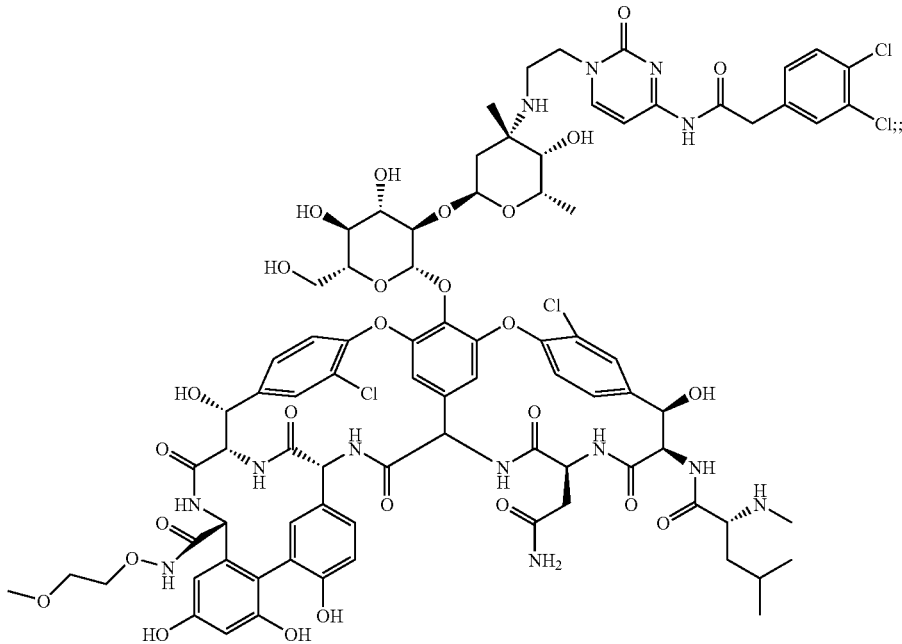

(2) The compound according to (1) or a pharmaceutically acceptable salt or solvate thereof, wherein $R^Y$ is selected from the group consisting of hydrogen, optionally substituted lower alkyl, C(=NH)NH$_2$, CSNH$_2$, COCONH$_2$, CN, optionally substituted heterocyclic group, and optionally substituted carbamoyl;

(3) The compound according to (1) or a pharmaceutically acceptable salt or solvate thereof,
wherein
$R^B$ is

—NHNR$^X$R$^Y$ wherein $R^X$ is hydrogen; $R^Y$ is hydrogen, optionally substituted lower alkyl or optionally substituted carbamoyl); or

—NR$^Z$OR$^W$ wherein $R^Z$ is hydrogen; $R^W$ is hydrogen or optionally substituted lower alkyl;

(4) The compound according to (1) or a pharmaceutically acceptable salt or solvate thereof,
wherein
$R^B$ is

—NHNR$^X$R$^Y$ wherein
$R^X$ is hydrogen;
$R^Y$ is hydrogen, or lower alkyl substituted with OH or lower alkoxy, or carbamoyl substituted with lower alkyl; or

—NR$^Z$OR$^W$ wherein
$R^Z$ is hydrogen;
$R^W$ is hydrogen, or lower alkyl substituted with OH or lower alkoxy;

(5) The compound according to (1) or a pharmaceutically acceptable salt or solvate thereof, wherein Y is —NR$^2$CO— or —CONR$^2$— wherein R$^2$ is hydrogen or lower alkyl;

(6) The compound according to (1) or a pharmaceutically acceptable salt or solvate thereof, wherein Ar$^1$ is optionally substituted phenyl or optionally substituted five- to seven-membered nitrogen atom-containing heterocyclic group;

(7) The compound according to (1) or a pharmaceutically acceptable salt or solvate thereof, wherein Ar$^1$ is phenyl or five- to seven-membered nitrogen atom-containing heterocyclic group optionally substituted with oxo;

(8) The compound according to (1) or a pharmaceutically acceptable salt or solvate thereof, wherein Ar$^1$ is a group represented by any one of the formulae:

[Chemical Formula 12]

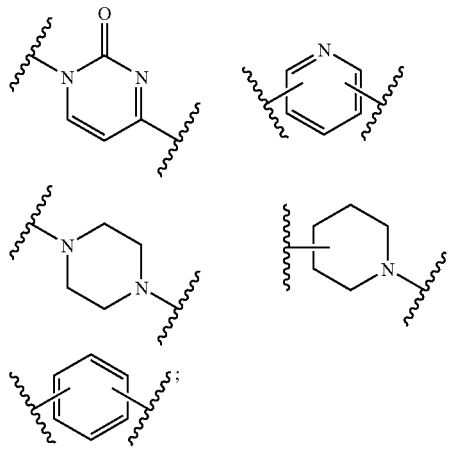

(9) The compound according to (1) or a pharmaceutically acceptable salt or solvate thereof, wherein Ar$^2$ is optionally substituted phenyl;

(10) The compound according to (1) or a pharmaceutically acceptable salt or solvate thereof, wherein Ar$^2$ is phenyl substituted with same or different one or two substituents selected from the group consisting of halogen and halogenated lower alkoxy;

(11) The compound according to (1) or a pharmaceutically acceptable salt or solvate thereof, wherein Ar² is a group represented by any one of the formulae:

[Chemical Formula 13]

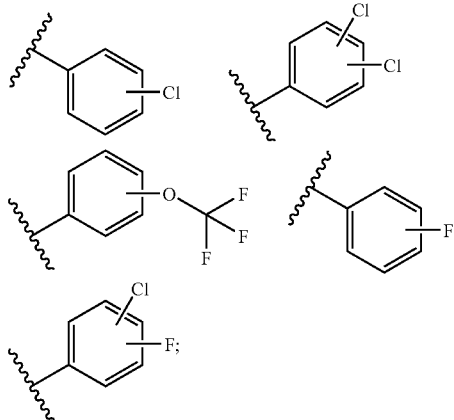

(12) The compound according to (1) or a pharmaceutically acceptable salt or solvate thereof, wherein
X¹ and X³ are independently
a) single bond,
b) heteroatom-containing group selected from the group consisting of —N═, ═N—, —NR¹— (wherein R¹ is hydrogen or lower alkyl), —O—, —S—, —SO— and —SO₂—, or a linkage thereof; or
c) lower alkylene or lower alkenylene optionally interrupted by one or more of same or different heteroatom-containing group of (b); and
X² is a single bond;

(13) The compound according to (1) or a pharmaceutically acceptable salt or solvate thereof, wherein X¹ and X³ are independently single bond, lower alkylene or lower alkenylene; and X² is a single bond;

(14) The compound according to (1) or a pharmaceutically acceptable salt or solvate thereof, wherein $R^C$ is hydrogen and/or R is —CH(NHR$^D$)CH₂CH(CH₃)₂ wherein $R^D$ is hydrogen or lower alkyl;

(15) The compound according to (1) or a pharmaceutically acceptable salt or solvate thereof,
wherein
$R^B$ is

—NHNR$^X$R$^Y$ wherein R$^X$ is hydrogen; R$^Y$ is hydrogen, optionally substituted lower alkyl or optionally substituted carbamoyl; or

—NR$^Z$OR$^W$ wherein R$^Z$ is hydrogen; R$^W$ is hydrogen or optionally substituted lower alkyl;
Y is —NR²CO— or —CONR²— wherein R² is hydrogen or lower alkyl;
Ar¹ is optionally substituted phenyl or optionally substituted five- to seven-membered nitrogen atom-containing heterocyclic group;
Ar² is optionally substituted phenyl;

X¹ and X³ are independently
a) single bond,
b) heteroatom-containing group selected from the group consisting of —N═, ═N—, —NR¹— (wherein R¹ is hydrogen or lower alkyl), —O—, —S—, —SO— and —SO₂—, or a linkage thereof; or
c) lower alkylene or lower alkenylene optionally interrupted by one or more of same or different heteroatom-containing group of (b); and
X² is a single bond;
$R^C$ is hydrogen;
R is —CH(NHR$^D$)CH₂CH(CH₃)₂ wherein $R^D$ is hydrogen or lower alkyl;

(16) The compound according to (1) or a pharmaceutically acceptable salt or solvate thereof,
wherein
$R^B$ is

—NHNR$^X$R$^Y$ wherein R$^X$ is hydrogen; R$^Y$ is hydrogen, optionally substituted lower alkyl, or optionally substituted carbamoyl); or

—NR$^Z$OR$^W$ wherein R$^Z$ is hydrogen; R$^W$ is hydrogen or optionally substituted lower alkyl;
Y is —NR²CO— or —CONR²— wherein R² is hydrogen or lower alkyl;
Ar¹ is phenyl or five- to seven-membered nitrogen atom-containing heterocyclic group optionally substituted with oxo;
Ar² is phenyl substituted with same or different one or two substituents selected from the group consisting of halogen and halogenated lower alkoxy;
X¹ and X³ are independently single bond, lower alkylene or lower alkenylene;
X² is a single bond;
$R^C$ is hydrogen;
R is —CH(NHR$^D$)CH₂CH(CH₃)₂ wherein $R^D$ is hydrogen or lower alkyl;

(17) The compound according to (1) or a pharmaceutically acceptable salt or solvate thereof,
wherein
$R^B$ is

—NHNR$^X$R$^Y$ wherein R$^X$ is hydrogen; R$^Y$ is hydrogen, lower alkyl substituted with OH or lower alkoxy, or carbamoyl substituted with lower alkyl; or

—NR$^Z$OR$^W$ wherein R$^Z$ is hydrogen; R$^W$ is hydrogen, or lower alkyl substituted with OH or lower alkoxy;
Y is —NHCO— or —CONH—;
Ar¹ is a group represented by any one of the formulae:

[Chemical Formula 14]

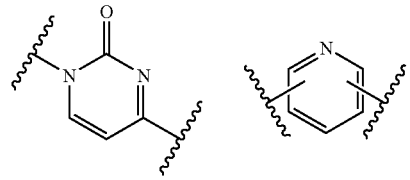

-continued

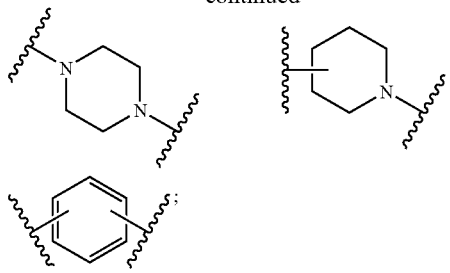

$Ar^2$ is a group represented by any one of the formulae:

[Chemical Formula 15]

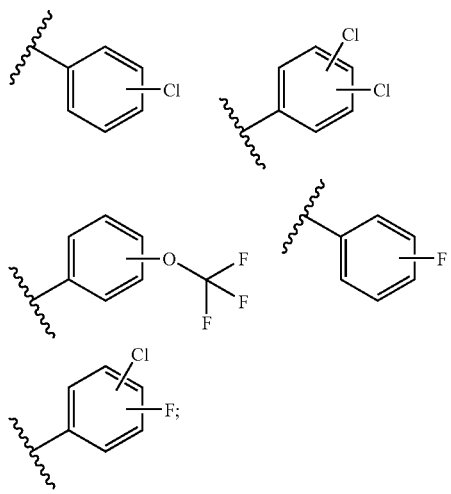

$X^1$ and $X^3$ are independently single bond, lower alkylene or lower alkenylene;
$X^2$ is a single bond;
$R^C$ is hydrogen; and
R is —CH(NHR$^D$)CH$_2$CH(CH$_3$)$_2$ wherein $R^D$ is hydrogen or lower alkyl;
(18) The compound according to (1) or a pharmaceutically acceptable salt or solvate thereof,
wherein
$R^B$ is

—NHNR$^X$R$^Y$ wherein $R^X$ is hydrogen; $R^Y$ is hydrogen, optionally substituted lower alkyl, —COCONH$_2$, or lower alkylcarbonyl; or

—NR$^Z$OR$^W$ wherein $R^Z$ is hydrogen; $R^W$ is hydrogen or optionally substituted lower alkyl;
Y is —NR$^2$CO— or —CONR$^2$— wherein R$^2$ is hydrogen or lower alkyl;
Ar$^1$ is phenyl or five- to seven-membered nitrogen atom-containing heterocyclic group optionally substituted with oxo;
Ar$^2$ is phenyl substituted with same or different one or two substituents selected from the group consisting of halogen, halogenated lower alkoxy, and lower alkyl;
$X^1$ and $X^3$ are independently single bond, lower alkylene or lower alkenylene;
$X^2$ is a single bond;
$R^C$ is hydrogen;
R is —CH(NHR$^D$)CH$_2$CH(CH$_3$)$_2$ wherein $R^D$ is hydrogen or lower alkyl; and
(19) The compound according to (1) or a pharmaceutically acceptable salt or solvate thereof,
wherein
$R^B$ is

—NHNR$^X$R$^Y$ wherein $R^X$ is hydrogen; $R^Y$ is —CH$_2$CH$_2$OH, —COCONH$_2$, —COCH$_3$, or —NHOH;
Y is —NR$^2$CO— or —CONR$^2$— wherein R$^2$ is hydrogen or lower alkyl;
Ar$^1$ is phenyl or five- to seven-membered nitrogen atom-containing heterocyclic group optionally substituted with oxo;
Ar$^2$ is phenyl substituted with same or different one or two substituents selected from the group consisting of halogen and halogenated lower alkoxy;
$X^1$ is lower alkylene;
$X^3$ is a single bond, lower alkylene or lower alkenylene;
$X^2$ is a single bond;
$R^C$ is hydrogen; and
R is —CH(NHR$^D$)CH$_2$CH(CH$_3$)$_2$ wherein $R^D$ is hydrogen or lower alkyl.

The present invention also relates to a pharmaceutical composition comprising the compound of the invention as described above, or a pharmaceutically acceptable salt or solvate thereof, preferably an antimicrobial drug.

Effect Of The Invention

The glycopeptide antibiotic derivative of the invention, a pharmaceutically acceptable salt, or solvate thereof shows an antimicrobial activity against various microorganisms such as *staphylococcus* including MRSA, *streptococcus*, pneumococcus and *enterococcus*. The compound is also effective against vancomycin-resistant strains thereof, particularly vancomycin-resistant *enterococcus* (VRE) and vancomycin-resistant *staphylococcus aureus* (VRSA). Thus, the compound is useful in the treatment or prevention of various bacterial infectious diseases such as meningitis, sepsis, pneumonia, arthritis, peritonitis, bronchitis, empyema and the like. The more preferred compound of the invention is highly water-soluble and shows good pharmacokinetics and/or is safe with respect to toxicity.

DETAILED DESCRIPTION OF THE PREFERRED EMBODIMENTS

In order to describe the compound of the invention, the terms as used herein have the following meaning solely or in combination with other terms as used herein.

The term "lower alkyl" refers to a saturated straight or branched hydrocarbon mono radical having 1 to 6 carbons, and includes methyl, ethyl, n-propyl, isopropyl, n-butyl, isobutyl, sec-butyl, tert-butyl, n-pentyl, isopentyl, neopentyl, tert-pentyl, N-hexyl, isohexyl.

The term "linking group" in the definition for $X^1$, $X^2$ and $X^3$ refers to a linking group that comprises a hetero atom selected from the group consisting of —N═, ═N—, —NR$^1$— (wherein R$^1$ is hydrogen or lower alkyl), —O—, —S—, —SO— and —SO$_2$— selected from the group, and includes for example —S—S—, —NR$^1$CO—, —NR$^1$O—, —NR$^1$S—, —OSO$_2$—, —OCO—, —SO$_2$NR$^1$—, etc.

The term "alkylene" refers to a saturated straight or branched hydrocarbon diradical having 1 to 6 carbons, and includes for example methylene, ethylene, trimethylene, propylene, tetramethylene, ethylethylene, pentamethylene or hexamethylene, etc. A saturated straight or branched alkylene having one to four carbon atoms, such as methylene, ethylene, trimethylene or tetramethylene is preferred. Preferred is methylene.

The term "alkenylene" refers to an unsaturated straight or branched hydrocarbon diradical of 2 to 6 carbons, having one or more double bond in the above "alkylene", and includes for example vinylene, propenylene or butenylene. A straight chain alkenylene of 2 or 3 carbons, such as vinylene or propenylene, is preferred.

The term "optionally substituted alkylene or alkenylene" refers to alkylene or alkenylene having 1 to 5 substituents, preferably 1 to 3 substituents, wherein said substituent is selected from the group consisting of: optionally substituted alkyl (e.g., methyl, ethyl, isopropyl, benzyl, carbamoylalkyl (e.g., carbamoylmethyl), mono- or di-alkylcarbamoylalkyl (e.g., dimethylcarbamoylethyl), hydroxyalkyl, heterocyclealkyl (e.g., morpholinoethyl, tetrahydropyranylethyl), alkoxycarbonylalkyl (e.g., ethoxycarbonylmethyl, ethoxycarbonylethyl), mono- or di-alkylaminoalkyl (e.g., dimethylamminioethyl) etc), alkoxyalkyl (e.g., methoxyethyl, ethoxymethyl, ethoxyethyl, i-propoxyethyl etc), acyl (e.g., formyl, optionally substituted alkylcarbonyl (e.g., acetyl, propionyl, butyryl, isobutyryl, valeryl, isovaleryl, pivaloyl, hexanoyl, octanoyl, methoxyethylcarbonyl, 2,2,2-trifluoroethylcarbonyl, ethoxycarbonylmethylcarbonyl, alkoxyalkylcarbonyl (e.g., methoxyethylcarbonyl), alkylcarbamoylalkylcarbonyl (e.g., methylcarbamoylethylcarbonyl), alkoxycarbonylacetyl etc), optionally substituted arylcarbonyl (e.g., benzoyl, toluoyl etc)), optionally substituted aralkyl (e.g., benzyl, 4-F-benzyl etc), hydroxy, optionally substituted alkylsulfonyl (e.g., methanesulfonyl, ethanesulphonyl, isopropylsulphonyl, 2,2,2-trifluoroethanesulphonyl, benzylsulphonyl, methoxyethylsulphonyl etc), arylsulfonyl optionally substituted with alkyl or halo (e.g., benzenesulfonyl, toluenesulfonyl, 4-fluorobenzenesulfonyl), cycloalkyl (e.g., cyclopropyl etc), aryl optionally substituted with alkyl (e.g., 4-methylphenyl etc), alkylaminosulphonyl (e.g., methylaminosulphonyl, dimethylamminiosulphonyl etc), alkylaminocarbonyl (e.g., dimethylaminocarbonyl etc), alkoxycarbonyl (e.g., ethoxycarbonyl etc), cycloalkylcarbonyl (e.g., cyclopropylcarbonyl, cyclohexylcarbonyl etc), optionally substituted sulfamoyl (e.g., sulfamoyl, methylsulfamoyl, dimethylsulfamoyl etc), alkylcarbonylamino (e.g., methylcarbonylamino), heterocycle (e.g., morpholino, tetrahydropyranyl), optionally substituted amino (e.g., mono- or di-alkylamino (such as dimethylamminio), formylamino).

Thus, "optionally substituted alkylene or alkenylene optionally interrupted by one or more same or different heteroatomic group" refers to alkylene or alkenylene optionally substituted and optionally interrupted by one or more same or different of a heteroatom-containing group selected from the group consisting of —N═, ═N—, —NR$^1$— (wherein R$^1$ is hydrogen or lower alkyl), —O—, —S—, —SO— and —SO$_2$—. In this regard, "interrupted" means the presence of a heteroatomic group between carbon atoms composing such alkylene or alkenylene or between said carbon atom and Ar$^1$, Y or Ar$^2$. For example, —O—CH$_2$—, —CH$_2$—O—, —CH$_2$—O—CH$_2$—, CH$_2$—NH—CH$_2$—, —O—CH$_2$—O—, —CH$_2$—O—CH$_2$—NH—CH$_2$—, CH$_2$—N═CH—, —CH$_2$—O—CH═N—CH$_2$—, and —O—CH═CH—, —CH═CH—O—, —CH═CH—O—CH$_2$—, CH$_2$—NH— CH═CH—, —O—CH═CH—O—, or —(CH$_2$—O)— Ar$^1$—(O—CH$_2$—O)—Y—(O—CH$_2$)—Ar$^2$, etc. are exemplified. Also, in the case that alkylene is substituted with oxo, —CO— is preferably exemplified.

X$^1$ is preferably C$_1$-C$_3$ alkylene.

X$^2$ is preferably a single bond, C$_1$-C$_3$ alkylene, O or NH, more preferably, single bond or NH.

Y is preferably, —NHCO—, —CONH—, —NMeCO—, —CONMe- or a radical as follows:

[Chemical Formula 16]

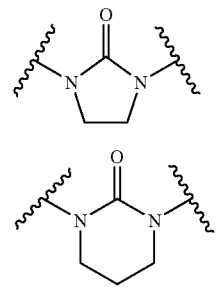

Q1

Q2

Also, Y may be a piperazine ring group, and more preferably, —NHCO— or —CONH—.

X$^3$ is preferably a single bond, C$_1$-C$_3$ alkylene, C$_2$-C$_3$ alkenylene, O or NH, more preferably a single bond, CH$_2$, or CH═CH.

Also, —Y—X$^3$— and —X$^2$—Y— may form a structure of the formula:

[Chemical Formula 17]

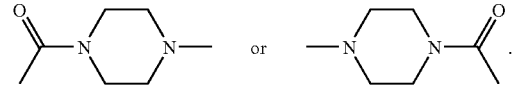

Ar$^1$ and Ar$^2$ are each a carbocycle or a heterocycle that may be substituted or unsaturated.

The term "optionally unsaturated carbocycle" in the definition for Ar$^1$ and Ar$^2$ refers to a cycloalkyl of 3-10 carbons or a cycloalkenyl or aryl of 3-10 carbons.

The term "cycloalkyl" includes, for example, cyclopropyl, cyclobutyl, cyclopentyl, cyclohexyl, cycloheptyl, cyclooctyl, etc. Cycloalkyl of 3-6 carbon atoms, such as cyclopentyl, cyclohexyl, is preferred.

The term "cycloalkenyl" includes, for example, cyclopropenyl (e.g., 1-cyclopropenyl), cyclobutenyl (e.g., 1-cyclobutenyl), cyclopentenyl (e.g., 1-cyclopentene-1-yl, 2-cyclopentene-1-yl, 3-cyclopentene-1-yl), cyclohexenyl (e.g., 1-cyclohexene-1-yl, 2-cyclohexene-1-yl, 3-cyclohexene-1-yl), cycloheptenyl (e.g., 1-cycloheptenyl), cyclooctenyl (e.g., 1-cyclooctenyl). Particularly, 1-cyclohexene-1-yl, 2-cyclohexene-1-yl, 3-cyclohexene-1-yl are preferred.

The term "aryl" refers to a monocyclic aromatic hydrocarbon group (phenyl) and a polycyclic aromatic hydrocarbon group (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl etc). Phenyl or naphthyl (e.g., 1-naphthyl, 2-naphthyl) is preferred.

The term "optionally unsaturated heterocycle" in the definition for Ar$^1$ and Ar$^2$ means a heterocycle or a heteroaryl.

The term "heterocycle" refers to a five- to eight-membered nonaromatic heterocyclic group having at least one N, O or S atom within the ring, the ring being optionally substituted at a substitutable position. Examples are 1-pyrrolinyl, 2-pyrrolinyl, 3-pyrrolinyl, 1-pyrrolindinyl, 2-pyrrolindinyl, 3-pyrrolindinyl, 1-imidazolinyl, 2-imidazolinyl, 4-imidazolinyl, 1-imidazolidinyl, 2-imidazolidinyl, 4-imidazolidinyl, 1-pyrazolynyl, 3-pyrazolynyl, 4-pyrazolynyl, 1-pyrazolidinyl, 3-pyrazolidinyl, 4-pyrazolidinyl, piperidino, 2-piperidyl, 3-piperidyl, 4-piperidyl, 1-piperazinyl, 2-piperazinyl, 2-morpholinyl, 3-morpholinyl, morpholino, tetrahydropyranyl etc. The "a nonaromatic heterocyclic group" may be saturated or unsaturated so long as it is not aromatic.

The term "heteroaryl" refers to a monocyclic aromatic heterocyclic group and a condensed aromatic heterocyclic group. The monocyclic aromatic heterocyclic group is that optionally substituted at a substitutable position and derived from a 5-8 membered aromatic ring that may contain one to four O, S, and/or N atoms within the ring. The condensed aromatic heterocyclic group is that optionally substituted at a substitutable position and wherein a 5-8 membered aromatic ring containing one to four O, S, and/or N atoms within the ring is condensed with one to four 5-8 membered aromatic carbocycles or another 5-8 membered aromatic hetero ring.

The "heteroaryl" includes, for example, furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazole-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzthienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzoimidazolyl, 2-benzoimidazolyl, 4-benzoimidazolyl, 5-benzoimidazolyl), dibenzofuryl, benzoxazolyl, quinoxalyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl) or phenothiazinyl (e.g., 1-phenothiazinyl, 2-phenothiazinyl, 3-phenothiazinyl, 4-phenothiazinyl), etc.

The carbocycle and/or heterocycle in $Ar_1$ and $Ar_2$ also include those wherein an aromatic ring is condensed with a nonaromatic ring.

As obvious from the definition of $R^4$, $Ar^1$ is a divalent group, and therefore, a carbon atom or a hetero atom, which constitutes the carbocycle or heterocycle as described above as a monovalent substituent, should further be involved with additional linkage to another group.

Substituent for "a carbocycle or heterocycle which is optionally substituted and may have an unsaturated bond" in the definition for $Ar^1$ and $Ar^2$ include lower alkyl, hydroxy lower alkyl, optionally substituted lower alkoxy (example of substituent: hydroxy, phenyloxy, optionally substituted heterocycle (preferably 5-6 membered ring), lower alkoxy, optionally substituted amino (example of substituent: lower alkyl, lower alkenyl, cyano, phenyl), optionally substituted lower alkoxy lower alkyl (example of substituent: hydroxy, lower alkoxy, optionally substituted heterocycle (preferably 5-6 membered ring)), cycloalkyl, optionally substituted aryloxy, optionally substituted aralkyloxy, optionally substituted aryloxy lower alkyl, optionally substituted aryloxycarbonyl, lower alkoxycarbonyl, nitro, hydroxy, carboxy, lower alkoxycarbonyl, cyano, oxo, carboxy lower alkenyl, $SO_2$-cyclic amino (preferably 5-6 membered ring), lower alkylsulfonylamino, optionally substituted amino (example of substituent: lower alkyl, lower alkoxy, acyl (e.g., lower alkylcarbonyl, amino lower alkylcarbonyl, lower alkylamino lower alkylcarbonyl), heterocycle (preferably 5-6 membered ring)), optionally substituted amino lower alkyl, optionally substituted carbamoyl (example of substituent: lower alkyl, CN, OH), optionally substituted carbamoyloxy, halo, lower alkyl halide, lower alkoxy halide, lower alkylthio halide, lower alkylcarbonyl halide, heterocyclo lower alkyl, heterocyclo lower alkoxy, cycloalkyl lower alkoxy, optionally substituted aralkyloxy, optionally substituted heteroaryl (preferably 5-6 membered ring), optionally substituted heteroaryl-lower alkyl, optionally substituted heteroaryl-lower alkyloxy, optionally substituted heterocycle, optionally substituted heterocycle lower alkyl, optionally substituted heterocycle lower alkyloxy, optionally substituted heterocyclecarbonyl lower alkenyl, optionally substituted heterocycleamino, optionally substituted aryl, and optionally substituted heterocyclecarbonyl lower alkenyl, $SCO_2R$, $OC(=S)OR$, $OC(=O)SR$, $C(=S)OR$, $SC(=O)SR$, $SC(=S)SR$, $OC(=S)NH_2$, $SC(=O)NH_2$, $SC(=S)NH_2$, $OC(=S)NHR$, $SC(=O)NHR$, $SC(=S)NHR$, $OSO_2NHR$, $OSO_2NHPh$, $OC(=S)NR_2$, $SC(=O)NR_2$, $SC(=S)NR_2$, $C(=S)NH_2$, $C(=S)NHR$, $C(=S)NR_2$ (R is lower alkyl), CONHCN, CONHOH, etc. The optionally substituted amino as described above is for example amino, mono- or di-lower alkylamino, phenylamino, N-alkyl-n-phenylamino, mono- or di-lower alkoxy lower alkylamino, mono- or di-hydroxy lower alkylamino, lower alkoxycarbonylamino, lower alkylcarbamoylamino, lower alkylcarbonylamino, $NHC(=O)SR$, $NHC(=S)OR$, $NHC(=S)SR$, $NHC(=S)R$, $NH(CH_2)_2OH$, $N[(CH_2)_2OH]_2$ (R is lower alkyl), optionally substituted heterocycleamino (substituent: lower alkyl), optionally substituted acetylamino (example of substituent: optionally substituted heterocycle (substituent: e.g., lower alkyl), amino, alkylamino), etc. The substituent of the above optionally substituted aryl, aralkyl, heteroaryl, heterocycle includes, lower alkyl, lower alkoxy, lower alkoxy lower alkyl, heterocycle (preferably 5-6 membered ring), cyano, etc.

The substituent for "carbocycle or heterocycle which may have an unsaturated bond" in the definition for $Ar^1$ and $Ar^2$ is, more specifically, methyl, ethyl, n-propyl, isopropyl, n-butyl, isobutyl, t-butyl, vinyl, allyl, propargyl, OH, methoxy, ethoxy, n-propyloxy, isopropyloxy, n-butyloxy, isobutyloxy, t-butyloxy, vinyloxy, allyloxy, propargyloxy, benzyloxy, 2,3,4-picolyloxy, furfuryloxy, thiophenemethyloxy, imidazolylmethyloxy, pyrazolylmethyloxy, triazolylmethyloxy, thiazolylmethyloxy, oxazolylmethyloxy, isoxazolylmethyloxy, phenylethyloxy, 2,3,4-pyridylethyloxy, furylethyloxy, thiopheneethyloxy, imidazolylethyloxy, pyrazolylethyloxy, triazolylethyloxy, thiazolylethyloxy, oxazolylethyloxy, isoxazolylethyloxy, cyclopropylmethyloxy, cyclopentylmethyloxy, cyclohexylmethyloxy, tetrahydropyran-4-ylmethyloxy, [1,3]dioxolan-2-ylmethyloxy, $OCO_2Me$, $NHCO_2Me$, $OCONHMe$, $NHCONHMe$, $NHCOMe$, $CONH_2$, $CONHMe$, $CONMe_2$, $OCONHPh$, $SCO_2Me$, $OC(=S)OMe$, $OC(=O)SMe$, $C(=S)OMe$, $SC(=O)SMe$, $SC(=S)SMe$, $NHC(=O)SMe$, $NHC(=S)OMe$, $NHC(=S)SMe$, $OC(=S)NH_2$, $SO_2NH_2$, $SO_2Me$, $SC(=O)NH_2$, $SC(=S)NH_2$, $OC(=S)NHMe$, $SC(=O)NHMe$, $SC(=S)NHMe$, $OSO_2NHMe$, $OSO_2NHPh$, $OC(=S)NMe_2$, $SC(=O)NMe_2$, $SC(=S)NMe_2$, $NHC(=S)Me$, $C(=S)NH_2$, $C(=S)NHMe$, $C(=S)NMe_2$, $NO_2$, $NH_2$, $NHMe$, $NMe_2$, $NHEt$, $NEt_2$, $NH(CH_2)_2OH$, $N[(CH_2)_2OH]_2$, piperazinyl, 4-alkylpiperadino (e.g., 4-methylpiperadino), piperidinyl, morpholino, F, Cl, Br, $CF_3$, $OCF_3$, $OCH_2CF_3$, CN, oxo, etc.

$Ar^1$ or $Ar^2$ may contain preferably one to three of these substituents.

One preferred embodiment of $Ar^1$ is optionally substituted phenylene. Preferred substituent on phenylene include halo, hydroxy, hydroxy lower alkyl, optionally substituted lower alkoxy, optionally substituted amino (substituent: e.g., lower alkyl, heterocycle, heterocycle lower alkyl, lower alkoxy lower alkyl, hydroxy lower alkyl, lower alkylsulfonyl), optionally substituted amino lower alkyl, optionally substituted heterocycle, optionally substituted heterocycle lower alkyl, phenylene optionally substituted with optionally substituted heterocycle lower alkyl, optionally substituted carbamoyl (substituent: e.g., lower alkyl), optionally substituted carbamoyl lower alkenyl. Preferred heterocycle is a heterocycle optionally substituted with lower alkyl (e.g., morpholino, piperadino, piperidino), pyridyl etc.

One preferred embodiment of $Ar^1$ is optionally substituted 5 to 7-membered heterocycle containing one to two N atoms. Preferred substituent on the heterocycle includes lower alkyl, oxo, halo, amino lower alkyl, mono- or di-lower alkylamino lower alkyl, lower alkoxy lower alkyl, and oxo is especially preferred.

One preferred embodiment of $Ar^2$ is aryl or heterocycle optionally substituted with one or more substituent selected from the group consisting of halo, mono-, di- or tri-halogenated lower alkyl, mono-, di-, tri- or tetra-halogenated lower alkoxy, mono-, di-, tri- or tetra-halogenated lower alkylthio, mono- or di-lower alkylamino, cycloalkylmethyloxy, optionally substituted benzyloxy, lower alkoxycarbonylamino, nitro, heterocycle (e.g., morpholino, piperadino, piperidino, pyrrolidino optionally substituted independently with lower alkyl etc.), optionally substituted acetylamino, optionally substituted lower alkoxy, acyl (e.g., optionally substituted lower alkylcarbonyl), and optionally substituted lower alkyloxycarbonyl. Particularly, substituted phenyl (substituent: halo, halogenated lower alkoxy) is preferred.

The term "aralkyloxy" refers to a group wherein oxygen atom is substituted the above "alkyl" substituted with the above "aryl" and, for example, benzyloxy, diphenylmethyloxy, triphenylmethyloxy, phenetyloxy, 1-naphthylmethyloxy, 2-naphthylmethyloxy, etc.

The term "lower alkoxy" refers to a group wherein O atom is substituted with the above "lower alkyl", and for example, methoxy, ethoxy, n-propoxy, isopropoxy, n-butoxy, isobutoxy, tert-butoxy, etc. Particularly, methoxy, ethoxy are preferred.

The term "aryloxy" refers to a group wherein O atom is substituted with the above "aryl".

The term "optionally substituted amino" is an amino substituted or unsubstituted.

The term "optionally substituted carbamoyl" is a carbamoyl substituted or unsubstituted.

For substituents of "optionally substituted amino" and "optionally substituted carbamoyl" include, optionally substituted alkyl (e.g., methyl, ethyl, isopropyl, benzyl, carbamoylalkyl (e.g., carbamoylmethyl), mono- or di-alkylcarbamoylalkyl (e.g., dimethylcarbamoylethyl), hydroxyalkyl, heterocyclealkyl (e.g., morpholinoethyl, tetrahydropyranylethyl), alkoxycarbonylalkyl (e.g., ethoxycarbonylmethyl, ethoxycarbonylethyl), mono- or di-alkylaminoalkyl (e.g., dimethylamminioethyl) etc), alkoxyalkyl (e.g., methoxyethyl, ethoxymethyl, ethoxyethyl, i-propoxyethyl etc), acyl (e.g., formyl, optionally substituted alkylcarbonyl (e.g., acetyl, propionyl, butyryl, isobutyryl, valeryl, isovaleryl, pivaloyl, hexanoyl, octanoyl, methoxyethylcarbonyl, 2,2,2-trifluoroethylcarbonyl, ethoxycarbonylmethylcarbonyl, alkoxyalkylcarbonyl (e.g., methoxyethylcarbonyl), alkylcarbamoylalkylcarbonyl (e.g., methylcarbamoylethylcarbonyl), alkoxycarbonylacetyl etc), optionally substituted arylcarbonyl (e.g., benzoyl, toluoyl etc)), optionally substituted aralkyl (e.g., benzyl, 4-F-benzyl etc), hydroxy, optionally substituted alkylsulfonyl (e.g., methanesulfonyl, ethanesulphonyl, isopropylsulphonyl, 2,2,2-trifluoroethanesulphonyl, benzylsulphonyl, methoxyethylsulphonyl etc), arylsulfonyl optionally substituted with alkyl or halo (e.g., benzenesulfonyl, toluenesulfonyl, 4-fluorobenzenesulfonyl), cycloalkyl (e.g., cyclopropyl etc), aryl optionally substituted with alkyl (e.g., 4-methylphenyl etc), alkylaminosulphonyl (e.g., methylaminosulphonyl, dimethylamminiosulphonyl etc), alkylaminocarbonyl (e.g., dimethylaminocarbonyl etc), alkoxycarbonyl (e.g., ethoxycarbonyl etc), cycloalkylcarbonyl (e.g., cyclopropylcarbonyl, cyclohexylcarbonyl etc), optionally substituted sulfamoyl (e.g., sulfamoyl, methylsulfamoyl, dimethylsulfamoyl etc), alkylcarbonylamino (e.g., methylcarbonylamino), heterocycle (e.g., morpholino, tetrahydropyranyl), optionally substituted amino (e.g., mono- or di-alkylamino (e.g., dimethylamminio), formylamino), etc. It may be mono- or di-substituted with the above substituent.

The amino group of "optionally substituted amino" and "optionally substituted carbamoyl" may be substituted with alkylene such as trimethylene, tetramethylene, pentamethylene, and may form a ring optionally containing O and/or S atom together with the nitrogen atom of the amino group.

For the amino group of "optionally substituted amino" and "optionally substituted carbamoyl", the two substituents of the amino group may be taken together with a nitrogen atom to which they are attached to form a nitrogen containing heterocycle that may contain S and/or O atom within the ring, preferably 5- to 7-membered and preferably saturated, and said ring may be substituted with oxo, lower alkyl or hydroxy etc. The ring may be substituted at S atom with oxo. For example, 5- or 6-membered rings such as piperidino, piperadino, morpholino, pyrrolidino, thiazinan-2-yl, 2-oxopiperidino, 2-oxopyrrolidino, 1,1-dioxido-1,2-thiazinan-2-yl, 4-hydroxymorpholino are preferred.

Substituent of "optionally substituted aryl" and "optionally substituted heteroaryl" is as defined above for "optionally substituted amino group".

$Ar^1$ especially preferred in the present invention is selected from the following groups:

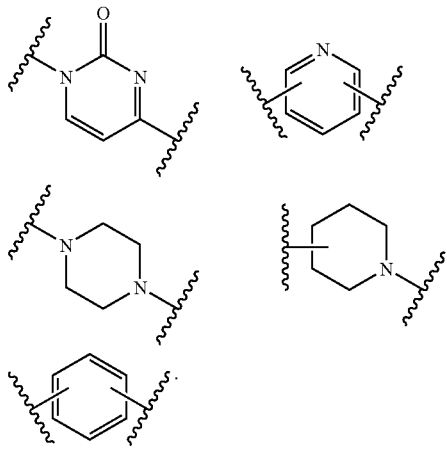

Ar² is preferably aryl optionally substituted, specifically phenyl optionally substituted. Ar² especially preferred in the present invention is selected from the following groups:

[Chemical Formula 19]

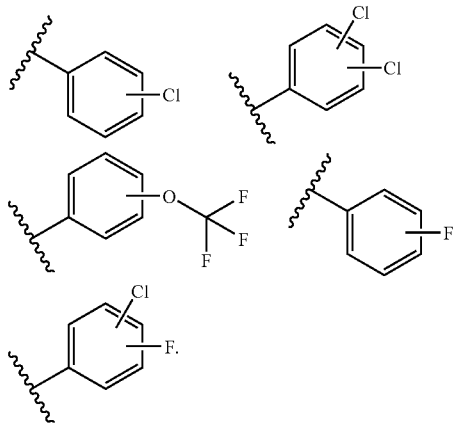

Preferred embodiments of the group of the formula: —X¹—Ar¹—X²—Y—X³—Ar² for R⁴ are as follows:

(1) —CH$_2$-(substituted)Ph-CONR-(substituted Ph)
(2) —CH$_2$-(substituted)Ph-NRCO-(substituted Ph)
(3) —CH$_2$-(substituted)Ph-CH$_2$—CONR-(substituted Ph)
(4) —CH$_2$-(substituted)Ph-CH$_2$—NRCO-(substituted Ph)
(5) —CH$_2$-(substituted)Ph-X—CONR-(substituted Ph)
(6) —CH$_2$-(substituted)Ph-X—NRCO-(substituted Ph)
(7) —CH$_2$-(substituted)Ph-Q-(substituted Ph)
(8) —CH$_2$-(substituted)Het-CONR-(substituted Ph)
(9) —CH$_2$-(substituted)Het-NRCO-(substituted Ph)
(10) —CH$_2$-(substituted)Ph-CONR—CH$_2$-(substituted Ph)
(11) —CH$_2$-(substituted)Ph-NRCO—CH$_2$-(substituted Ph)
(12) —CH$_2$-(substituted)Ph-CH$_2$—CONR—CH$_2$-(substituted Ph)
(13) —CH$_2$-(substituted)Ph-CH$_2$—NRCO—CH$_2$-(substituted Ph)
(14) —CH$_2$-(substituted)Ph-X—CONR—CH$_2$-(substituted Ph)
(15) —CH$_2$-(substituted)Ph-X—NRCO—CH$_2$-(substituted Ph)
(16) —CH$_2$-(substituted)Ph-Q-CH$_2$-(substituted Ph)
(17) —CH$_2$-(substituted)Het-CONR—CH$_2$-(substituted Ph)
(18) —CH$_2$-(substituted)Het-NRCO—CH$_2$-(substituted Ph)
(19) —(CH$_2$)$_m$-(substituted)Ph-CONR-(substituted Ph)
(20) —(CH$_2$)$_m$-(substituted)Ph-NRCO-(substituted Ph)
(21) —(CH$_2$)$_m$-(substituted)Ph-CH$_2$—CONR-(substituted Ph)
(22) —(CH$_2$)$_m$-(substituted)Ph-CH$_2$—NRCO-(substituted Ph)
(23) —(CH$_2$)$_m$-(substituted)Ph-X—CONR-(substituted Ph)
(24) —(CH$_2$)$_m$-(substituted)Ph-X—NRCO-(substituted Ph)
(25) —(CH$_2$)$_m$-(substituted)Ph-Q-(substituted Ph)
(26) —(CH$_2$)$_m$-(substituted)Het-CONR-(substituted Ph)
(27) —(CH$_2$)$_m$-(substituted)Het-NRCO-(substituted Ph)
(28) —(CH$_2$)$_m$-(substituted)Het-NRCO—CH$_2$-(substituted Ph)
(29) —(CH$_2$)$_m$-(substituted)Het-NRCO—CH=CH-(substituted Ph)

wherein, Ph=phenyl; R=hydrogen or lower alkyl; X=O or NH; Q is Q1 or Q2 as defined above; Het is heteroaryl or heterocycle (preferably five- or seven-membered ring containing one or two nitrogen atom and having oxo as a substituent on Het); m is 2 or 3; "(substituted)" means "optionally substituted".

In one embodiment of the invention, R$^B$ is a group of the formula —NHNR$^X$R$^Y$. For R$^X$, it can be hydrogen, lower alkyl, etc. For R$^Y$, it can be hydrogen, optionally substituted lower alkyl, lower alkylcarbonyl, C(=NH)NH$_2$, CSNH$_2$, COCONH$_2$, CN, optionally substituted heterocyclic group, or optionally substituted carbamoyl etc. Preferred substituent of the lower alkyl can be OH, CN, lower alkoxy, amino, =O, halogen, heterocyclic group etc., and preferably —OH. The heterocyclic group in "optionally substituted heterocyclic group" can be a group as recited above for "heterocycle" and "heteroaryl", and preferably five- or six-membered heterocyclic group such as morpholinyl, imidazoyl, tetrahydropyranyl. Substituent for "optionally substituted heterocycle" includes hydroxy, amino, carboxy, lower alkyl, amino lower alkyl, quaternary ammonium lower alkyl. The lower alkyl group on the quaternary ammonium radical may be substituted with a substituted alkyl (substituent: carboxy, hydroxy, quaternary ammonium). Substituent for "optionally substituted carbamoyl" includes alkyl (e.g., methyl, ethyl, dimethyl, etc.), alkoxycarbonyl (methoxycarbonyl, ethoxycarbonyl etc.), alkoxyalkyl (e.g. ethoxymethyl, ethoxyethyl etc.), acyl (e.g., formyl, acetyl, benzoyl, toluoyl etc.), aralkyl (e.g. benzyl etc.), hydroxy, alkylsulfonyl (e.g., methanesulfonyl, ethanesulphonyl etc.), SO$_2$NH$_2$, arylsulfonyl optionally substituted with alkyl (e.g., benzenesulfonyl, toluenesulfonyl), cycloalkyl (e.g., cyclopropyl etc.), alkylene (e.g., trimethylene, tetramethylene, pentamethylene), aryl optionally substituted with alkyl (e.g., phenyl, trityl etc.). $R^Y$ especially preferred is optionally substituted lower alkyl, or lower alkylcarbonyl.

In further embodiment of the invention, $R^B$ is a group of the formula —$NR^ZOR^W$. For $R^Z$, it can be hydrogen, lower alkyl etc. For $R^W$, it can be hydrogen, optionally substituted lower alkyl, optionally substituted lower alkenyl, optionally substituted heterocyclic group, optionally substituted heterocyclic carbonyl, or optionally substituted carbamoyl. Substituent for "optionally substituted lower alkyl" includes OH, a lower alkoxy, optionally substituted amino, =O, halogen, $SO_3H$, optionally substituted carbamoyl, heterocyclic group, etc. For such heterocyclic group, it can be as recited above for "heterocycle" and "heteroaryl", and preferably five- or six-membered heterocyclic group such as morpholinyl, imidazoyl, tetrahydropyranyl. Substituent for "optionally substituted heterocycle" and "optionally substituted heterocyclic carbonyl" includes hydroxy, amino, carboxy, amino lower alkyl, quaternary ammonium lower alkyl. The lower alkyl group for the quaternary ammonium radical may be substituted further with a substituted alkyl (substituent: carboxy, hydroxy, quaternary ammonium radical). Substituent for "optionally substituted lower alkenyl" includes OH, CN, lower alkoxy, amino, =O, halogen, $NH_3$, etc. Substituent for "optionally substituted amino" and "optionally substituted carbamoyl" includes alkyl (e.g., methyl, ethyl, dimethyl etc.), alkoxycarbonyl (methoxycarbonyl, ethoxycarbonyl etc.), alkoxyalkyl (e.g., ethoxymethyl, ethoxyethyl etc.), acyl (e.g., formyl, acetyl, benzoyl, toluoyl etc.), aralkyl (e.g., benzyl etc.), hydroxy, CN, alkylsulfonyl (e.g., methanesulfonyl, ethanesulphonyl etc.), $SO_2NH_2$, arylsulfonyl optionally substituted with alkyl (e.g., benzenesulfonyl, toluenesulfonyl), cycloalkyl (e.g., cyclopropyl etc.), alkylene (e.g., trimethylene, tetramethylene, pentamethylene), aryl optionally substituted with alkyl (e.g., phenyl, trityl etc.). For the amino group of "optionally substituted amino", the two substituents of the amino group may be taken together with a nitrogen atom to which they are attached to form a nitrogen containing heterocycle that may contain S atom within the ring, which may be substituted with oxo.

Preferred embodiments of the group of the formula: —$NHNR^XR^Y$ for $R^B$ are as follows:

(1) —$NHNH_2$
(2) —NHNH-[(substituted)lower alkyl]
(3) —NHNHC(=NH)$NH_2$
(4) —NHNH—$(CH_2)_m$—CN
(5) —NHNH—$(CH_2)_m$—OH
(6) —NHNHCO$NH_2$
(7) —NHNHCO-[(substituted) lower alkyl]
(8) —NHNHCO—$(CH_2)_m$—O—[(substituted) lower alkyl]
(9) —NHNHCOCO$NH_2$
(10) —NHNHCO—N[(substituted) lower alkyl]$_2$
(11) —NHNHCO—N[(substituted) lower alkyl]$_3^+$
(12) —NHNHCSNH—$(CH_2)_m$-Het
(13) —NHNH-Het
(14) —NHN[(substituted) lower alkyl]$_2$
(15) —NHN[(substituted) lower alkyl]C(=NH)$NH_2$
(16) —NHN[(substituted) lower alkyl]-$(CH_2)_m$—CN
(17) —NHN[(substituted) lower alkyl]-$(CH_2)_m$—OH
(18) —NHN[(substituted) lower alkyl]-CON$H_2$
(19) —NHN[(substituted) lower alkyl]-CO—[(substituted) lower alkyl]
(20) —NHN[(substituted) lower alkyl]-CO—$(CH_2)_m$—O-[(substituted) lower alkyl]
(21) —NHN[(substituted) lower alkyl]-COCON$H_2$
(22) —NHN[(substituted) lower alkyl]-CO—N[(substituted) lower alkyl]$_2$
(23) —NHN[(substituted) lower alkyl]-CO—N[(substituted) lower alkyl]$_3^+$
(24) —NHN[(substituted) lower alkyl]-CSNH—$(CH_2)_m$-Het
(25) —NHN[(substituted) lower alkyl]-Het wherein, Het is heteroaryl or heterocycle; m is an integer from 0 to 3; "(substituted)" means "optionally substituted with the substituent as described above".

Preferred embodiments of the group of the formula: —$NR^ZOR^W$ for $R^B$ are as follows:

(1) —NHOH
(2) —NHO-Het
(3) —NHO[(substituted) lower alkyl]
(4) —NHO[(substituted) lower alkylene]
(5) —NHO—$(CH_2)_m$—NH[(substituted) lower alkyl]
(6) —NHO—$(CH_2)_m$—N[(substituted) lower alkyl]$_2$
(7) —NHO—$(CH_2)_m$—$NH_2$
(8) —NHO—$(CH_2)_m$—NHCN
(9) —NHO—$(CH_2)_m$—NH[(substituted) lower alkyl]
(10) —NHO—$(CH_2)_m$-Het
(11) —NHO—$(CH_2)_m$—$SO_3H$
(12) —NHO—$(CH_2)_m$—NHCO-[(substituted) lower alkyl]
(13) —NHO—$(CH_2)_m$—$NHSO_2NH_2$
(14) —NHO—$(CH_2)_m$—O-[(substituted) lower alkyl]
(15) —NHO—$(CH_2)_m$-Het
(16) —NHO—$(CH_2)_m$—CO—NH[(substituted) lower alkyl]
(17) —NHO—$(CH_2)_m$—CO—N[(substituted) lower alkyl]$_2$
(18) —NHO—$(CH_2)_m$—CO—$NH_2$
(19) —NHO—$(CH_2)_m$—CO—NHCN
(20) —NHO—$(CH_2)_m$—CO—NH[(substituted) lower alkyl]
(21) —NHO—$(CH_2)_m$—CO-Het
(22) —NHO—$(CH_2)$—CO—$SO_3H$
(23) —N[(substituted) lower alkyl]OH
(24) —N[(substituted) lower alkyl]O-Het
(25) —N[(substituted) lower alkyl]O-[(substituted) lower alkyl]
(26) —N[(substituted) lower alkyl]O-(lower alkylene)
(27) —N[(substituted) lower alkyl]O—$(CH_2)_m$—NH[(substituted) lower alkyl]
(28) —N[(substituted) lower alkyl]O—$(CH_2)_m$—N[(substituted) lower alkyl]$_2$
(29) —N[(substituted) lower alkyl]O—$(CH_2)_m$—$NH_2$
(30) —N[(substituted) lower alkyl]O—$(CH_2)_m$—NHCN
(31) —N[(substituted) lower alkyl]O—$(CH_2)_m$—NH[(substituted) lower alkyl]
(32) —N[(substituted) lower alkyl]O—$(CH_2)_m$-Het
(33) —N[(substituted) lower alkyl]O—$(CH_2)_m$—$SO_3H$
(34) —N[(substituted) lower alkyl]O—$(CH_2)_m$—NHCO-[(substituted) lower alkyl]
(35) —N[(substituted) lower alkyl]O—$(CH_2)_m$—$NHSO_2NH_2$
(36) —N[(substituted) lower alkyl]O—$(CH_2)_m$—O-[(substituted) lower alkyl]

(37) —N[(substituted) lower alkyl]O—(CH$_2$)$_m$-Het
(38) —N[(substituted) lower alkyl]O—(CH$_2$)$_m$—CO—NH[(substituted) lower alkyl]
(39) —N[(substituted) lower alkyl]O—(CH$_2$)$_m$—CO—N[(substituted) lower alkyl]$_2$
(40) —N[(substituted) lower alkyl]O—(CH$_2$)$_m$—CO—NH$_2$
(41) —N[(substituted) lower alkyl]O—(CH$_2$)$_m$—CO—NHCN
(42) —N[(substituted) lower alkyl]O—(CH$_2$)$_m$—CO—NH[(substituted) lower alkyl]
(43) —N[(substituted) lower alkyl]O—(CH$_2$)$_m$—CO-Het
(44) —N[(substituted) lower alkyl]O—(CH$_2$)$_m$—CO—SO$_3$H wherein, Het is heteroaryl or heterocycle; m is an integer from 0 to 3; "(substituted)" means "optionally substituted with the substituent as described above".

R$^C$ is selected from the group consisting of the following (3-1)-(3-4):
(3-1) hydrogen;
(3-2) aminomethyl optionally substituted with alkyl, cycloalkyl or alkylene, wherein said alkyl, cycloalkyl and alkylene may be substituted with amino optionally substituted with alkyloxycarbonyl or aryloxycarbonyl, monoalkylamino, dialkylamino, trialkylammonium, aryl optionally substituted with cycloalkyl, hydroxy, guanidino, —O—(P=O)(OH)$_2$, carboxy, —N$^+$(R$^X$)$_2$(CH$_2$)$_m$N$^+$(R$^X$)$_3$, or —(C=O)—N$^-$—N$^+$(R$^X$)$_3$, in which m is 1 to 3, R$^X$ is C$_1$-C$_3$ alkyl, or combination thereof, and wherein alkyl of said monoalkylamino or dialkylamino is further optionally substituted with amino;
(3-3) alkynyl that may have a substituent wherein said substituent is amino optionally substituted with alkyloxycarbonyl or aryloxycarbonyl, or aryl;
(3-4) halo;

with the proviso that any aryl ring present in the groups in (3-2) and (3-3) may contain a heteroatom, and any carbon-carbon single bond may be interrupted with a heteroatom or a heterogroup selected from —O(P=O)(OR$^J$)O— (R$^J$ is hydrogen, alkyloxycarbonyl or aryloxycarbonyl), amido or imino.

R$^C$ is preferably hydrogen or optionally substituted alkyl. Substituent for such optionally substituted alkyl is preferably —NHR$^5$ as described above or substituents of the optionally substituted alkyl as defined for R$^5$.

R$^D$ is selected from the group consisting of the following (4-1)-(4-6):
(4-1) hydrogen;
(4-2) alkyl that may have a substituent, wherein said substituent is alkyloxycarbonyl, amino, optionally alkylated aryl, arylcarbonyl, carbamoyl, mono- or di-alkylcarbamoyl or mono- or di-arylalkylcarbamoyl, or combination thereof, and wherein alkyl or aryl in said substituent further may be substituted with amino optionally substituted with alkyloxycarbonyl or aryloxycarbonyl, or hydroxy;
(4-3) alkyloxycarbonyl that may be substituted with optionally alkylated aryl;
(4-4) arylamido or arylthioamido;
(4-5) amino or amidino optionally alkylated; and
(4-6) nitroso;

with the proviso that any aryl ring present in the groups in (4-2) to (4-5) may contain a heteroatom, and any carbon-carbon single bond may be interrupted with a heteroatom. R$^D$ is preferably hydrogen or optionally substituted alkyl. Also, the leucine residue at the N-terminal moiety may be removed to convert to —NH$_2$, and optionally further acylated, according to a procedure described in literatures such as Expert Opin. Ther. Patents (2004) 14, 141-173 (e.g., Table 110).

Especially preferred compounds of the invention are exemplified as follows:

[Chemical Formula 20]

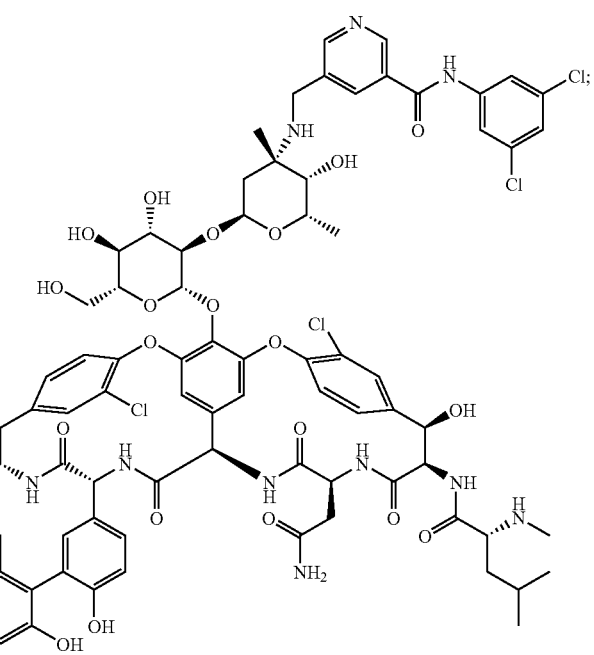

[Chemical Formula 21]
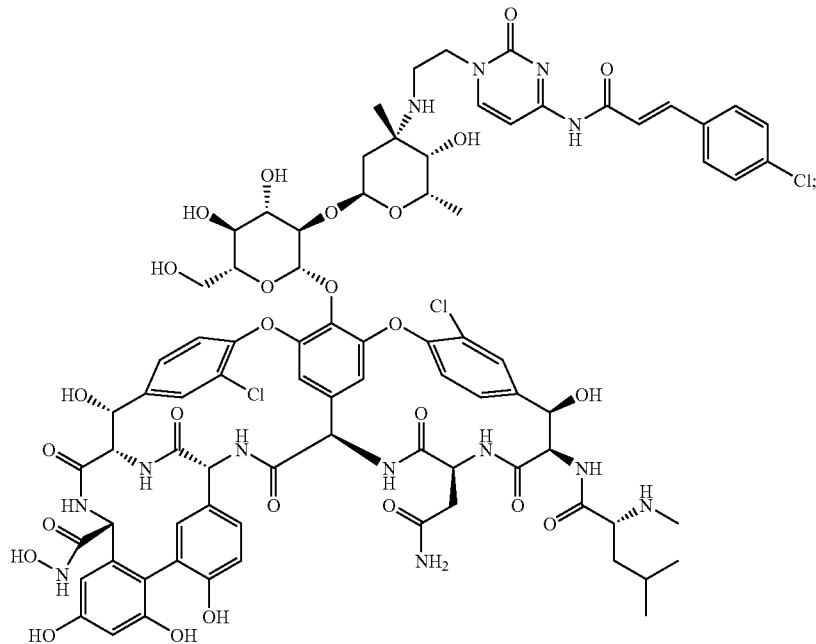
[Chemical Formula 22]
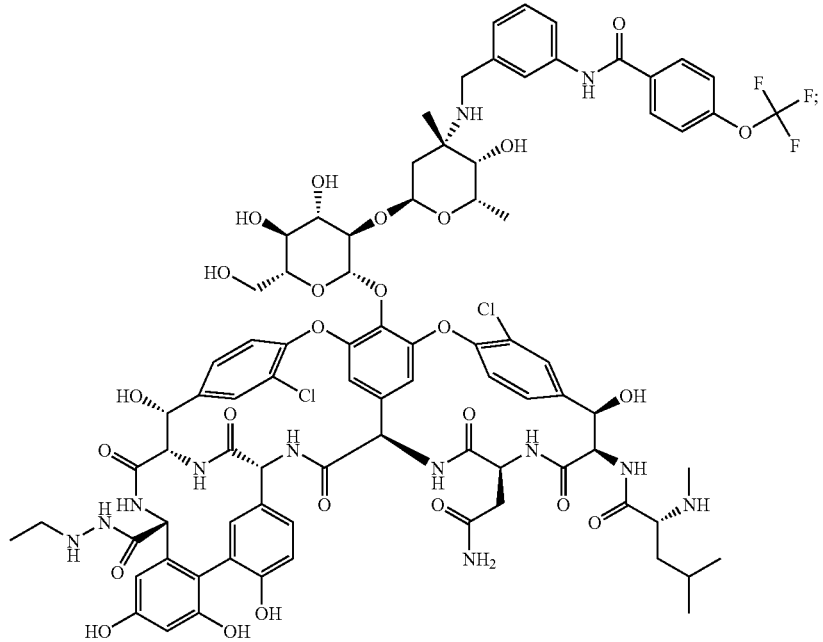

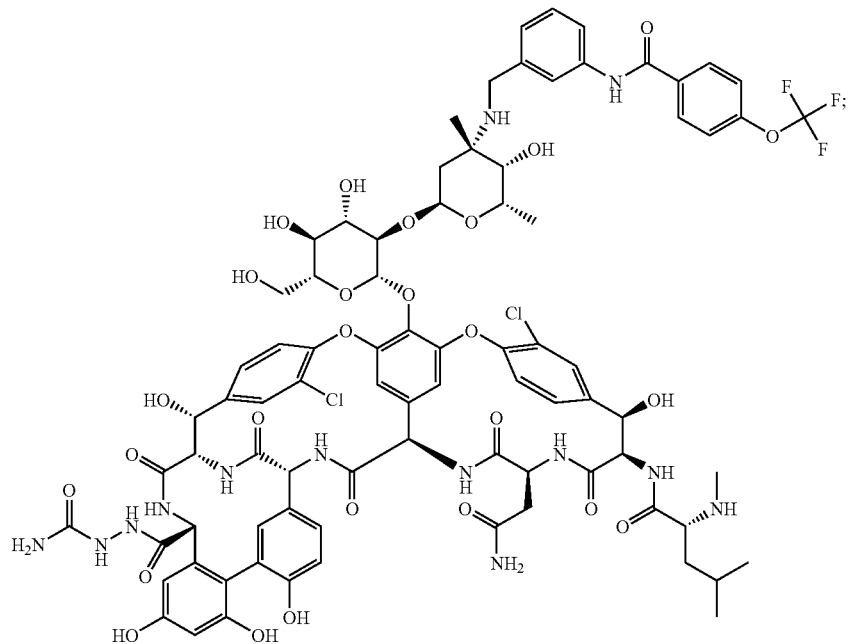
[Chemical Formula 23]
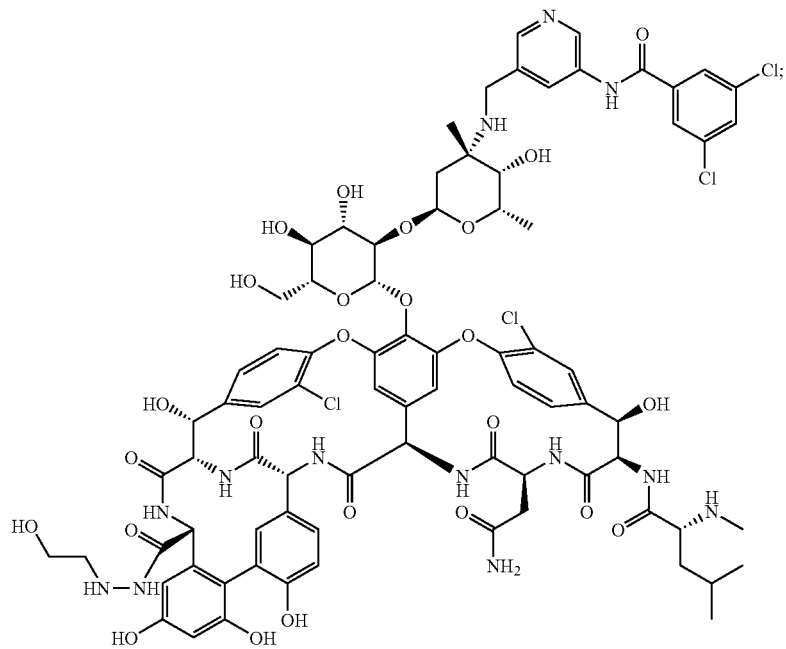
[Chemical Formula 24]
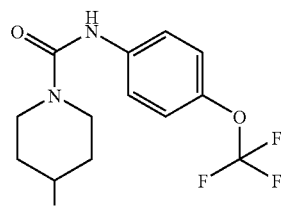
[Chemical Formula 25]

-continued

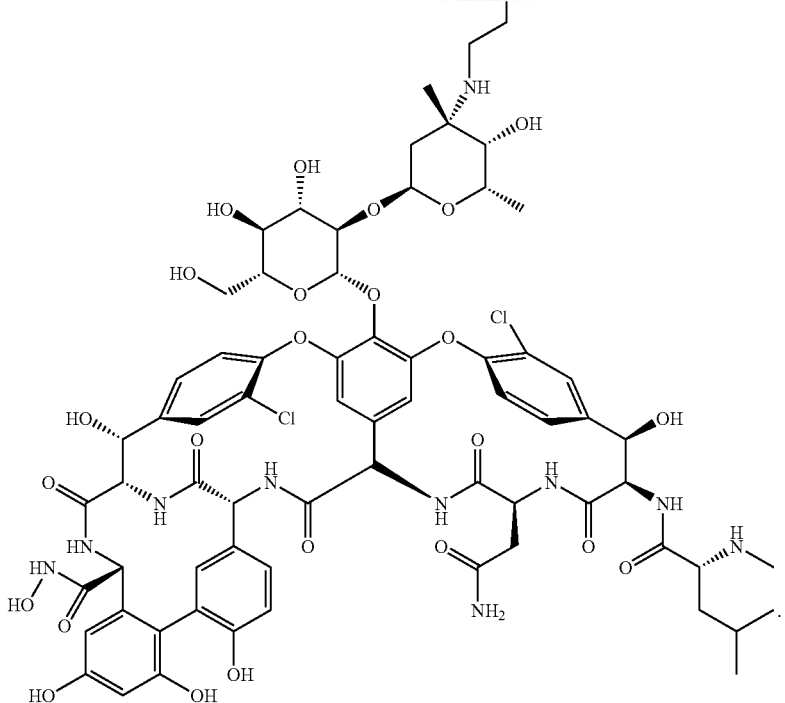

Another preferred compounds are Compound 200 to Compound 232, as described in the following Examples.

The present invention encompasses the compounds described above, a pharmaceutically acceptable salt and solvate thereof. Any theoretically available tautomer and geometric isomer of such compound are also within the scope of the present invention.

The term "pharmaceutically acceptable" means harmless with respect to the prevention and the treatment.

Pharmaceutically acceptable salts of a compound of the present invention include, as basic salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine salts, meglumine salt, diethanolamine salt or ethylenediamine salt; aralkyl amine salts such as N,N-dibenzylethylenediamine salts, benethamine salt; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Acid salts include, for example, inorganic acid salts such as hydrochloride, sulfates salts, nitrate salts, phosphates salts, carbonates salts, hydrogencarbonates or perchlorate; organic acid salts such as acetates, propionates, lactates, maleates, fumarates, tartrates, malates, citrates, or ascorbates; sulfonates such as methanesulfonates, isethionates, benzenesulfonates, or p-toluenesulfonates; and acidic amino acid salts such as aspartates or glutamates.

Furthermore, various solvates of a compound of the present invention, for example, monosolvate, disolvate, monohydrate or dihydrate are also within the scope of the present invention.

(2) General Procedure

Below is described a representative procedure for the production of a compound of the invention. The preparation of the compound is not intend to limit to such procedure, and of course, can be conducted by another procedure.

The compound of the invention may be synthesized using vancomycin or its known derivative as a starting material, by chemical modification of the amino moiety ($R^A$) at the amino sugar, or the C terminal ($R^B$), the resorcinol moiety ($R^C$), or the methylamino moiety at the N terminal ($R^D$). Such chemical modification can be conducted according to the procedure, for example, as disclosed in Japanese Patent Publication No. 7-258289, WO00/39156, Japanese Patent Publication No. 2001-163898. Specifically, it may be conducted in the following manner.

1) Modification of $R^A$ Moiety

Typically, vancomycin as a starting material may be reacted, optionally in the presence of a base, with a different aldehyde corresponding to $R^A$ moiety of the formula:

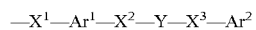

to form an intermediate Schiff base, followed by reduction to N-alkylate to afford a desired secondary amine.

Specifically, the Schiff base formation is conducted in a polar solvent such as dimethylformamide or methanol or mixture thereof, optionally under inert atmosphere such as nitrogen or argon gas and optionally in the presence of a base, at a temperature between about 25° C. and about 100° C. Preferably, the reaction is conducted at room temperature to 100° C., preferably about 60° C. to about 80° C., for about 30 minute to 2 hours. The base used in the reaction is, for example, alkylamine (e.g., diisopropylethylamine, etc).

The intermediate Schiff base, preferably without purification, may be reduced with a hydrogenated metal complex or subjected to a catalytic reduction. For such hydrogenated metal complex, a metal borohydride, such as sodium borohydride or sodium cyanoborohydride, may be used. The catalytic reduction may be conducted using hydrogen in the presence of homogeneous or heterogeneous catalysis such as Crabtree catalyst, Wilkinson catalyst, palladium on carbon, platinum on carbon or rhodium on carbon. The reduction reaction is conducted at about 25° C. to about 100° C. for about 1 to 24 hours. Preferably, the reaction is conducted in the above solvent, using an excessive amount (e.g., 3-5 equiv) of sodium cyanoborohydride at about 60° C. to about 80° C.

2) Modification of $R^B$ Moiety

Typically, the carboxylic acid moiety at the C terminal of the vancomycin skeleton may be amidated using an appropriate reagent according to a conventional procedure to provide a different amido derivative wherein $R^B$=—NHNR$^X$R$^Y$ or —NR$^Z$OR$^W$.

When $R^B$ is a group of the formula —NHNR$^X$R$^Y$, a compound of the formula NH$_2$NR$^X$R$^Y$ (wherein R$^X$ and R$^Y$ are as defined above) can be used to react in an appropriate solvent (dimethylformamide (DMF) etc.) with the carboxyl group at the C terminal of the vancomycin skeleton, in the presence of benztriazole-1-yl-oxy-tris-(pyrrolidino)phosphonium hexafluorophosphate (PyBOP), diisopropyl ethyl amine (DIPEA), etc.

When $R^B$ is a group of the formula —NR$^Z$OR$^W$, a compound of the formula NHR$^Z$OR$^V$ (wherein R$^Z$ is as defined above and R$^V$ is a hydroxy protecting group or R$^W$ as defined above) can be used to react in an appropriate solvent (dimethylformamide (DMF) etc.) with a carboxyl group at the C terminal of the vancomycin skeleton, in the presence of benztriazole-1-yl-oxy-tris-(pyrrolidino)phosphonium hexafluorophosphate (PyBOP), diisopropyl ethyl amine (DIPEA), etc.

The reagents used in the above reactions are commercially available or can be prepared readily according to procedures well known in the art using reagents as commercially available.

The amidation can be conducted preferably in a solvent such as dimethylformamide, etc. at room temperature or under heating for several minutes to several hours.

3) Modification of $R^C$ Moiety

Typically, vancomycin as a starting material may be subjected to alkylation of the resorcinol moiety, according to a conventional procedure.

4) Modification of $R^D$ Moiety

Typically, vancomycin as a starting material may be subjected to N-alkylation of the methylamine moiety at the N-terminal, according to a conventional procedure.

(3) Pharmaceutical Composition

The invention also provides a pharmaceutical formulation comprising a novel glycopeptide derivative of the invention. Thus, the glycopeptide compound in a form of pharmaceutically acceptable salt may be formulated preferably for oral or parenteral administration for therapeutic and prophylactic treatment of bacterial infection.

For oral administration, the compounds of the present invention can be used in any form of usual formulations, for example, formulations in a solid form such as tablets, powders, granules, capsules; formulations in a liquid form such as aqueous formulation; oily suspension; syrup or elixir. For parenteral administration, the compounds of the invention can be used in a form of aqueous or oily suspending injection, or nose drops. In the preparation of such formulation, conventional excipients, binding agents, lubricants, aqueous solvents, oleaginous solvents, emulsifying agents, suspending agents, preservatives, stabilizers, and the like can be optionally used. Oral formulations or intravenous injection is preferred for use as an antimicrobial drug.

The formulation of the invention may be prepared by combining (for example, admixing) a therapeutically effective amount of a compound of the invention with a pharmaceutically acceptable carrier or diluent. The formulation of the invention may be prepared in accordance with a procedure known in the art using ingredients well-known and easily available.

For the preparation of a pharmaceutical composition according to the present invention, an active ingredient is admixed or diluted with a carrier, or they are contained in a carrier in the form of capsule, sacheier, paper, or another container. In case that a carrier is served as a diluent, the carrier is a solid, semi-solid, or liquid material which functions as a medium. Accordingly, a formulation according to the present invention may be prepared in a form of tablet, pill, powder, intraoral formulation, elixir, suspension, emulsion, solution, syrup, aerosol (solid in liquid medium), and ointment. Such a formulation may contain up to 10% of an active compound. It is preferred to formulate the compound of the invention prior to administration thereof.

Any suitable carrier well known to those skilled in the art may be used for the present formulation. Such carrier may be in a form of solid, liquid or mixture thereof in the formulation. For instance, the compound of the invention is dissolved into an aqueous solution of 4% dextrose/0.5% sodium citrate for intravenous injection. Solid formulation can be powder, tablet, and capsule. Solid carrier can be one or more of material(s) that also serves as a fragrant, a lubricant, a dissolving agent, a suspending agent, a binder, a tablet disintegrator or a capsule. A tablet for oral administration contains a suitable excipient such as calcium carbonate, sodium carbonate, lactose, calcium phosphate, etc., together with a disintegrator such as corn starch, alginic acid, etc. and/or a binder such as gelatin, acacia, etc. and a lubricant such as magnesium stearate, stearic acid, talc, etc.

For powder formulation, the carrier can be a finely-divided solid to be blended with an active ingredient that has been finely-divided. In a tablet, an active ingredient has been admixed in a suitable ratio with a carrier having required binding property and solidified in a desired shape and size. Powder and tablet formulations contain about 1% to about 99% by weight of the active ingredient, which is a novel compound of the invention. Example for a suitable solid carrier is magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

A liquid formulation can be suspension, emulsion, syrup, or elixir. An active ingredient may be dissolved or suspended in a pharmaceutically acceptable carrier such as sterile water, a sterile organic solvent, or a mixture thereof. Often, the active ingredient may be dissolved in a suitable organic solvent such as propylene glycol aqueous solution. Other compositions may be prepared by dispersing a finely-divided active ingredient in an aqueous starch, sodium carboxylmethylcellulose solution or suitable oil.

For oral administration, daily dosage of the compound of the invention can be between approximately 0.1-7000 mg, preferably approximately 0.5-2000 mg, for an adult, while such dosage varies depending on the administration route therefor, age, body weight and conditions of the patient, and disease in the patient. The dosage may be divided for administration. In case of parenteral administration, the daily dosage for an adult can be between approximately 0.1-1000 mg, preferably approximately 0.5-500 mg.

EXAMPLES

The present invention is further explained by the following Examples, which are not intended to limit the scope of the present invention in any way.

Example 1

Preparation of Compound 1
(Step 1)

[Chemical Formula 26]

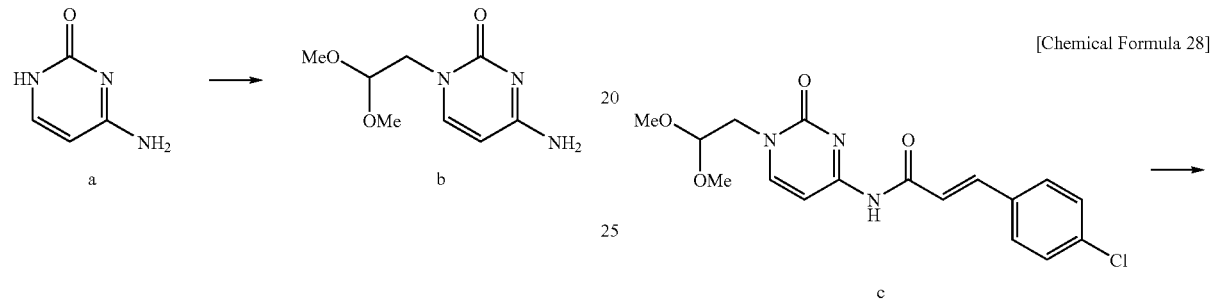

Cytosine (a, 51 g, 0.46M), 2-bromo-1,1-dimethoxyethane (93 g, 0.55M) and potassium carbonate (127 g, 0.92M) were suspended in N,N-dimethylformamide (250 mL) and the mixture was stirred vigorously for 21 hours at 130° C. After the reaction mixture was cooled to room temperature, precipitate was filtered and washed with N,N-dimethylformamide (300 mL) and diethylether (300 mL). The obtained powder was extracted with hot ethanol (3×500 mL), followed by removing the solvent in vacuo to afford 30.4 g of the desired compound 4-amino-1-(2,2-diethoxy-ethyl)-1H-pyrimidin-2-one (b) (yield 33%, brown crystal).

(Step 2)

[Chemical Formula 27]

P-chloro cinnamic acid (1.84 g, 10 mM), 4-amino-1-(2,2-diethoxyethyl)-1H-pyrimidin-2-one (b, 3.00 g, 15 mM), 1-hydroxybenztriazolemonohydrate (2.30 g, 15 mM) and 1-ethyl-3-(3'-dimethylaminopropyl)carbodiimide hydrochloride (2.90 g, 15 mM) were suspended in N,N-dimethylformamide (20 mL) and stirred at 70° C. for 5 hours. After the reaction mixture was cooled to room temperature, water (20 mL) was added and stirred at room temperature. The crystal precipitated from the reaction mixture was filtered to afford 2.48 g of the desired compound (E)-3-(4-chlorophenyl)-N-[1-(2,2-diethoxyethyl)-2-oxo-1,2-dihydropyrimidin-4-yl]-acrylamide (c) (yield 68%, colorless crystal).

(Step 3)

[Chemical Formula 28]

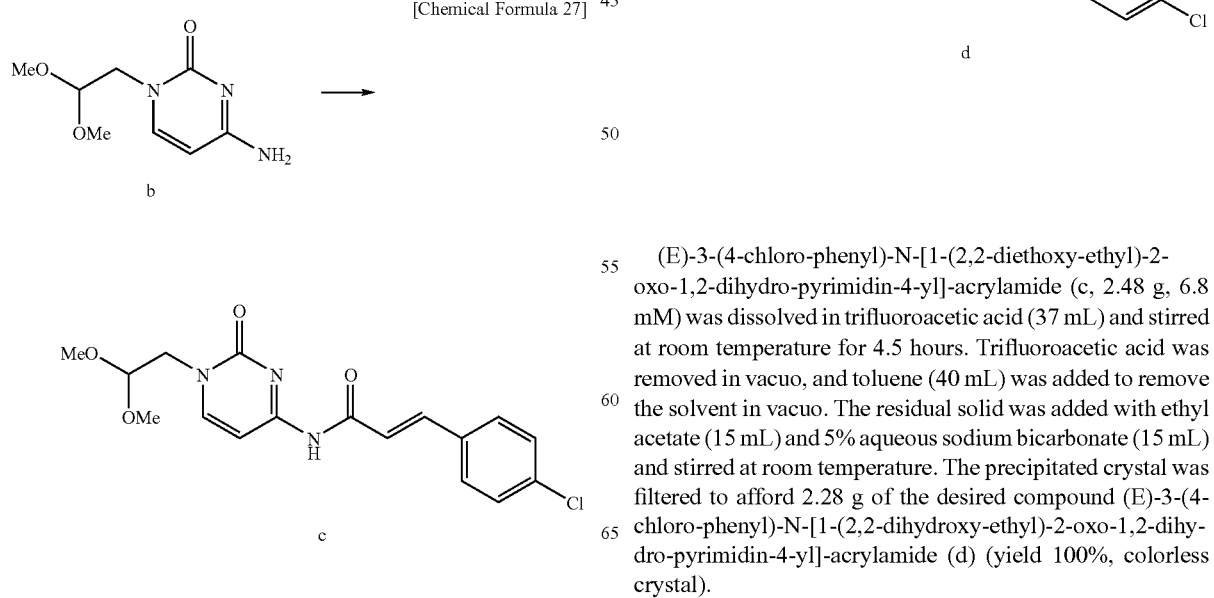

(E)-3-(4-chloro-phenyl)-N-[1-(2,2-diethoxy-ethyl)-2-oxo-1,2-dihydro-pyrimidin-4-yl]-acrylamide (c, 2.48 g, 6.8 mM) was dissolved in trifluoroacetic acid (37 mL) and stirred at room temperature for 4.5 hours. Trifluoroacetic acid was removed in vacuo, and toluene (40 mL) was added to remove the solvent in vacuo. The residual solid was added with ethyl acetate (15 mL) and 5% aqueous sodium bicarbonate (15 mL) and stirred at room temperature. The precipitated crystal was filtered to afford 2.28 g of the desired compound (E)-3-(4-chloro-phenyl)-N-[1-(2,2-dihydroxy-ethyl)-2-oxo-1,2-dihydro-pyrimidin-4-yl]-acrylamide (d) (yield 100%, colorless crystal).

(Step 4)

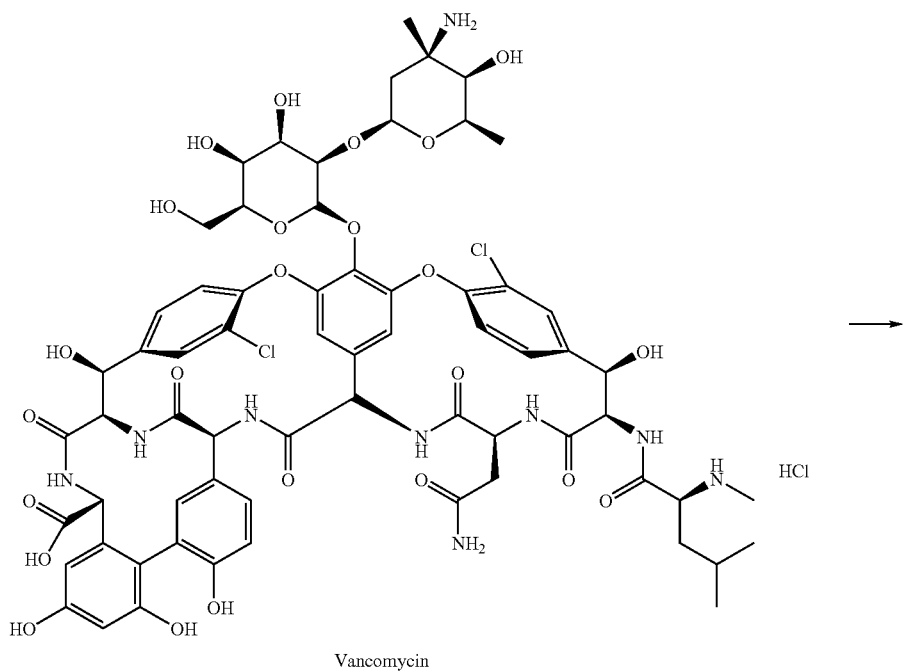

Vancomycin

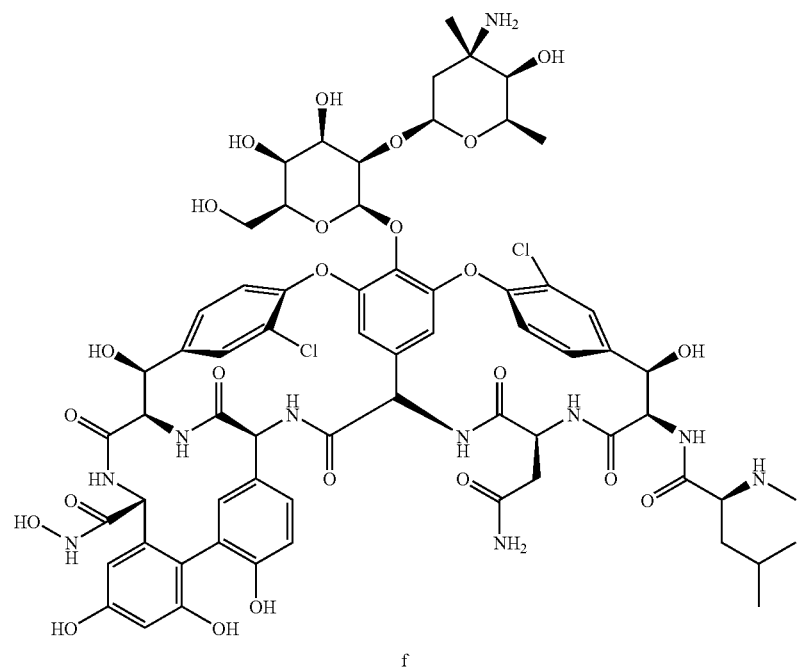

f

Vancomycin hydrochloride (42.1 g, 28.3 mM) and benztriazole-1-yl-oxy-tris-(pyrrolidino)phosphonium hexafluorophosphate (7.36 g, 14.2 mM) were suspended in N,N-dimethylformamide (400 mL), and a solution of hydroxylammonium chloride (3.94 g, 56.7 mM) and diisopropylethylamine (14.8 mL, 85 mM) in N,N-dimethylformamide (10 mL) was added to the suspension and stirred at room temperature for 30 minutes.

The reaction mixture is added to ethyl acetate (3 L), and the precipitate was filtered. The powder thus obtained was purified by ODS column chromatography to afford 16.2 g of the desired vancomycin derivative having a modification at the C-terminal (f) (titer 0.8, yield 31%, colorless powder).

(Step 5)
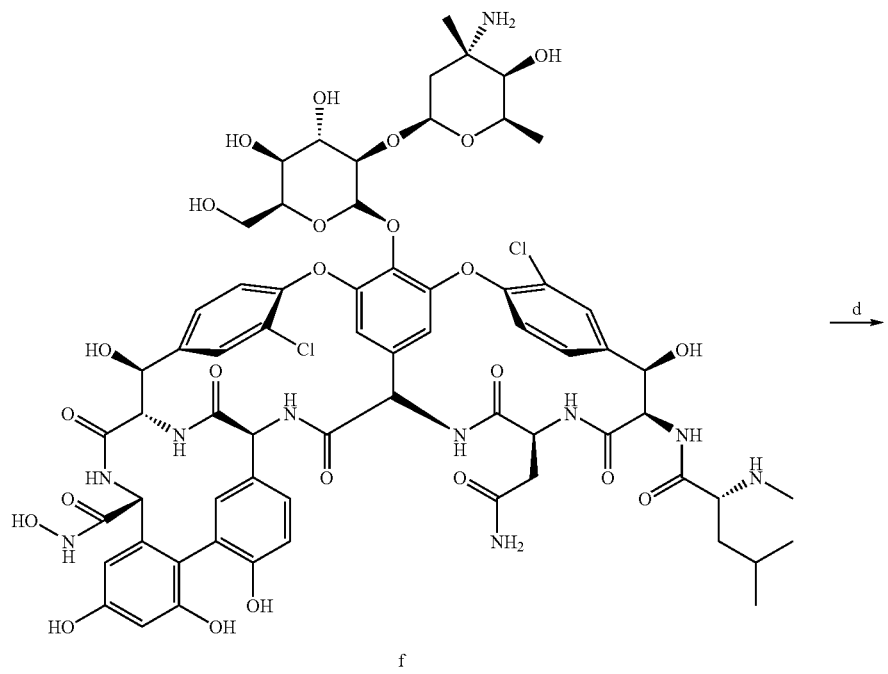
f
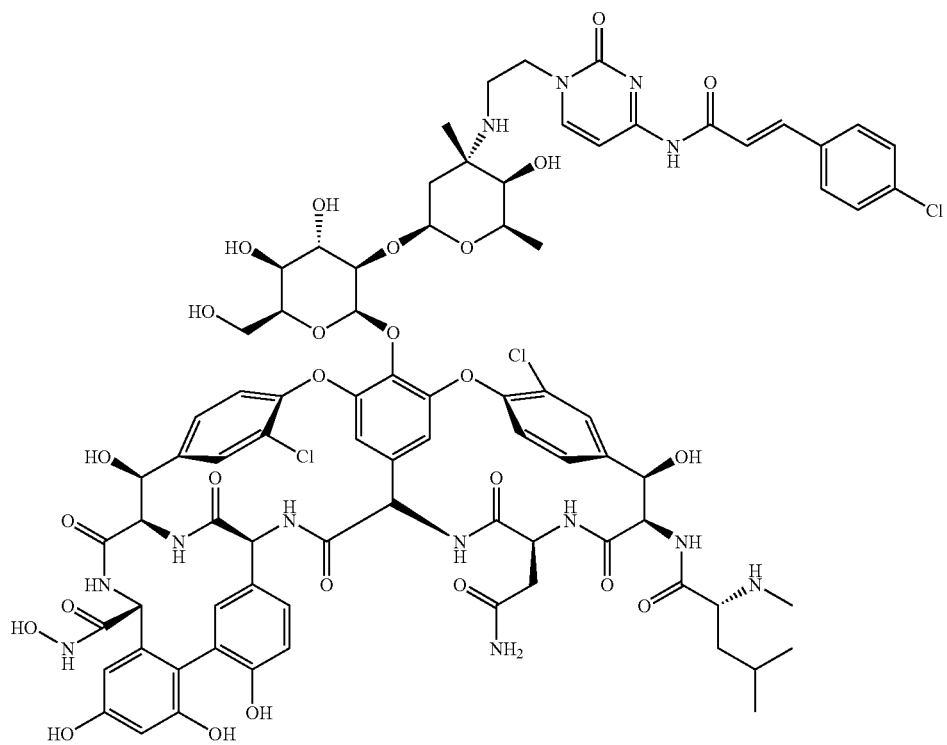
Compound 1

The vancomycin derivative having a modification at the C-terminal prepared in the above Step 4 (f, 1.78 g, F=0.8, 0.96 mM) and (E)-3-(4-chlorophenyl)-N-[1-(2,2-dihydroxyethyl)-2-oxo-1,2-dihydro-pyrimidin-4-yl]-acrylamide (d, 0.37 g, 1.2 mM) prepared in the above Step 3 were suspended in N,N-dimethylformamide (27 mL), and diisopropylethylamine (0.33 mL, 1.9 mM) was added to the suspension and stirred at 70° C. for 3.5 hours.

The mixture was cooled on ice and added with trifluoroacetic acid (0.14 mL, 1.9 mM), sodium cyanoborohydride (90 mg, 1.44 mM) and methanol (9 mL) and stirred at room temperature for 5 hours. To the reaction mixture, 5% aqueous sodium chloride (200 mL) was added, and the precipitate was filtered. The precipitate was washed with acetonitrile (23 ml) and filtered. The obtained powder was purified by ODS column chromatography to afford 330 mg of the desired compound (Compound 1) (titer 0.8, yield 16%, colorless powder).

[M+H]$^+$=1764

Anal calcd. for $C_{81}H_{88}Cl_3N_{13}O_{26}\cdot 11.1H_2O\cdot 2.4HCl$: C, 47.38%; H, 5.53%; N, 8.87%; Cl, 9.32%. Found: C, 47.35%; H, 5.52%; N, 8.97%; Cl, 9.32%.

Example 2

Preparation of Compound 2

(Step 1)

[Chemical Formula 31]

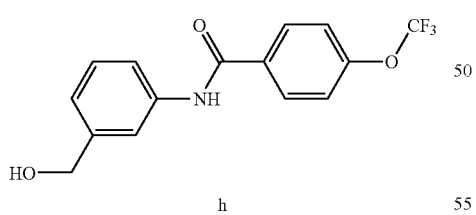

3-amino benzyl alcohol (18.85 g, 0.15 mol) was dissolved in 190 mL of tetrahydrofuran. After cooling on ice, 29 mL of diisopropyl ethylamine was added dropwise, and a solution of 4-trifluoromethoxy benzoyl chloride (g) (24 mL, 0.15 mol) in tetrahydrofuran (30 mL) was added dropwise with maintaining the temperature bellow 10° C. The mixture was then stirred at room temperature for 10 hours. The mixture was pored into ice water (900 mL), extracted with 900 mL of ethyl acetate, and followed by dryness on anhydrous magnesium sulfate. After the desiccant agent was removed by filtration, the filtrate was concentrated in vacuo. The crude solid obtained was dissolved in acetone and added with 15 g of activated carbon. After standing for 10 minutes at room temperature, the mixture was filtered to remove the activated carbon, and the filtrate was concentrated in vacuo. The obtained crude solid was subjected to recrystallization from diisopropyl ether afforded 42.08 g of the titled compound (N-(3-hydroxymethylphenyl)-4-trifluoromethoxy-benzamide: h) as colorless crystal (yield 90%).

(Step 2)

[Chemical Formula 32]

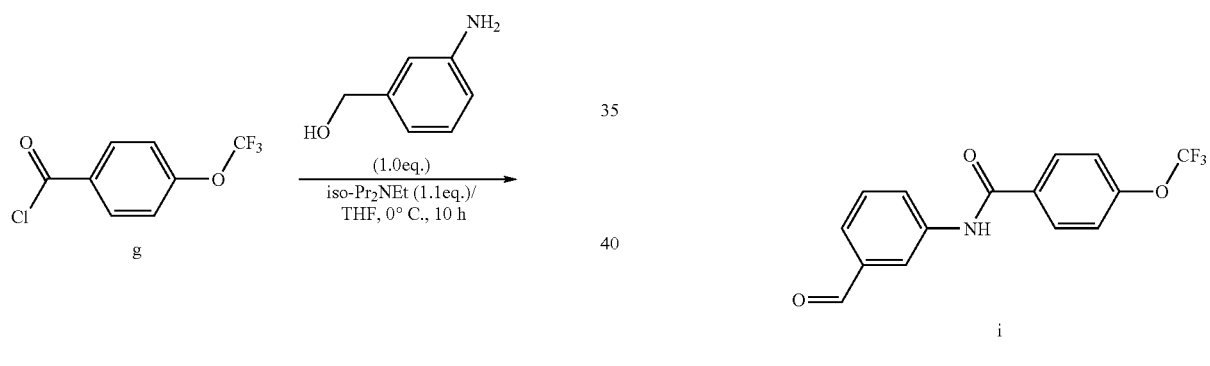

51.22 g of N-(3-hydroxymethylphenyl)-4-trifluoromethoxybenzamide (h, 0.164 mol) as prepared in Step 1 was dissolved in 100 mL of tetrahydrofuran. To the mixture, 102.4 g of manganese dioxide was added and stirred at room temperature for 36 hours. The mixture was filtered using Hyflo Super-Cel to remove manganese dioxide, and the filter residue was rinsed with acetone (1.0 L). The obtained yellow filtrate was added with activated carbon (20 g) and left stand for 10 minutes at room temperature. After the activated carbon was filtered off to concentrate the filtrate in vacuo, recrystallization of the obtained crude solid from acetone-hexane afforded 46.05 g of the titled compound (i) as colorless crystal (yield 91%).

(Step 3)

[Chemical Formula 33]

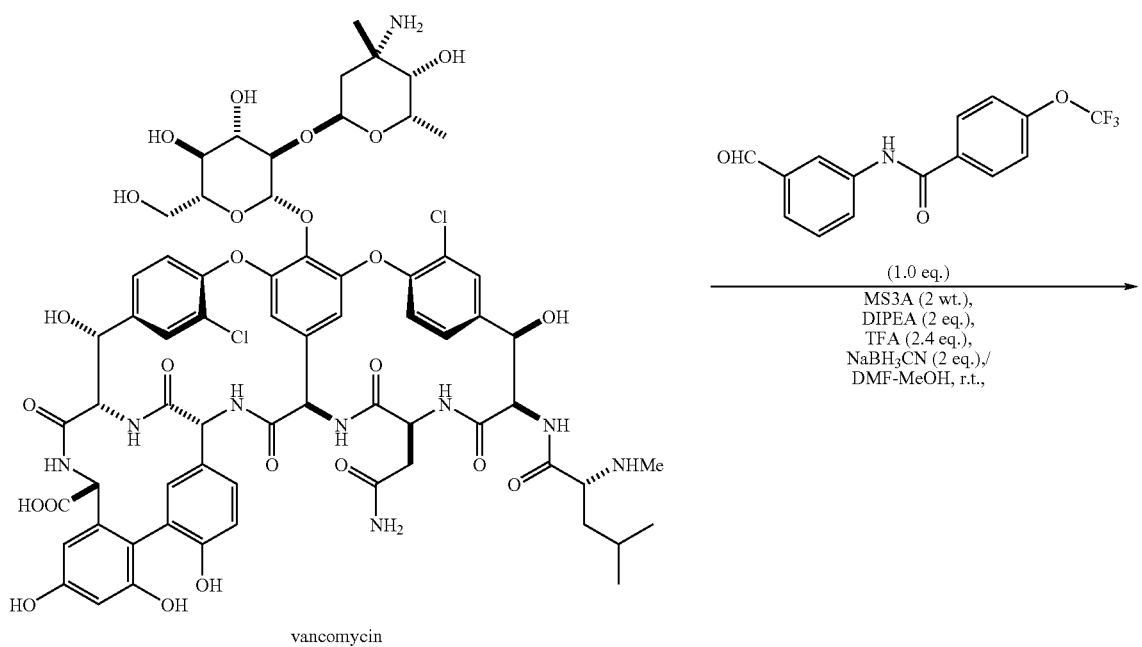

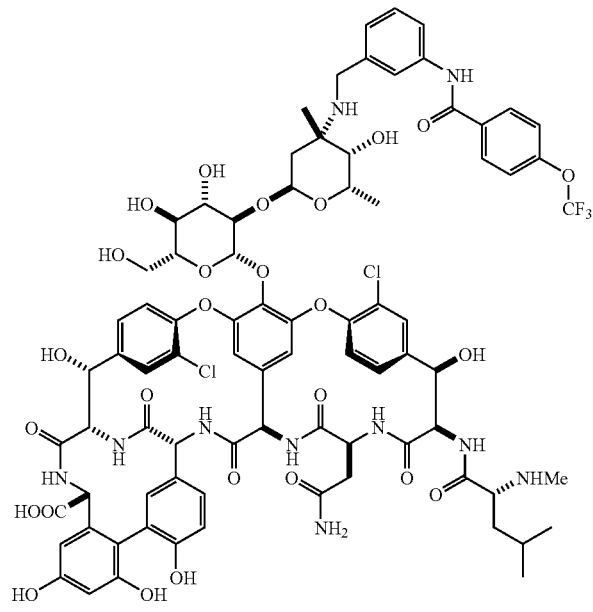

40 g of vancomycin hydrochloride (j, 26.9 mmol) and 8.32 g of N-(3-formylphenyl)-4-trifluoromethoxybenzamide (26.9 mmol) were dissolved in dimethylformamide (800 mL), and molecular sieves 3 Å (80 g) was suspended in the solution. After the mixture was stirred at room temperature for 30 minutes, diisopropylethylamine (9.37 mL) was added and stirred at room temperature for 4 hours. The mixture was added with methanol (800 mL), trifluoroacetic acid (5 mL) dropwise slowly, and sodium cyanoborohydride (3.76 g), and stirred at room temperature for 2 hours. Molecular sieves were removed by filtration through a cotton-plugged funnel, and methanol was removed in vacuo from the filtrate, which was then pored into ethyl acetate. The precipitate was collected by filtration, and the obtained crude solid was rinsed with 10% saline to remove sodium cyanoborohydride. The crude solid was purified by reverse phase column chromatography to afford 18.78 g of the titled compound (j) as a colorless solid (yield 40%).

(Step 4)

[Chemical Formula 34]

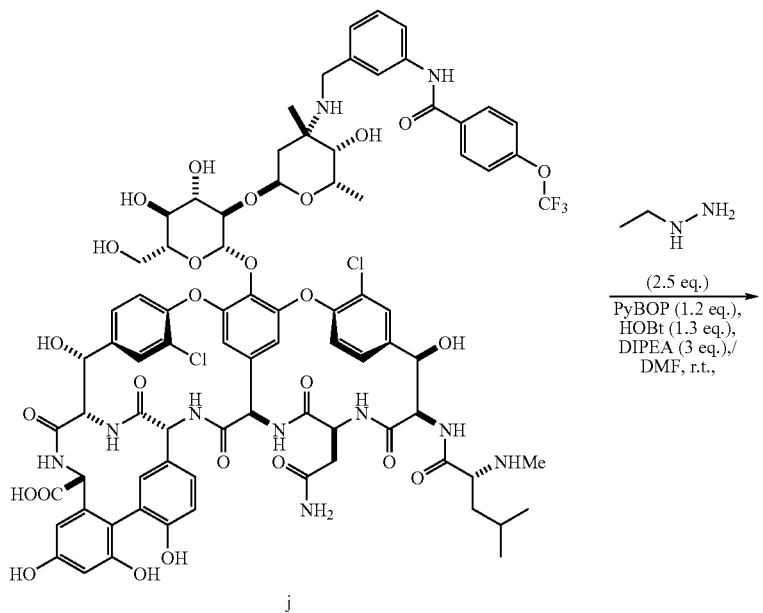

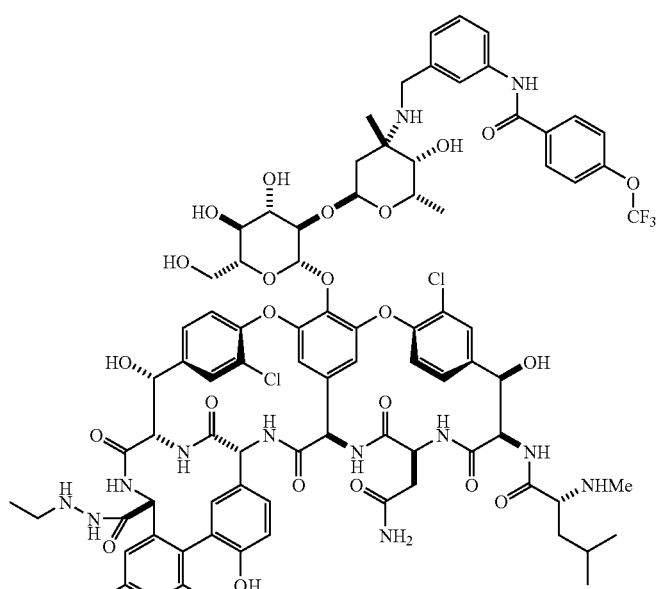

1.97 g (1.13 mmol) of the compound (j) as prepared in Step 3, 706 mg (1.36 mmol) of benztriazole-1-yl-oxy-tris-(pyrrolidino)phosphonium hexafluoro phosphate, and 199 mg (1.47 mmol) of benztriazole-1-ol were dissolved in 40 mL of dimethylformamide, and the mixture was stirred at room temperature for 1.5 hours. Diisopropylethylamine (0.59 mL) and ethylhydrazine (170 mg) were then added sequentially at room temperature, and the reaction mixture was stirred at the same temperature for 24 hours. The mixture was added dropwise to 400 mL of ethyl acetate, and the precipitate formed was collected by filtration and purified by reverse phase column chromatography to afford 1.30 g of the titled compound (Compound 2) as colorless solid (yield 64%).

[M+H]+=1783

Anal calcd. for $C_{83}H_{91}Cl_2F_3N_{12}O_{25}\cdot11H_2O\cdot2.3HCl$: C, 48.24%; H, 5.62%; N, 8.13%; Cl, 7.38%; F, 2.76%. Found: C, 48.33%; H, 5.51%; N, 8.15%; Cl, 7.39%; F, 2.69%.

Example 3

Preparation of Compound 3
(Step 1)

[Chemical Formula 35]

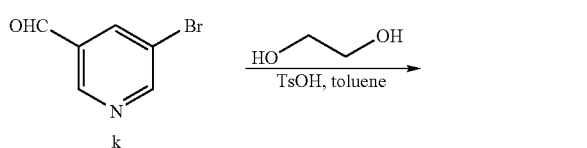

5-bromo-pyridine-3-carbaldehyde (k) (11.98 g), p-toluenesulfonic acid (1.23 g) and ethyleneglycol (39.98 g) were dissolved in 200 mL of toluene, and the mixture was heated under reflux for 3 hours with dehydration using a Dean Stark trap. The reaction mixture was poured into 5% aqueous NaHCO$_3$, and extracted with toluene and subsequently worked up according to conventional procedure to afford 13.82 g of the titled compound (5-bromo-5-[1,3]dioxolan-2-yl-pyridine: m) as a brown oil (yield 93%).

(Step 2)

[Chemical Formula 36]

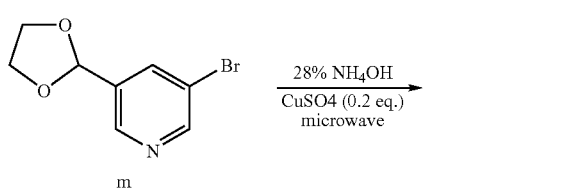

5-bromo-5-[1,3]dioxolan-2-yl-pyridine (m) (1.15 g) prepared in Step 1 and copper sulfate (II) (0.25 g) were suspended in 28% ammonia water and subjected to reaction in a microwave reactor (Emrys Optimizer, Amersham Bio-Sciences) at 150° C. for 1 hour. The reaction mixture was poured into water, extracted with ethyl acetate, and subsequently worked up according to conventional procedure to afford 0.696 g of the titled compound (5-[1,3]dioxolan-2-yl-pyridine-3-ylamine: n) as a yellow oil (yield 84%).

(Step 3)

[Chemical Formula 37]

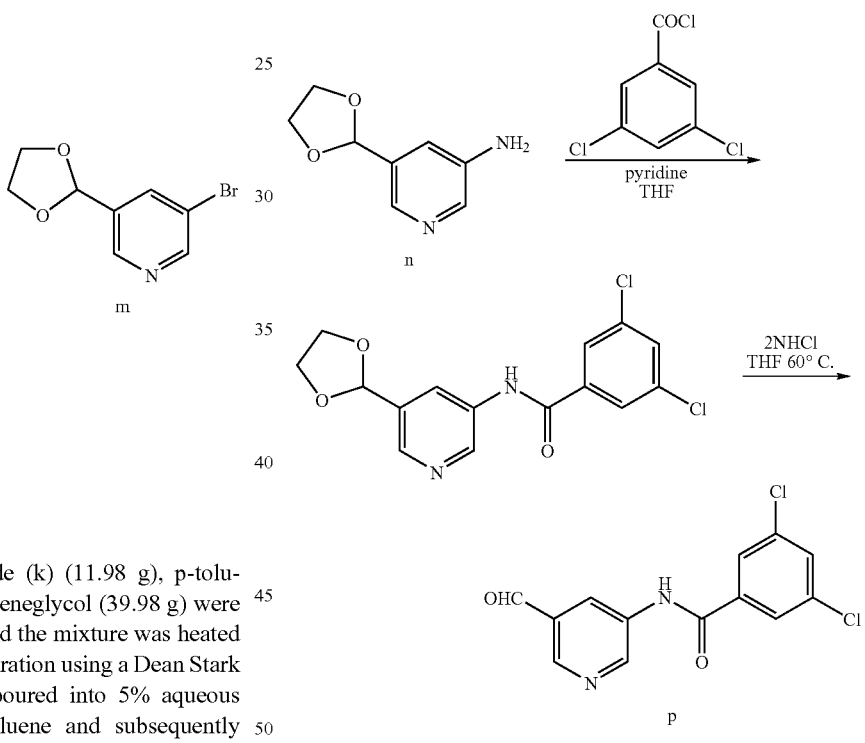

8.75 g of 5-[1,3]dioxolan-2-yl-pyridine-3-ylamine (n) prepared in Step 2 and pyridine (5.00 g) were dissolved in 100 mL of tetrahydrofuran, and 3,5-dichloro-benzoyl chloride (12.14 g) was added dropwise to the mixture over 0.5 hour. After the mixture was stirred for 15 minutes at room temperature, it was poured into water and extracted with ethyl acetate. The extract was dried over anhydrous magnesium sulfate, and the solvent was evaporated to obtain the residue. The obtained residue was dissolved in a mixed solution of 2N hydrochloric acid (100 mL)-tetrahydrofuran (100 mL) and stirred at 60° C. for 8 hours. After tetrahydrofuran was removed in vacuo, the reaction mixture was neutralized by 2N sodium hydroxide. The precipitate was collected by filtration to afford 12.74 g of the titled compound (3,5-dichloro-N-(5-formyl-pyridine-3-yl)-benzamide: p) as a colorless powder (yield 82%).

(Step 4)

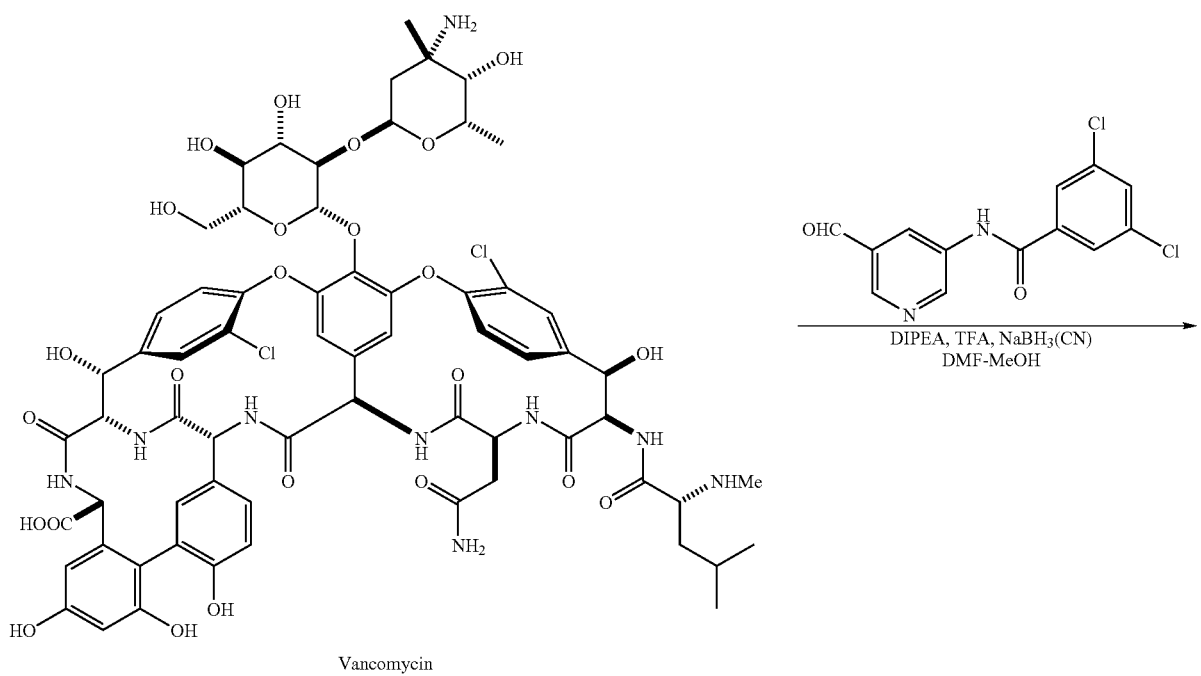

Vancomycin

[Chemical Formula 38]

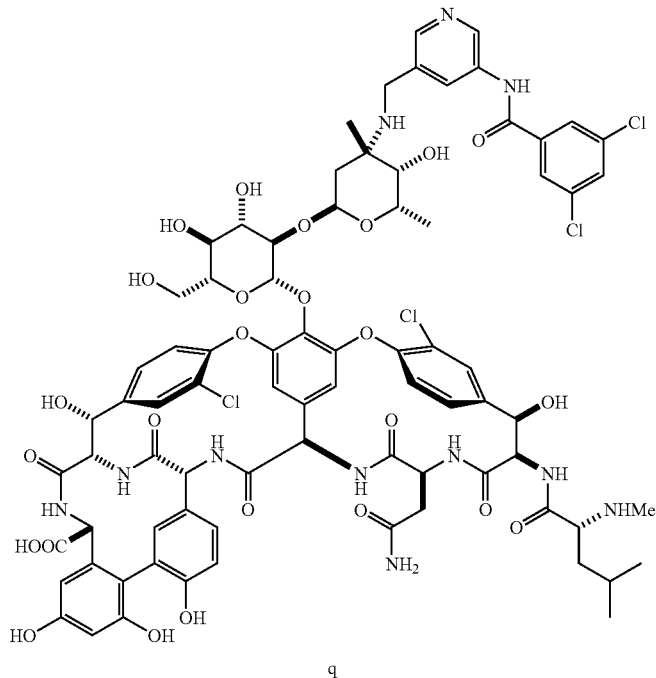

q

Vancomycin hydrochloride (7.43 g) prepared in Step 3,3,5-dichloro-N-(5-formyl-pyridine-3-yl)-benzamide (p) (1.475 g) and diisopropyl ethylamine (1.29 g) were suspended in dimethylformamide (50 mL)-methanol (50 mL) and stirred at room temperature for 2 hours. To the reaction mixture, trifluoroacetic acid (1.37 g) and sodium cyanoborohydride (0.628 g) were added sequentially at room temperature and stirred for 1 hours at this temperature. After methanol was removed in vacuo, the mixture was poured into ethyl acetate and filtered to collect the precipitate, which was then washed with 10% aqueous NaCl. The obtained residue was purified by reverse phase column chromatography to afford 2.73 g (yield 32%) of the titled compound (q).

(Step 5)
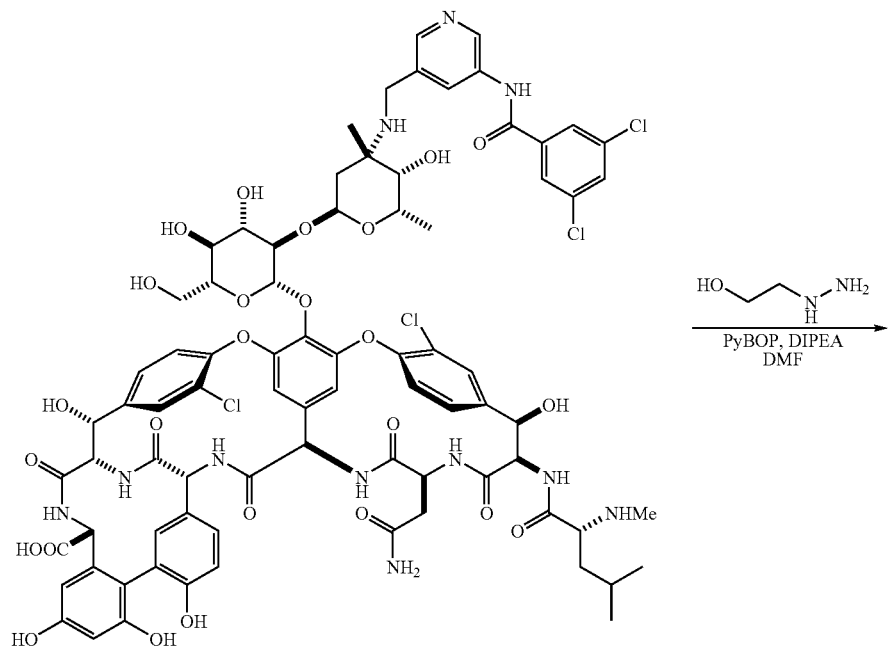
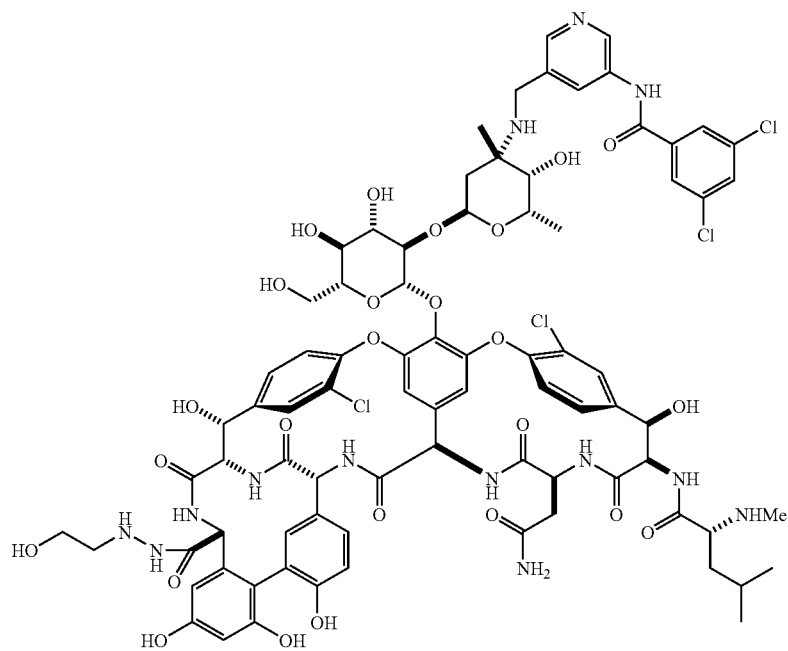

The compound (q) (14.40 g) prepared in Step 4, benztriazole-1-yl-oxy-tris-(pyrrolidino)phosphonium hexafluorophosphate (6.09 g) were dissolved in dimethylformamide (100 mL) and stirred for 0.5 hour at room temperature. Diisopropyl ethyl amine (5.38 g) and 2-hydrazino ethanol (1.27 g) were added sequentially at room temperature and stirred for 1 hour at this temperature. The reaction mixture was poured into ethyl acetate and filtered to collect the precipitate, which was then purified by reverse phase column chromatography to afford 8.57 g of the titled compound (Compound 3) (yield 58%).

$[M+H]^+=1786$

Anal calcd. for $C_{81}H_{89}Cl_4N_{13}O_{25} \cdot 11.2H_2O \cdot 2.4HCl$: C, 46.87%; H, 5.53%; N, 8.77%; Cl, 10.93%. Found: C, 46.88%; H, 5.41%; N, 8.75%; Cl, 10.84%.

Example 4

Preparation of Compound 4
(Step 1)

[Chemical Formula 40]

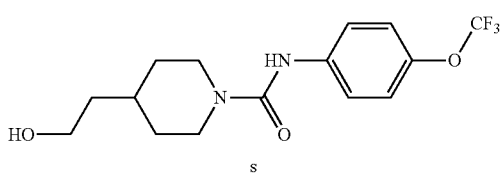

Under nitrogen gas stream, 50 g of 2-piperidine-4-ylethanol (r) (0.387 mol) was dissolved in tetrahydrofuran (1 L), and after ice cooling, 78.6 g of 1-isocyanate-4-trifluoromethoxy-benzene (0.387 mol) was added dropwise to keep the mixture at the temperature bellow 10° C. and then stirred at this temperature for 1 hour. The mixture was concentrated in vacuo to achieve ⅓ of the total volume. The residue was added with diisopropyl ether and stirred for 5 minutes, and then filtered to collect the precipitate, which was rinsed with diisopropyl ether and dried to afford 120.1 g of the titled compound (4-(2-hydroxyethyl)-piperazine-1-carboxylic acid (4-trifluoromethoxyphenyl) amide: s) as colorless crystal (yield 93%).

(Step 2)

[Chemical Formula 41]

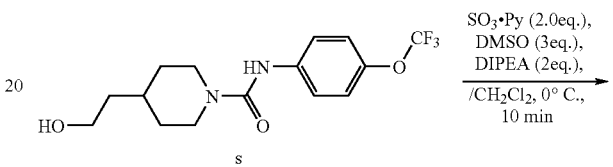

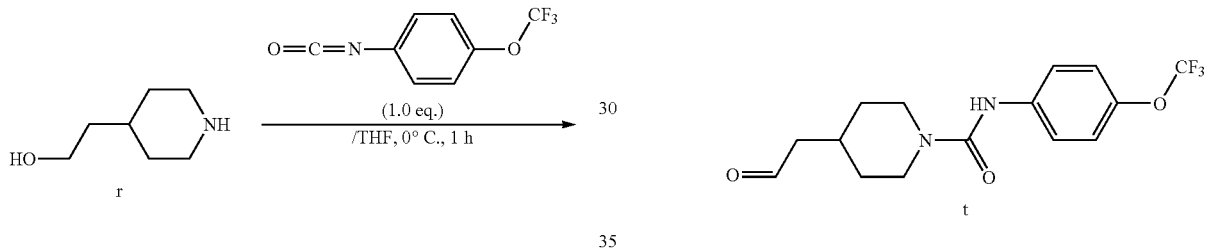

4-(2-hydroxyethyl)-piperazine-1-carboxylic acid (4-trifluoromethoxyphenyl)-amide (s) (8.0 g, 24.1 mmol) was suspended in dichloromethane (80 mL). After ice cooling, 8.38 mL of diisopropylethylamine (48.1 mmol) and 10.1 mL of dimethylsulfoxide (72.3 mmol) were added sequentially. Sulfur trioxidepyridine complex (7.66 g, 48.1 mmol) was then added portionwise to keep the temperature bellow 10° C., and the mixture was stirred for 10 minutes. Water (80 mL) was added to quench the reaction, and the mixture was extracted with ethyl acetate. The extract layer was washed sequentially with saturated sodium bicarbonate and saturated saline, and dried on anhydrous magnesium sulfate. The desiccant was removed by filtration, and the filtrate was concentrated in vacuo to afford 10.6 g of the titled compound (4-(2-oxoethyl)-piperidin-1-carboxylic acid (4-trifluoromethoxy-phenyl)amide: t) as yellow crude solid. Titer was 0.65, and the yield was 87%, as confirmed by $^1$H-NMR spectroscopic analysis.

(Step 3)

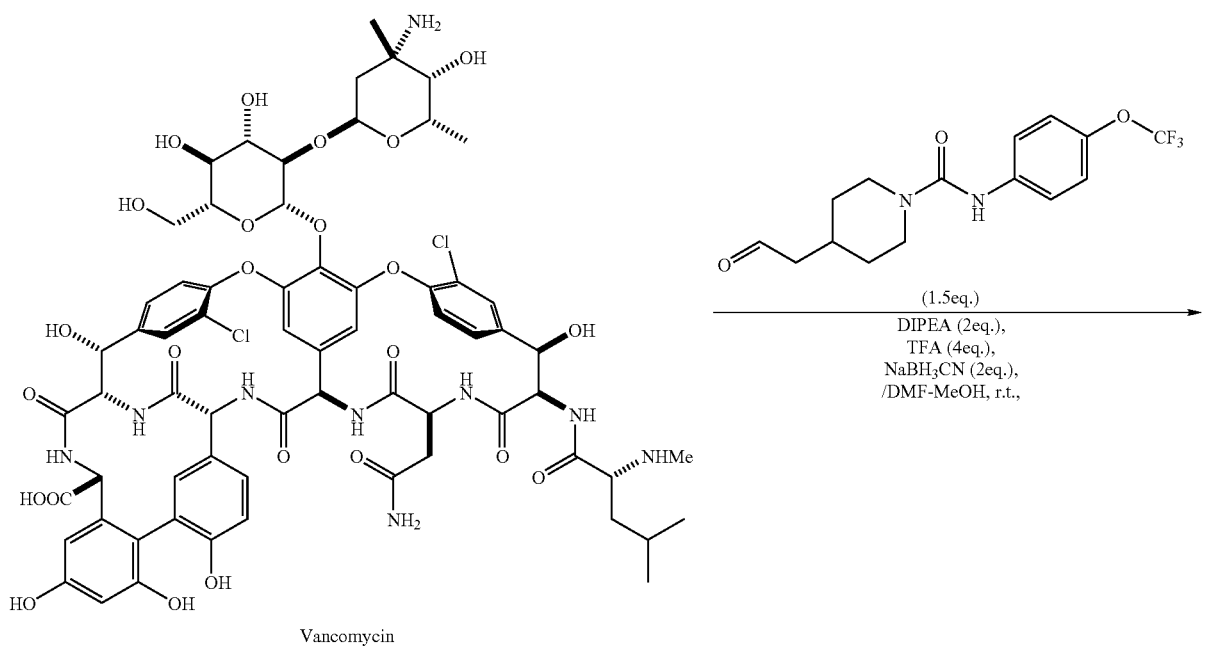

Vancomycin

[Chemical Formula 42]

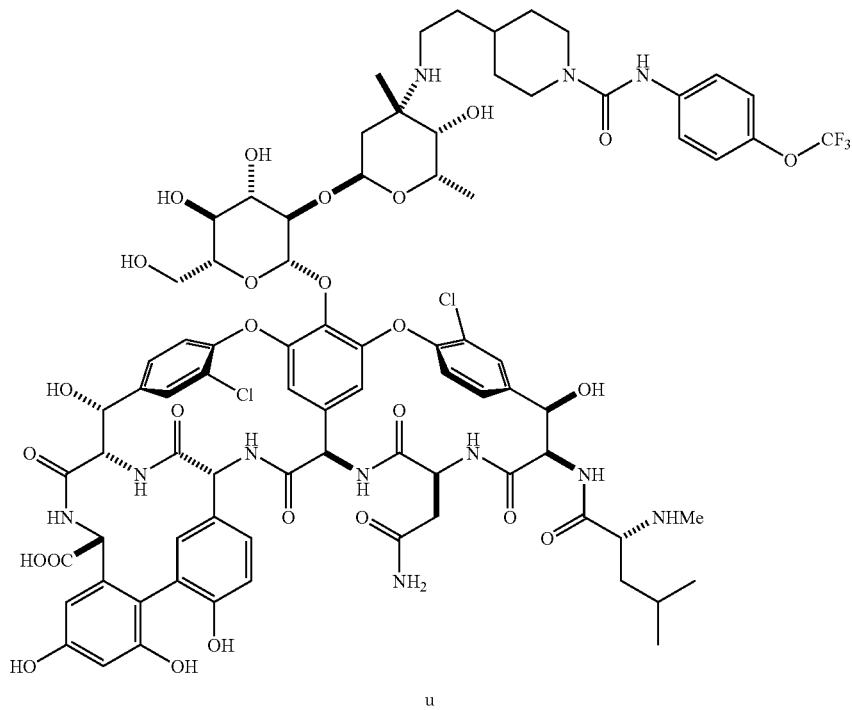

Vancomycin hydrochloride (20.8 g, 14 mmol) and 4-(2-oxoethyl)-piperidin-1-carboxylic acid (4-trifluoromethoxyphenyl)amide (t) (6.94 g, 21 mmol) prepared in Step 2 were dissolved in dimethylformamide (208 mL), and diisopropylethylamine (9.37 mL) was added to the mixture and stirred at room temperature for 75 minutes. To the mixture, trifluoroacetic acid (4.3 mL) was added slowly dropwise over 10 minutes. The mixture was then added with methanol (208 mL) and further sodium cyanoborohydride (1.76 g) and stirred at room temperature for 3 hours. Methanol was removed in vacuo, and the residue was poured into 2.0 L of ethyl acetate. The precipitate was collected by filtration, and the obtained crude solid was rinsed with 10% saline to remove sodium cyanoborohydride. The crude solid was purified by reverse phase column chromatography to afford 10.19 g of the titled compound (u) (yield 41%).
(Step 4)

and the mixture was stirred at this temperature for 1.5 hours. The mixture was poured into 60 mL of diethylether, and the precipitate was collected by filtration. The crude solid thus obtained was dissolved in a mixed solvent of acetonitrile (8 mL) and 0.5N hydrochloric acid (6 mL), and the mixture was stirred at room temperature for 1.5 hours. The mixture was subjected to purification by reverse phase column chroma-

[Chemical Formula 43]

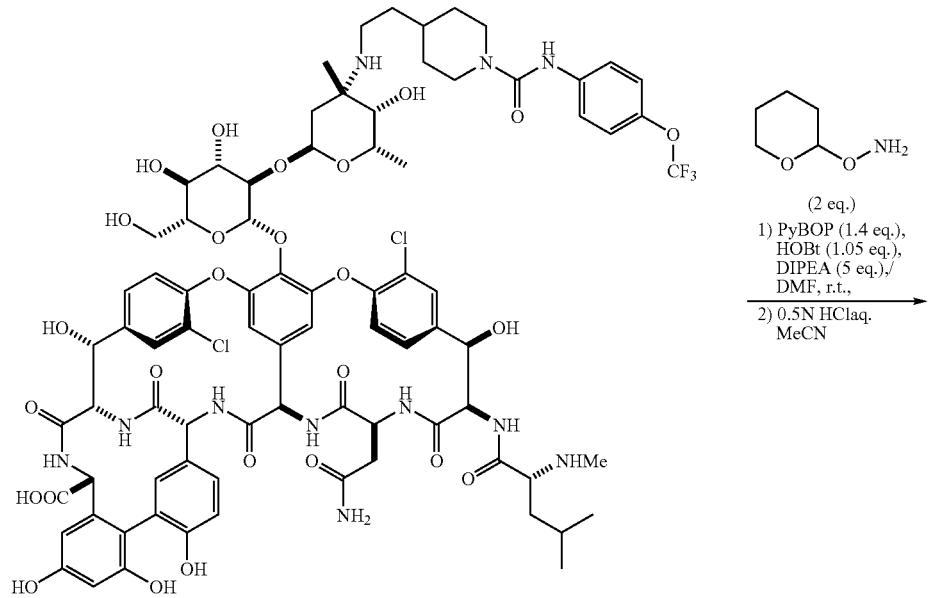

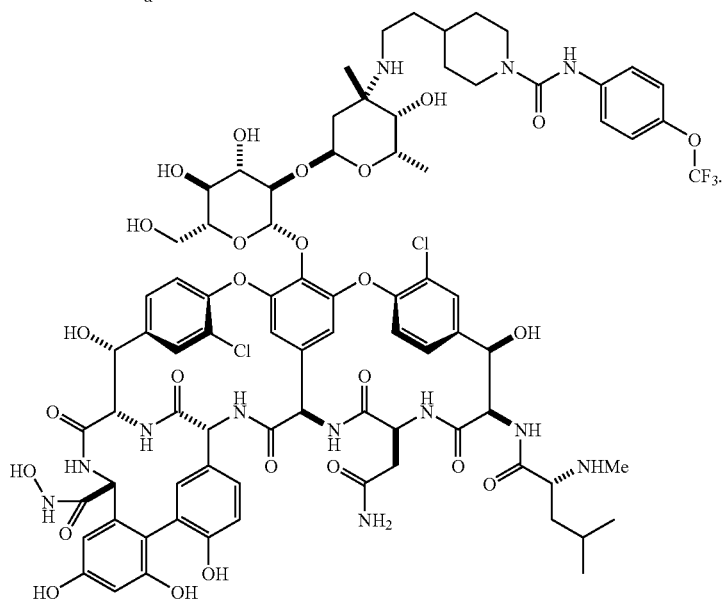

The compound (u) as prepared in Step 3 (485 mg, 0.275 mmol), benztriazole-1-yl-oxy-tris-(pyrrolidino)phosphonium hexafluorophosphate (200 mg, 0.385 mmol) and benztriazole-1-ol (38 mg, 0.289 mmol) were dissolved in dimethylformamide (8 mL), and the mixture was stirred at room temperature for 1.5 hours. Diisopropyl ethylamine (0.24 mL) and o-(tetrahydro-2H-pyran-2-yl)hydroxylamine (64 mg, 0.55 mmol) were added sequentially at room temperature, tography to afford 202 mg of the titled compound (Compound 4) as colorless solid (yield 41%).

$[M+H]^+=1777$

Anal calcd. for $C_{81}H_{93}Cl_2F_3N_{12}O_{26}\cdot 11.3H_2O_2\cdot 2.0HCl$: C, 47.34%; H, 5.77%; Cl, 6.90%; F, 2.77%; N, 8.18%. Found: C, 47.42%; H, 5.77%; Cl, 6.85%; F, 2.64%; N, 8.21%.

The following compounds were prepared in a similar manner as described in the above Examples.

Compound 5
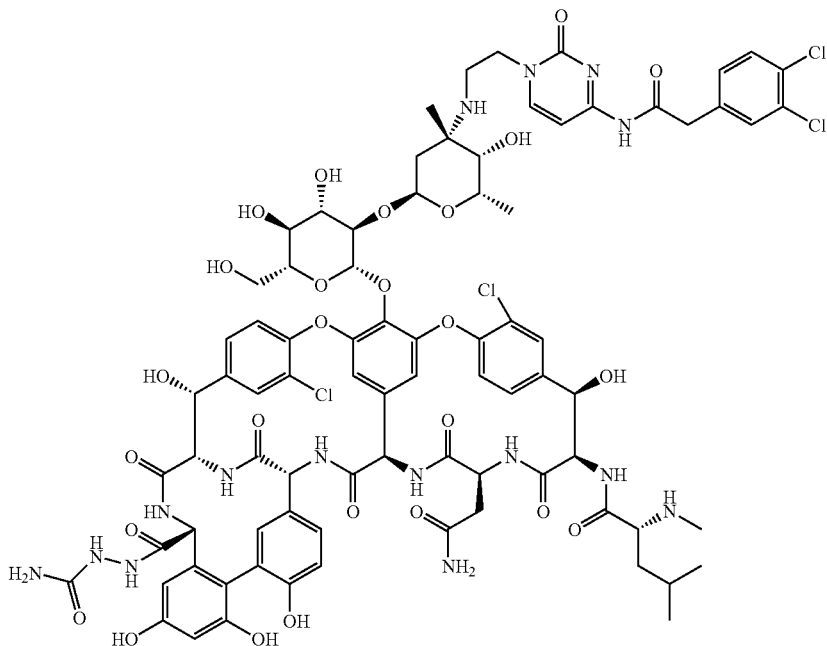
[Chemical Formula 44]
[M+H]⁺=1828
Anal. calcd. for $C_{81}H_{89}Cl_4N_{15}O_{26} \cdot 11.2H_2O \cdot 1.7HCl$: C, 46.45%; H, 5.44%; N, 10.03%; Cl, 9.65%. Found: C, 46.48%; H, 5.34%; N, 9.77%; Cl, 9.69%.
Compound 6
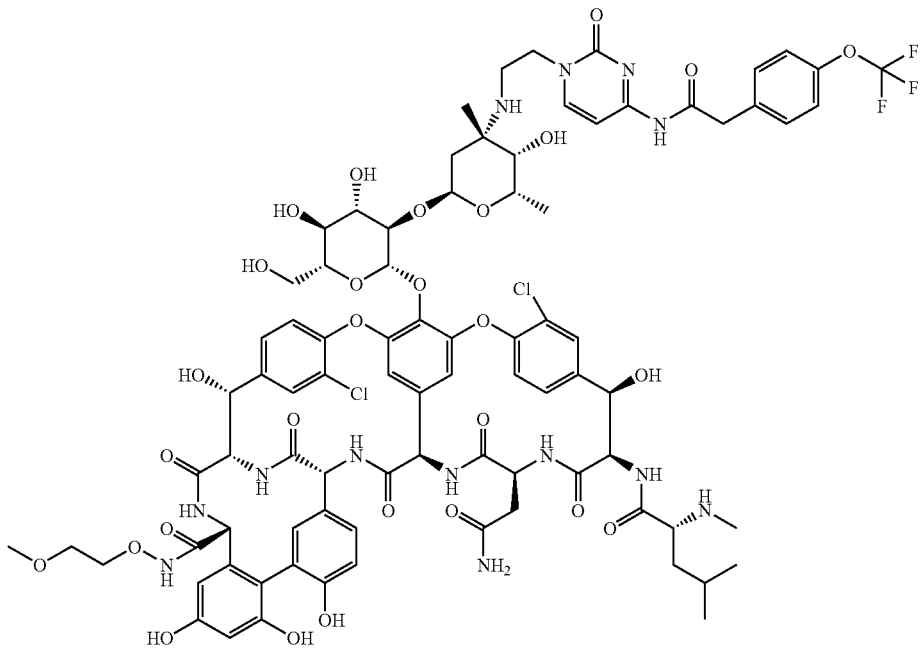
[Chemical Formula 45]

[M+H]⁺=1860
Anal calcd. for $C_{84}H_{94}Cl_2F_3N_{13}O_{28} \cdot 10.0H_2O \cdot 2.5HCl$: C, 47.30%; H, 5.51%; N, 8.54%; Cl, 7.48%; F, 2.67%. Found: C, 47.24%; H, 5.42%; N, 8.67%; Cl, 7.50%; F, 2.70%.
Compound 7
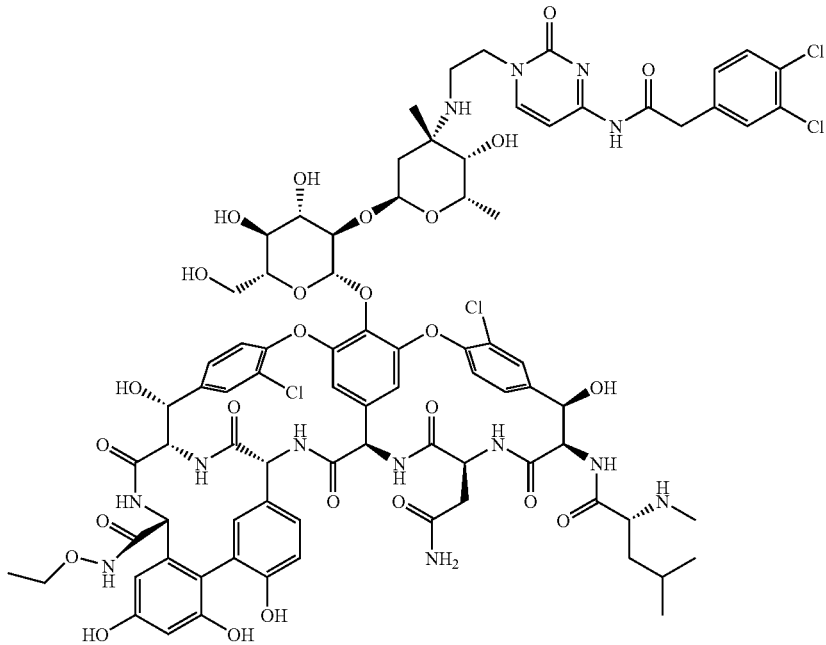
[Chemical Formula 46]
[M+H]⁺=1814
Anal calcd. for $C_{82}H_{91}Cl_4N_{13}O_{26} \cdot 10.4H_2O \cdot 2.2HCl$: C, 47.26%; H, 5.51%; N, 8.74%; Cl, 10.55%. Found: C, 47.25%; H, 5.38%; N, 8.78%; Cl, 10.62%.
Compound 8
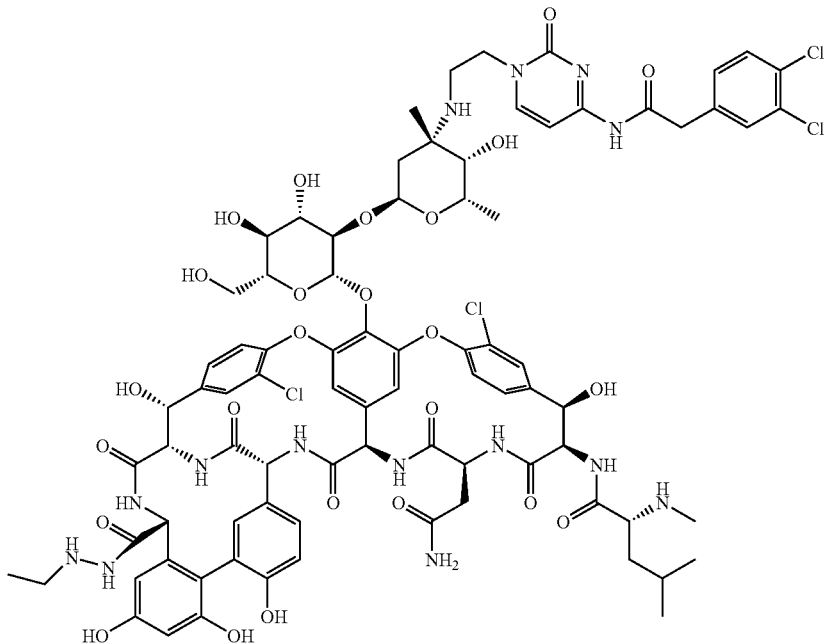
[Chemical Formula 47]

[M+H]⁺=1813
Anal calcd. for $C_{82}H_{92}Cl_4N_{14}O_{25} \cdot 10.4H_2O \cdot 2.4HCl$: C, 47.12%; H, 5.55%; N, 9.38%; Cl, 10.85%. Found: C, 47.07%; H, 5.49%; N, 9.44%; Cl, 10.83%.
Compound 9
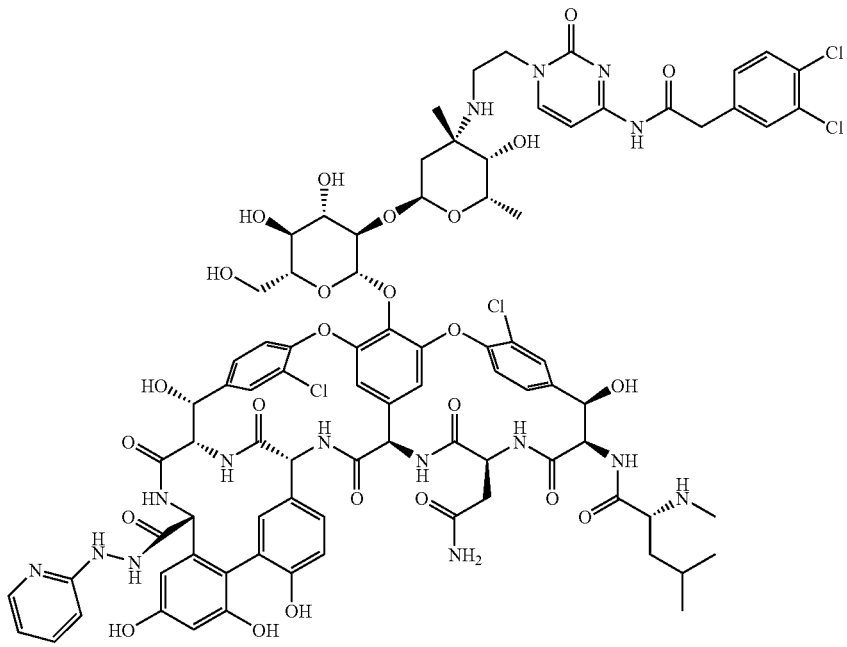
[Chemical Formula 48]
[M+H]⁺=1862
Anal calcd. for $C_{85}H_{91}Cl_4N_{15}O_{25} \cdot 12.7H_2O \cdot 2.4HCl$: C, 46.81%; H, 5.49%; N, 9.63%; Cl, 10.40%. Found: C, 46.75%; H, 5.19%; N, 9.78%; Cl, 10.46%.
Compound 10
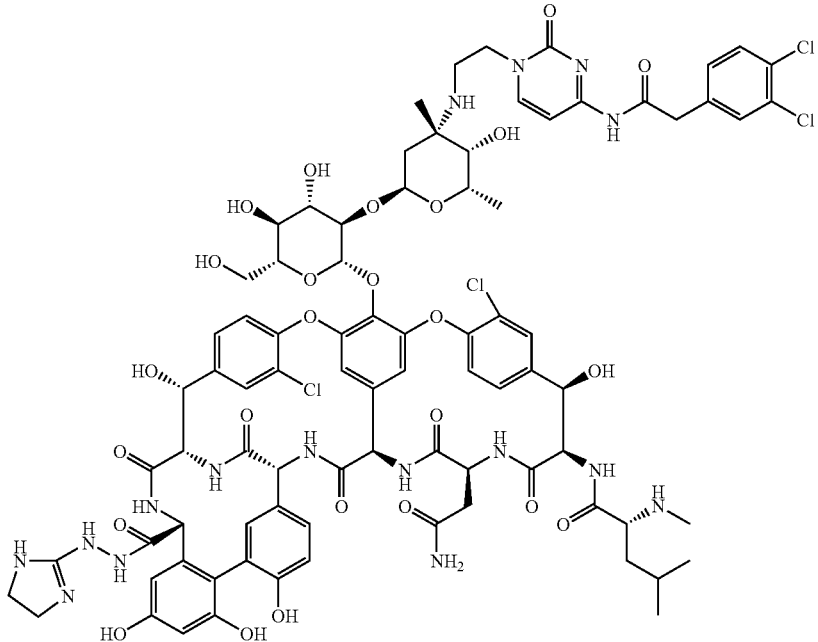
[Chemical Formula 49]

[M+H]$^+$=1853
Anal calcd. for $C_{83}H_{92}Cl_4N_{16}O_{25}\cdot 13.7H_2O\cdot 1.8HCl$: C, 45.98%; H, 5.63%; N, 10.34%; Cl, 9.48%. Found: C, 45.96%; H, 5.34%; N, 10.44%; Cl, 9.55%.
Compound 11
[Chemical Formula 50]
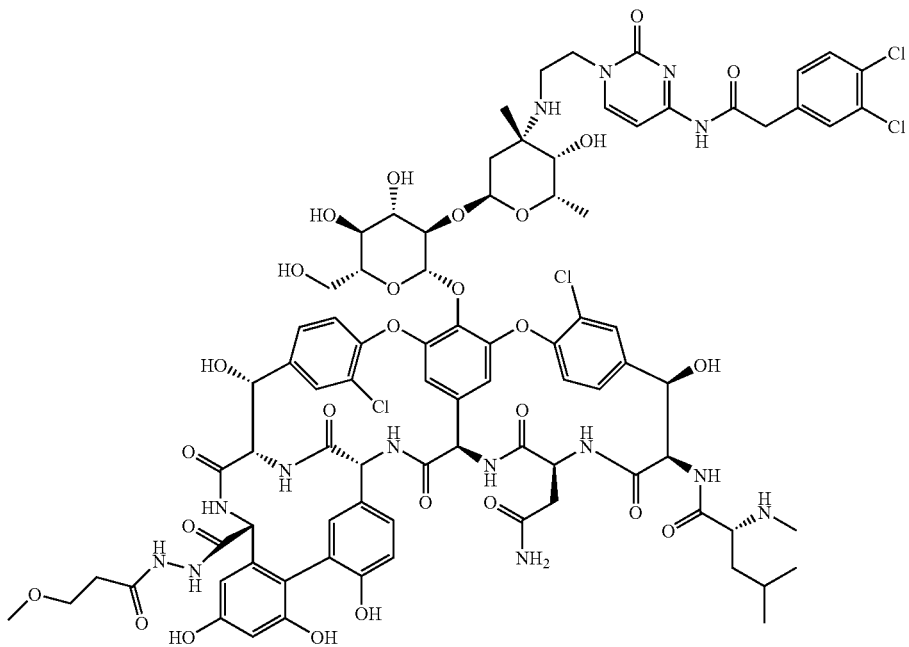
[M+H]$^+$=1871
Anal calcd. for $C_{84}H_{94}Cl_4N_{14}O_{27}\cdot 10.0H_2O\cdot 1.9HCl$: C, 47.52%; H, 5.50%; N, 9.24%; Cl, 9.85%. Found: C, 47.50%; H, 5.47%; N, 9.29%; Cl, 9.87%.
Compound 12
[Chemical Formula 51]
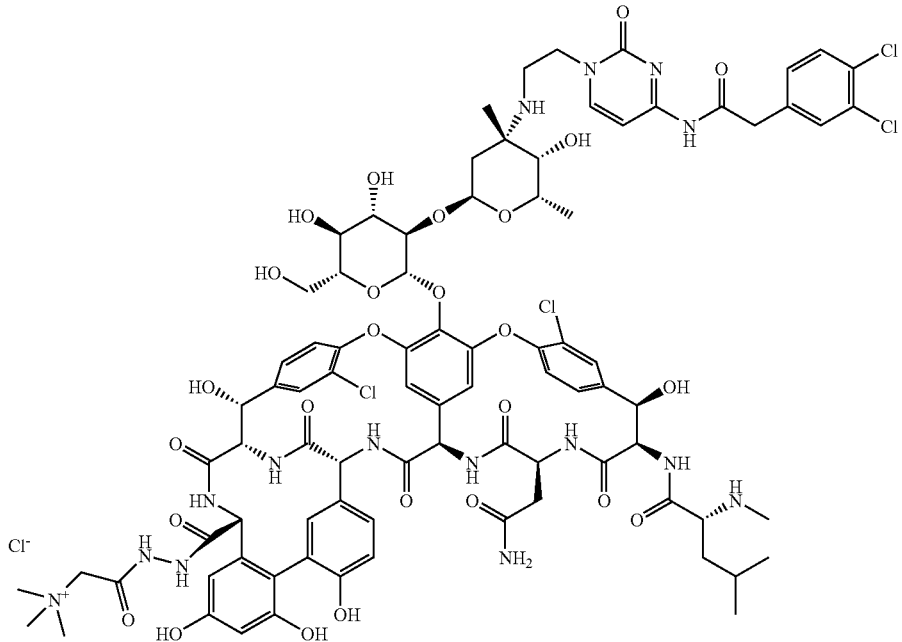

[M]+=1884
Anal calcd. for $C_{85}H_{98}Cl_5N_{15}O_{26}\cdot 12.1H_2O\cdot 2.4HCl$: C, 45.81%; H, 5.64%; N, 9.43%; Cl, 11.77%. Found: C, 45.78%; H, 5.59%; N, 9.62%; Cl, 11.69%.
Compound 13
[Chemical Formula 52]
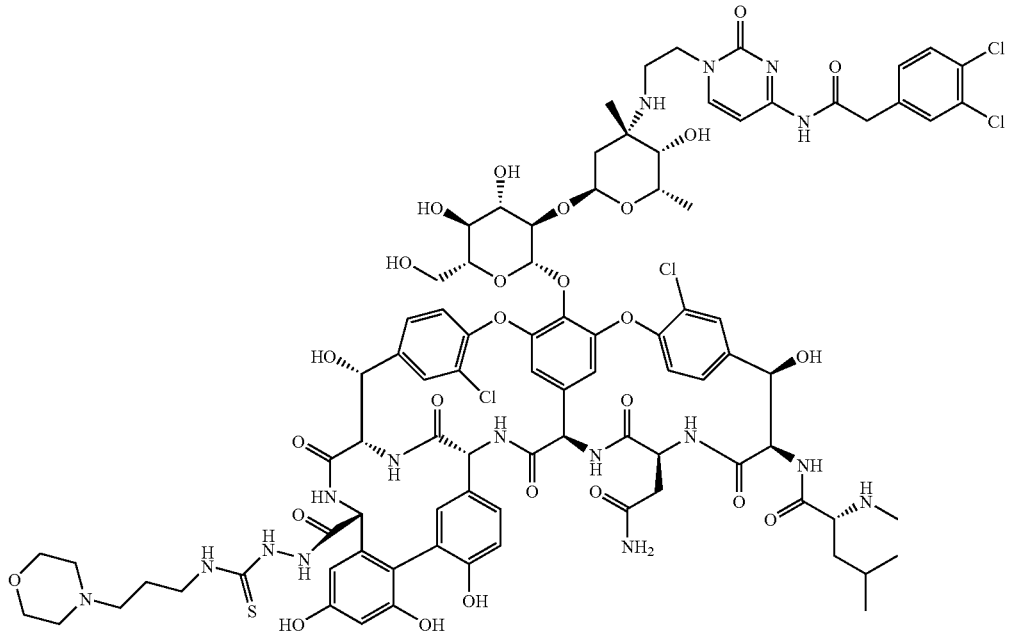
[M+H]+=1971
Anal calcd. for $C_{88}H_{102}Cl_4N_{16}O_{26}S\cdot 12.1H_2O\cdot 3.1HCl$: C, 45.86%; H, 5.65%; N, 9.72%; Cl, 10.92%; S, 1.39%. Found: C, 45.80%; H, 5.53%; N, 9.79%; Cl, 10.98%; S, 1.42%.
Compound 14
[Chemical Formula 53]
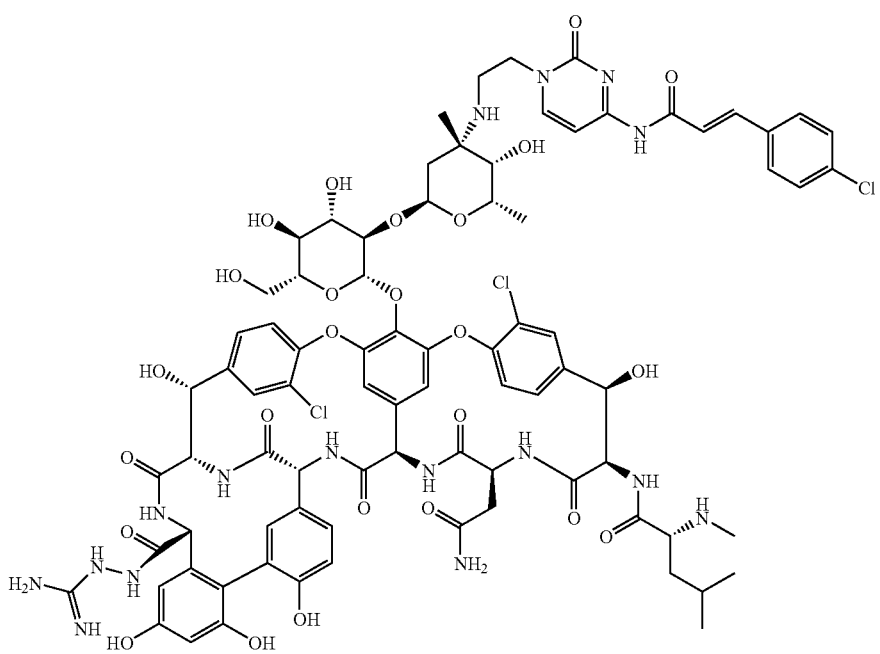

[M+H]$^+$=1805
Anal calcd. for $C_{82}H_{91}Cl_3N_{16}O_{25}\cdot11.9H_2O\cdot2.8HCl$: C, 46.38%; H, 5.58%; N, 10.55%; Cl, 9.68%. Found: C, 46.50%; H, 5.51%; N, 10.09%; Cl, 9.71%.
Compound 15
[Chemical Formula 54]
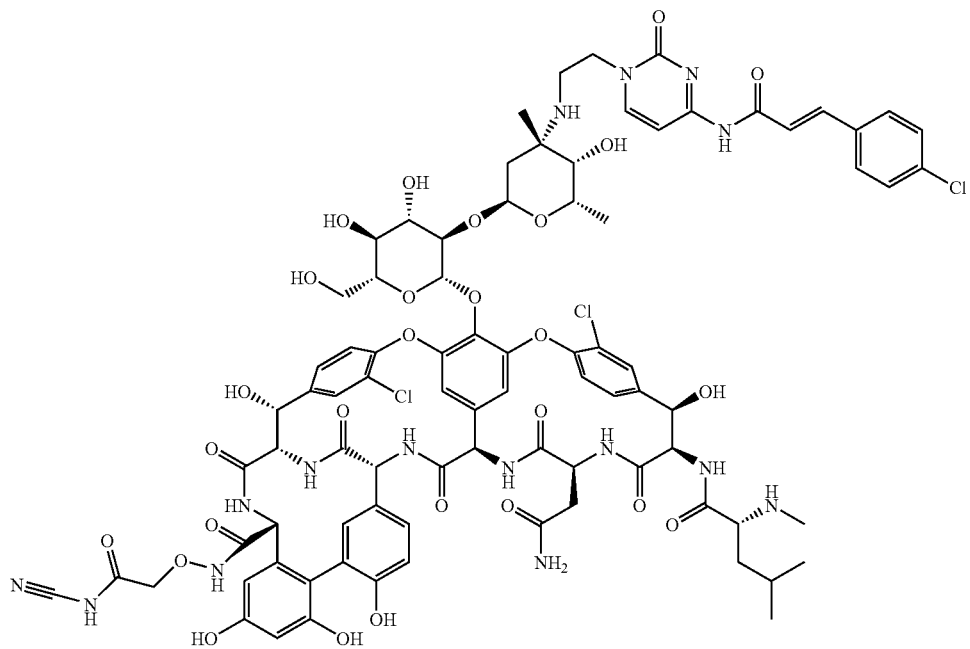
[M+H]$^+$=1846
Anal calcd. for $C_{84}H_{90}Cl_3N_{15}O_{27}\cdot10.3H_2O\cdot2.3HCl$: C, 47.65%; H, 5.37%; N, 9.92%; Cl, 8.87%. Found: C, 47.64%; H, 5.30%; N, 9.94%; Cl, 8.90%.
Compound 16
[Chemical Formula 55]
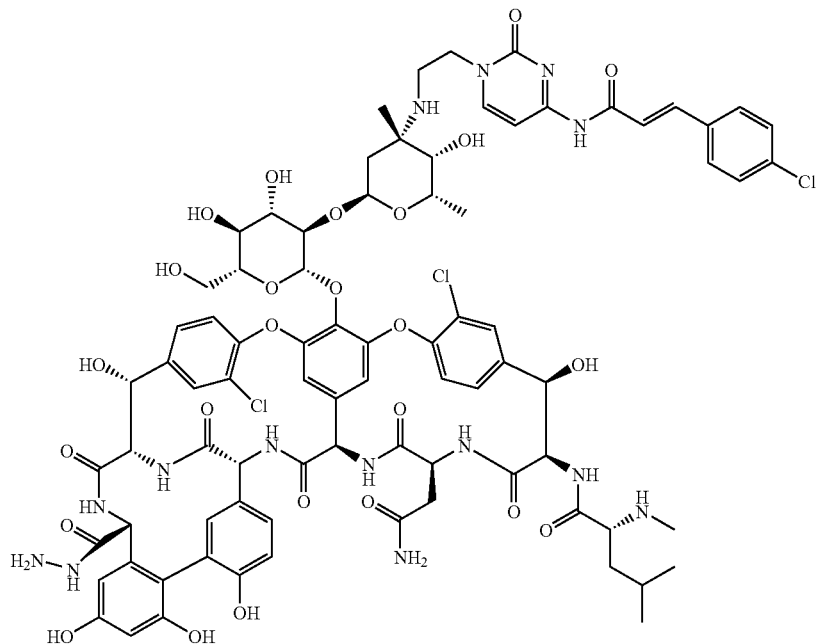

$[M+H]^+=1763$
Anal calcd. for $C_{81}H_{89}Cl_3N_{14}O_{25} \cdot 10.9H_2O \cdot 2.6HCl$: C, 47.31%; H, 5.56%; N, 9.54%; Cl, 9.66%. Found: C, 47.30%; H, 5.56%; N, 9.66%; Cl, 9.68%.
Compound 17
[Chemical Formula 56]
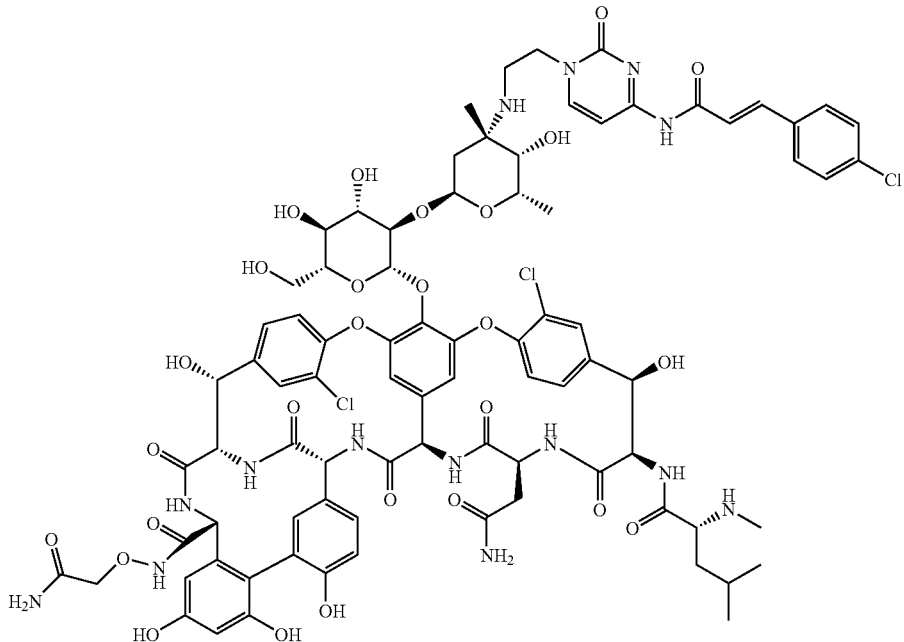
$[M+H]^+=1821$
Anal calcd. for $C_{83}H_{91}Cl_3N_{14}O_{27} \cdot 9.9H_2O \cdot 2.2HCl$: C, 47.89%; H, 5.47%; N, 9.42%; Cl, 8.86%. Found: C, 47.92%; H, 5.45%; N, 9.31%; Cl, 8.92%.
Compound 18
[Chemical Formula 57]
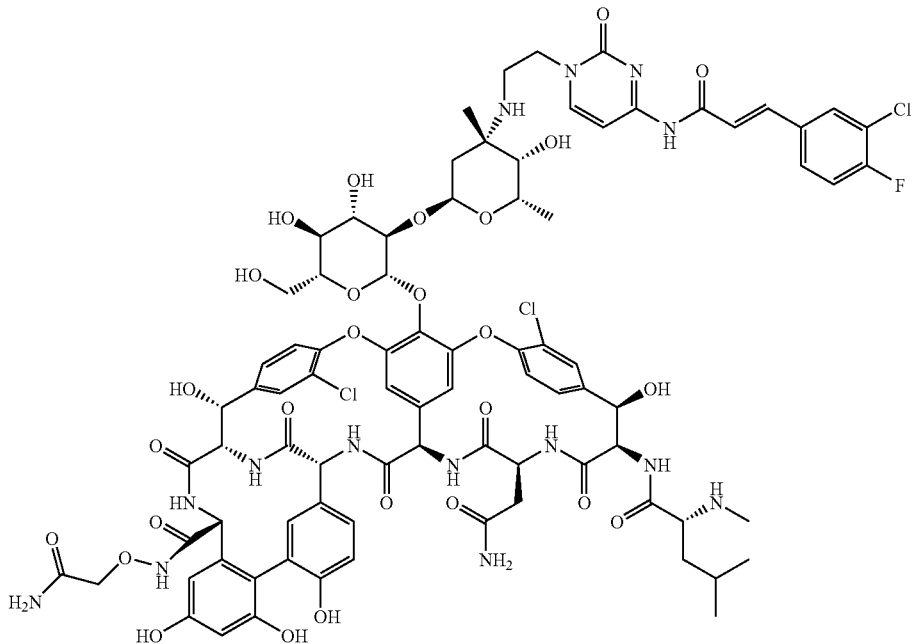

[M+H]$^+$=1839
Anal calcd. for $C_{83}H_{90}Cl_3FN_{14}O_{27} \cdot 9.6H_2O \cdot 2.3HCl$: C, 47.52%; H, 5.36%; N, 9.35%; Cl, 8.96%; F, 0.91%. Found: C, 47.52%; H, 5.40%; N, 9.18%; Cl, 8.94%; F, 1.09%.
Compound 19
[Chemical Formula 58]
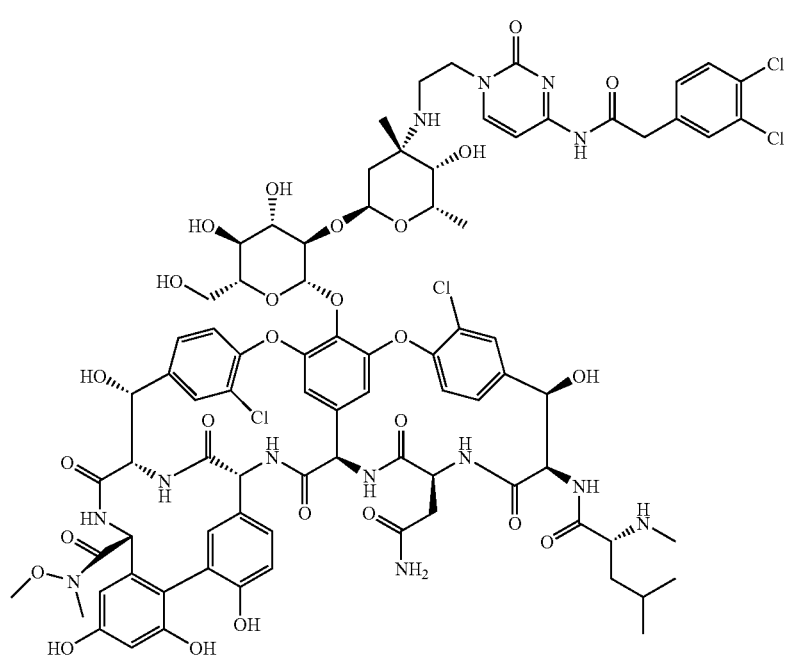
[M+H]$^+$=1814
Anal calcd. for $C_{82}H_{91}Cl_4N_{13}O_{26} \cdot 9.5H_2O \cdot 2.3HCl$: C, 47.54%; H, 5.46%; N, 8.79%; Cl, 10.78%. Found: C, 47.53%; H, 5.41%; N, 8.79%; Cl, 10.82%.
Compound 20
[Chemical Formula 59]
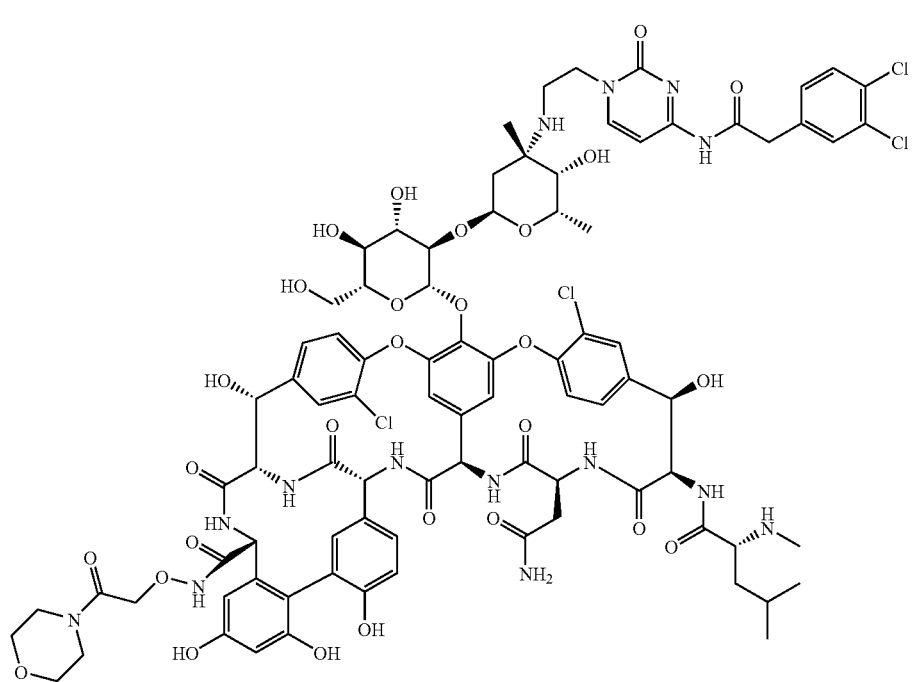

[M+H]⁺=1913
Anal calcd. for $C_{86}H_{96}Cl_4N_{14}O_{28} \cdot 10.1H_2O \cdot 2.0HCl$: C, 47.59%; H, 5.49%; N, 9.03%; Cl, 9.80%. Found: C, 47.62%; H, 5.43%; N, 8.84%; Cl, 9.74%.
Compound 21
[Chemical Formula 60]
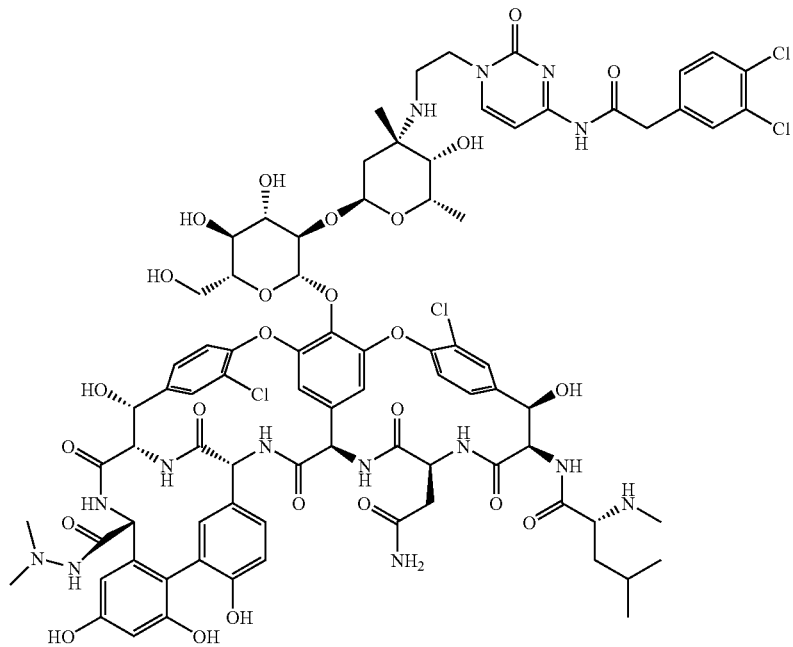
[M+H]⁺=1813
Anal calcd. for $C_{82}H_{92}Cl_4N_{14}O_{25} \cdot 11.1H_2O \cdot 2.2HCl$: C, 47.00%; H, 5.60%; N, 9.36%; Cl, 10.49%. Found: C, 47.01%; H, 5.51%; N, 9.29%; Cl, 10.51%.
Compound 22
[Chemical Formula 61]
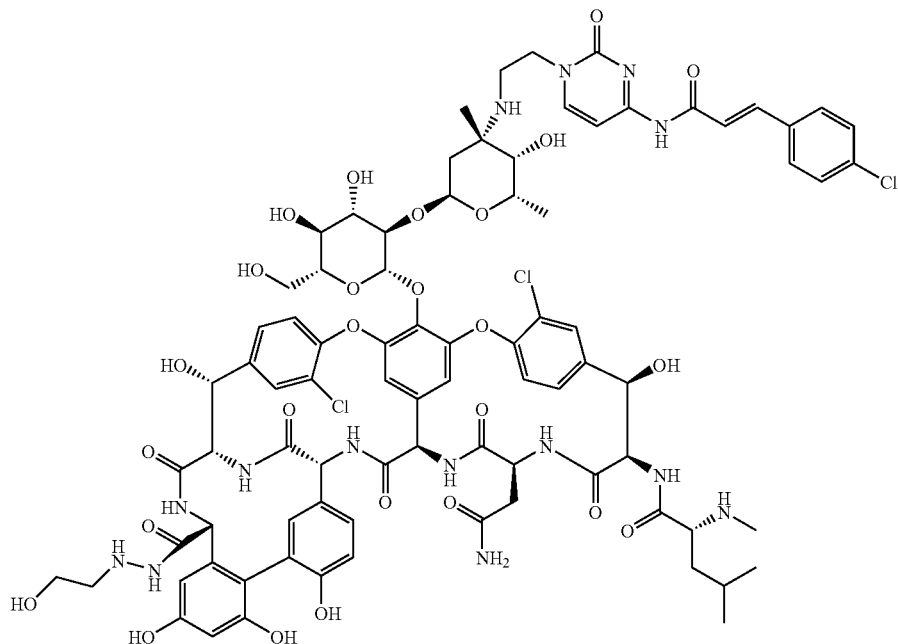

[M+H]⁺=1807
Anal calcd. for $C_{83}H_{93}Cl_3N_{14}O_{26} \cdot 10.5H_2O \cdot 2.3HCl$: C, 47.88%; H, 5.63%; N, 9.42%; Cl, 9.02%. Found: C, 47.90%; H, 5.50%; N, 9.39%; Cl, 9.04%.
Compound 23
[Chemical Formula 62]
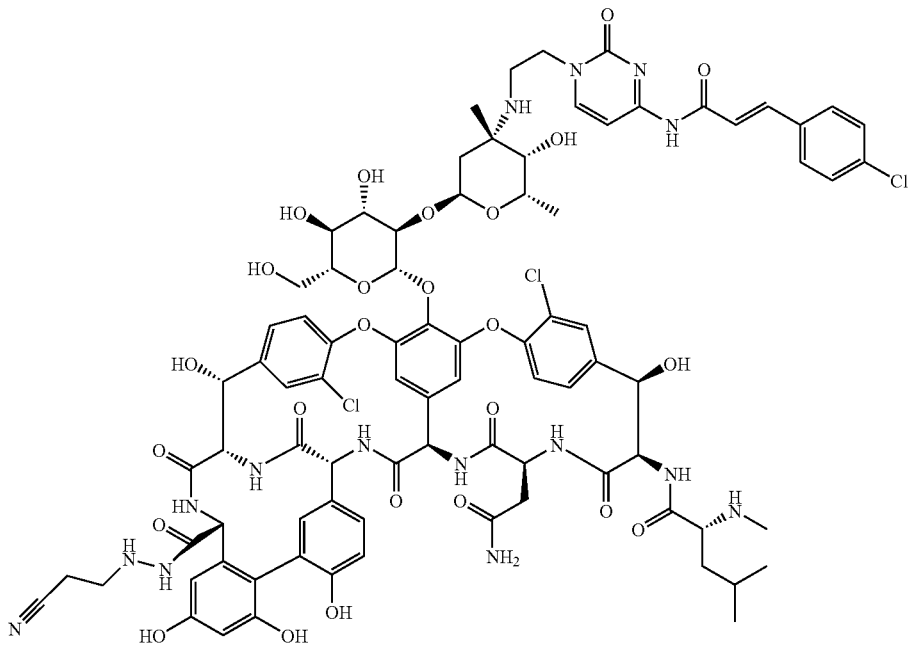
[M+H]⁺=1816
Anal calcd. for $C_{84}H_{92}Cl_3N_{15}O_{25} \cdot 9.3H_2O \cdot 2.8HCl$: C, 48.33%; H, 5.47%; N, 10.06%; Cl, 9.85%. Found: C, 48.32%; H, 5.42%; N, 9.77%; Cl, 9.93%.
Compound 24
[Chemical Formula 63]
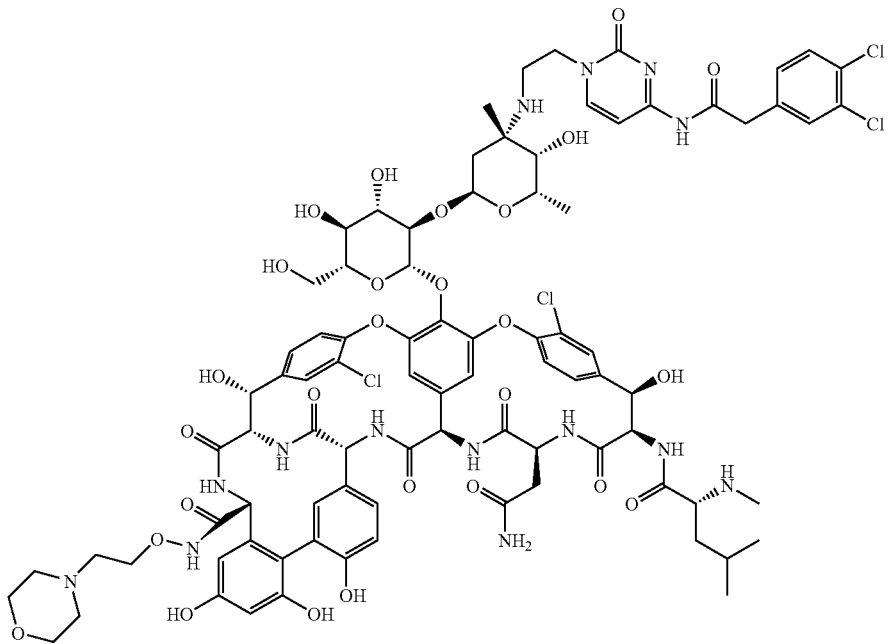

[M+H]$^+$=1899
Anal calcd. for $C_{86}H_{98}Cl_4N_{14}O_{27}\cdot10.8H_2O\cdot3.0HCl$: C, 46.83%; H, 5.60%; N, 8.89%; Cl, 11.25%. Found: C, 46.84%; H, 5.55%; N, 8.94%; Cl, 11.20%.
Compound 25
[Chemical Formula 64]
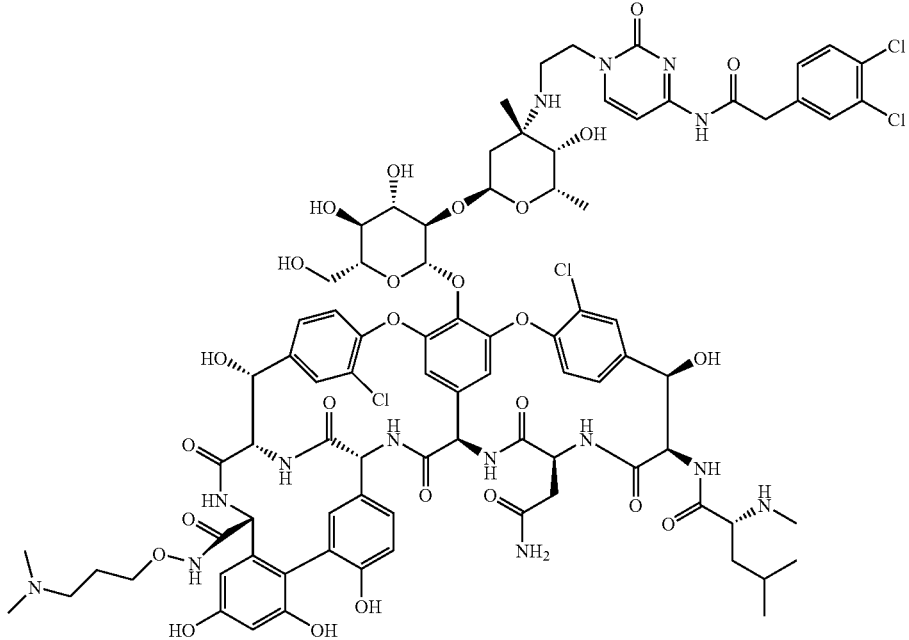
[M+H]$^+$=1871
Anal calcd. for $C_{85}H_{98}Cl_4N_{14}O_{26}\cdot11.0H_2O\cdot3.0HCl$: C, 46.81%; H, 5.68%; N, 8.99%; Cl, 11.38%. Found: C, 46.77%; H, 5.71%; N, 9.03%; Cl, 11.48%.
Compound 26
[Chemical Formula 65]
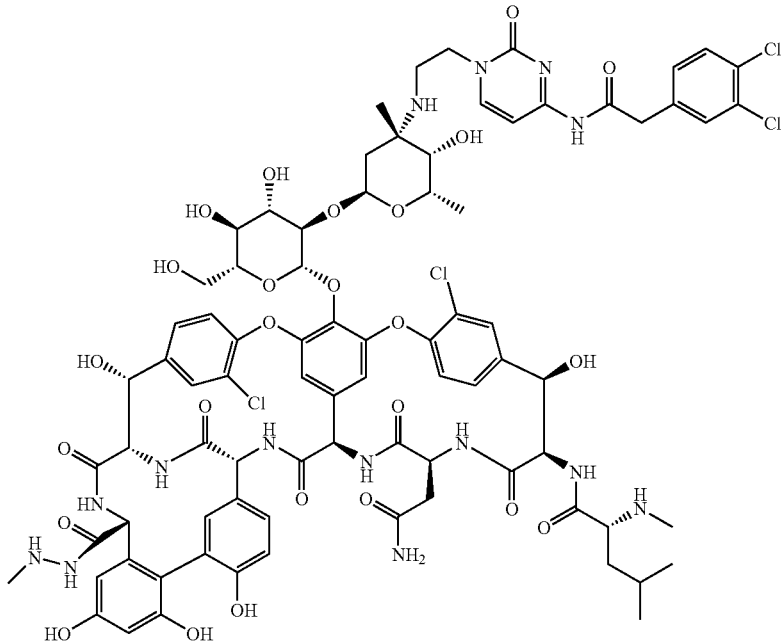

[M+H]$^+$=1799
Anal calcd. for $C_{81}H_{90}Cl_4N_{14}O_{25}\cdot10.3H_2O\cdot2.5HCl$: C, 46.81%; H, 5.49%; N, 9.44%; Cl, 11.09%. Found: C, 46.82%; H, 5.52%; N, 9.51%; Cl, 11.06%.
Compound 27
[Chemical Formula 66]
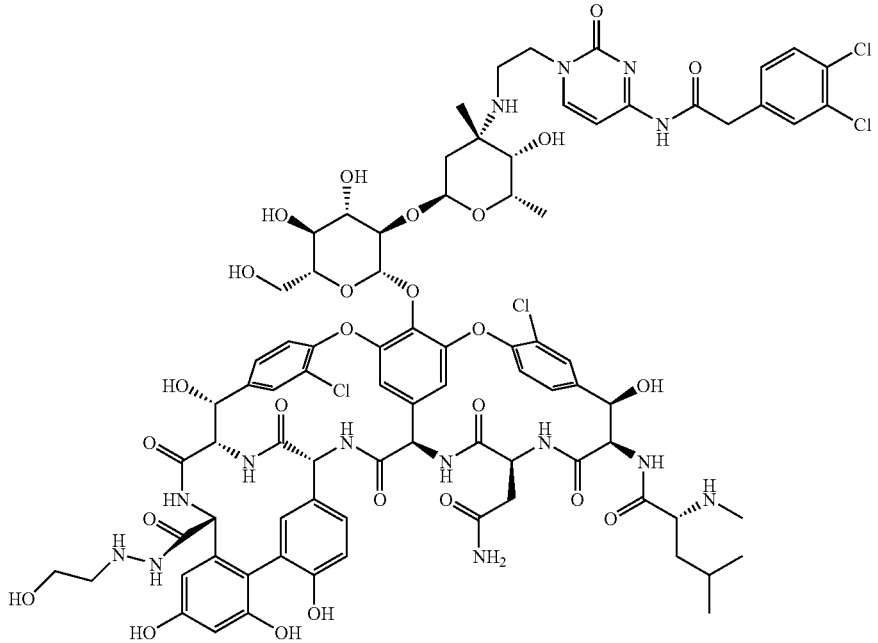
[M+H]$^+$=1829
Anal calcd. for $C_{82}H_{92}Cl_4N_{14}O_{26}\cdot10.4H_2O\cdot2.7HCl$: C, 46.52%; H, 5.50%; N, 9.26%; Cl, 11.22%. Found: C, 46.53%; H, 5.42%; N, 9.26%; Cl, 11.19%.
Compound 28
[Chemical Formula 67]
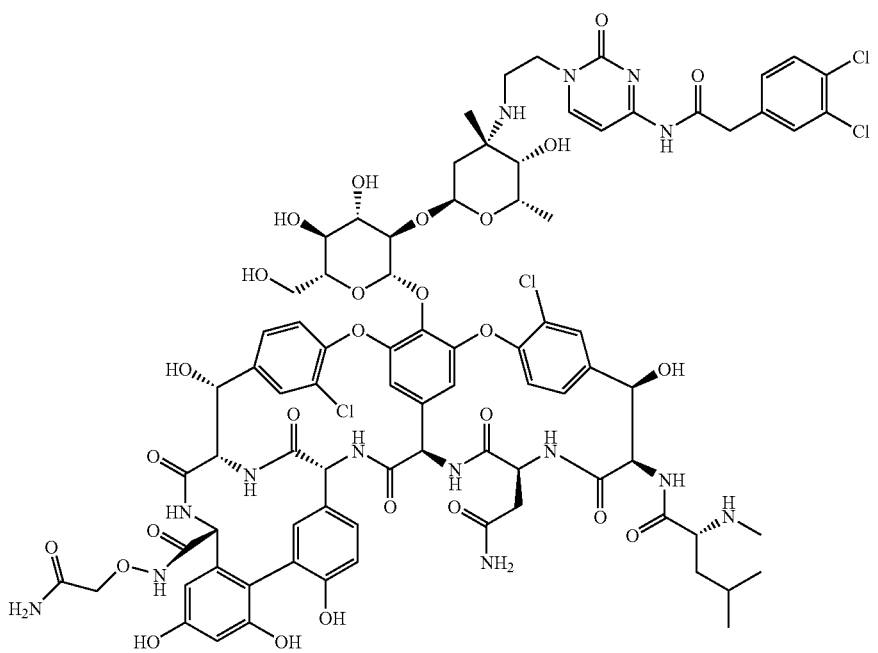

[M+H]$^+$=1843
Anal calcd. for $C_{82}H_{90}Cl_4N_{14}O_{27} \cdot 9.8H_2O \cdot 2.3HCl$: C, 46.77%; H, 5.36%; N, 9.31%; Cl, 10.61%. Found: C, 46.75%; H, 5.46%; N, 9.33%; Cl, 10.61%.
Compound 29
[Chemical Formula 68]
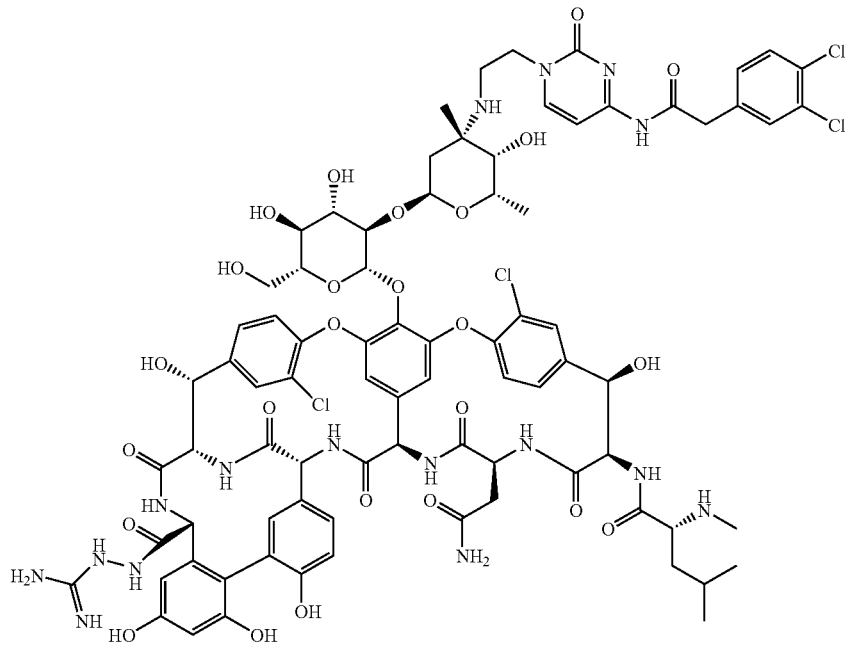
[M+H]$^+$=1827
Anal calcd. for $C_{81}H_{90}Cl_4N_{16}O_{25} \cdot 10.6H_2O \cdot 2.6HCl$: C, 45.99%; H, 5.42%; N, 10.59%; Cl, 11.06%. Found: C, 45.98%; H, 5.37%; N, 10.33%; Cl, 11.13%.
Compound 30
[Chemical Formula 69]
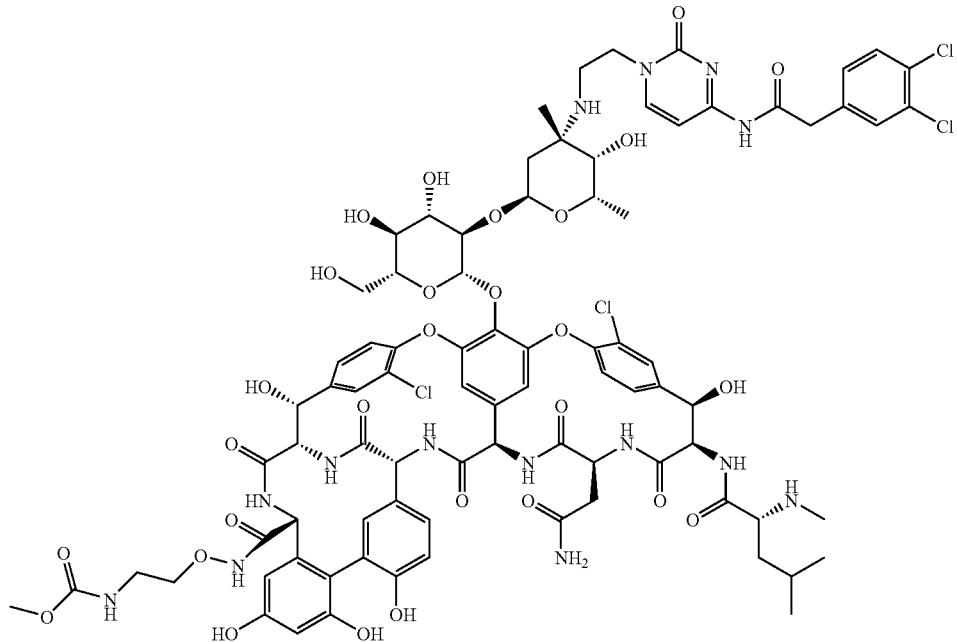

$[M+H]^+=1887$
Anal calcd. for $C_{84}H_{94}Cl_4N_{14}O_{28}\cdot 9.4H_2O\cdot 2.4HCl$: C, 47.00%; H, 5.41%; N, 9.14%; Cl, 10.57%. Found: C, 46.98%; H, 5.38%; N, 9.29%; Cl, 10.64%.
Compound 31
[Chemical Formula 70]
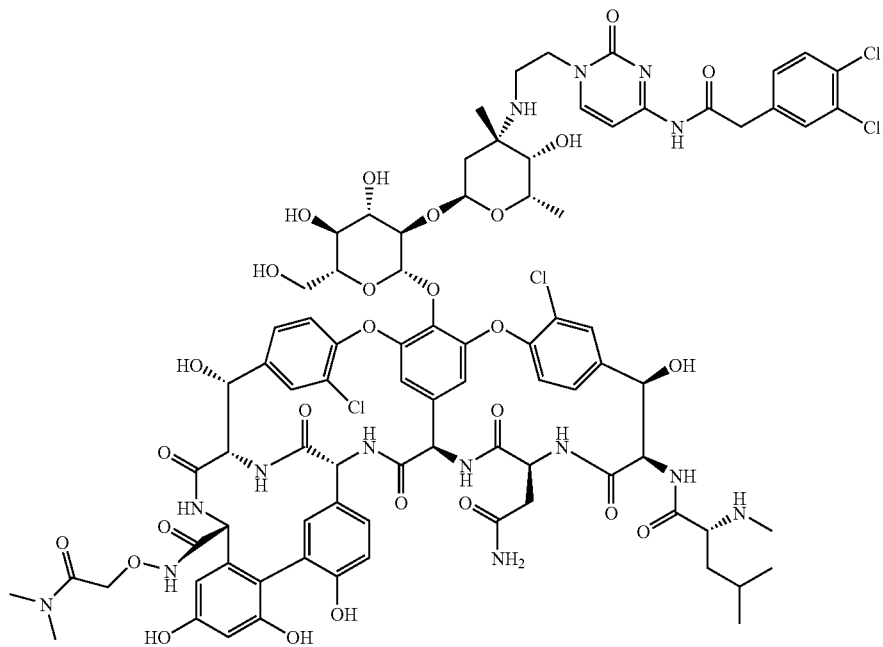
$[M+H]^+=1871$
Anal calcd. for $C_{84}H_{94}Cl_4N_{14}O_{27}\cdot 10.3H_2O\cdot 2.4HCl$: C, 47.00%; H, 5.49%; N, 9.14%; Cl, 10.57%. Found: C, 46.99%; H, 5.36%; N, 9.26%; Cl, 10.64%.
Compound 32
[Chemical Formula 71]
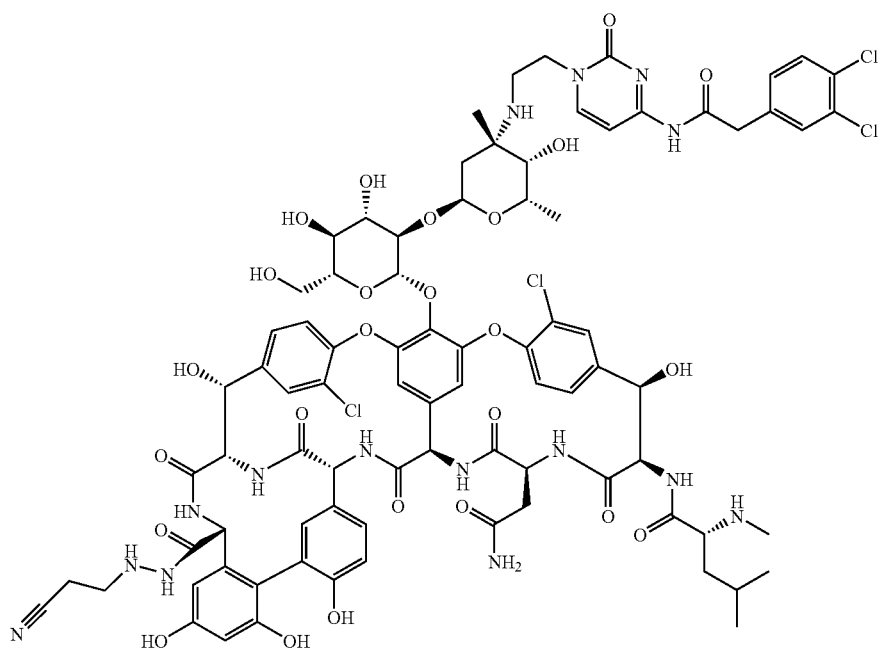

[M+H]$^+$=1838
Anal calcd. for $C_{83}H_{91}Cl_4N_{15}O_{25} \cdot 9.0H_2O \cdot 2.4HCl$: C, 47.69%; H, 5.37%; N, 10.05%; Cl, 10.86%. Found: C, 47.67%; H, 5.33%; N, 10.27%; Cl, 10.88%.
Compound 33
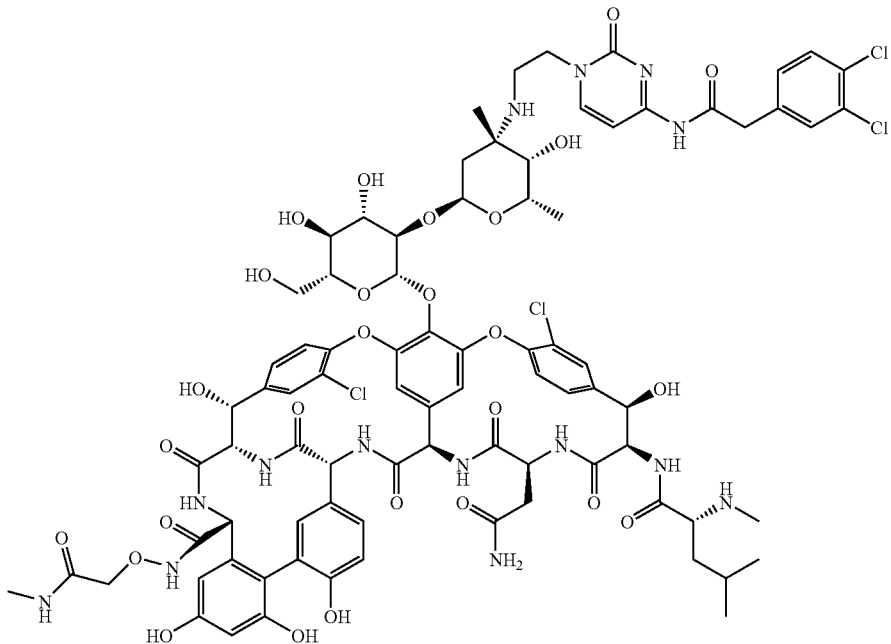
[Chemical Formula 72]
[M+H]$^+$=1857
Anal calcd. for $C_{83}H_{92}Cl_4N_{14}O_{27} \cdot 9.8H_2O \cdot 2.4HCl$: C, 46.94%; H, 5.41%; N, 9.23%; Cl, 10.68%. Found: C, 46.96%; H, 5.40%; N, 9.17%; Cl, 10.57%.
Compound 34
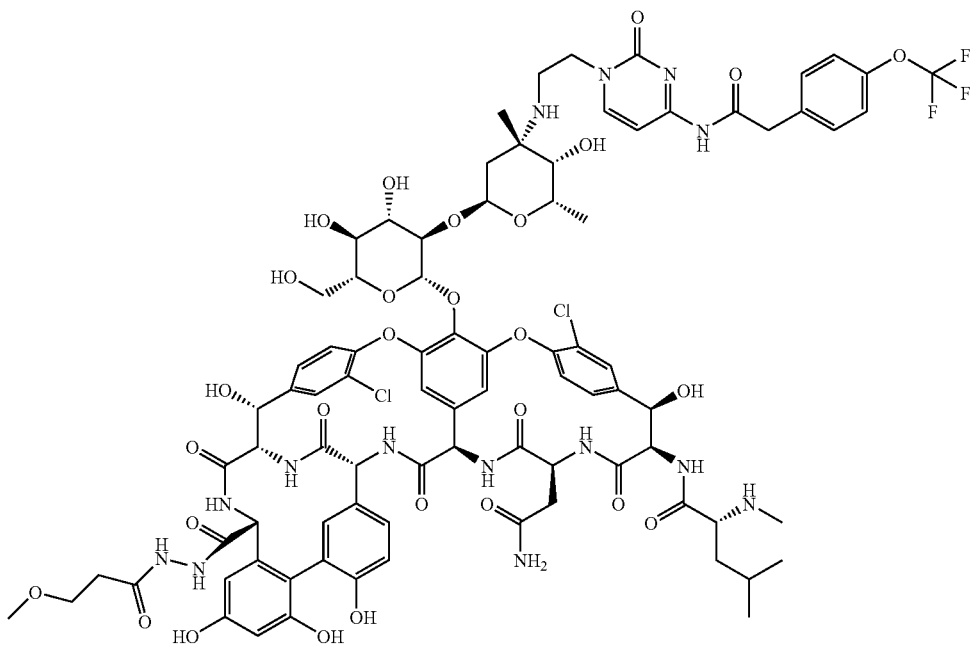
[Chemical Formula 73]

[M+H]$^+$=1887
Anal calcd. for $C_{85}H_{95}Cl_2F_3N_{14}O_{28} \cdot 10.2H_2O \cdot 2.3HCl$: C, 47.35%; H, 5.50%; N, 9.09%; Cl, 7.07%; F, 2.64%. Found: C, 47.38%; H, 5.54%; N, 9.09%; Cl, 7.09%; F, 2.53%.
Compound 35
[Chemical Formula 74]
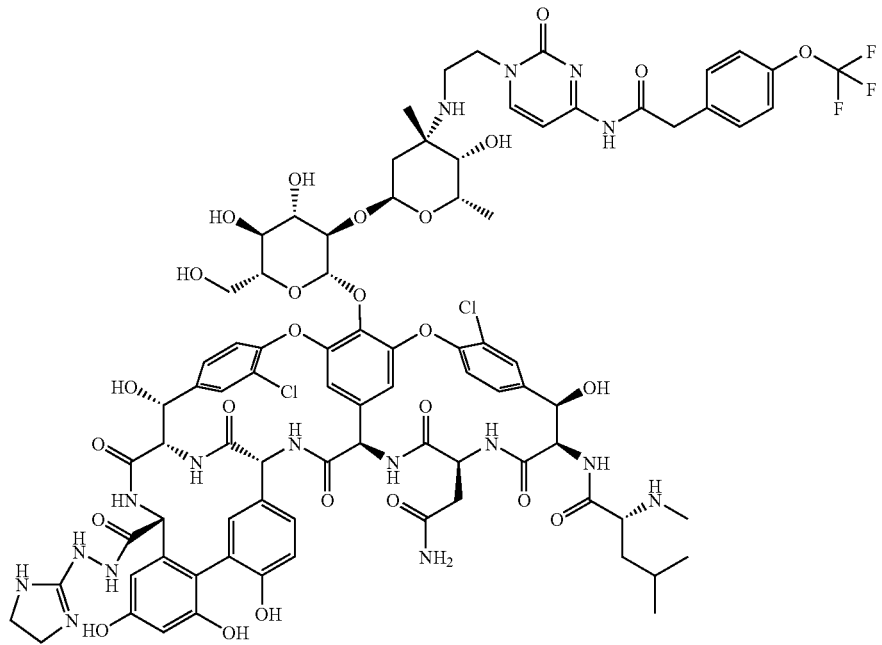
[M+H]$^+$=1869
Anal calcd. for $C_{84}H_{93}Cl_2F_3N_{16}O_{26} \cdot 11.2H_2O \cdot 3.2HCl$: C, 46.09%; H, 5.46%; N, 10.24%; Cl, 8.42%; F, 2.60%. Found: C, 46.11%; H, 5.43%; N, 10.35%; Cl, 8.34%; F, 2.41%.
Compound 36
[Chemical Formula 75]
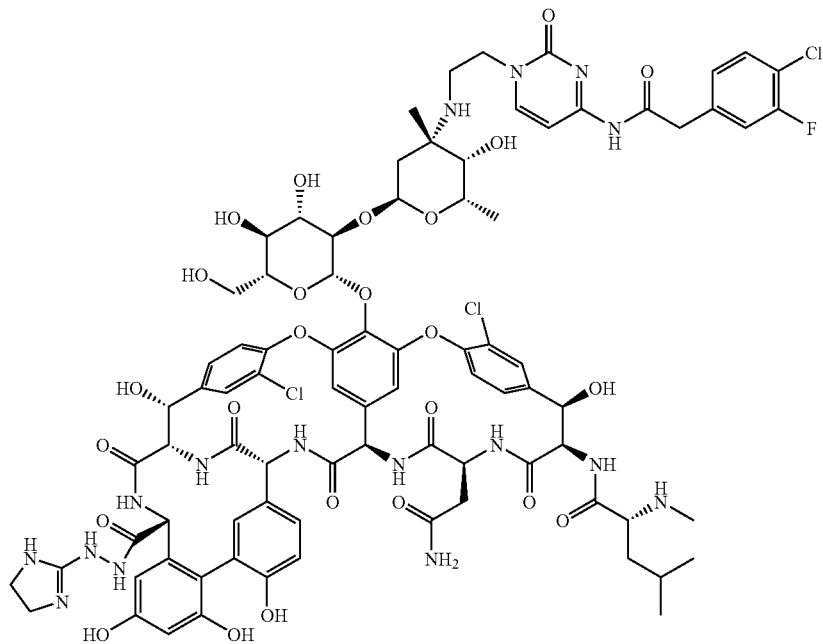

[M+H]$^+$=1837
Anal calcd. for $C_{83}H_{92}Cl_3FN_{16}O_{25} \cdot 11.6H_2O \cdot 3.1HCl$: C, 46.13%; H, 5.52%; N, 10.37%; Cl, 10.01%; F, 0.88%. Found: C, 46.10%; H, 5.46%; N, 10.48%; Cl, 10.02%; F, 0.90%.
Compound 37
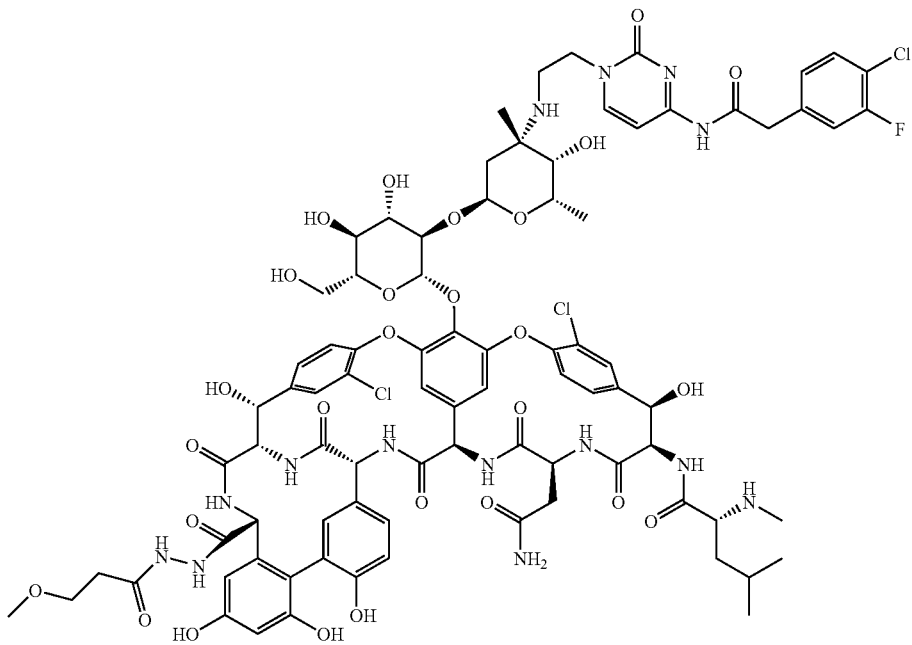
[Chemical Formula 76]
[M+H]$^+$=1855
Anal calcd. for $C_{84}H_{94}Cl_3FN_{14}O_{27} \cdot 10.9H_2O \cdot 2.0HCl$: C, 47.45%; H, 5.58%; N, 9.22%; Cl, 8.34%; F, 0.89%. Found: C, 47.45%; H, 5.54%; N, 9.26%; Cl, 8.43%; F, 0.94%.
Compound 38
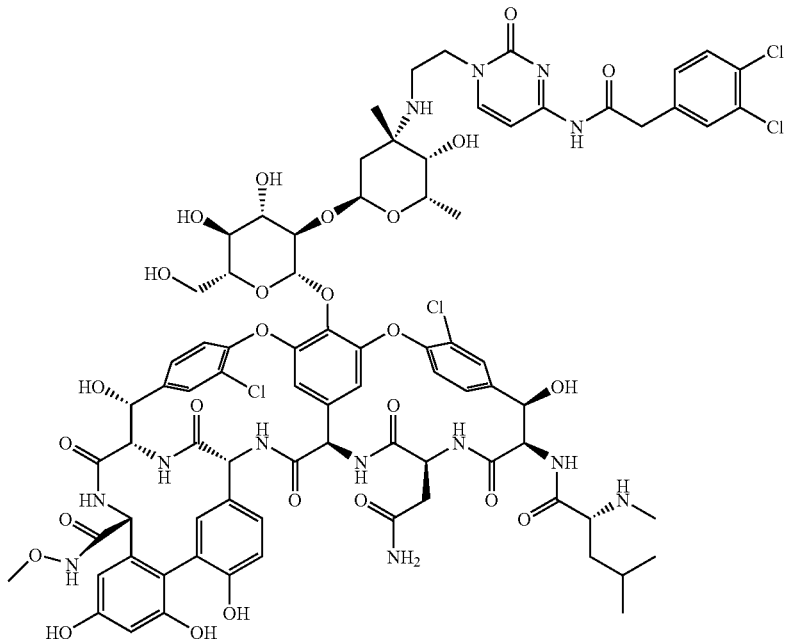
[Chemical Formula 77]

[M+H]⁺=1800
Anal calcd. for $C_{81}H_{89}Cl_4N_{13}O_{26} \cdot 11.0H_2O \cdot 2.2HCl$: C, 46.75%; H, 5.48%; N, 8.75%; Cl, 10.56%. Found: C, 46.71%; H, 5.42%; N, 8.81%; Cl, 10.52%.
Compound 39
[Chemical Formula 78]
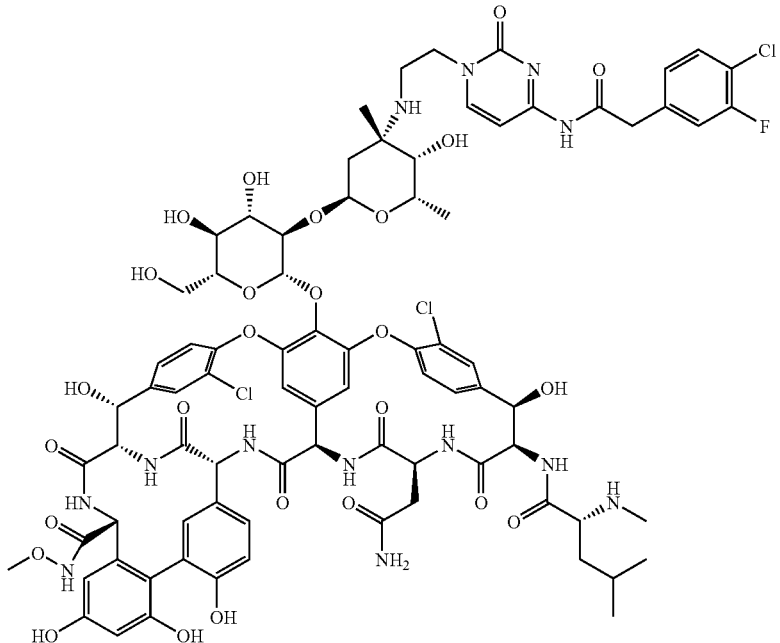
[M+H]⁺=1784
Anal calcd. for $C_{81}H_{89}Cl_3FN_{13}O_{26} \cdot 11.9H_2O \cdot 2.1HCl$: C, 46.84%; H, 5.58%; N, 8.77%; Cl, 8.71%; F, 0.91%. Found: C, 46.79%; H, 5.57%; N, 8.96%; Cl, 8.76%; F, 0.95%.
Compound 40
[Chemical Formula 79]
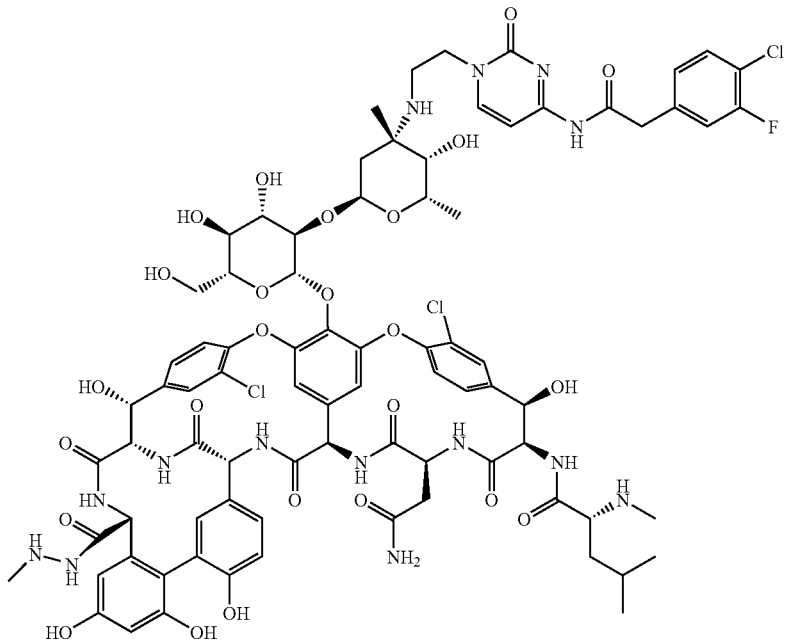

[M+H]$^+$=1783
Anal calcd. for $C_{81}H_{90}Cl_3FN_{14}O_{25}\cdot 12.6H_2O\cdot 2.7HCl$: C, 46.10%; H, 5.63%; N, 9.29%; Cl, 9.58%; F, 0.90%. Found: C, 46.10%; H, 5.48%; N, 9.36%; Cl, 9.63%; F, 0.92%.
Compound 41
[Chemical Formula 80]
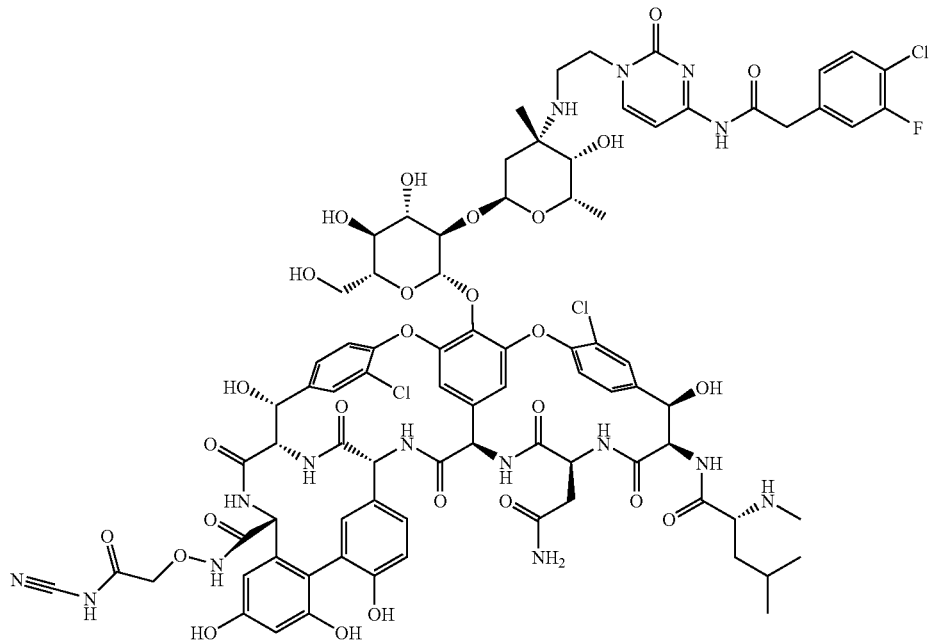
[M+H]$^+$=1852
Anal calcd. for $C_{83}H_{89}Cl_3FN_{15}O_{27}\cdot 12.6H_2O\cdot 2.1HCl$: C, 46.20%; H, 5.43%; N, 9.74%; Cl, 8.38%; F, 0.88%. Found: C, 46.15%; H, 5.32%; N, 9.99%; Cl, 8.34%; F, 0.92%.
Compound 42
[Chemical Formula 81]
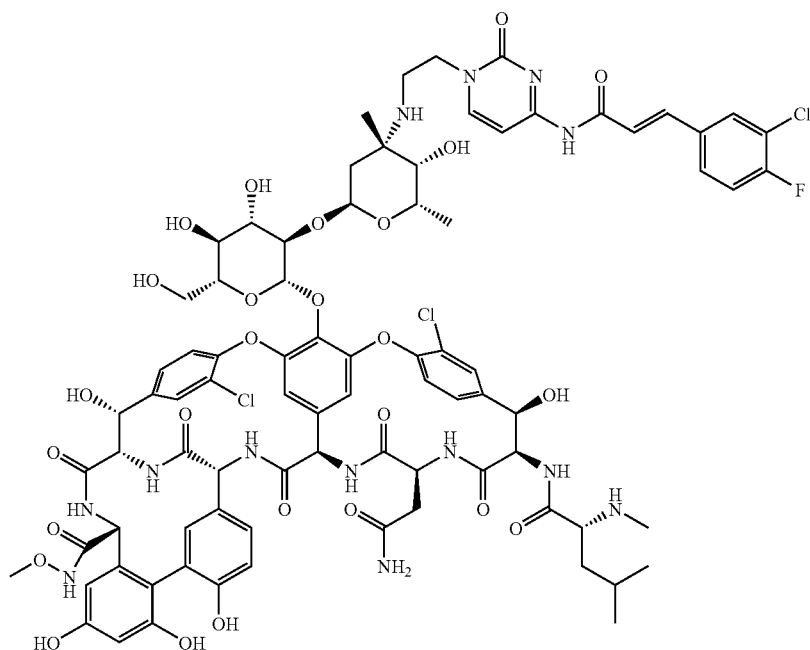

[M+H]$^+$=1796
Anal calcd. for $C_{82}H_{89}Cl_3FN_{13}O_{26} \cdot 11.5H_2O \cdot 2.1HCl$: C, 47.31%; H, 5.52%; N, 8.75%; Cl, 8.69%; F, 0.91%. Found: C, 47.30%; H, 5.48%; N, 8.80%; Cl, 8.65%; F, 0.96%.
Compound 43
[Chemical Formula 82]
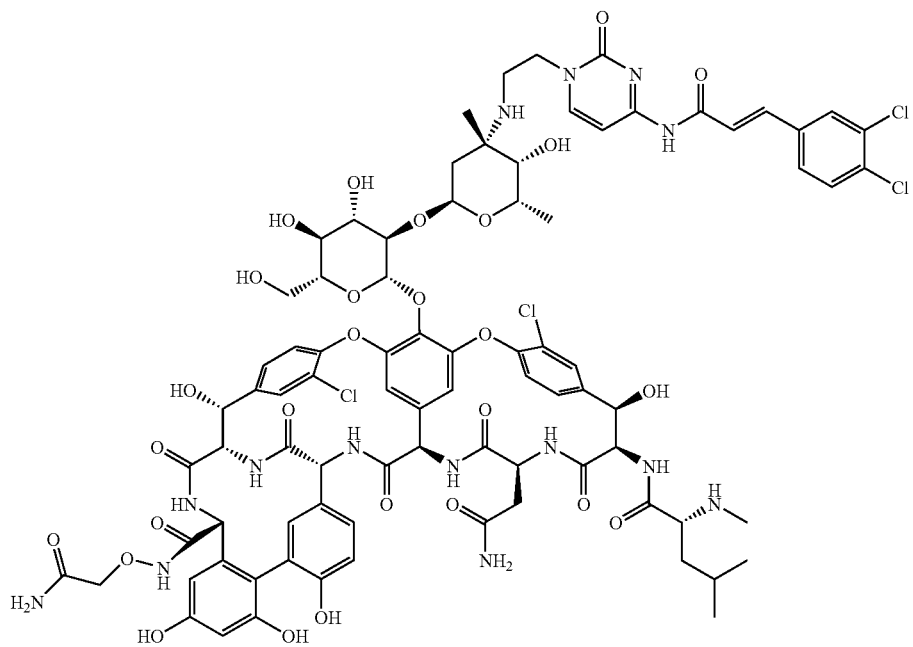
[M+H]$^+$=1855
Anal calcd. for $C_{83}H_{90}Cl_4N_{14}O_{27} \cdot 10.4H_2O \cdot 2.1HCl$: C, 46.99%; H, 5.36%; N, 9.24%; Cl, 10.19%. Found: C, 46.96%; H, 5.32%; N, 9.26%; Cl, 10.16%.
Compound 44
[Chemical Formula 83]
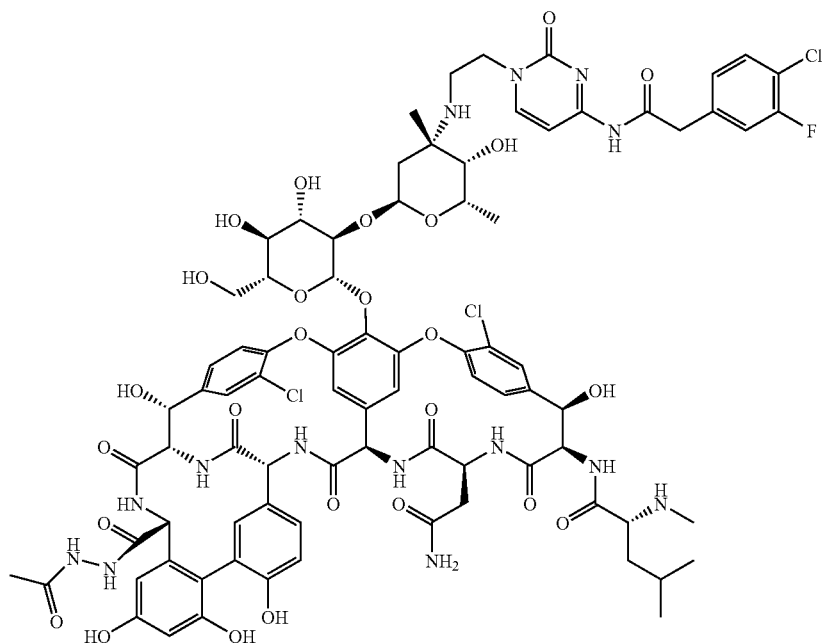

[M+H]⁺=1811
Anal calcd. for $C_{82}H_{90}Cl_3FN_{14}O_{26} \cdot 10.4H_2O \cdot 2.2HCl$: C, 47.34%; H, 5.47%; N, 9.42%; Cl, 8.86%; F, 0.91%. Found: C, 47.32%; H, 5.42%; N, 9.36%; Cl, 8.89%; F, 0.98%.
Compound 45
[Chemical Formula 84]
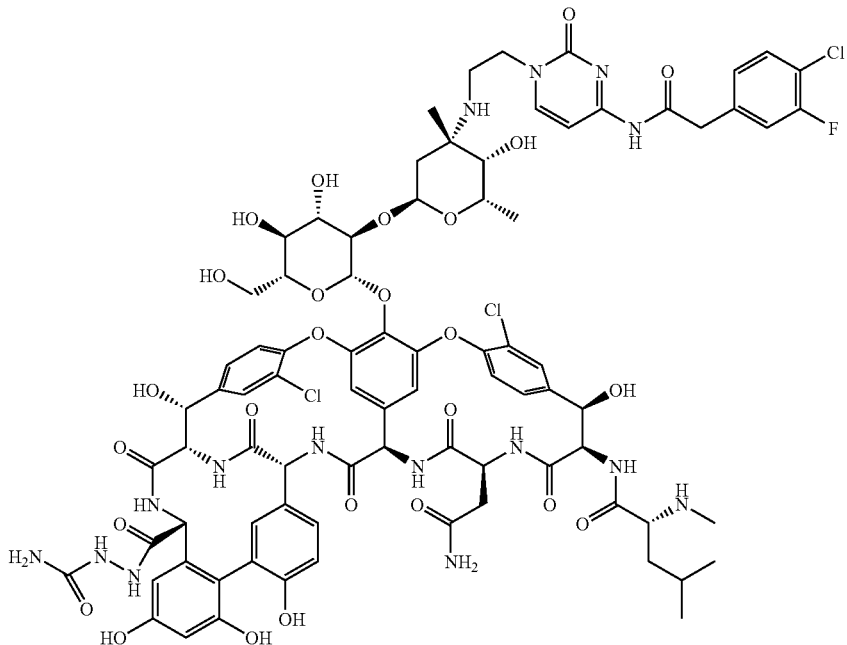
[M+H]⁺=1812
Anal calcd. for $C_{81}H_{89}Cl_3FN_{15}O_{26} \cdot 11.0H_2O \cdot 2.2HCl$: C, 46.50%; H, 5.45%; N, 10.04%; Cl, 8.81%; F, 0.91%. Found: C, 46.14%; H, 5.47%; N, 10.78%; Cl, 8.78%; F, 0.88%.
Compound 46
[Chemical Formula 85]
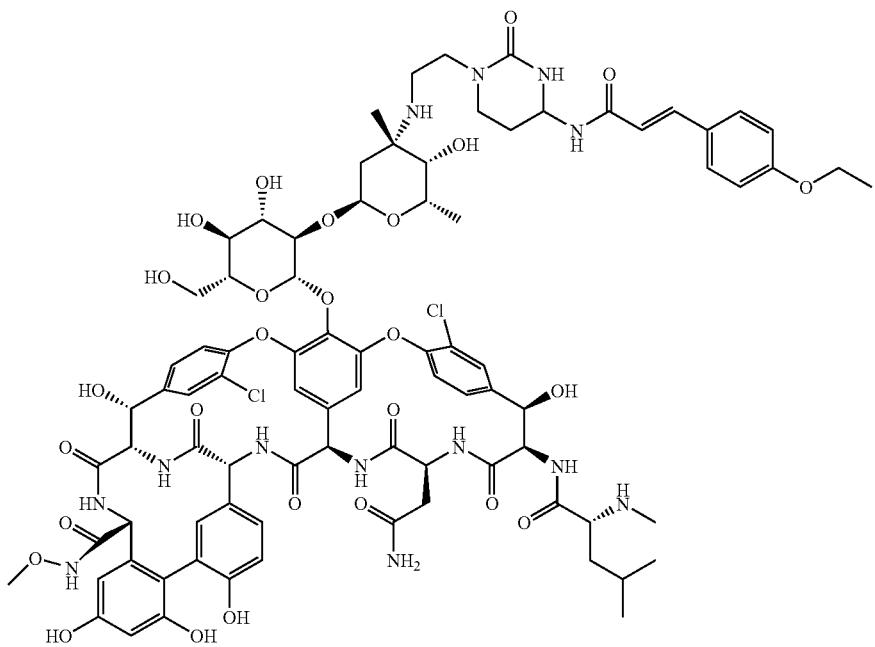

[M+H]⁺=1792
Anal calcd. for $C_{84}H_{99}Cl_2N_{13}O_{27} \cdot 10.1H_2O \cdot 2.0HCl$: C, 49.25%; H, 5.96%; N, 8.89%; Cl, 6.92%. Found: C, 49.13%; H, 5.91%; N, 9.35%; Cl, 6.91%.
Compound 47
[Chemical Formula 86]
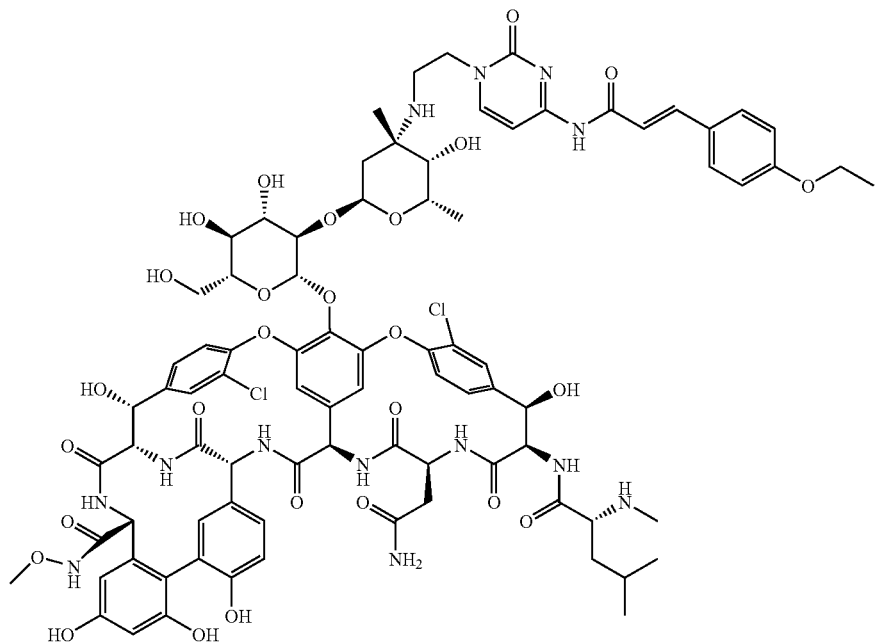
[M+H]⁺=1788
Anal calcd. for $C_{84}H_{95}Cl_2N_{13}O_{27} \cdot 10.5H_2O \cdot 23HCl$: C, 48.91%; H, 5.78%; N, 8.83%; Cl, 7.39%. Found: C, 48.75%; H, 5.75%; N, 9.44%; Cl, 7.48%.
Compound 48
[Chemical Formula 87]
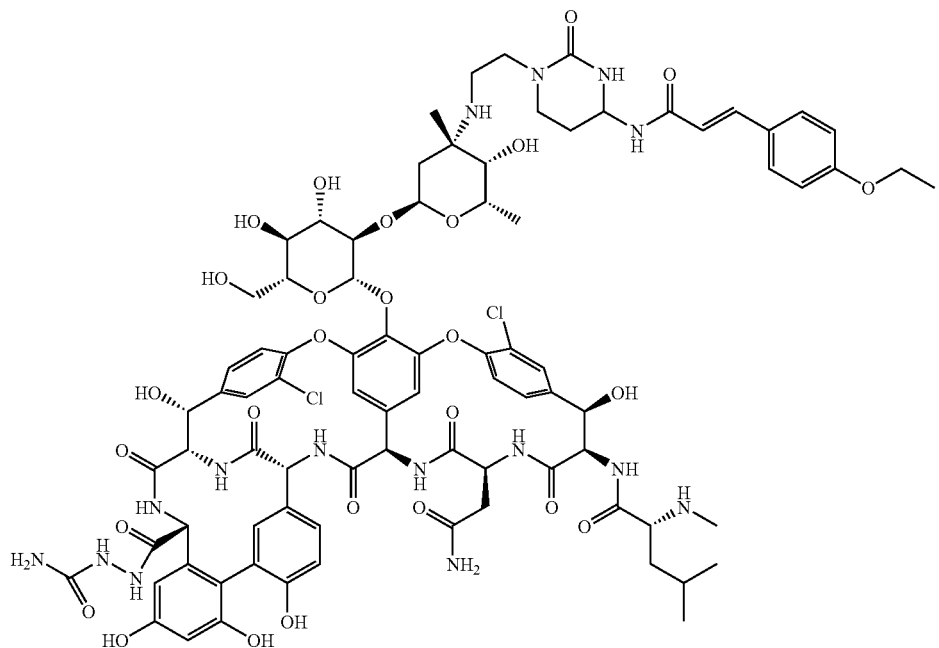

[M+H]⁺=1820
Anal calcd. for $C_{84}H_{99}Cl_2N_{15}O_{27}\cdot10.3H_2O\cdot2.0HCl$: C, 48.50%; H, 5.89%; N, 10.10%; Cl, 6.82%. Found: C, 48.33%; H, 5.82%; N, 10.64%; Cl, 6.89%.
Compound 49
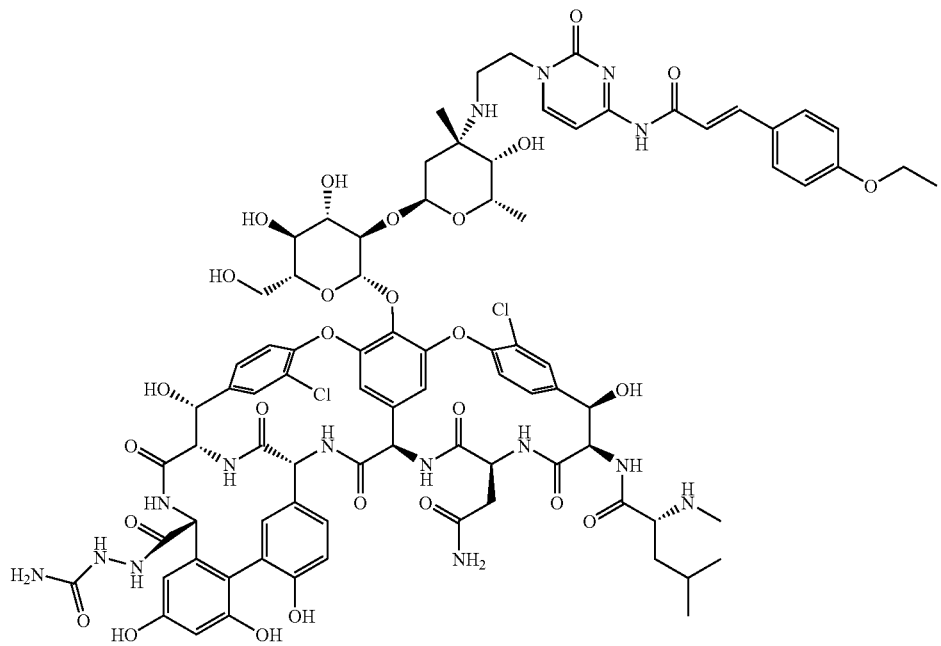
[Chemical Formula 88]
[M+H]⁺=1816
Anal calcd. for $C_{84}H_{95}Cl_2N_{15}O_{27}\cdot10.2H_2O\cdot2.4HCl$: C, 48.30%; H, 5.68%; N, 10.06%; Cl, 7.47%. Found: C, 48.16%; H, 5.64%; N, 10.57%; Cl, 7.46%.
Compound 50
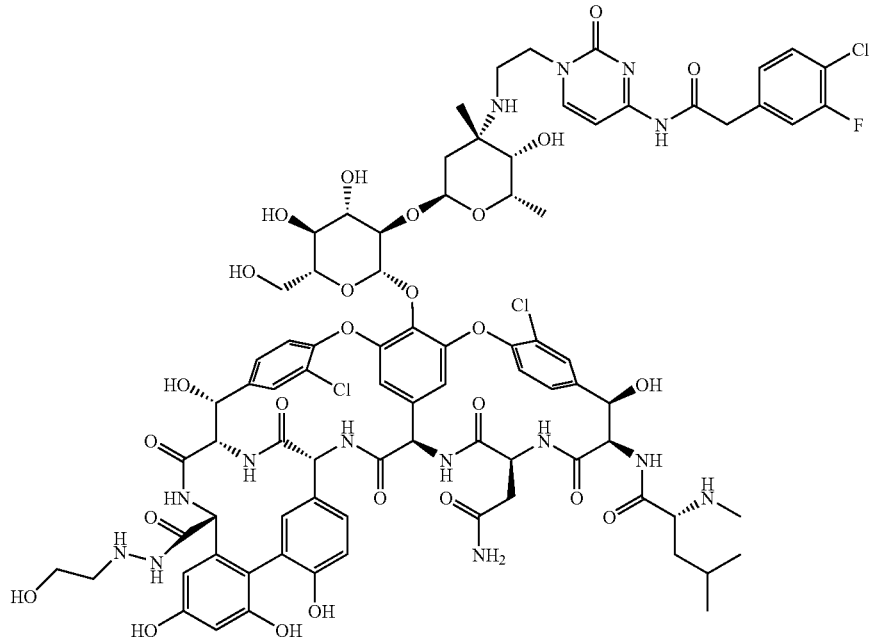
[Chemical Formula 89]

[M+H]$^+$=1813
Anal calcd. for $C_{82}H_{92}Cl_3FN_{14}O_{26} \cdot 9.5H_2O \cdot 2.4HCl$: C, 47.49%; H, 5.51%; N, 9.46%; Cl, 9.23%; F, 0.92%. Found: C, 47.40%; H, 5.48%; N, 10.09%; Cl, 9.25%; F, 0.96
Compound 51
[Chemical Formula 90]
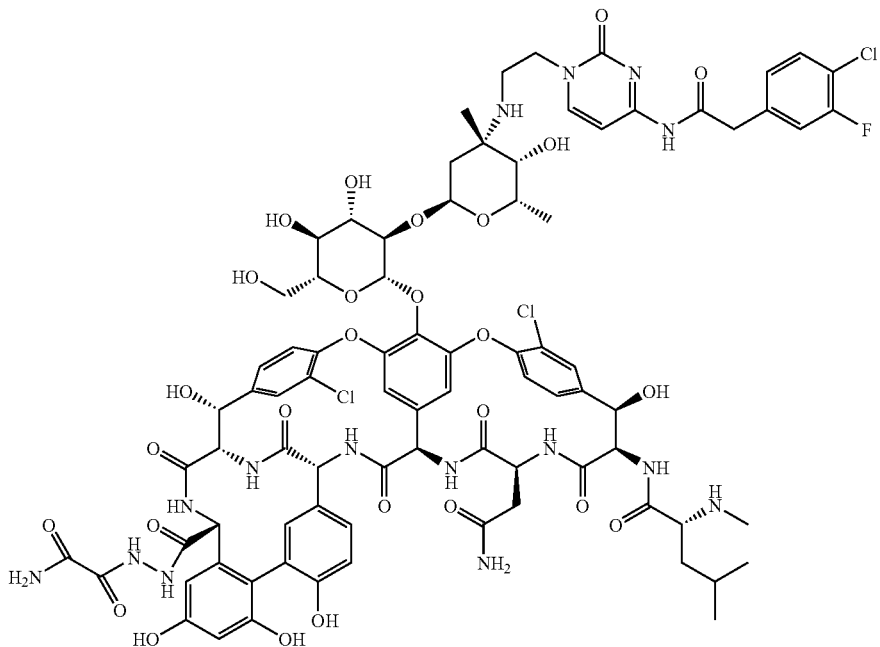
[M+H]$^+$=1840
Anal calcd. for $C_{82}H_{89}Cl_3FN_{15}O_{27} \cdot 13.0H_2O \cdot 2.2HCl$: C, 45.67%; H, 5.48%; N, 9.74%; Cl, 8.55%; F, 0.88%. Found: C, 45.70%; H, 5.45%; N, 9.72%; Cl, 8.46%; F, 0.88%.
Compound 52
[Chemical Formula 91]
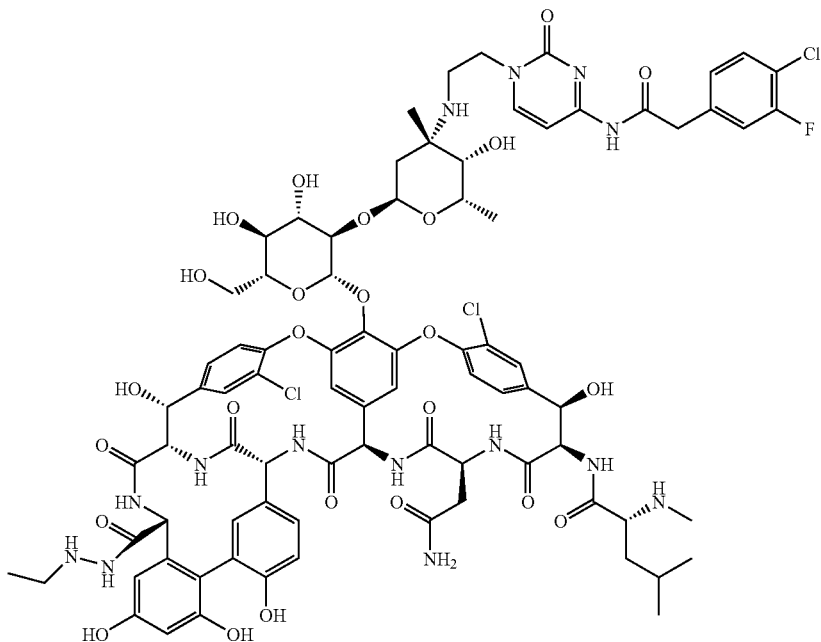

[M+H]⁺=1797
Anal calcd. for $C_{82}H_{92}Cl_3FN_{14}O_{25} \cdot 12.5H_2O \cdot 2.7HCl$: C, 46.40%; H, 5.68%; N, 9.24%; Cl, 9.52%; F, 0.90%. Found: C, 46.37%; H, 5.64%; N, 9.38%; Cl, 9.38%; F, 0.90%.
Compound 53
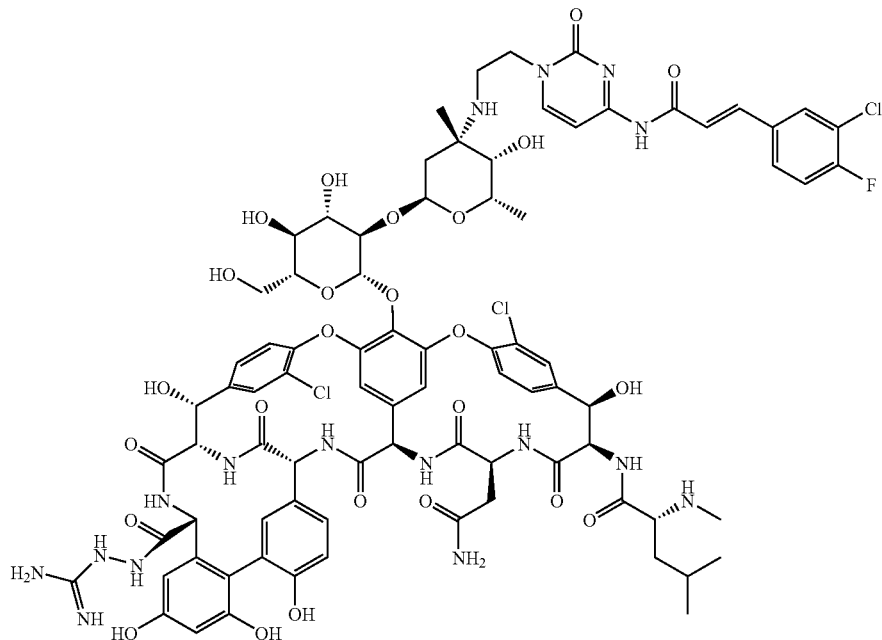
[Chemical Formula 92]
[M+H]⁺=1823
Anal calcd. for $C_{82}H_{90}Cl_3FN_{16}O_{25} \cdot 9.5H_2O \cdot 2.4HCl$: C, 47.27%; H, 5.39%; N, 10.76%; Cl, 9.19%; F, 0.91%. Found: C, 47.13%; H, 5.23%; N, 11.20%; Cl, 9.25%; F, 0.85%.
Compound 54
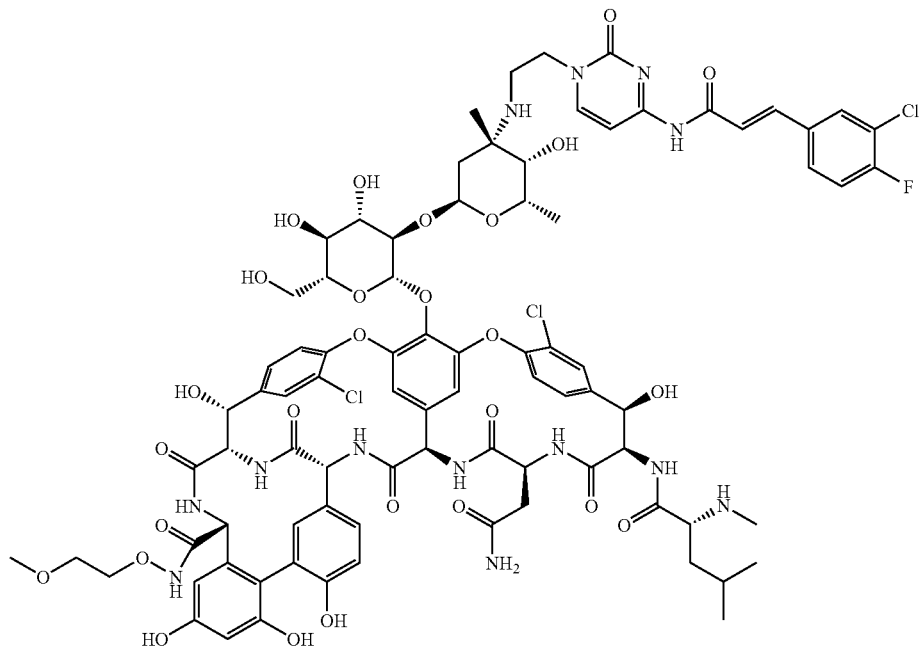
[Chemical Formula 93]

[M+H]$^+$=1840
Anal calcd. for $C_{84}H_{93}Cl_3FN_{13}O_{27} \cdot 10.6H_2O \cdot 2.4HCl$: C, 47.58%; H, 5.54%; N, 8.59%; Cl, 9.03%; F, 0.90%. Found: C, 47.56%; H, 5.48%; N, 8.68%; Cl, 9.04%; F, 0.99%.
Compound 55
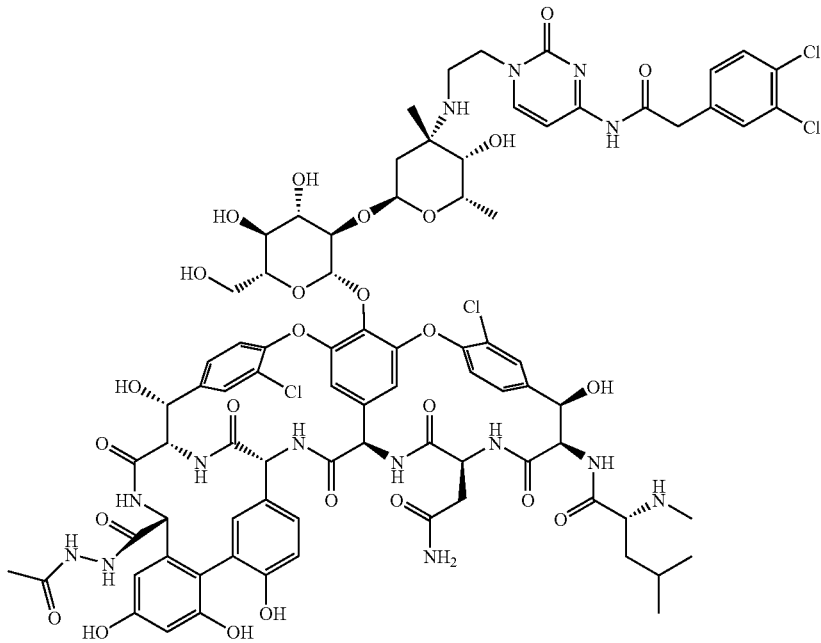
[Chemical Formula 94]
[M+H]$^+$=1827
Anal calcd. for $C_{82}H_{90}Cl_4N_{14}O_{26} \cdot 10.6H_2O \cdot 2.0HCl$: C, 47.05%; H, 5.45%; N, 9.37%; Cl, 10.16%. Found: C, 47.05%; H, 5.31%; N, 9.39%; Cl, 10.08%.
Compound 56
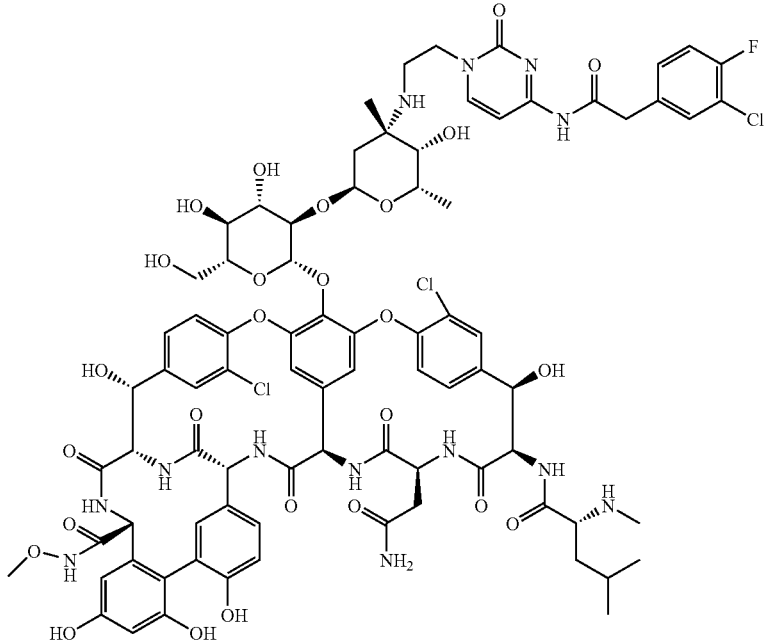
[Chemical Formula 95]

[M+H]$^+$=1784
Anal calcd. for $C_{81}H_{89}Cl_3FN_{13}O_{26} \cdot 10.6H_2O \cdot 2.1HCl$: C, 47.38%; H, 5.51%; N, 8.87%; Cl, 8.80%; F, 0.93%. Found: C, 47.37%; H, 5.42%; N, 9.02%; Cl, 8.82%; F, 0.98%.
Compound 57
[Chemical Formula 96]
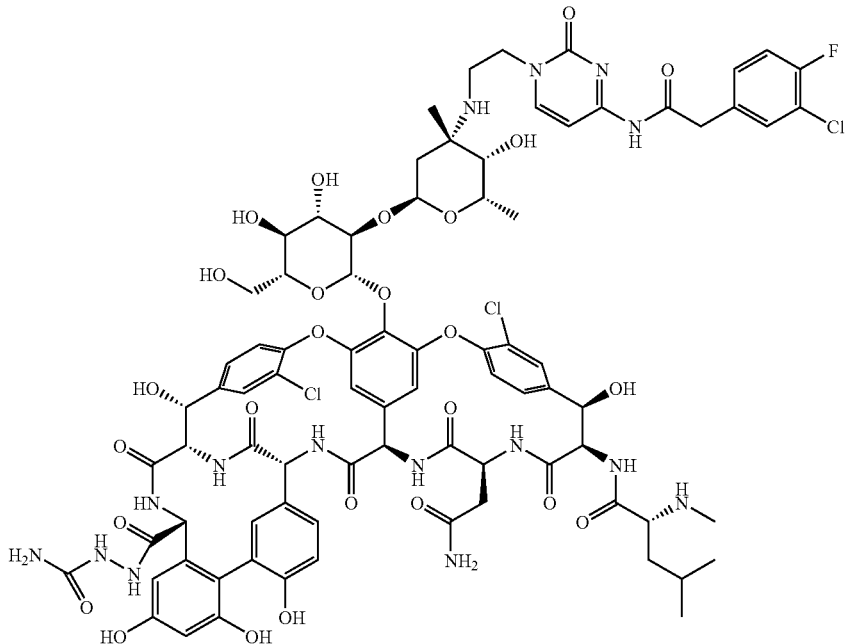
[M+H]$^+$=1812
Anal calcd. for $C_{81}H_{89}Cl_3FN_{15}O_{26} \cdot 10.2H_2O \cdot 2.2HCl$: C, 46.82%; H, 5.41%; N, 10.11%; Cl, 8.87%; F, 0.91%. Found: C, 46.81%; H, 5.35%; N, 10.16%; Cl, 8.83%; F, 0.96%.
Compound 58
[Chemical Formula 97]
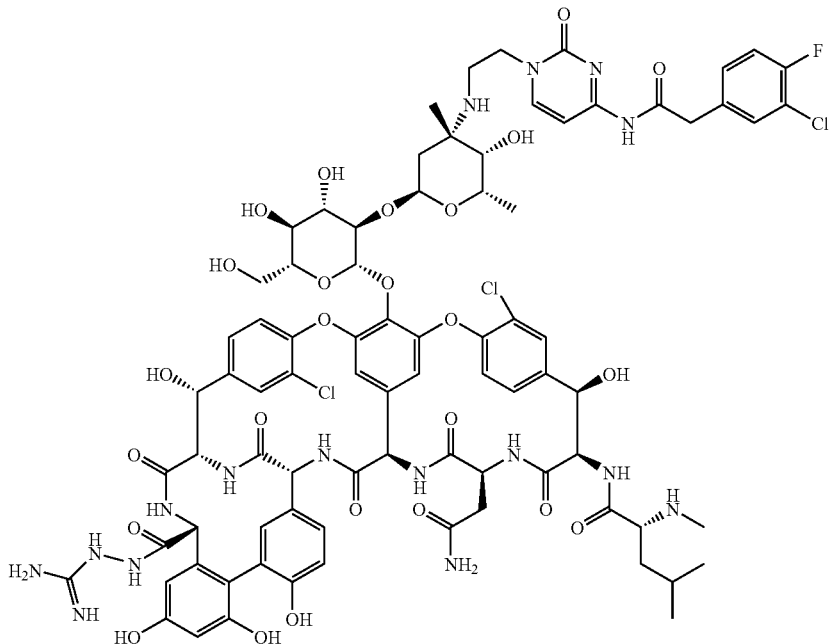

[M+H]$^+$=1811
Anal calcd. for $C_{81}H_{90}Cl_3FN_{16}O_{25} \cdot 11.9H_2O \cdot 3.2HCl$: C, 45.37%; H, 5.50%; N, 10.45%; Cl, 10.25%; F, 0.89%. Found: C, 45.39%; H, 5.47%; N, 10.32%; Cl, 10.28%; F, 0.86%.
Compound 59
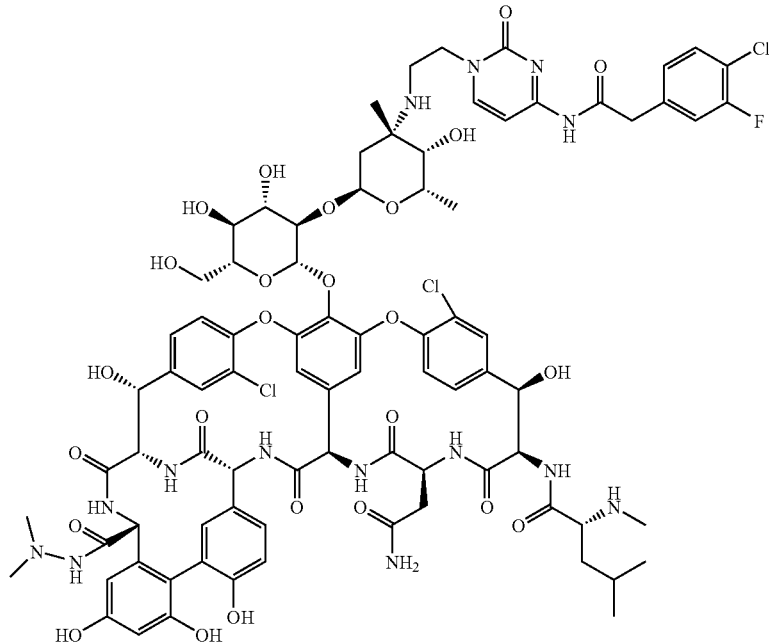
[Chemical Formula 98]
[M+H]$^+$=1797
Anal calcd. for $C_{82}H_{92}Cl_3FN_{14}O_{25} \cdot 11.1H_2O \cdot 2.2HCl$: C, 47.37%; H, 5.64%; N, 9.43%; Cl, 8.87%; F, 0.91%. Found: C, 47.34%; H, 5.64%; N, 9.58%; Cl, 8.89%; F, 0.97%.
Compound 60
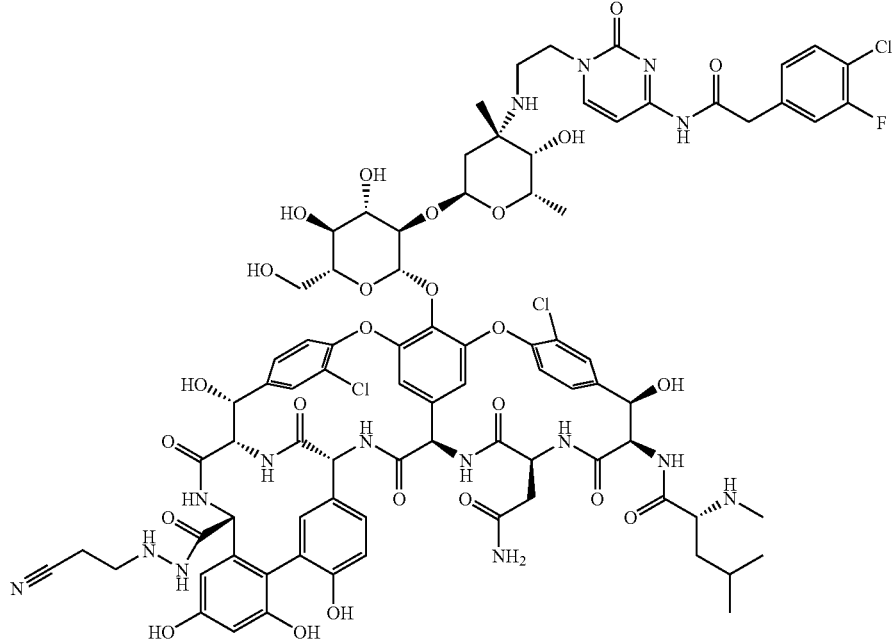
[Chemical Formula 99]

[M+H]$^+$=1822
Anal calcd. for $C_{83}H_{91}Cl_3FN_{15}O_{25} \cdot 9.9H_2O \cdot 2.2HCl$: C, 47.87%; H, 5.47%; N, 10.09%; Cl, 8.85%; F, 0.91%. Found: C, 47.80%; H, 5.39%; N, 10.22%; Cl, 8.91%; F, 0.98%.
Compound 61
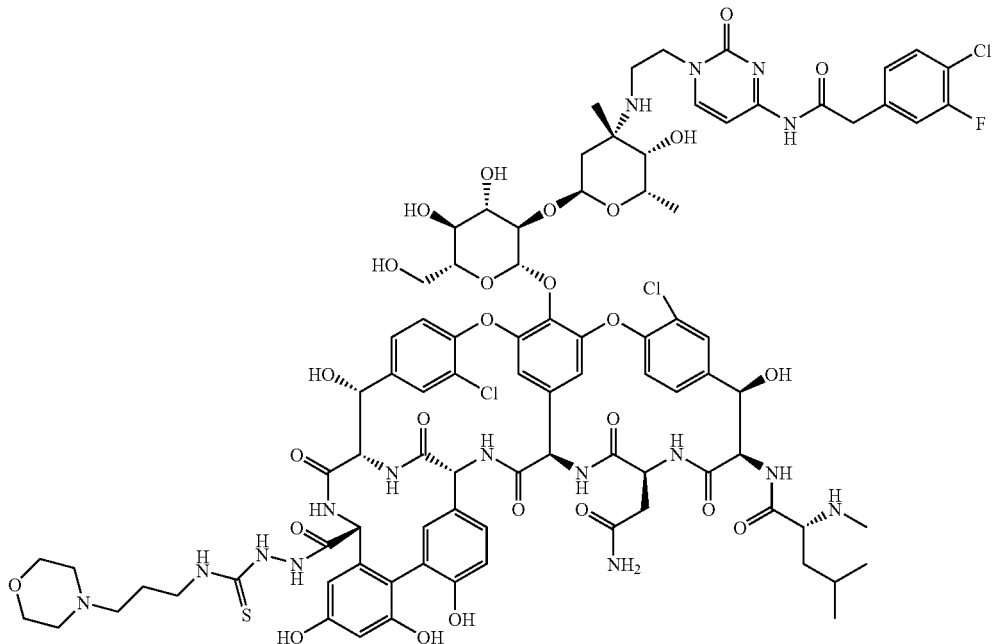
[Chemical Formula 100]
[M+H]$^+$=1955
Anal calcd. for $C_{88}H_{102}Cl_3FN_{16}O_{26}S \cdot 11.2H_2O \cdot 3.2HCl$: C, 46.44%; H, 5.65%; N, 9.85%; Cl, 9.66%; F, 0.83; S, 1.41%. Found: C, 46.36%; H, 5.63%; N, 10.01%; Cl, 9.69%; F, 0.90; S, 1.37%.
Compound 62
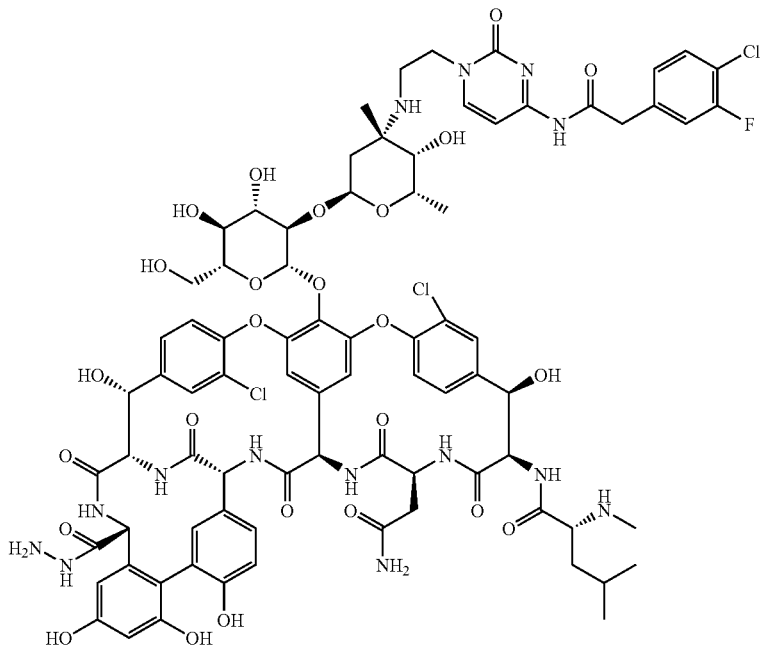
[Chemical Formula 101]

[M+H]⁺=1769
Anal calcd. for $C_{80}H_{88}Cl_3FN_{14}O_{25} \cdot 11.3H_2O \cdot 2.6HCl$: C, 46.43%; H, 5.51%; N, 9.48%; Cl, 9.59%; F, 0.92%. Found: C, 46.37%; H, 5.36%; N, 9.64%; Cl, 9.54%; F, 1.11%.
Compound 63
[Chemical Formula 102]
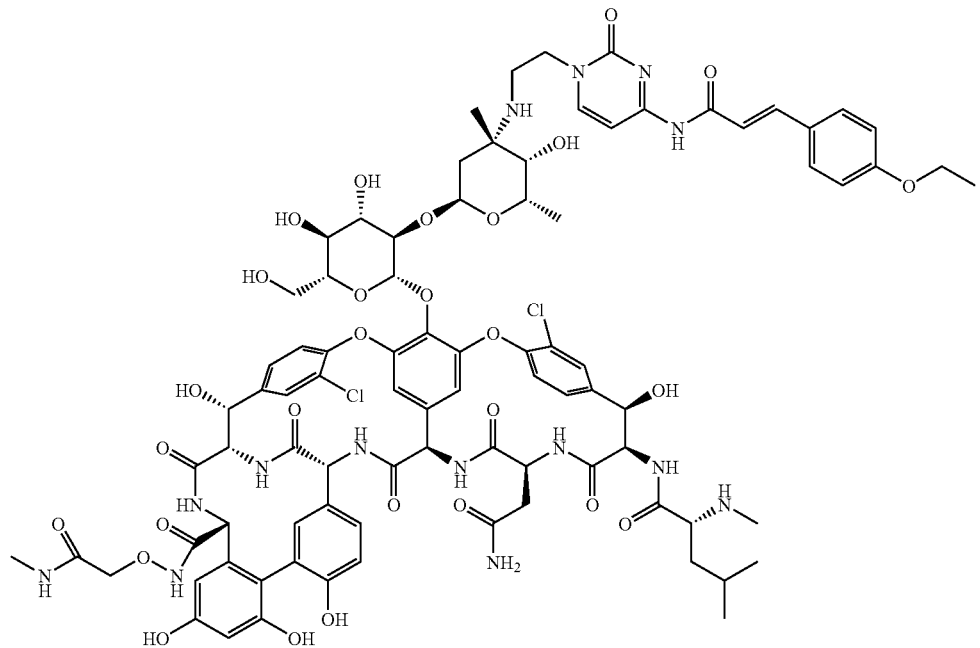
[M+H]⁺=1845
Anal calcd. for $C_{85}H_{96}Cl_2N_{14}O_{28} \cdot 10.4H_2O \cdot 2.6HCl$: C, 48.27%; H, 5.69%; N, 9.27%; Cl, 7.71%. Found: C, 48.25%; H, 5.65%; N, 9.45%; Cl, 7.75%.
Compound 64
[Chemical Formula 103]
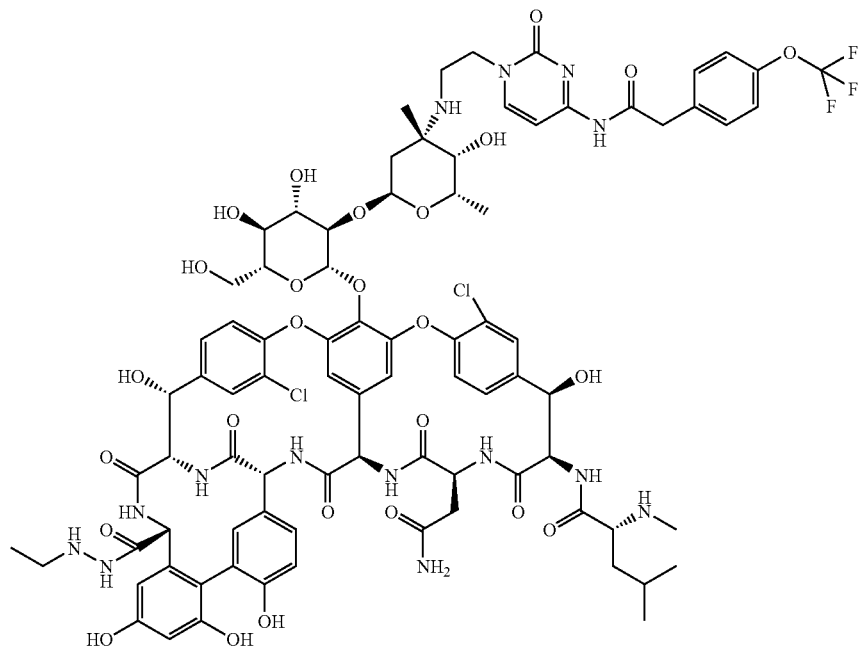

[M+H]$^+$=1829
Anal calcd. for $C_{83}H_{93}Cl_2F_3N_{14}O_{26} \cdot 9.8H_2O \cdot 2.3HCl$: C, 47.67%; H, 5.54%; N, 9.38%; Cl, 7.29%; F, 2.73%. Found: C, 47.64%; H, 5.59%; N, 9.43%; Cl, 7.30%; F, 2.71%.
Compound 65
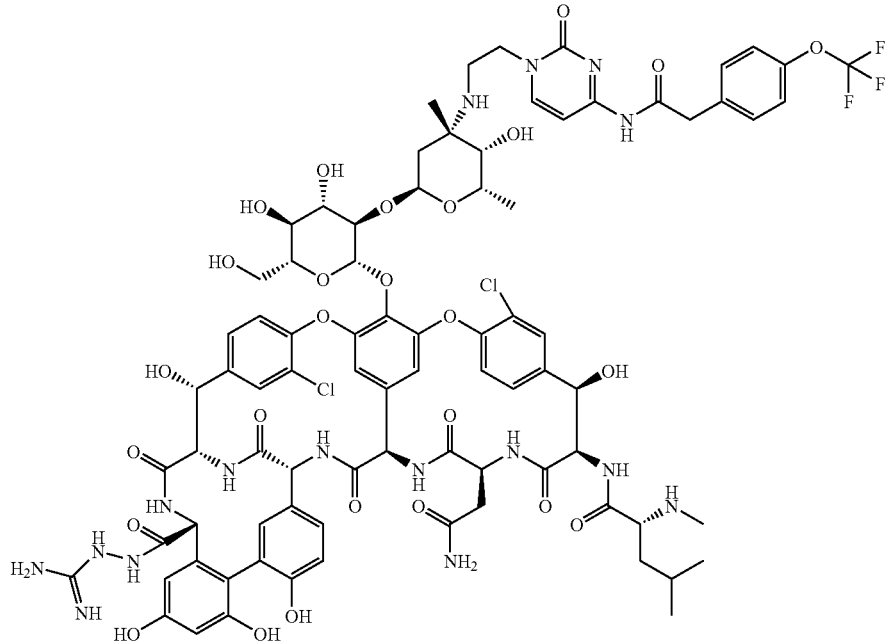
[Chemical Formula 104]
[M+H]$^+$=1843
Anal calcd. for $C_{82}H_{91}Cl_2F_3N_{16}O_{26} \cdot 11.0H_2O \cdot 2.9HCl$: C, 45.84%; H, 5.44%; N, 10.43%; Cl, 8.09%; F, 2.65%. Found: C, 46.05%; H, 5.49%; N, 9.62%; Cl, 8.09%; F, 2.41%.
Compound 66
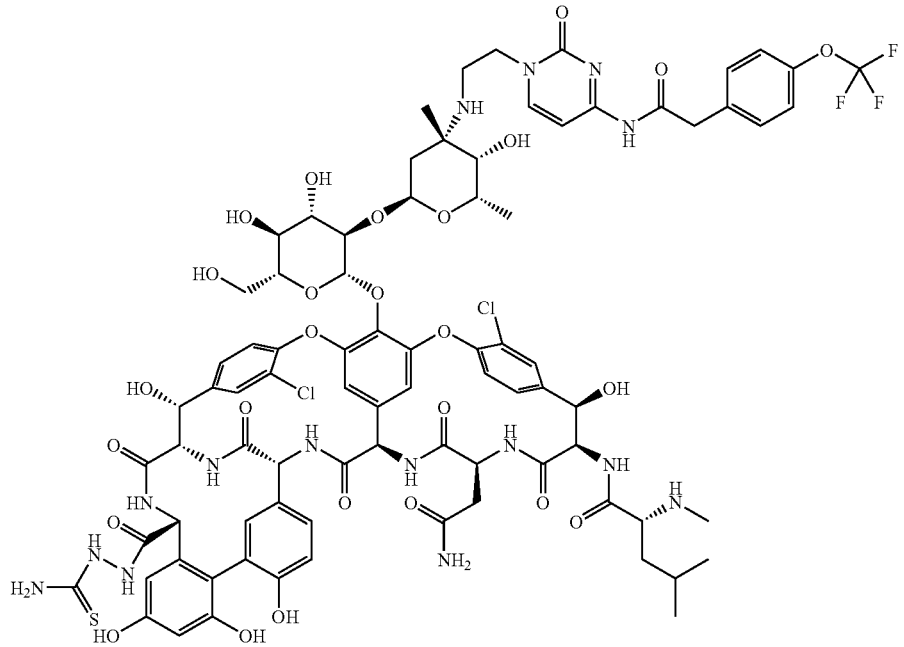
[Chemical Formula 105]

[M+H]⁺=1860
Anal calcd. for $C_{82}H_{90}Cl_2F_3N_{15}O_{26}S \cdot 10.8H_2O \cdot 1.9HCl$: C, 46.34%; H, 5.38%; N, 9.88%; Cl, 6.51%; F, 2.68%; S, 1.51%. Found: C, 46.41%; H, 5.30%; N, 9.42%; Cl, 6.50%; F, 2.87%; S, 1.22%.
Compound 67
[Chemical Formula 106]
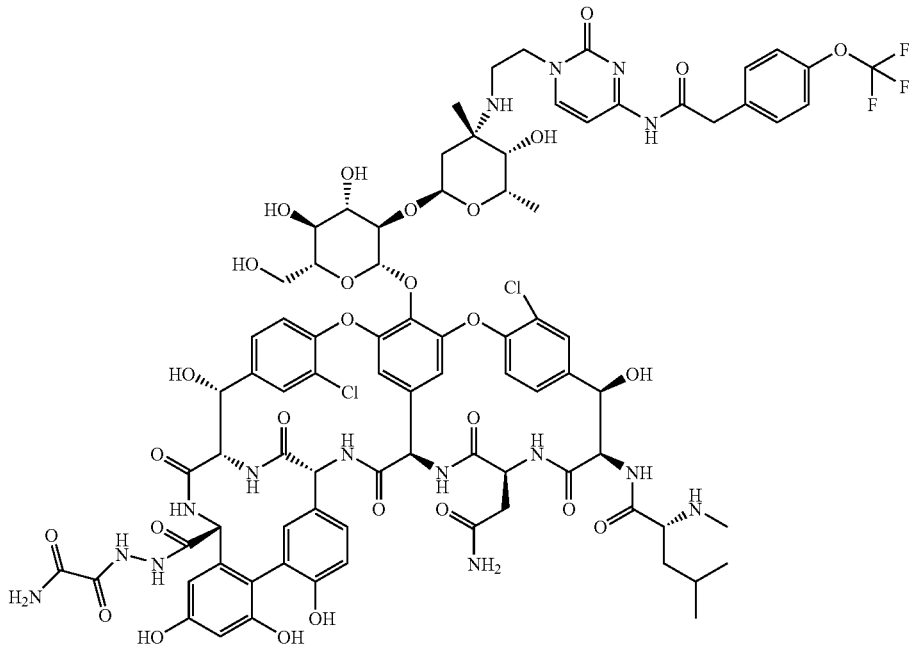
[M+H]⁺=1872
Anal calcd. for $C_{83}H_{90}Cl_2F_3N_{15}O_{28} \cdot 11.2H_2O \cdot 2.1HCl$: C, 46.33%; H, 5.36%; N, 9.76%; Cl, 6.75%; F, 2.65%. Found: C, 46.31%; H, 5.31%; N, 9.77%; Cl, 6.75%; F, 2.51%.
Compound 68
[Chemical Formula 107]
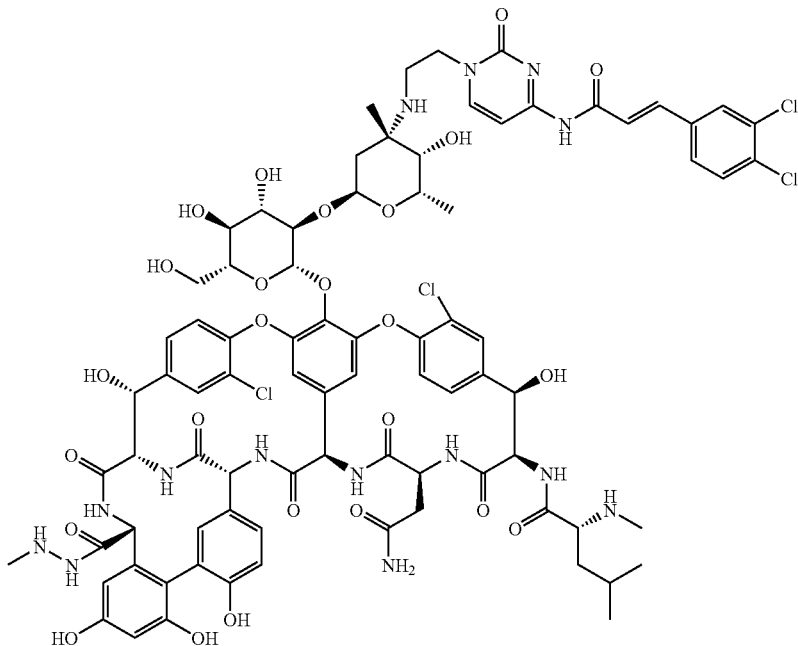

[M+H]$^+$=1811
Anal. calcd. for $C_{82}H_{90}Cl_4N_{14}O_{25} \cdot 11.4H_2O \cdot 2.7HCl$: C, 46.52%; H, 5.50%; N, 9.26%; Cl, 11.22%. Found: C, 46.54%; H, 5.53%; N, 9.30%; Cl, 11.18%.
Compound 69
[Chemical Formula 108]
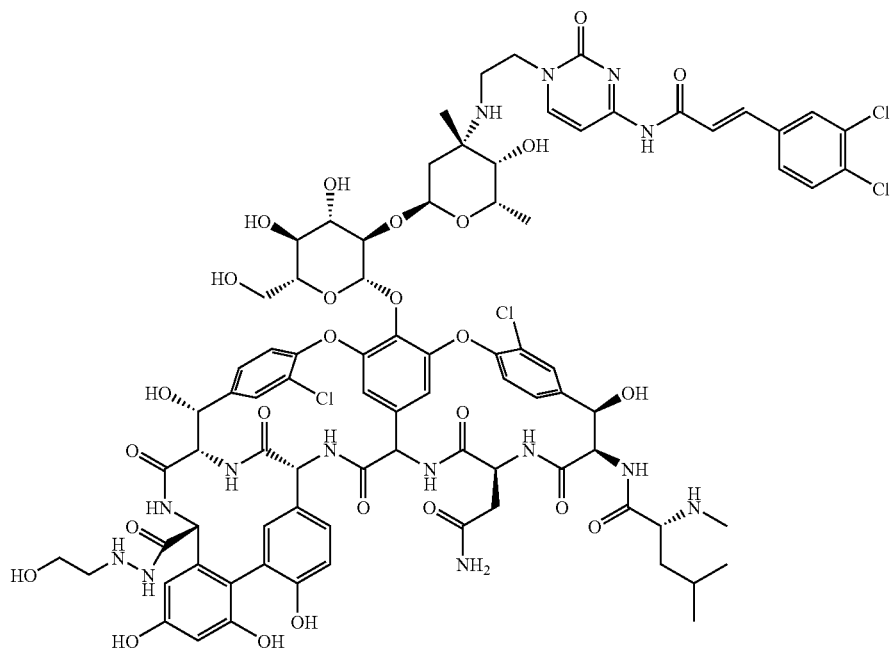
[M+H]$^+$=1841
Anal. calcd. for $C_{83}H_{92}Cl_4N_{14}O_{26} \cdot 11.3H_2O \cdot 2.9HCl$: C, 46.31%; H, 5.50%; N, 9.11%; Cl, 11.36%. Found: C, 46.28%; H, 5.39%; N, 9.21%; Cl, 11.38%.
Compound 70
[Chemical Formula 109]
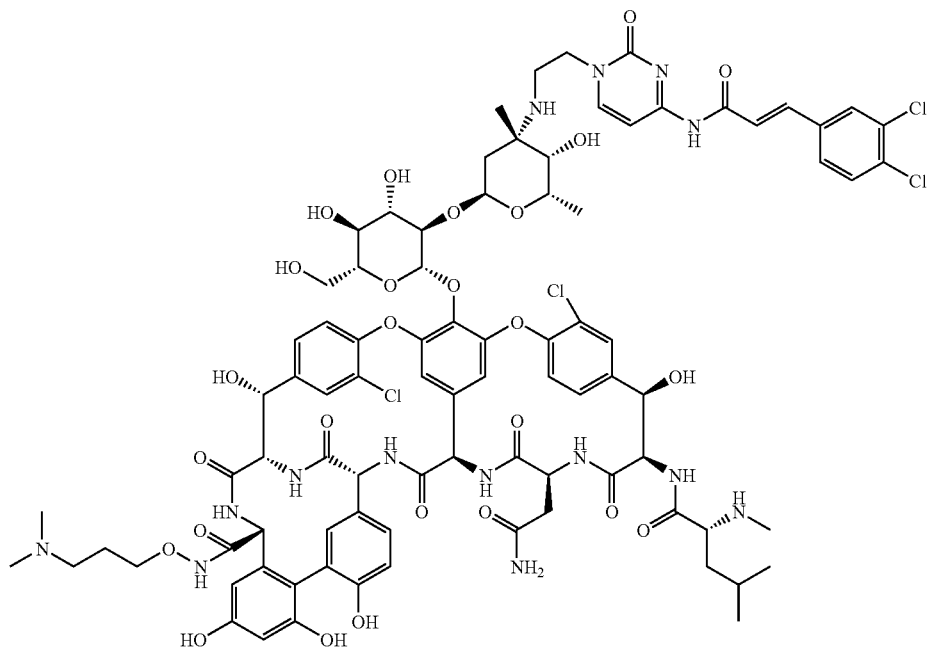

[M+H]⁺=1883
Anal. calcd. for $C_{86}H_{98}Cl_4N_{14}O_{26}\cdot 10.9H_2O\cdot 3.3HCl$: C, 46.90%; H, 5.63%; N, 8.90%; Cl, 11.75%. Found: C, 46.85%; H, 5.54%; N, 8.96%; Cl, 11.79%.
Compound 71
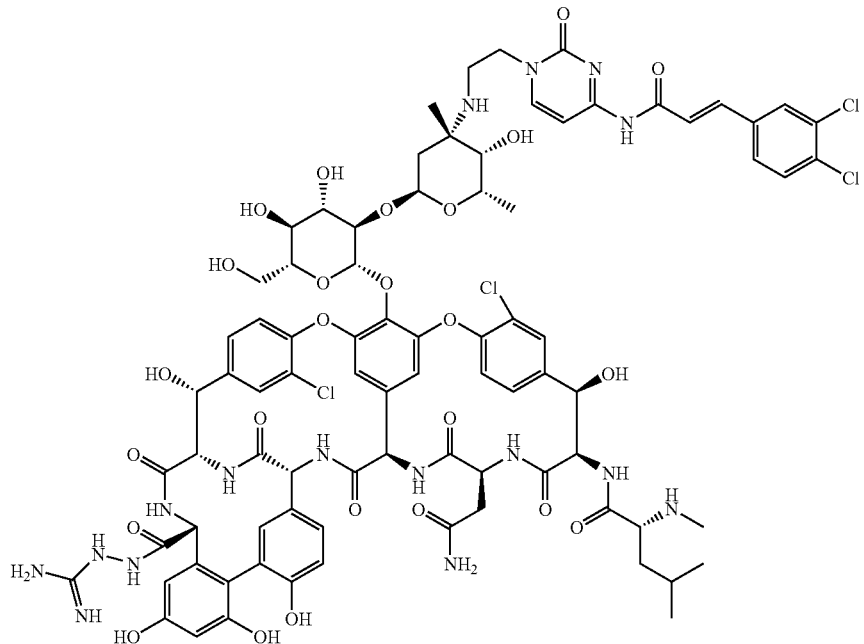
[Chemical Formula 110]
[M+H]⁺=1839
Anal. calcd. for $C_{82}H_{90}Cl_4N_{16}O_{25}\cdot 11.1H_2O\cdot 3.2HCl$: C, 45.64%; H, 5.39%; N, 10.38%; Cl, 11.83%. Found: C, 45.76%; H, 5.37%; N, 9.92%; Cl, 11.86%.
Compound 72
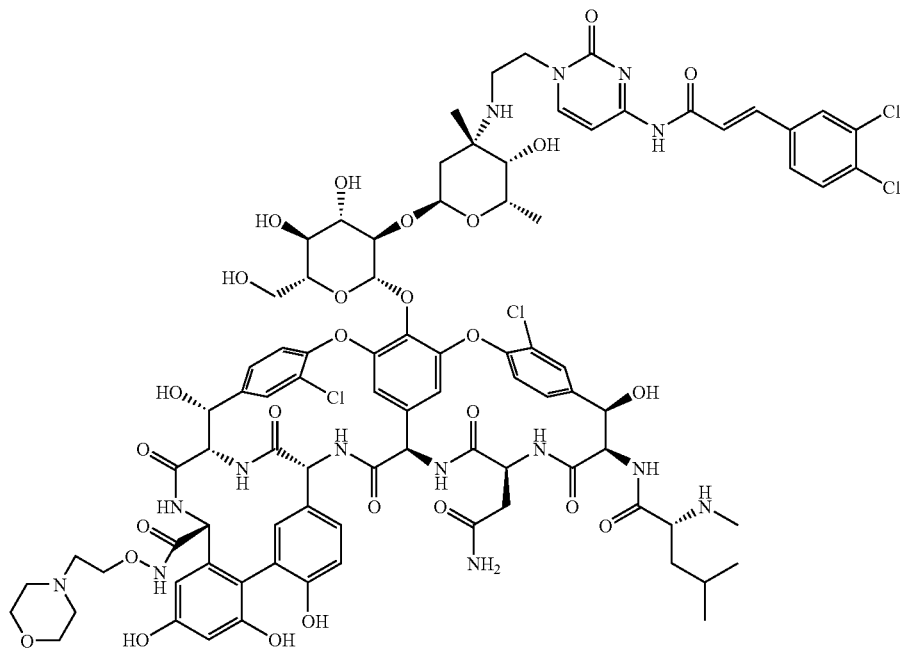
[Chemical Formula 111]

[M+H]⁺=1911
Anal. calcd. for $C_{87}H_{98}Cl_4N_{14}O_{27} \cdot 11.8H_2O \cdot 3.5HCl$: C, 46.36%; H, 5.59%; N, 8.70%; Cl, 11.80%. Found: C, 46.36%; H, 5.49%; N, 8.73%; Cl, 11.78%.
Compound 73
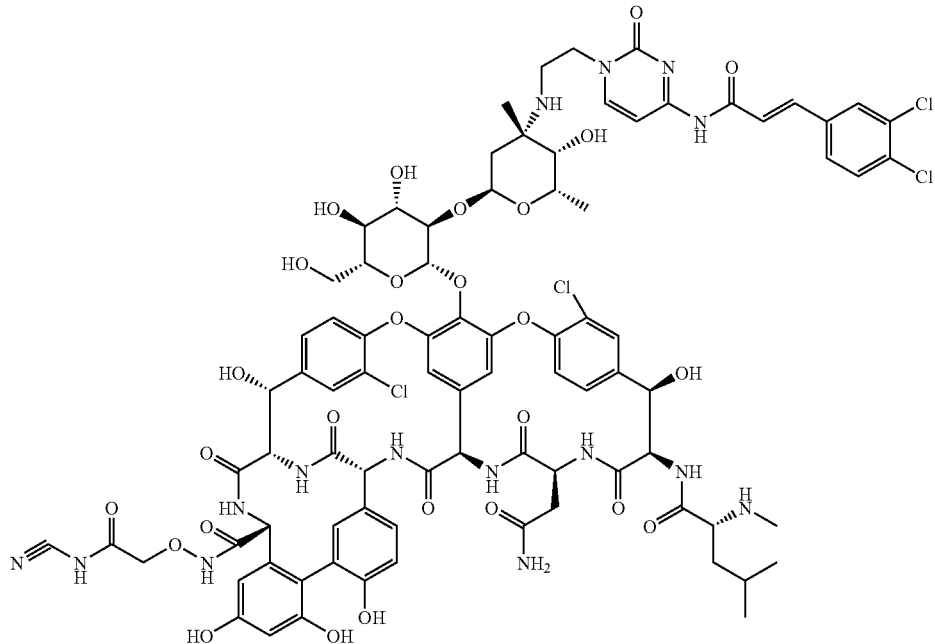
[Chemical Formula 112]
[M+H]⁺=1880
Anal. calcd. for $C_{84}H_{89}Cl_4N_{15}O_{27} \cdot 11.0H_2O \cdot 2.0HCl$: C, 46.85%; H, 5.29%; N, 9.76%; Cl, 9.88%. Found: C, 46.88%; H, 5.36%; N, 9.61%; Cl, 9.86%.
Compound 74
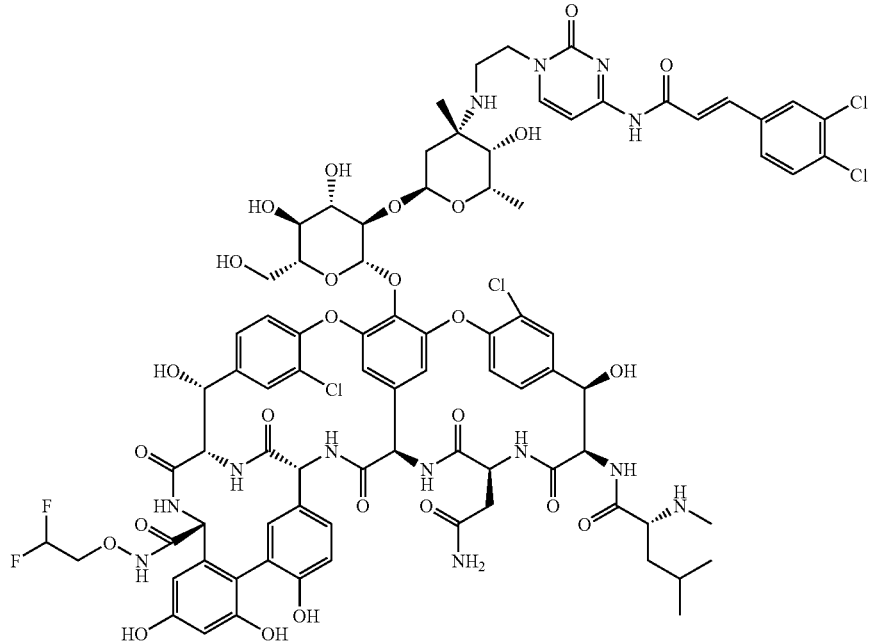
[Chemical Formula 113]

[M+H]⁺=1862
Anal calcd. for $C_{83}H_{89}Cl_4F_2N_{13}O_{26} \cdot 10.7H_2O \cdot 2.2HCl$: C, 46.64%; H, 5.31%; N, 8.52%; Cl, 10.28%; F, 1.78%. Found: C, 46.60%; H, 5.33%; N, 8.68%; Cl, 10.26%; F, 1.48%.
Compound 75
[Chemical Formula 114]
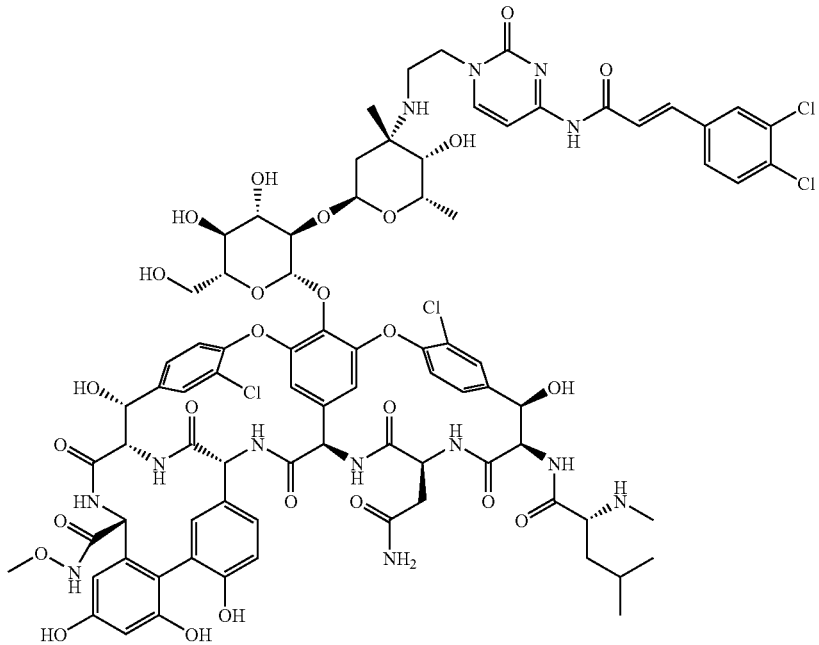
[M+H]⁺=1812
Anal calcd. for $C_{82}H_{89}Cl_4N_{13}O_{26} \cdot 11.6H_2O \cdot 2.2HCl$: C, 46.82%; H, 5.48%; N, 8.66%; Cl, 10.45%. Found: C, 46.82%; H, 5.43%; N, 8.65%; Cl, 10.46%.
Compound 76
[Chemical Formula 115]
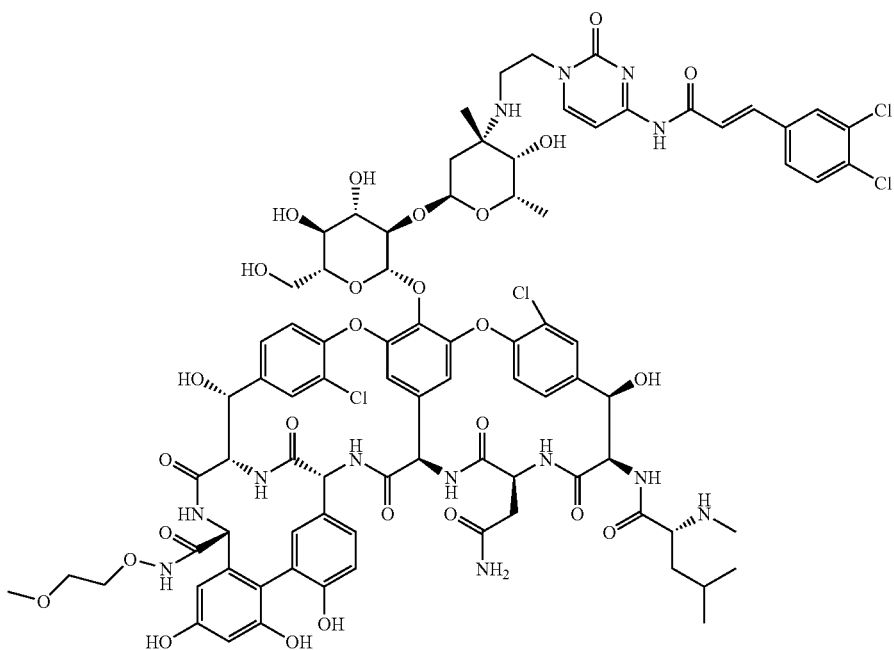

[M+H]⁺=1856
Anal calcd. for $C_{84}H_{93}Cl_4N_{13}O_{27}·10.3H_2O·2.6HCl$: C, 47.17%; H, 5.48%; N, 8.51%; Cl, 10.94%. Found: C, 47.17%; H, 5.48%; N, 8.63%; Cl, 10.90%.
Compound 77
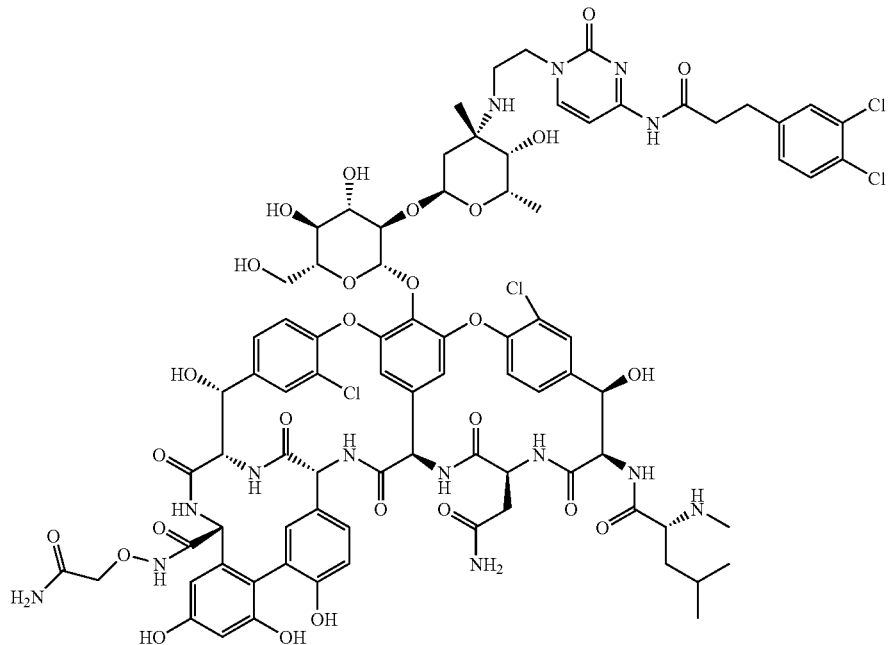
[Chemical Formula 116]
[M+H]⁺=1857
Anal calcd. for $C_{83}H_{92}Cl_4N_{14}O_{27}·10.2H_2O·3.0HCl$: C, 46.31%; H, 5.40%; N, 9.11%; Cl, 11.53%. Found: C, 46.36%; H, 5.48%; N, 9.01%; Cl, 11.48%.
Compound 78
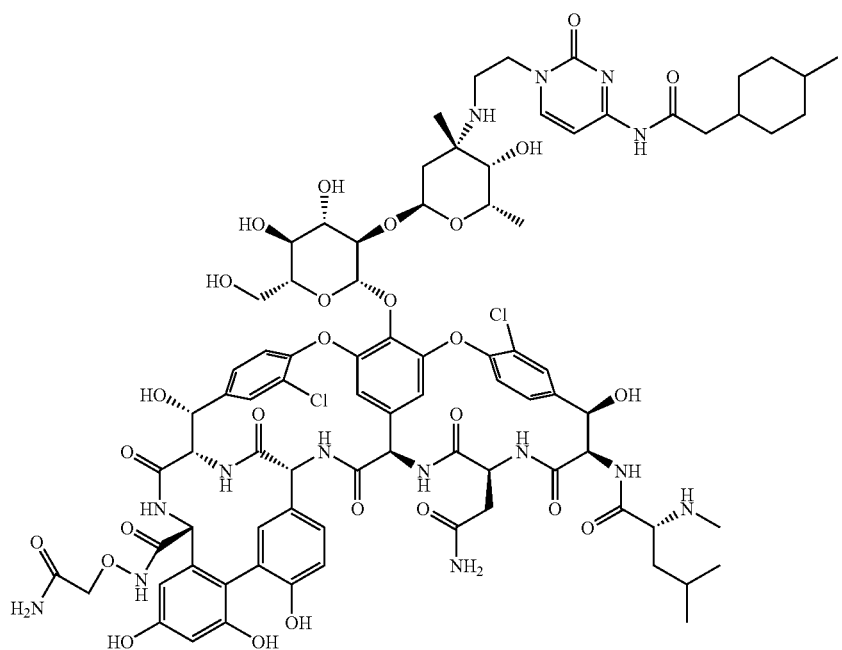
[Chemical Formula 117]

[M+H]⁺=1795
Anal calcd. for $C_{83}H_{100}Cl_2N_{14}O_{27}\cdot11.5H_2O\cdot2.4HCl$: C, 47.67%; H, 6.04%; N, 9.38%; Cl, 7.46%. Found: C, 47.67%; H, 5.91%; N, 9.47%; Cl, 7.47%.
Compound 79
[Chemical Formula 118]
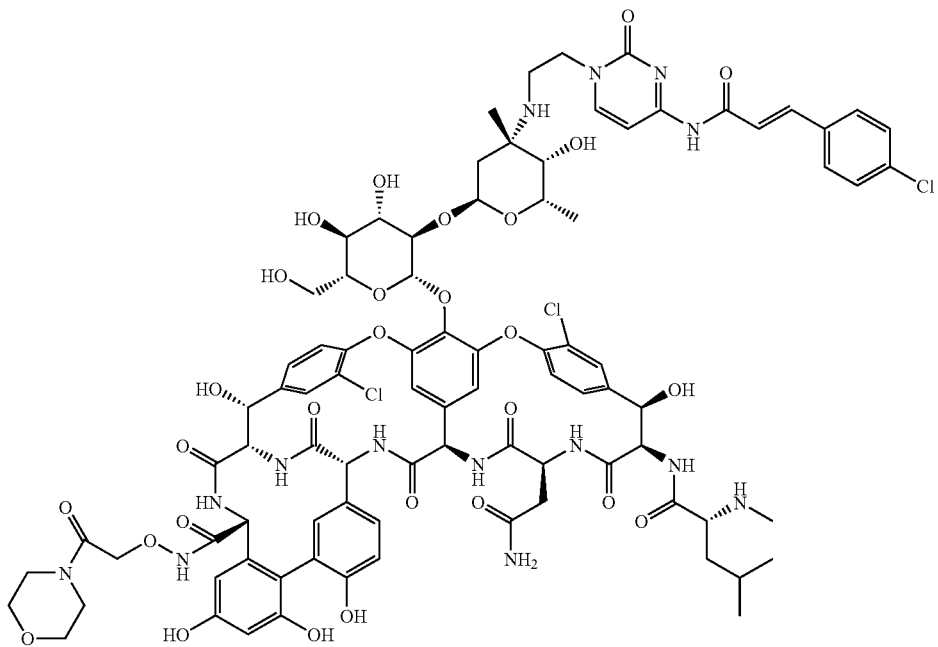
[M+H]⁺=1891
Anal calcd. for $C_{87}H_{97}Cl_3N_{14}O_{28}\cdot11.2H_2O\cdot2.4HCl$: C, 47.88%; H, 5.63%; N, 8.99%; Cl, 8.77%. Found: C, 47.84%; H, 5.64%; N, 9.15%; Cl, 8.75%.
Compound 80
[Chemical Formula 119]
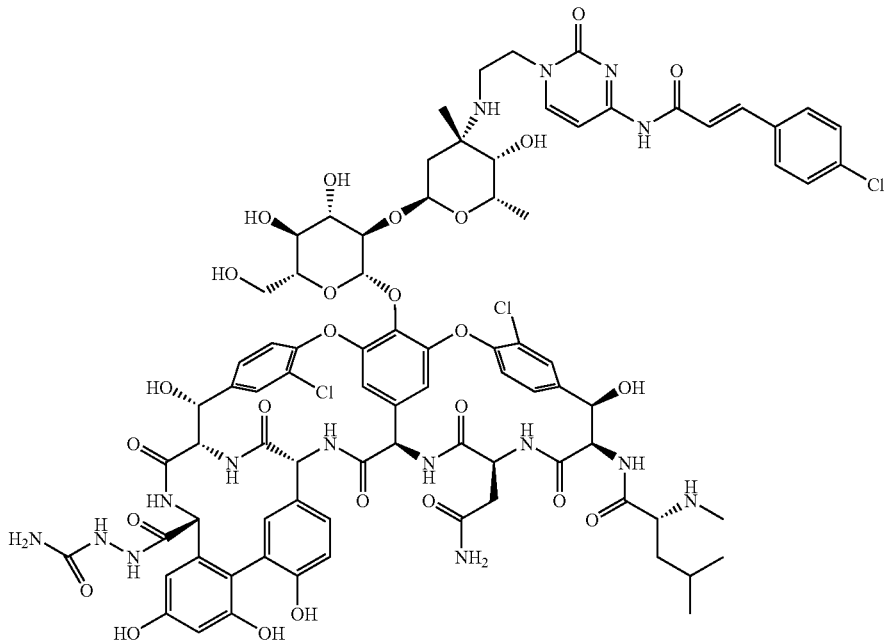

[M+H]⁺=1806
Anal. calcd. for $C_{82}H_{90}Cl_3N_{15}O_{26}\cdot10.6H_2O\cdot2.2HCl$: C, 47.37%; H, 5.50%; N, 10.10%; Cl, 8.87%. Found: C, 47.36%; H, 5.49%; N, 9.95%; Cl, 8.85%.
Compound 81
[Chemical Formula 120]
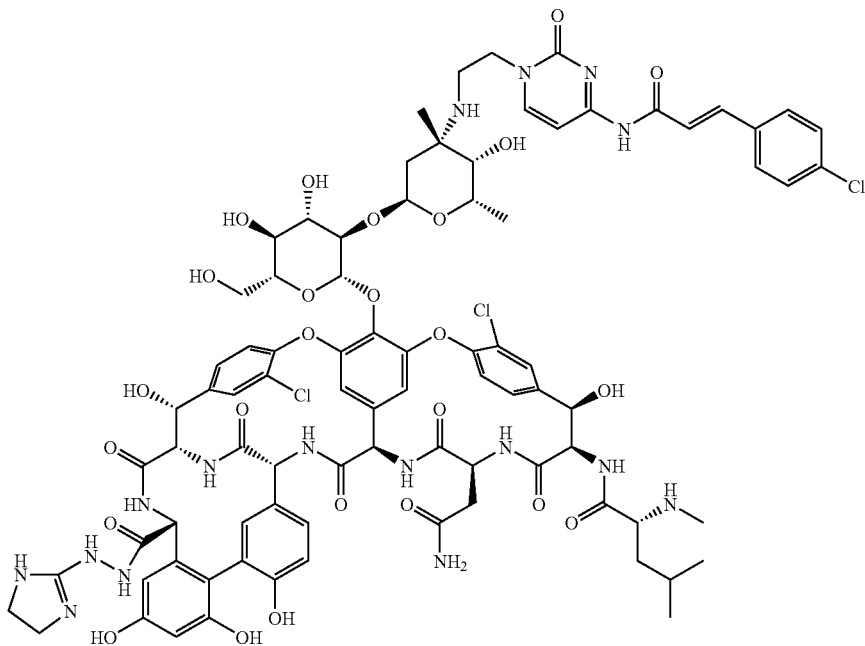
[M+H]⁺=1831
Anal. calcd. for $C_{84}H_{93}Cl_3N_{16}O_{25}\cdot10.2H_2O\cdot3.2HCl$: C, 47.29%; H, 5.51%; N, 10.50%; Cl, 10.30%. Found: C, 47.31%; H, 5.62%; N, 10.49%; Cl, 10.28%.
Compound 82
[Chemical Formula 121]
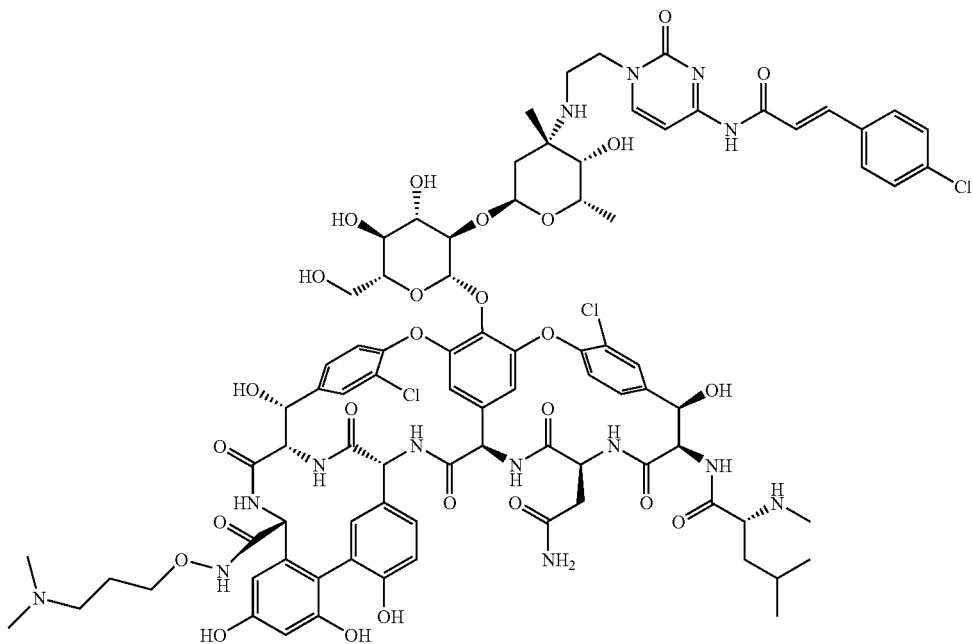

[M+H]$^+$=1849
Anal. calcd. for $C_{86}H_{99}Cl_3N_{14}O_{26} \cdot 12.2H_2O \cdot 3.2HCl$: C, 47.22%; H, 5.83%; N, 8.96%; Cl, 10.05%. Found: C, 47.20%; H, 5.75%; N, 9.07%; Cl, 10.07%.
Compound 83
[Chemical Formula 122]
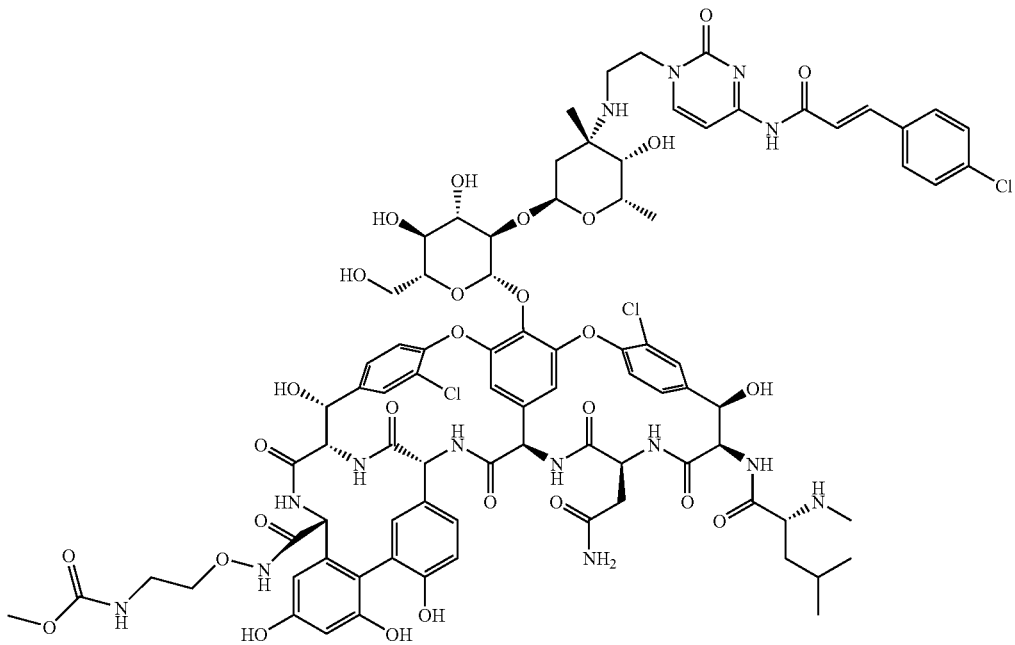
[M+H]$^+$=1865
Anal. calcd. for $C_{85}H_{95}Cl_3N_{14}O_{28} \cdot 11.0H_2O \cdot 2.4HCl$: C, 47.42%; H, 5.59%; N, 9.11%; Cl, 8.89%. Found: C, 47.44%; H, 5.52%; N, 9.03%; Cl, 8.96%.
Compound 84
[Chemical Formula 123]
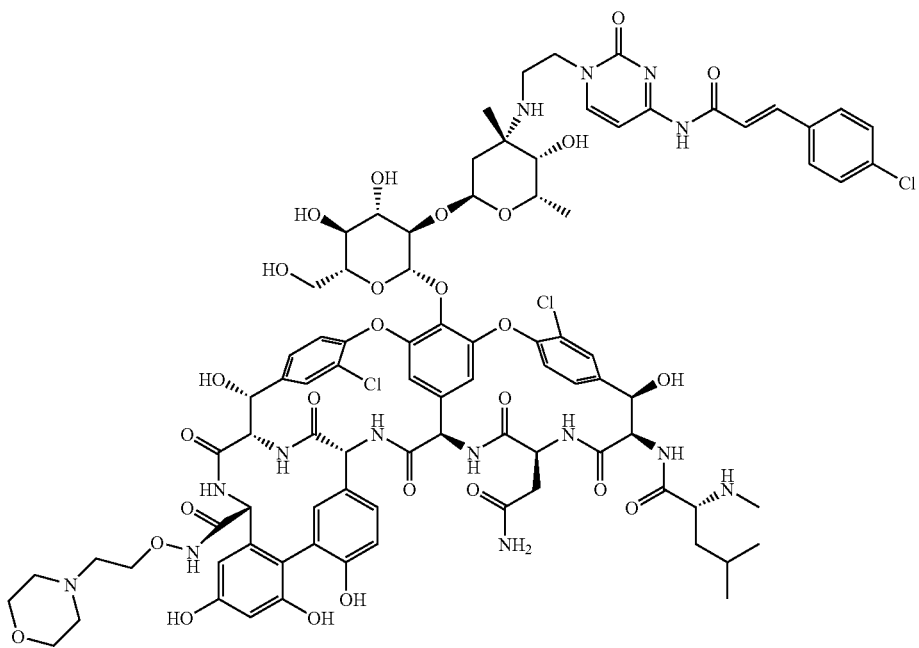

[M+H]⁺=1877
Anal calcd. for $C_{87}H_{99}Cl_3N_{14}O_{27} \cdot 11.5H_2O \cdot 3.1HCl$: C, 47.51%; H, 5.73%; N, 8.92%; Cl, 9.83%. Found: C, 47.53%; H, 5.70%; N, 9.10%; Cl, 9.78%.
Compound 85
[Chemical Formula 124]
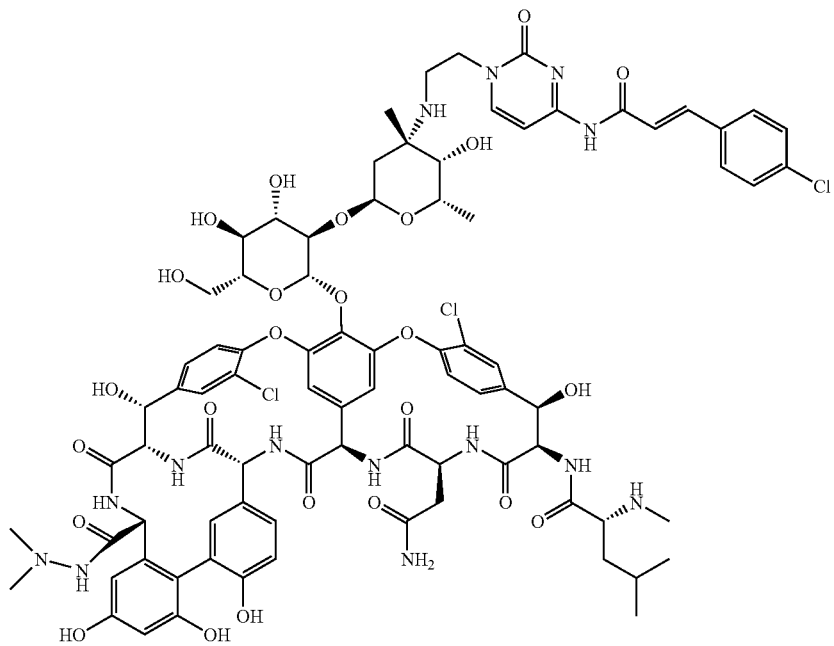
[M+H]⁺=1791
Anal calcd. for $C_{83}H_{93}Cl_3N_{14}O_{25} \cdot 11.5H_2O \cdot 2.1HCl$: C, 48.00%; H, 5.73%; N, 9.44%; Cl, 8.71%. Found: C, 48.01%; H, 5.67%; N, 9.39%; Cl, 8.66%.
Compound 86
[Chemical Formula 125]
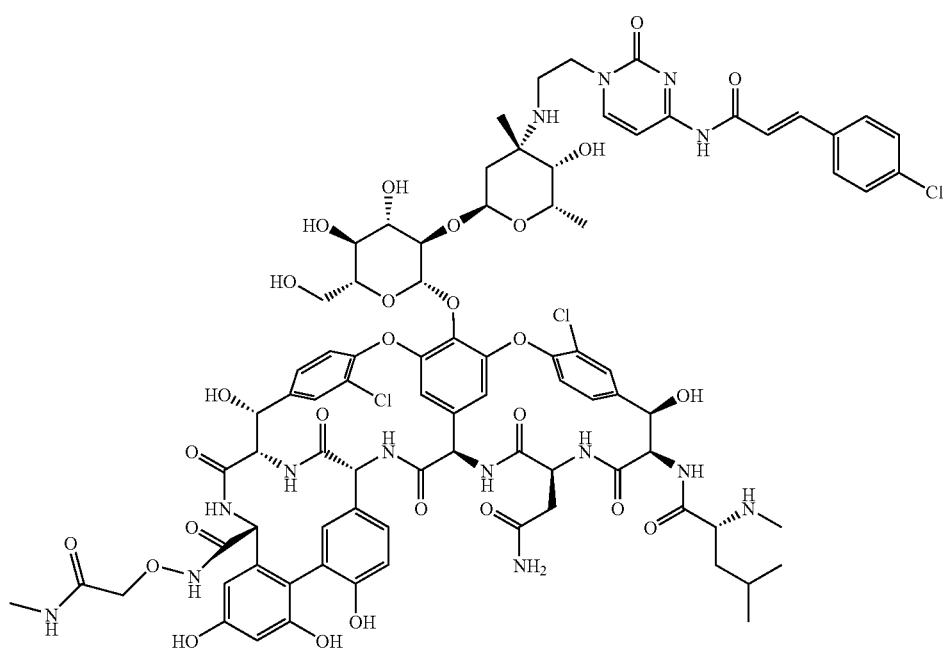

[M+H]$^+$=1835
Anal calcd. for $C_{84}H_{93}Cl_3N_{14}O_{27} \cdot 10.8H_2O \cdot 2.2HCl$: C, 47.77%; H, 5.57%; N, 9.29%; Cl, 8.73%. Found: C, 47.73%; H, 5.52%; N, 9.38%; Cl, 8.66%.
Compound 87.
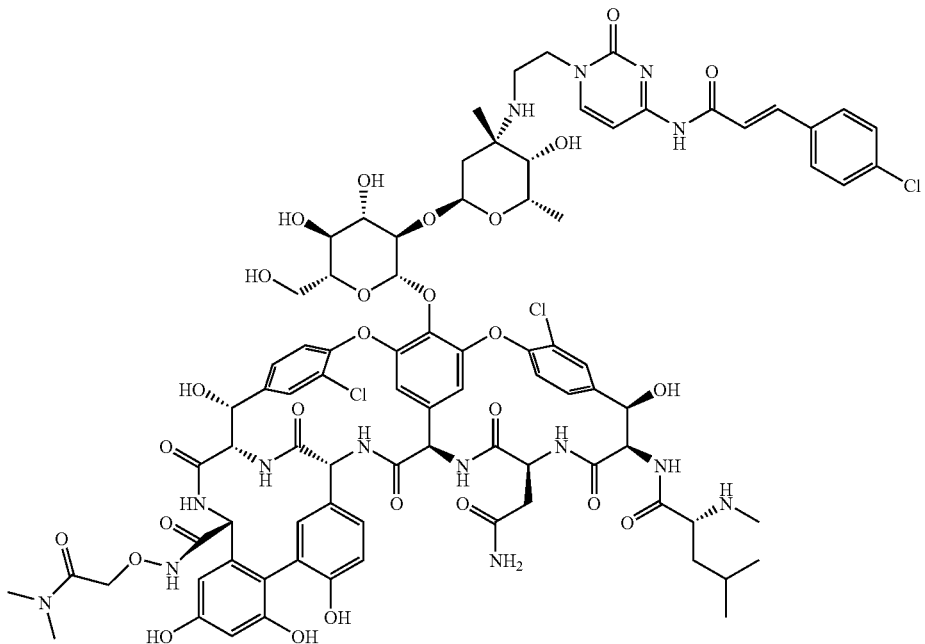
[Chemical Formula 126]
[M+H]$^+$=1849
Anal calcd. for $C_{85}H_{95}Cl_3N_{14}O_{27} \cdot 11.8H_2O \cdot 2.4HCl$: C, 47.46%; H, 5.67%; N, 9.12%; Cl, 8.90%. Found: C, 47.45%; H, 5.56%; N, 9.19%; Cl, 8.84%.
Compound 88
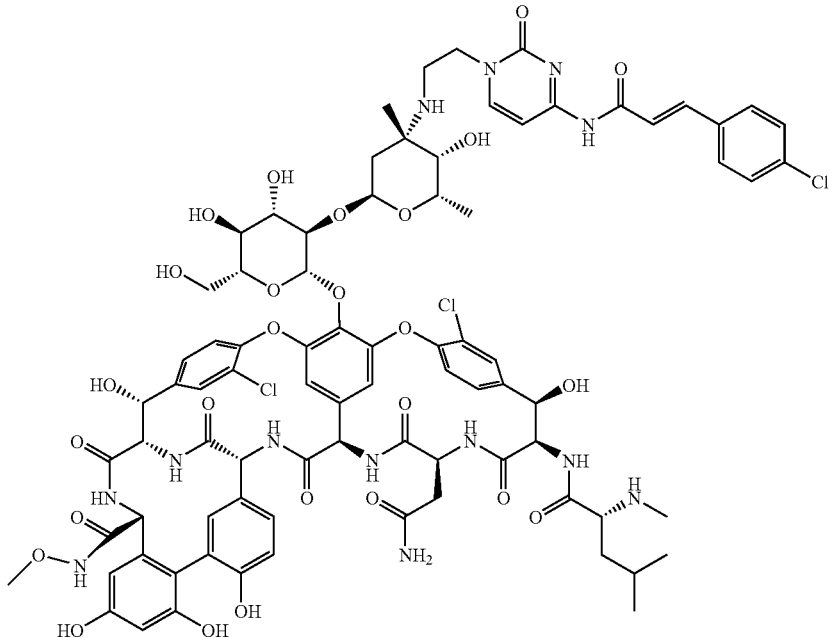
[Chemical Formula 127]

[M+H]⁺=1778
Anal calcd. for $C_{82}H_{90}Cl_3N_{13}O_{26}\cdot 11.5H_2O\cdot 2.3HCl$: C, 47.55%; H, 5.61%; N, 8.79%; Cl, 9.07%. Found: C, 47.51%; H, 5.57%; N, 9.01%; Cl, 9.12%.
Compound 89
[Chemical Formula 128]
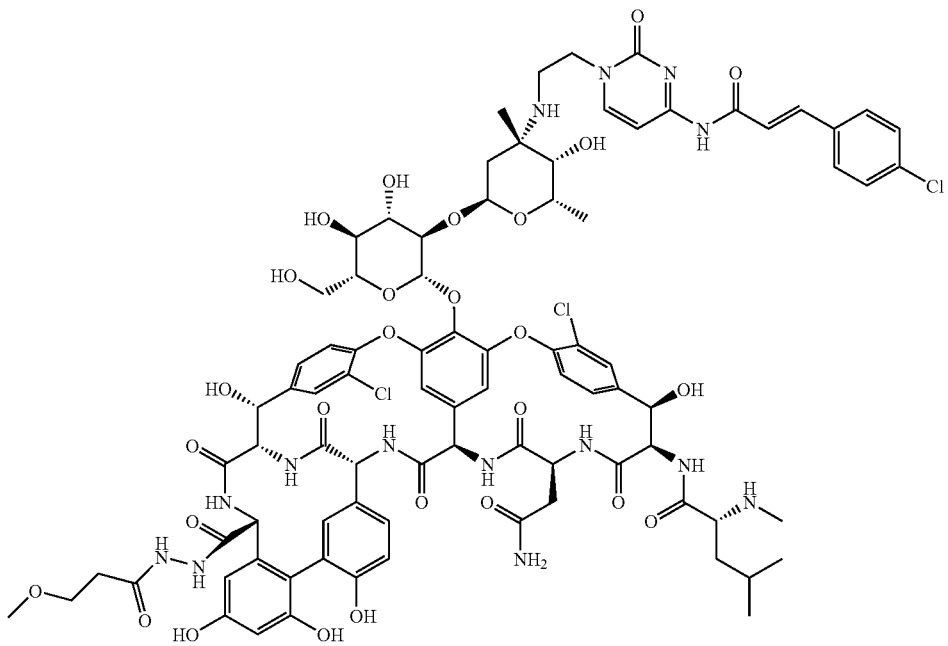
[M+H]⁺=1849
Anal calcd. for $C_{85}H_{95}Cl_3N_{14}O_{27}\cdot 11.4H_2O\cdot 2.2HCl$: C, 47.78%; H, 5.66%; N, 9.18%; Cl, 8.63%. Found: C, 47.75%; H, 5.60%; N, 9.29%; Cl, 8.66%.
Compound 90
[Chemical Formula 129]
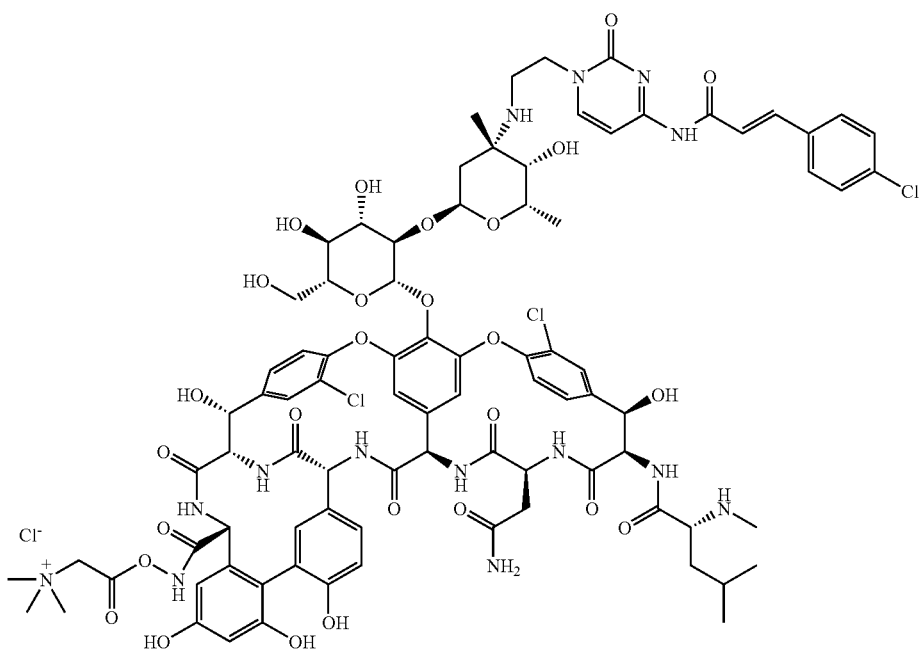

[M]⁺=1862
Anal calcd. for $C_{86}H_{99}Cl_4N_{15}O_{26}\cdot 13.2H_2O\cdot 2.0HCl$: C, 46.71%; H, 5.81%; N, 9.50%; Cl, 9.62%. Found: C, 46.69%; H, 5.78%; N, 9.59%; Cl, 9.65%.
Compound 91
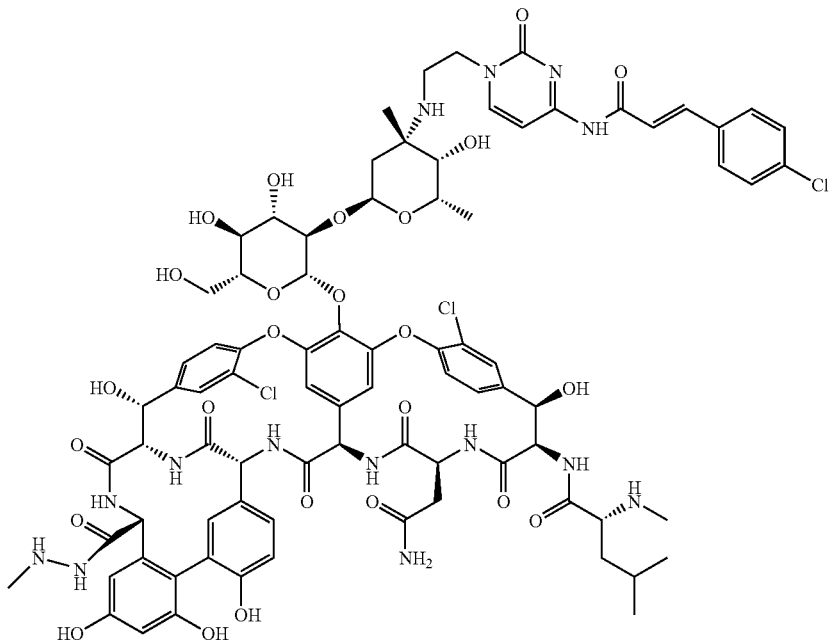
[Chemical Formula 130]
[M+H]⁺=1777
Anal calcd. for $C_{82}H_{91}Cl_3N_{14}O_{25}\cdot 12.1H_2O\cdot 3.1HCl$: C, 46.68%; H, 5.65%; N, 9.29%; Cl, 10.25%. Found: C, 46.65%; H, 5.68%; N, 9.42%; Cl, 10.32%.
Compound 92
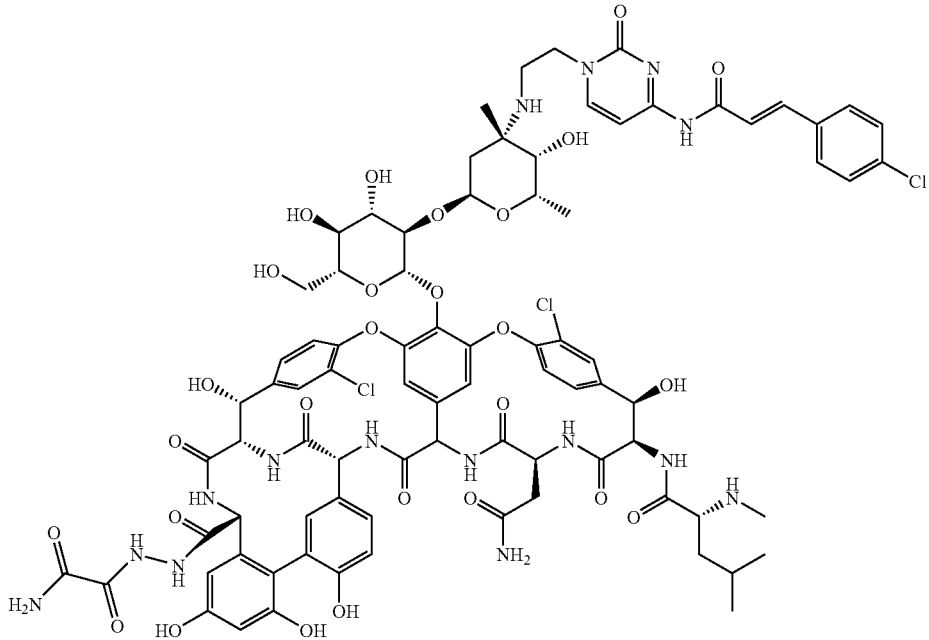
[Chemical Formula 131]

[M+H]⁺=1834
Anal calcd. for $C_{83}H_{90}Cl_3N_{15}O_{27}\cdot11.8H_2O\cdot2.2HCl$: C, 46.83%; H, 5.48%; N, 9.87%; Cl, 8.66%. Found: C, 46.81%; H, 5.48%; N, 9.86%; Cl, 8.67%.
Compound 93
[Chemical Formula 132]
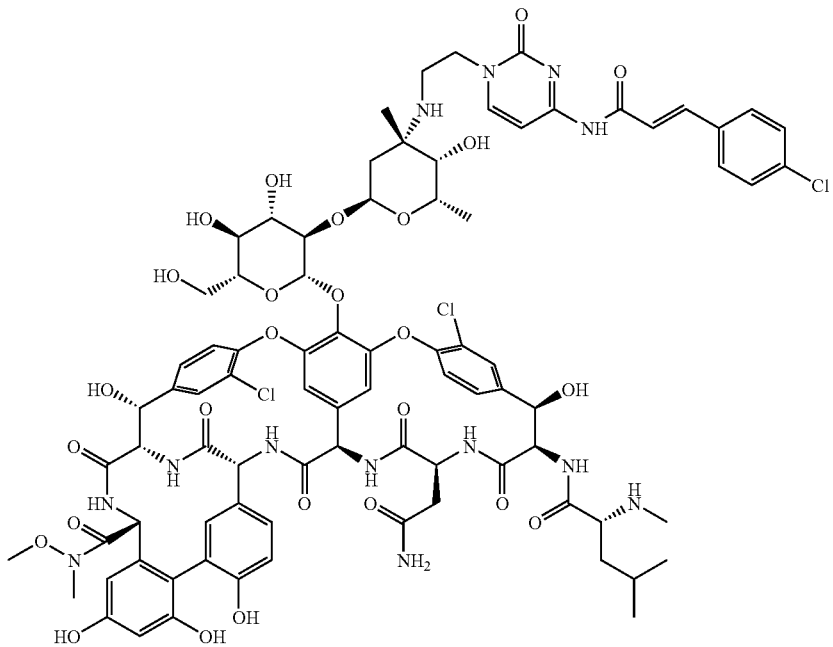
[M+H]⁺=1792
Anal calcd. for $C_{83}H_{92}Cl_3N_{13}O_{26}\cdot10.8H_2O\cdot2.5HCl$: C, 47.93%; H, 5.63%; N, 8.76%; Cl, 9.38%. Found: C, 47.94%; H, 5.60%; N, 8.77%; Cl, 9.43%.
Compound 94
[Chemical Formula 133]
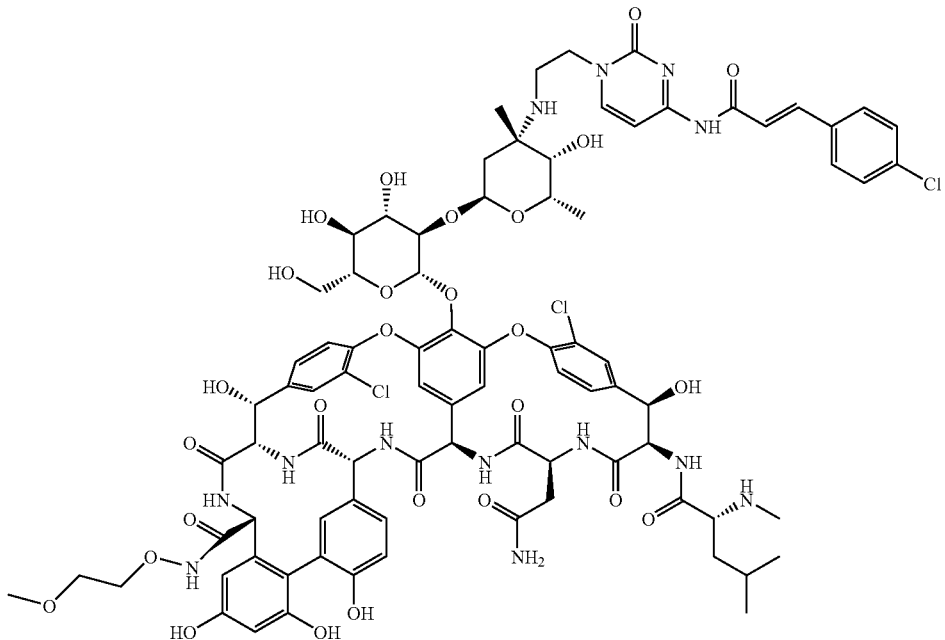

$[M+H]^+=1822$
Anal calcd. for $C_{84}H_{94}Cl_3N_{13}O_{27}\cdot11.6H_2O\cdot2.5HCl$: C, 47.50%; H, 5.68%; N, 8.57%; Cl, 9.18%. Found: C, 47.45%; H, 5.55%; N, 8.66%; Cl, 9.21%.
Compound 95
[Chemical Formula 134]
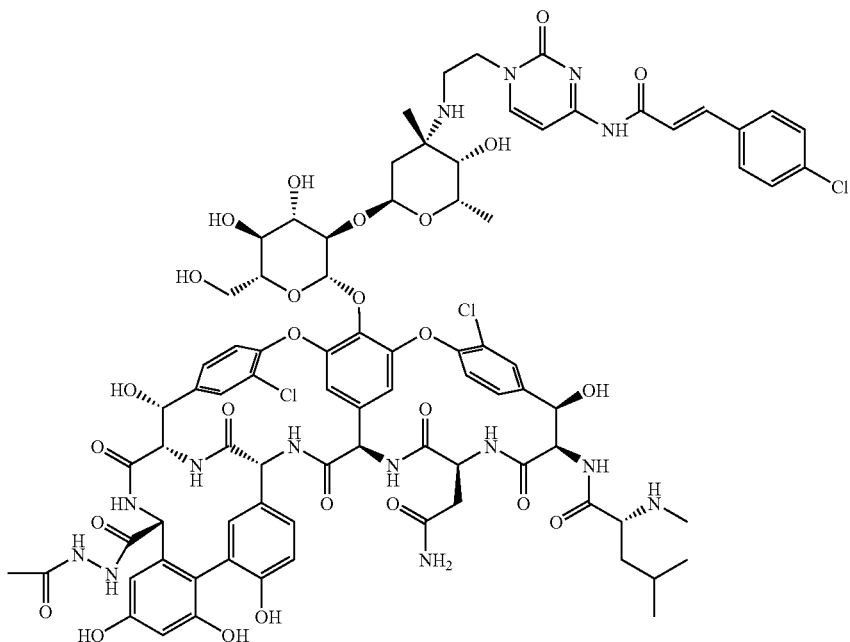
$[M+H]^+=1805$
Anal calcd. for $C_{83}H_{91}Cl_3N_{14}O_{26}\cdot12.5H_2O\cdot2.3HCl$: C, 47.11%; H, 5.63%; N, 9.27%; Cl, 8.88%. Found: C, 47.13%; H, 5.51%; N, 9.25%; Cl, 8.87%.
Compound 96
[Chemical Formula 135]
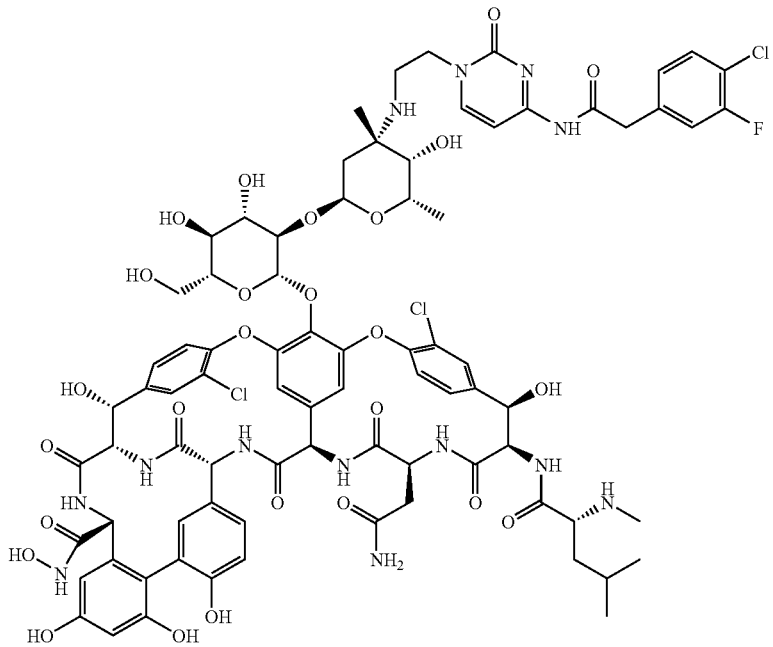

[M+H]⁺=1770
Anal calcd. for $C_{80}H_{87}Cl_3FN_{13}O_{26}\cdot 11.9H_2O\cdot 2.2HCl$: C, 46.50%; H, 5.51%; N, 8.81%; Cl, 8.92%; F, 0.92%. Found: C, 46.47%; H, 5.42%; N, 8.86%; Cl, 8.88%; F, 0.94%.
Compound 97
[Chemical Formula 136]
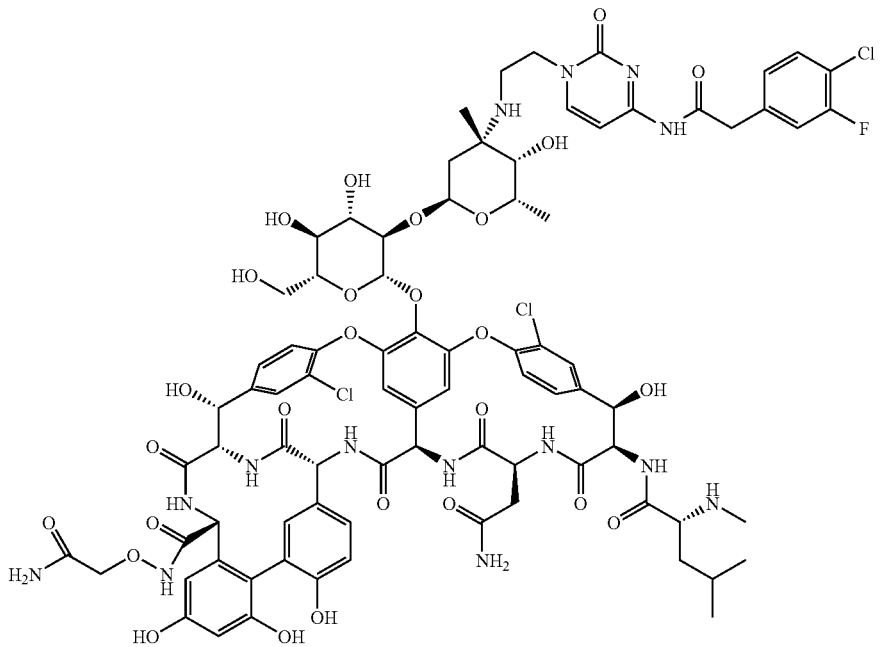
[M+H]⁺=1827
Anal calcd. for $C_{82}H_{90}Cl_3FN_{14}O_{27}\cdot 11.7H_2O\cdot 2.3HCl$: C, 46.38%; H, 5.49%; N, 9.23%; Cl, 8.85%; F, 0.89%. Found: C, 46.37%; H, 5.33%; N, 9.24%; Cl, 8.83%; F, 0.95%.
Compound 98
[Chemical Formula 137]
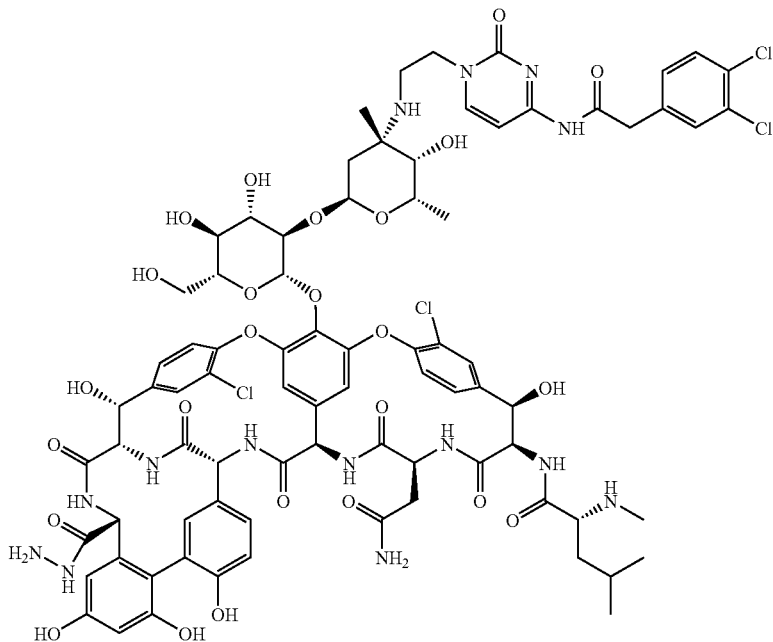

[M+H]⁺=1785
Anal. calcd. for $C_{80}H_{88}Cl_4N_{14}O_{25} \cdot 12.6H_2O \cdot 2.6HCl$: C, 45.55%; H, 5.53%; N, 9.30%; Cl, 11.09%. Found: C, 45.53%; H, 5.49%; N, 9.45%; Cl, 11.05%.
Compound 99
[Chemical Formula 138]
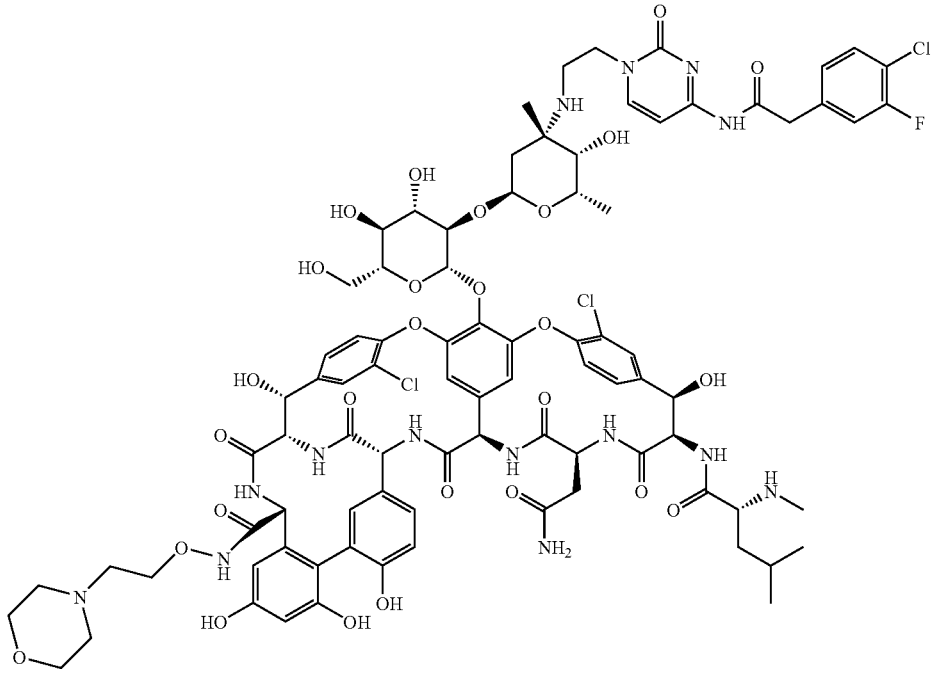
[M+H]⁺=1883
Anal. calcd. for $C_{86}H_{98}Cl_3FN_{14}O_{27} \cdot 11.6H_2O \cdot 3.5HCl$: C, 46.49%; H, 5.66%; N, 8.83%; Cl, 10.37%; F, 0.86%. Found: C, 46.46%; H, 5.65%; N, 9.23%; Cl, 10.43%; F, 0.92%.
Compound 100
[Chemical Formula 139]
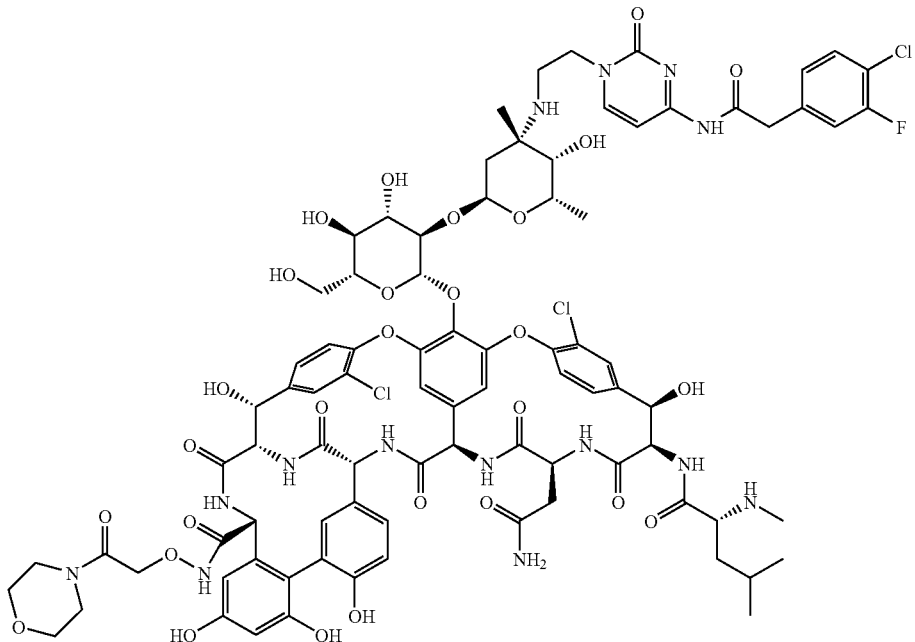

[M+H]$^+$=1897
Anal calcd. for $C_{86}H_{96}Cl_3FN_{14}O_{28}$·10.9$H_2O$·2.3HCl: C, 47.40%; H, 5.55%; N, 9.00%; Cl, 8.62%; F, 0.87%. Found: C, 47.23%; H, 5.52%; N, 9.30%; Cl, 8.55%; F, 0.90%.
Compound 101
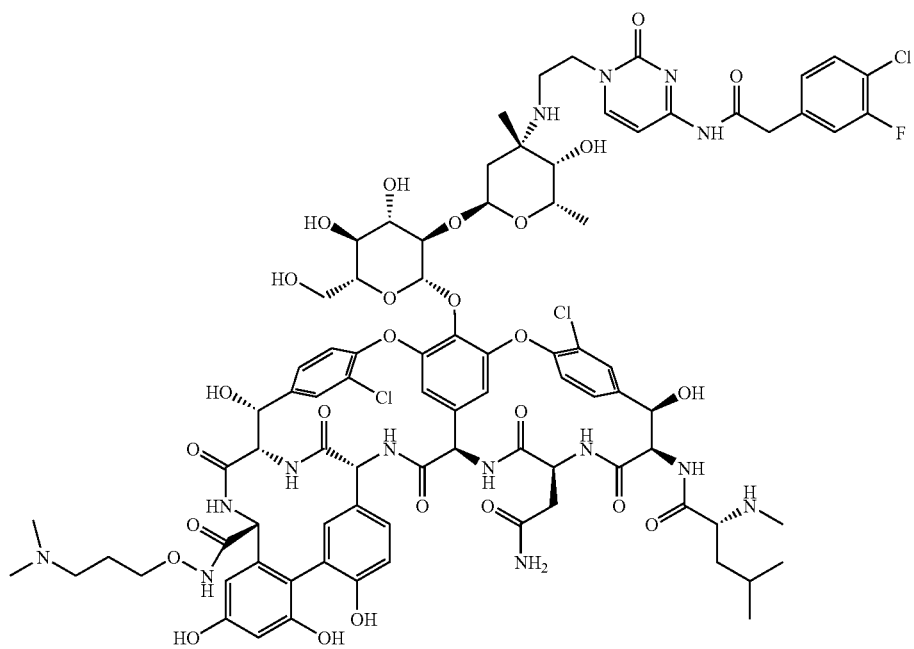
[Chemical Formula 140]

[M+H]$^+$=1855
Anal calcd. for $C_{85}H_{98}Cl_3FN_{14}O_{26} \cdot 11.4H_2O \cdot 3.2HCl$: C, 46.85%; H, 5.74%; N, 9.00%; Cl, 10.09%; F, 0.87%. Found: C, 46.57%; H, 5.83%; N, 9.30%; Cl, 10.18%; F, 0.89%.
Compound 102
[Chemical Formula 141]
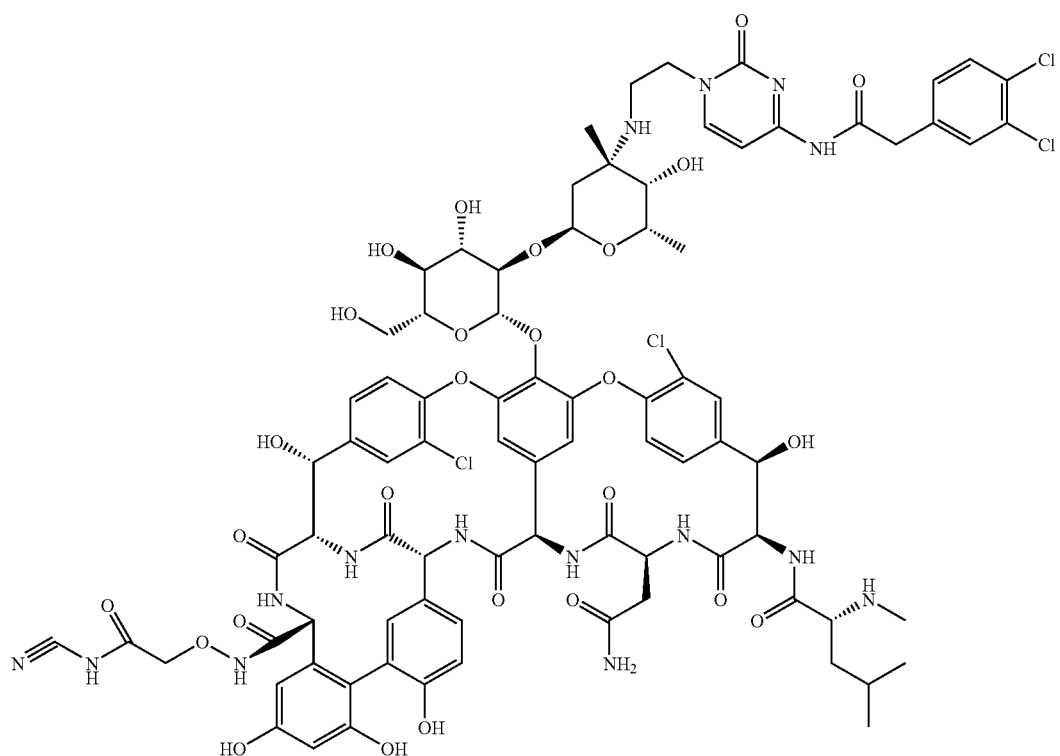

[M+H]⁺=1868
Anal calcd. for $C_{83}H_{88}Cl_4N_{15}O_{27}\cdot11.8H_2O\cdot1.9HCl$: C, 46.34%; H, 5.32%; N, 9.77%; Cl, 9.72%. Found: C, 46.32%; H, 5.33%; N, 10.03%; Cl, 9.65%.
Compound 103
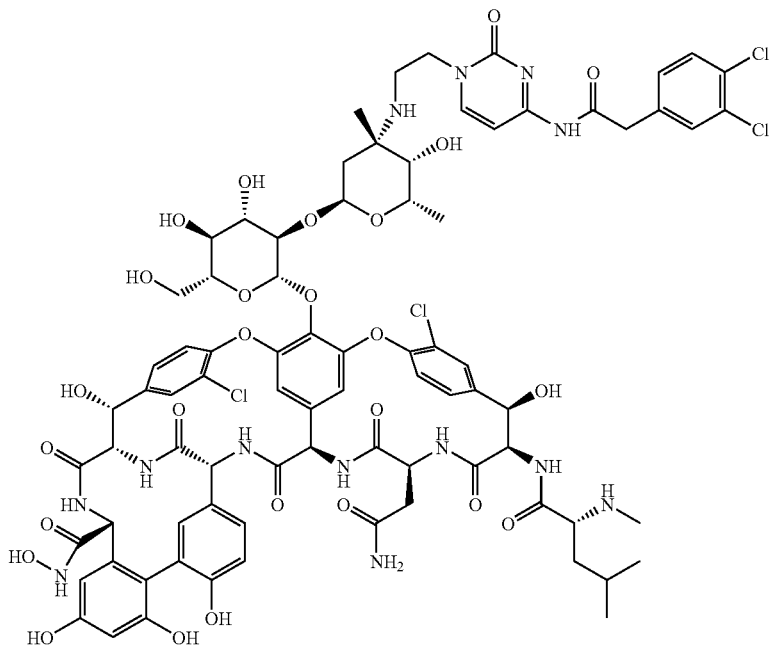
[Chemical Formula 142]

[M+H]$^+$=1786
Anal calcd. for $C_{80}H_{87}Cl_4N_{13}O_{26}\cdot 11.1H_2O\cdot 2.7HCl$: C, 46.04%; H, 5.40%; N, 8.73%; Cl, 11.38%. Found: C, 45.90%; H, 5.38%; N, 9.32%; Cl, 11.31%.
Compound 104
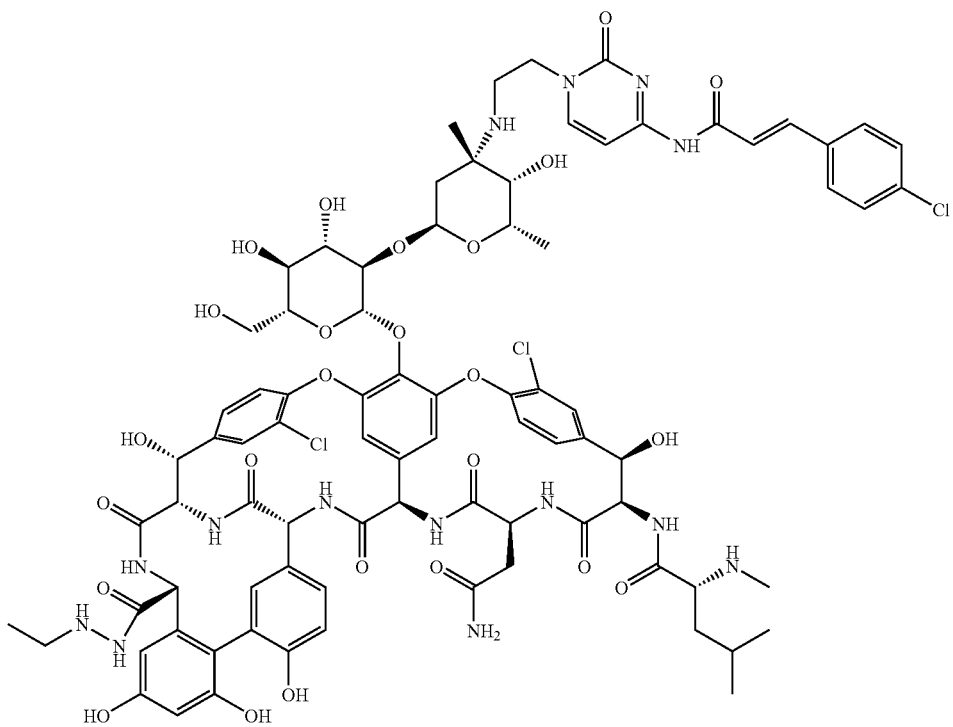
[Chemical Formula 143]

[M+H]⁺=1791
Anal calcd. for $C_{83}H_{93}Cl_3N_{14}O_{25}\cdot12.1H_2O\cdot2.2HCl$: C, 47.67%; H, 5.75%; N, 9.38%; Cl, 8.82%. Found: C, 47.63%; H, 5.75%; N, 9.53%; Cl, 8.80%.
Compound 105
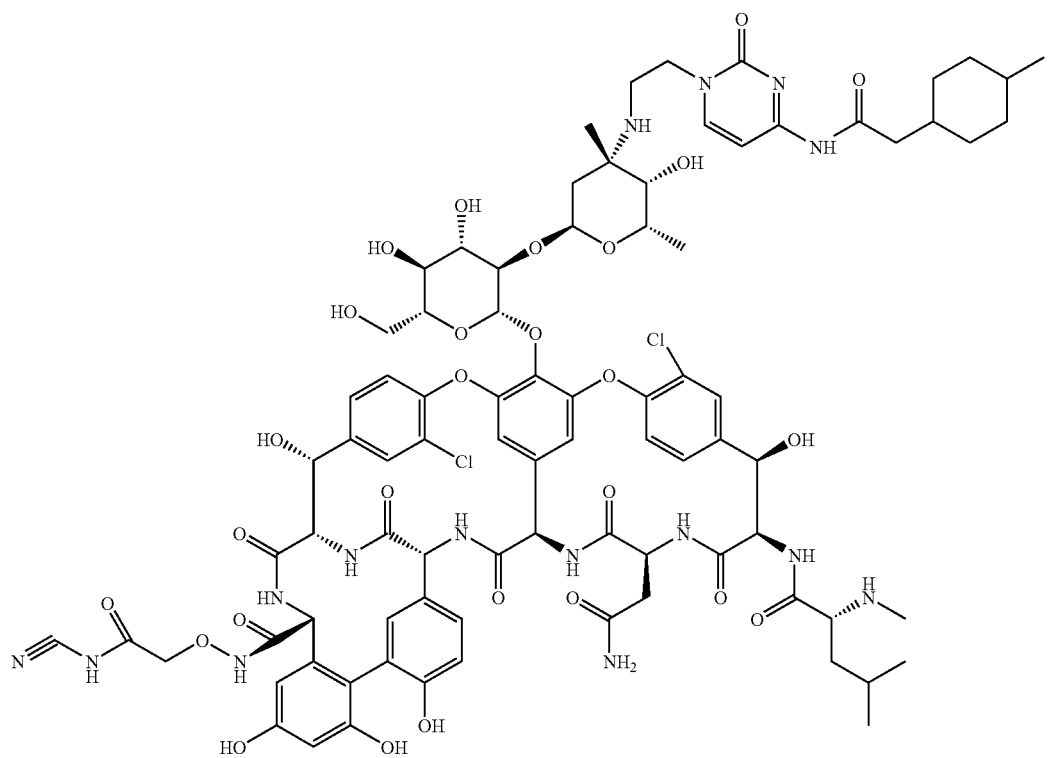
[Chemical Formula 144]

[M+H]$^+$=1820
Anal calcd. for $C_{84}H_{99}Cl_2N_{15}O_{27} \cdot 11.3H_2O \cdot 1.7HCl$: C, 48.34%; H, 5.95%; N, 10.07%; Cl, 6.28%. Found: C, 48.35%; H, 5.95%; N, 10.24%; Cl, 6.23%.
Compound 106
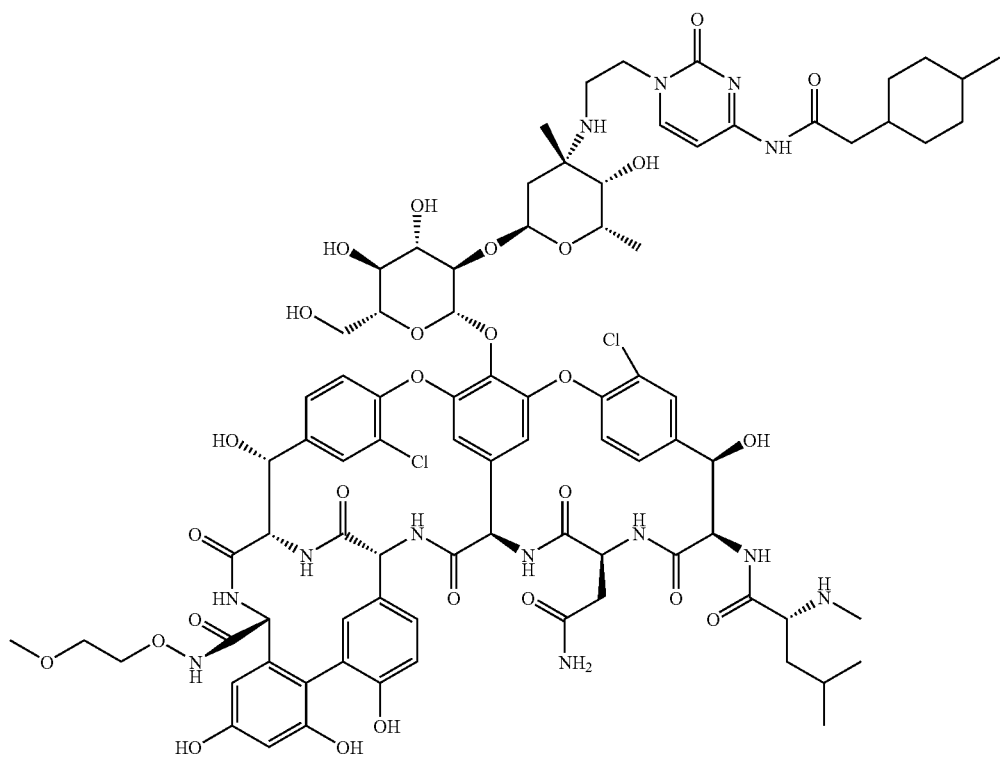
[Chemical Formula 145]

[M+H]⁺=1796
Anal calcd. for $C_{84}H_{103}Cl_2N_{13}O_{27} \cdot 11.4H_2O \cdot 2.3HCl$: C, 48.34%; H, 6.19%; N, 8.73%; Cl, 7.30%. Found: C, 48.35%; H, 6.13%; N, 8.85%; Cl, 7.30%.
Compound 107
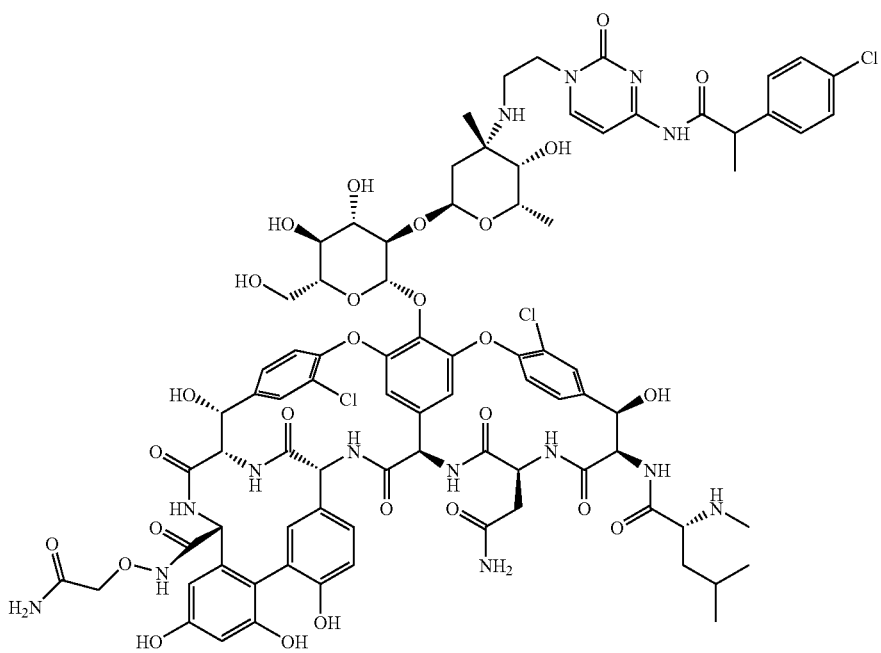
[Chemical Formula 146]

[M+H]⁺=1823
Anal calcd. for $C_{83}H_{93}Cl_3N_{14}O_{27} \cdot 11.8H_2O \cdot 2.2HCl$: C, 47.07%; H, 5.65%; N, 9.26%; Cl, 8.70%. Found: C, 47.05%; H, 5.50%; N, 9.34%; Cl, 8.62%.
Compound 108
[Chemical Formula 147]
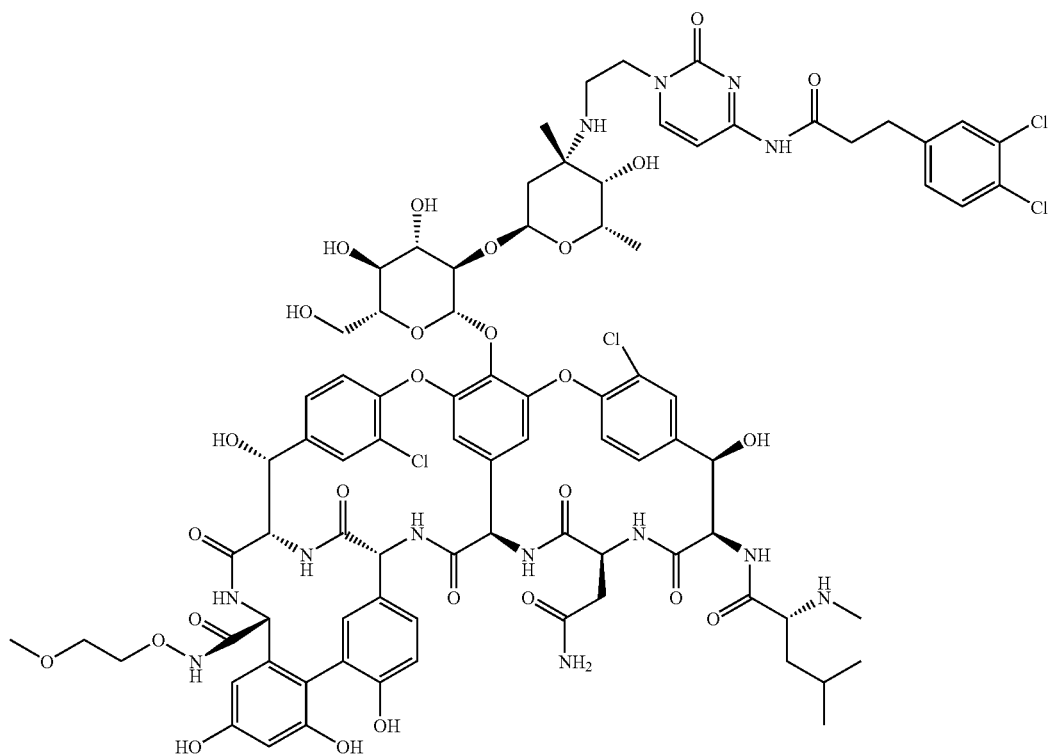

[M+H]+=1858
Anal. calcd. for $C_{84}H_{95}Cl_4N_{13}O_{27} \cdot 11.5H_2O \cdot 2.1HCl$: C, 47.05%; H, 5.65%; N, 8.49%; Cl, 10.09%. Found: C, 46.99%; H, 5.66%; N, 8.76%; Cl, 10.16%.
Compound 109
[Chemical Formula 148]
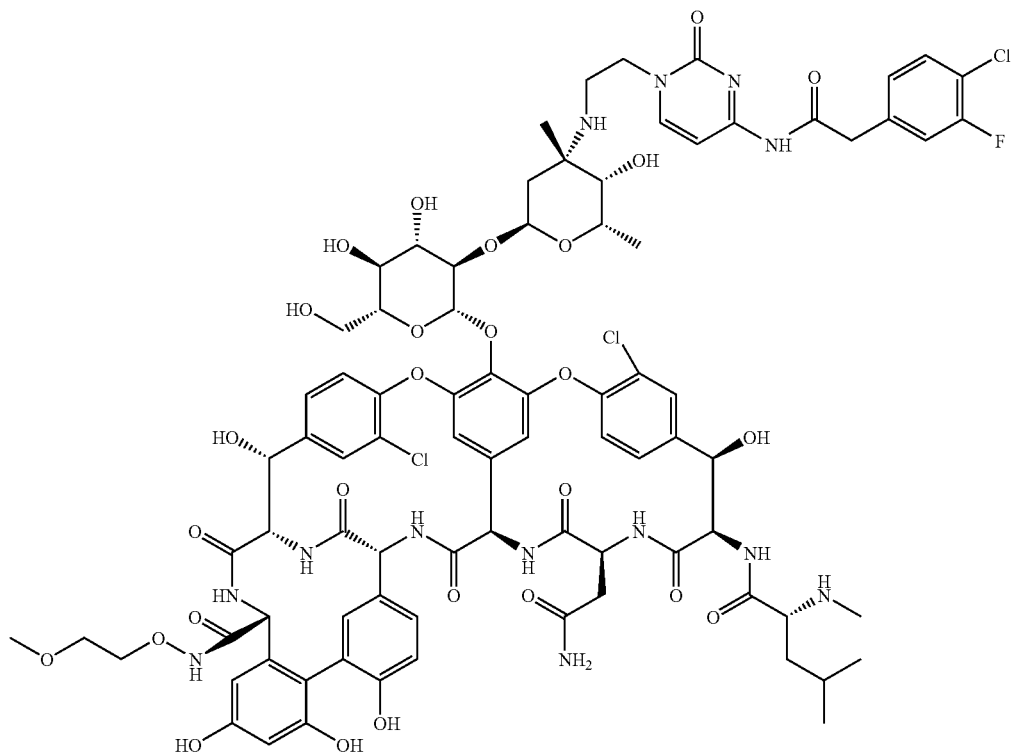

[M+H]⁺=1828
Anal calcd. for $C_{83}H_{93}Cl_3FN_{13}O_{27}\cdot11.9H_2O\cdot1.9HCl$: C, 47.16%; H, 5.66%; N, 8.61%; Cl, 8.22%; F, 0.90%. Found: C, 47.13%; H, 5.55%; N, 8.79%; Cl, 8.22%; F, 1.20%.
Compound 110
[Chemical Formula 149]
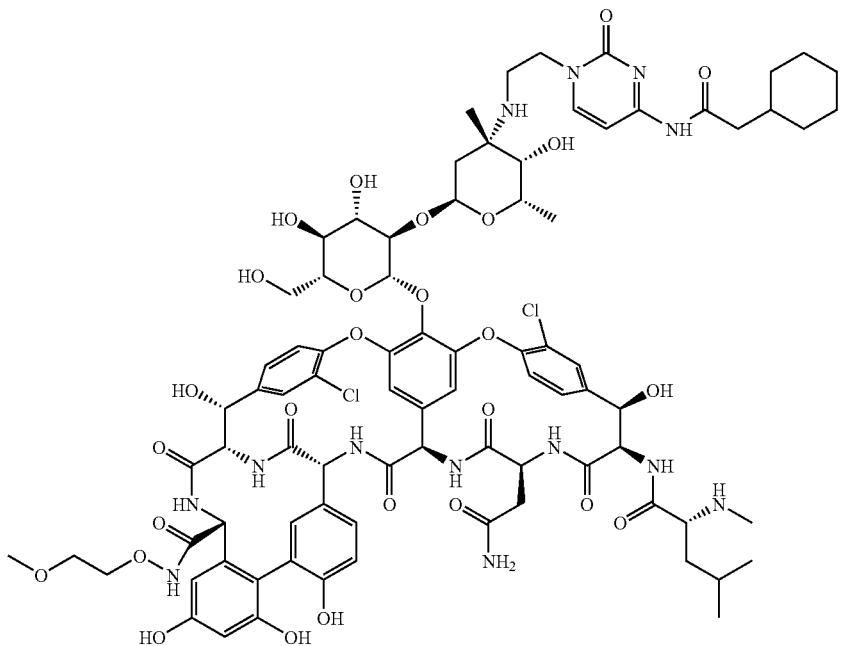
[M+H]⁺=1782
Anal calcd. for $C_{83}H_{101}Cl_2N_{13}O_{27}\cdot11.5H_2O\cdot2.3HCl$: C, 48.05%; H, 6.14%; N, 8.78%; Cl, 7.35%. Found: C, 47.98%; H, 6.20%; N, 9.13%; Cl, 7.33%.
Compound 111
[Chemical Formula 150]
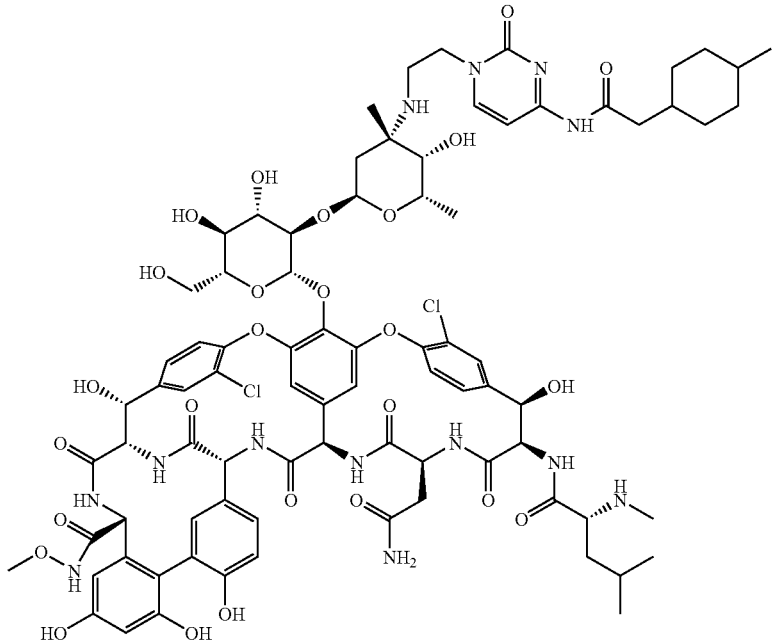

[M+H]$^+$=1752
Anal calcd. for $C_{82}H_{99}Cl_2N_{13}O_{26}\cdot11.7H_2O\cdot2.2HCl$: C, 48.17%; H, 6.14%; N, 8.91%; Cl, 7.28%. Found: C, 48.16%; H, 6.06%; N, 8.83%; Cl, 7.24%.
Compound 112
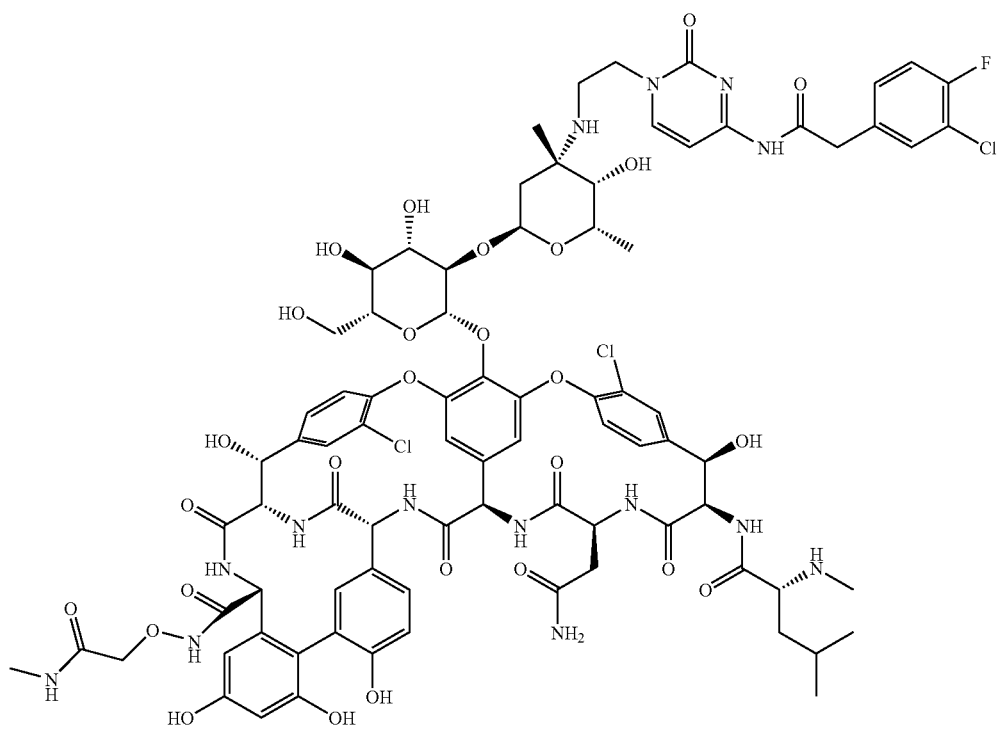
[Chemical Formula 151]

[M+H]$^+$=1841
Anal calcd. for $C_{83}H_{92}Cl_3FN_{14}O_{27}\cdot 11.9H_2O\cdot 2.0HCl$: C, 46.79%; H, 5.57%; N, 9.20%; Cl, 8.32%; F, 0.89%. Found: C, 46.81%; H, 5.51%; N, 9.20%; Cl, 8.28%; F, 0.90%.
Compound 113
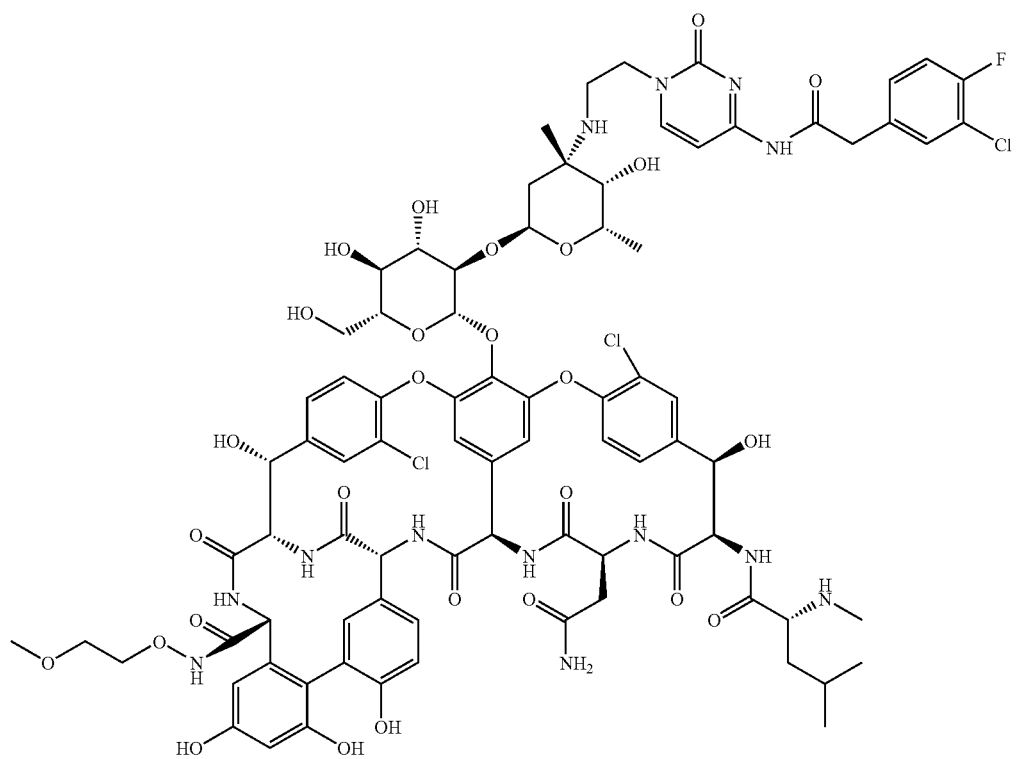
[Chemical Formula 152]

[M+H]$^+$=1828
Anal calcd. for $C_{83}H_{93}Cl_3FN_{13}O_{27} \cdot 10.6H_2O \cdot 2.4HCl$: C, 47.28%; H, 5.57%; N, 8.64%; Cl, 9.08%; F, 0.90%. Found: C, 47.22%; H, 5.48%; N, 8.78%; Cl, 9.02%; F, 0.95%.
Compound 114
[Chemical Formula 153]
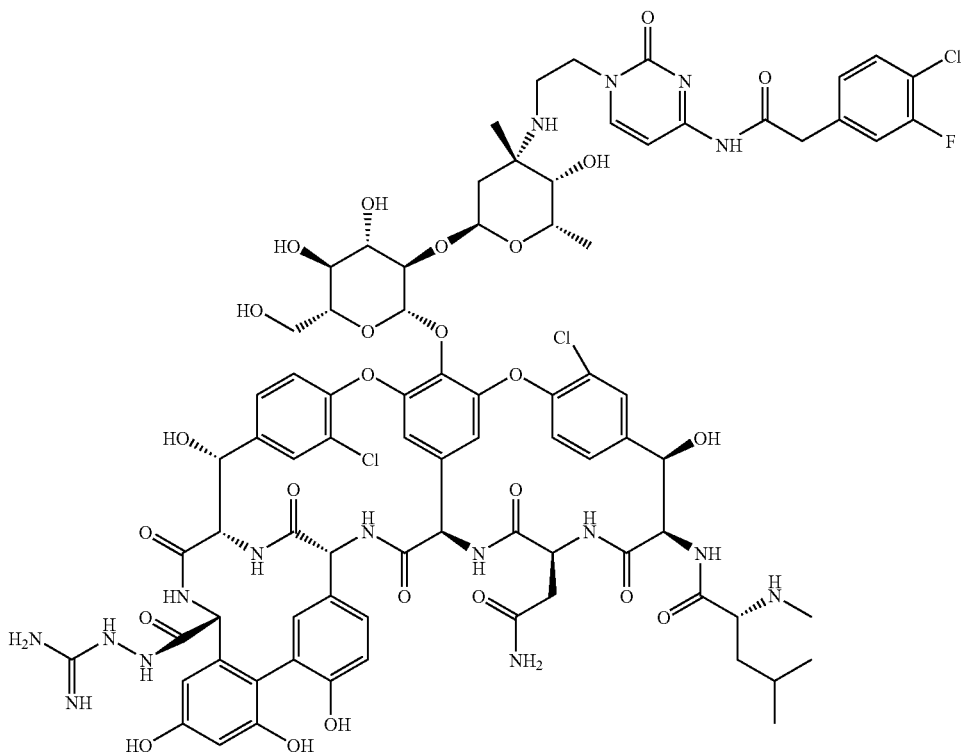

[M+H]⁺=1811
Anal calcd. for $C_{81}H_{90}Cl_3FN_{16}O_{25} \cdot 11.8H_2O \cdot 2.8HCl$: C, 45.72%; H, 5.51%; N, 10.53%; Cl, 9.66%; F, 0.89%. Found: C, 45.65%; H, 5.41%; N, 10.62%; Cl, 9.73%; F, 0.90%.
Compound 115
[Chemical Formula 154]
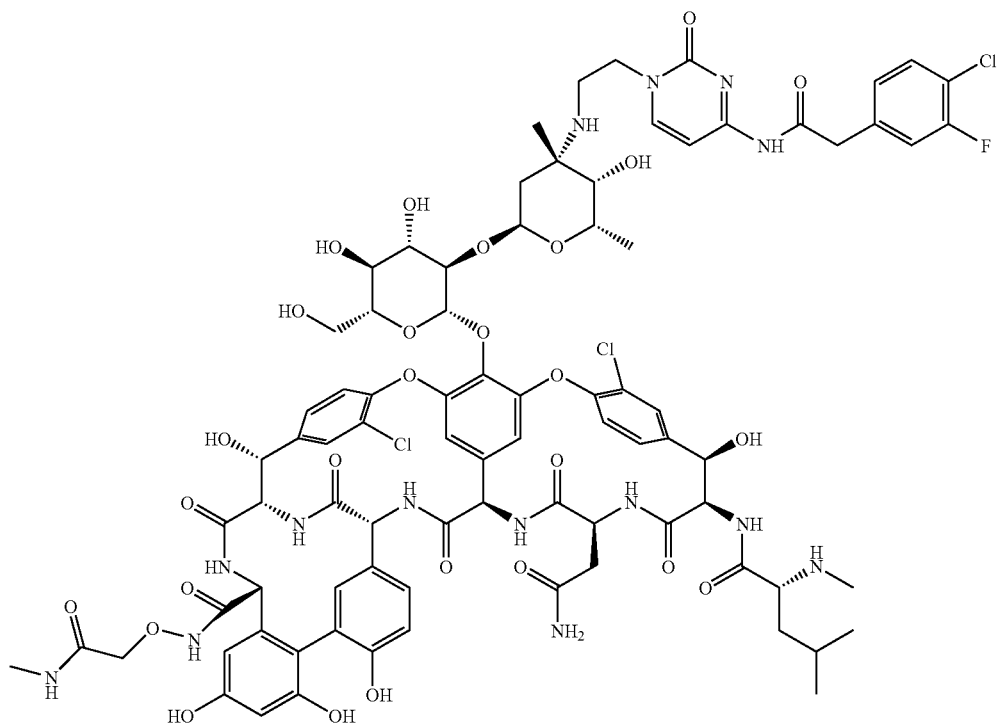

[M+H]$^+$=1841
Anal calcd. for $C_{83}H_{92}Cl_3FN_{14}O_{27} \cdot 10.1H_2O \cdot 2.1HCl$: C, 47.44%; H, 5.48%; N, 9.33%; Cl, 8.60%; F, 0.90%. Found: C, 47.28%; H, 5.37%; N, 9.63%; Cl, 8.59%; F, 1.16%.
Compound 116
[Chemical Formula 155]
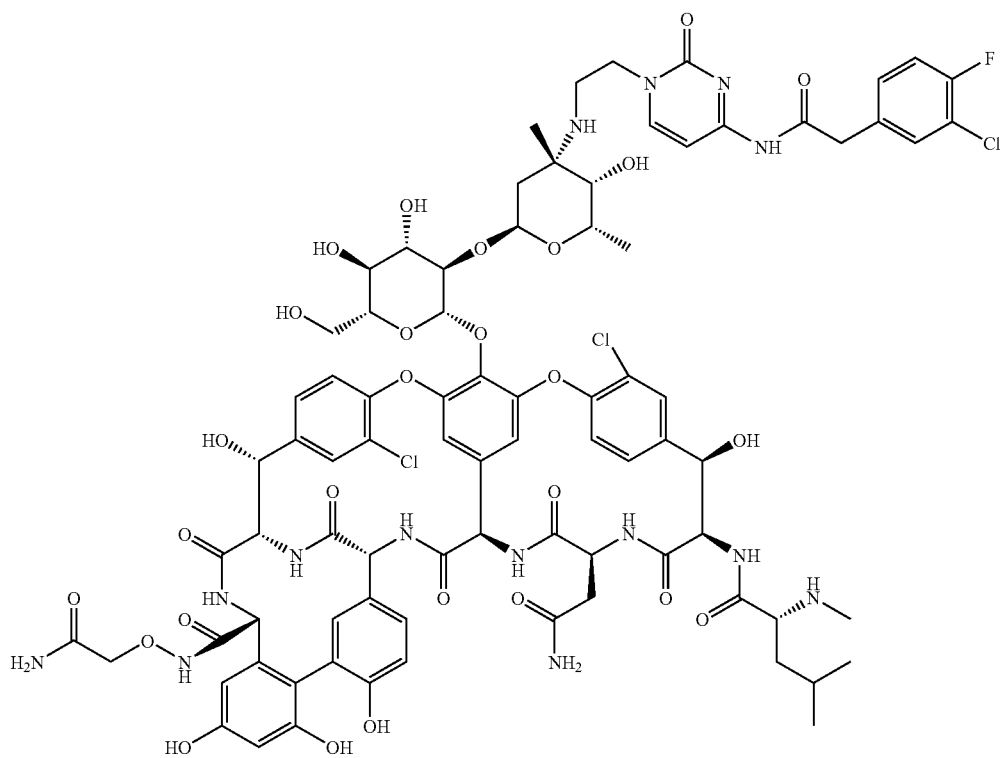

[M+H]$^+$=1827
Anal calcd. for $C_{82}H_{90}Cl_3FN_{14}O_{27} \cdot 11.5H_2O \cdot 2.5HCl$: C, 46.30%; H, 5.47%; N, 9.22%; Cl, 9.17%; F, 0.89%. Found: C, 46.27%; H, 5.36%; N, 9.38%; Cl, 9.24%; F, 0.94%.
Compound 117
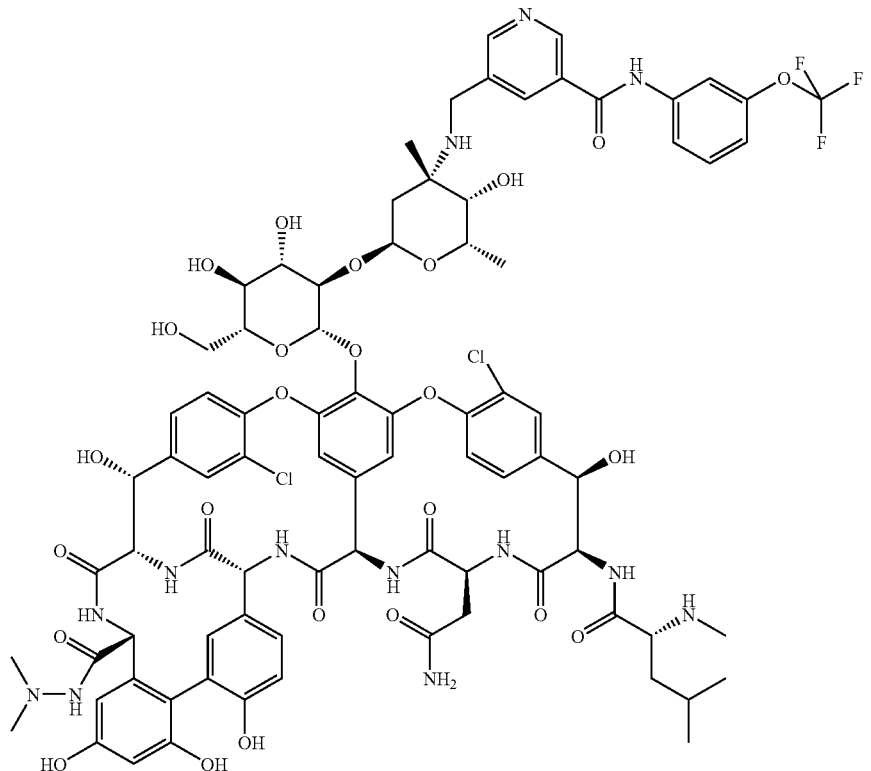
[Chemical Formula 156]

[M+H]⁺=1786
Anal calcd. for $C_{82}H_{90}Cl_2F_3N_{13}O_{25} \cdot 10.0H_2O \cdot 2.4HCl$: C, 47.97%; H, 5.52%; N, 8.87%; Cl, 7.60%; F, 2.78%. Found: C, 47.98%; H, 5.39%; N, 8.98%; Cl, 7.61%; F, 2.82%.
Compound 118
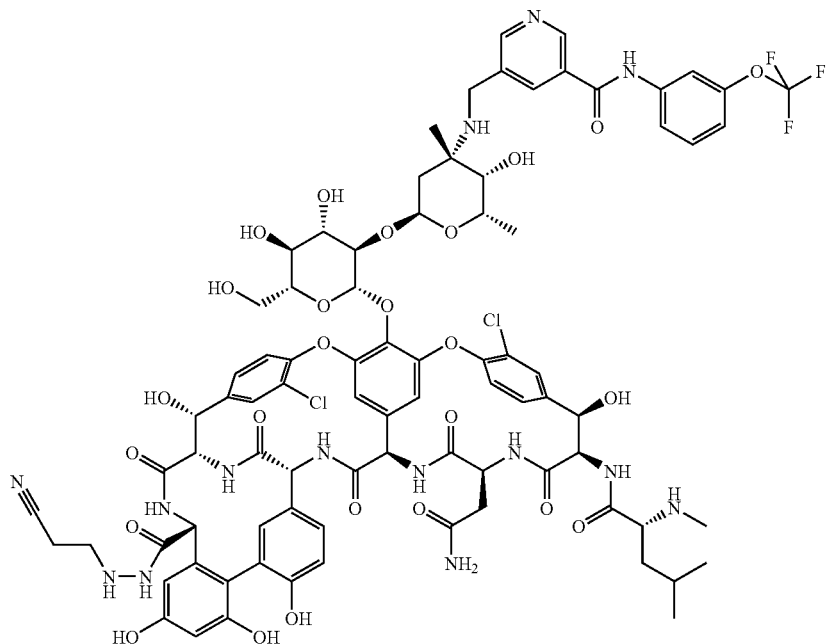
[Chemical Formula 157]

[M+H]⁺=1811
Anal calcd. for $C_{83}H_{89}Cl_2F_3N_{14}O_{25} \cdot 10.7H_2O \cdot 2.3HCl$: C, 47.76%; H, 5.44%; N, 9.40%; Cl, 7.30%; F, 2.73%. Found: C, 47.75%; H, 5.24%; N, 9.41%; Cl, 7.29%; F, 2.77%.
Compound 119
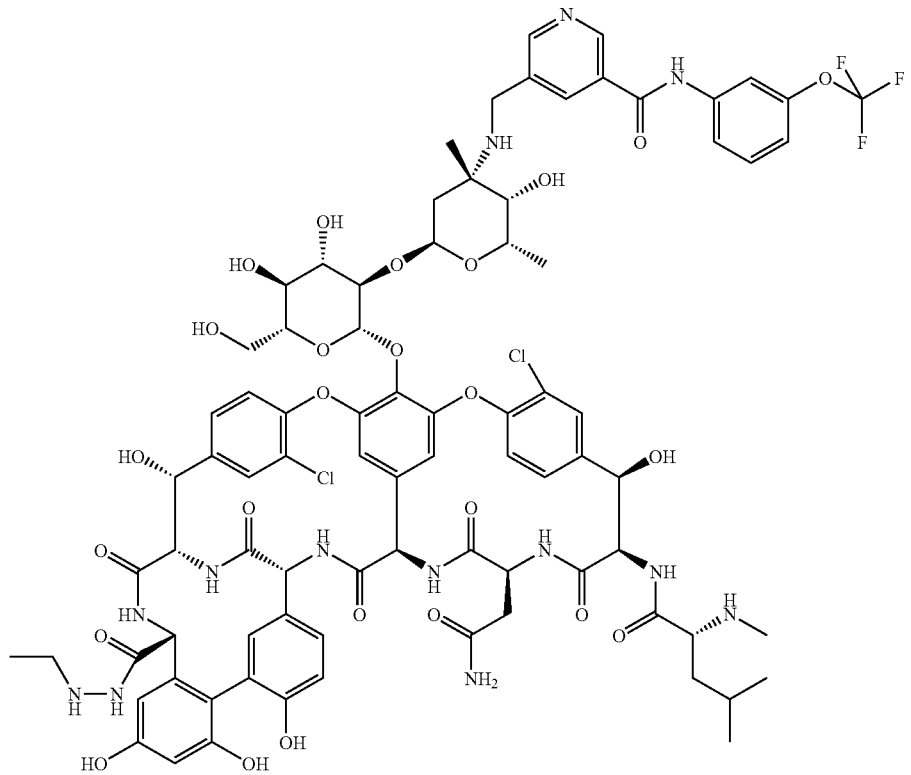
[Chemical Formula 158]

[M+H]⁺=1786
Anal calcd. for $C_{82}H_{90}Cl_2F_3N_{13}O_{25}\cdot 10.3H_2O\cdot 2.4HCl$: C, 47.84%; H, 5.53%; N, 8.85%; Cl, 7.58%; F, 2.77%. Found: C, 47.80%; H, 5.45%; N, 8.92%; Cl, 7.53%; F, 2.87%.
Compound 120
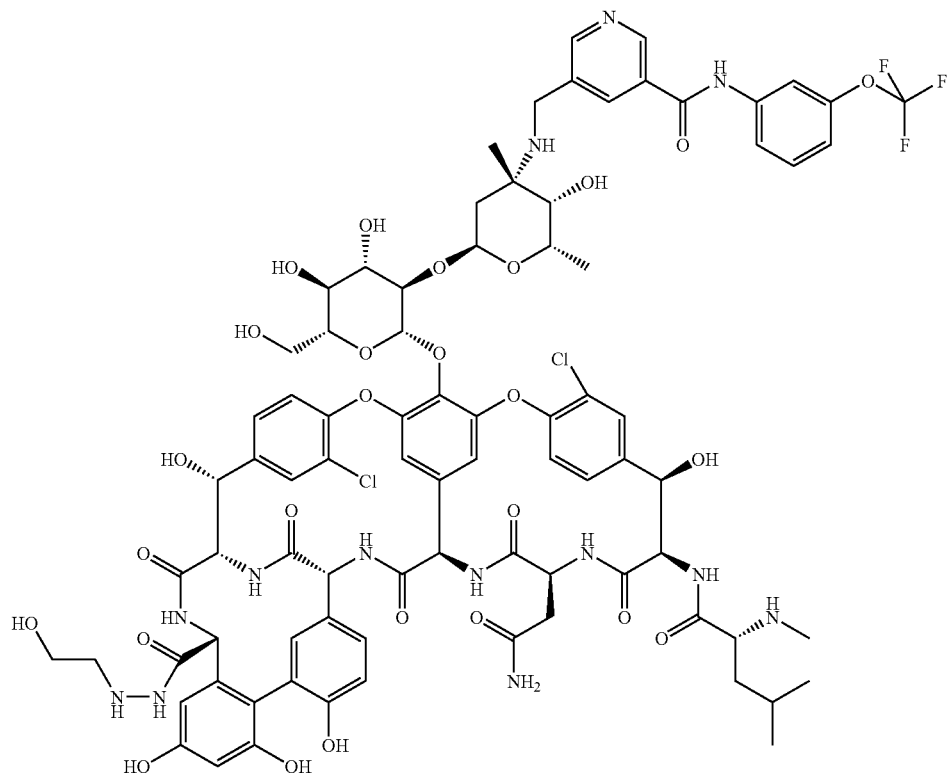
[Chemical Formula 159]

[M+H]⁺=1802
Anal calcd. for $C_{82}H_{90}Cl_2F_3N_{13}O_{26}\cdot 10.5H_2O\cdot 2.3HCl$: C, 47.47%; H, 5.50%; N, 8.78%; Cl, 7.35%; F, 2.75%. Found: C, 47.46%; H, 5.40%; N, 8.88%; Cl, 7.37%; F, 2.68%.
Compound 121
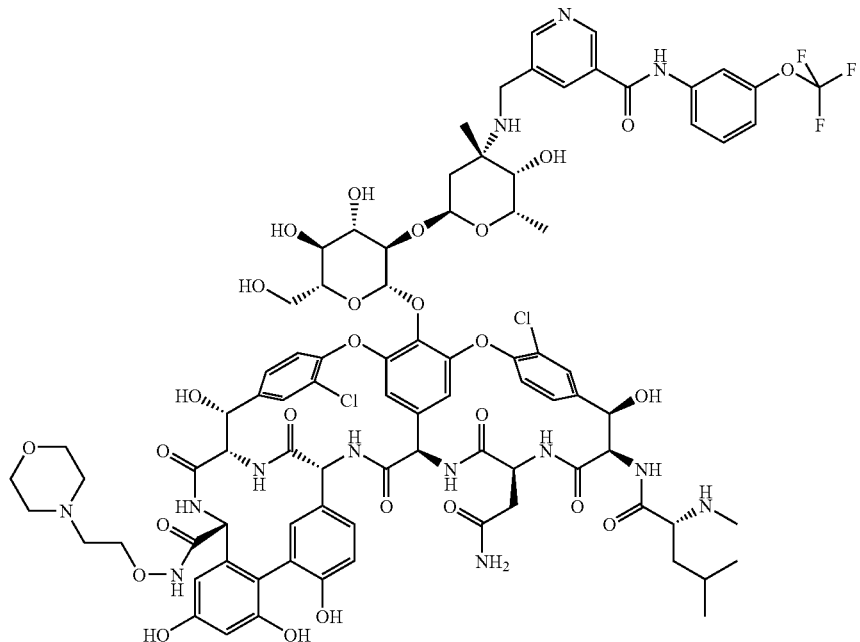
[Chemical Formula 160]

[M+H]⁺=1872
Anal calcd. for $C_{86}H_{96}Cl_2F_3N_{13}O_{27} \cdot 11.4H_2O \cdot 3.6HCl$: C, 46.77%; H, 5.59%; N, 8.25%; Cl, 8.99%; F, 2.58%. Found: C, 46.73%; H, 5.45%; N, 8.37%; Cl, 8.97%; F, 2.66%.
Compound 122
[Chemical Formula 161]
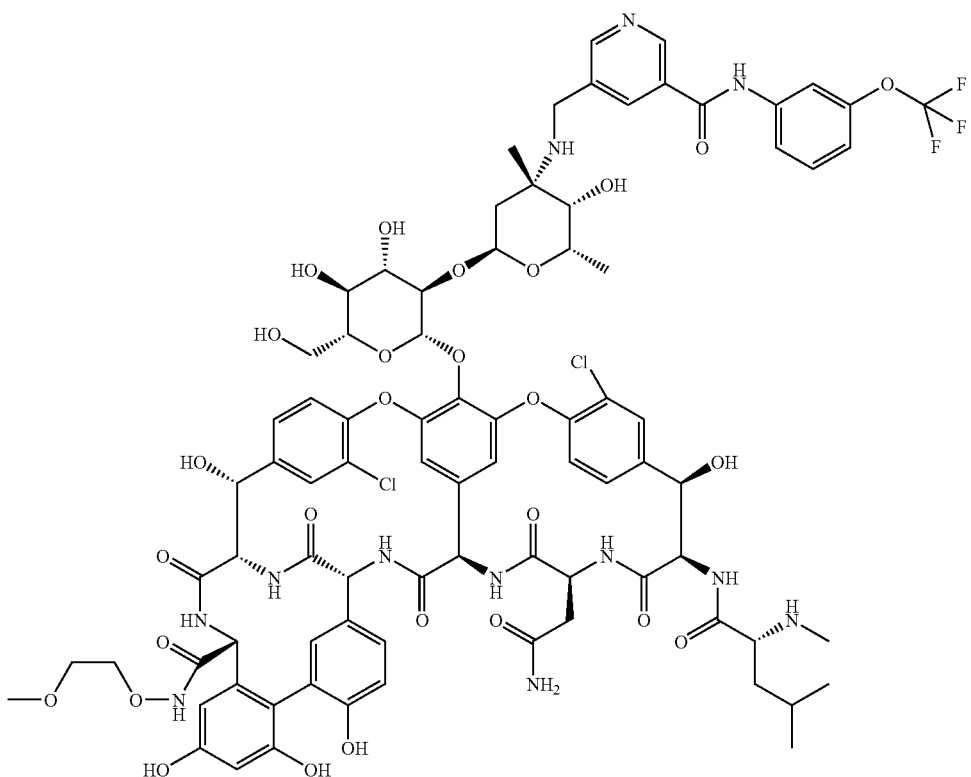

[M+H]⁺=1817
Anal calcd. for $C_{83}H_{91}Cl_2F_3N_{12}O_{27} \cdot 10.8H_2O \cdot 2.7HCl$: C, 47.26%; H, 5.51%; N, 7.97%; Cl, 7.90%; F, 2.70%. Found: C, 47.25%; H, 5.43%; N, 8.03%; Cl, 7.94%; F, 2.76%.
Compound 123
[Chemical Formula 162]
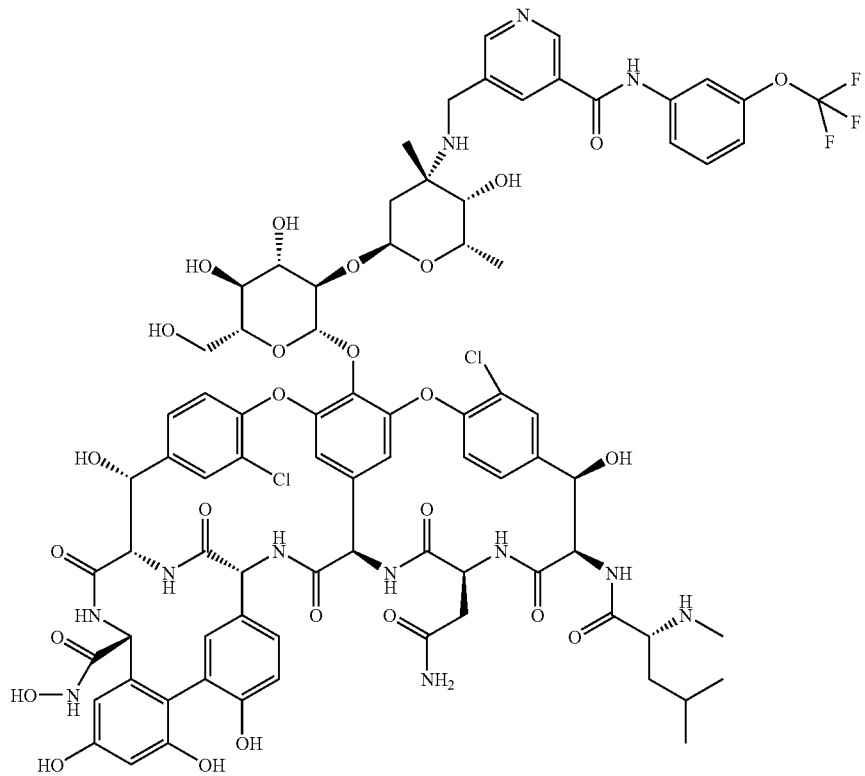

[M+H]⁺=1759
Anal calcd. for $C_{80}H_{85}Cl_2F_3N_{12}O_{26}\cdot 10.0H_2O\cdot 3.1HCl$: C, 46.83%; H, 5.31%; N, 8.19%; Cl, 8.81%; F, 2.78%. Found: C, 46.81%; H, 5.26%; N, 8.23%; Cl, 8.82%; F, 2.76%.
Compound 124
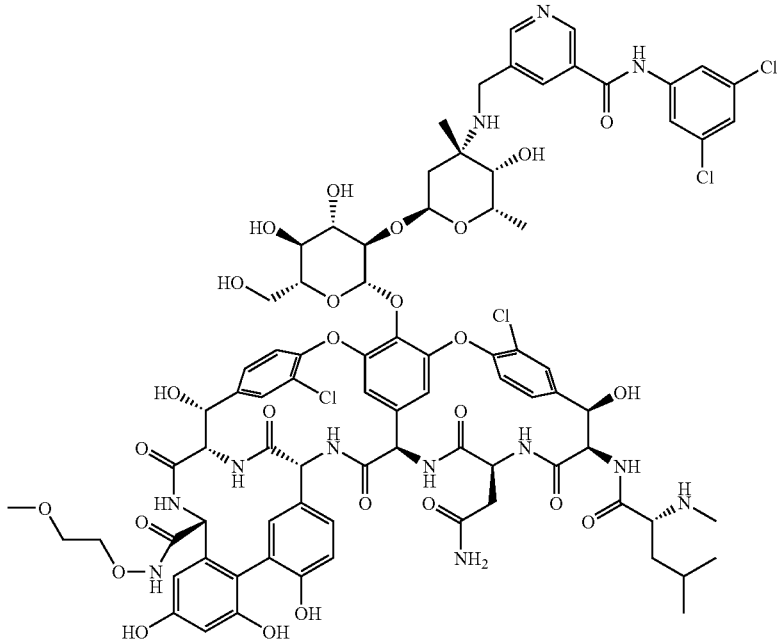
[Chemical Formula 163]
[M+H]⁺=1801
Anal calcd. for $C_{82}H_{90}Cl_4N_{12}O_{26}\cdot 9.9H_2O\cdot 3.0HCl$: C, 47.14%; H, 5.44%; N, 8.05%; Cl, 11.88%. Found: C, 47.11%; H, 5.36%; N, 8.30%; Cl, 11.83%.
Compound 125
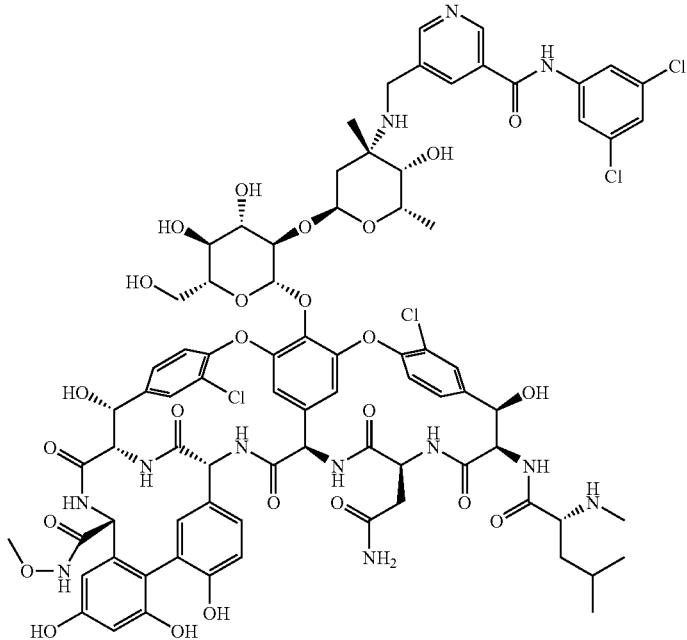
[Chemical Formula 164]

[M+H]⁺=1759
Anal calcd. for $C_{80}H_{86}Cl_4N_{12}O_{25}\cdot 11.5H_2O\cdot 2.2HCl$: C, 46.99%; H, 5.48%; N, 8.22%; Cl, 10.75%. Found: C, 46.96%; H, 5.36%; N, 8.33%; Cl, 10.72%.
Compound 126
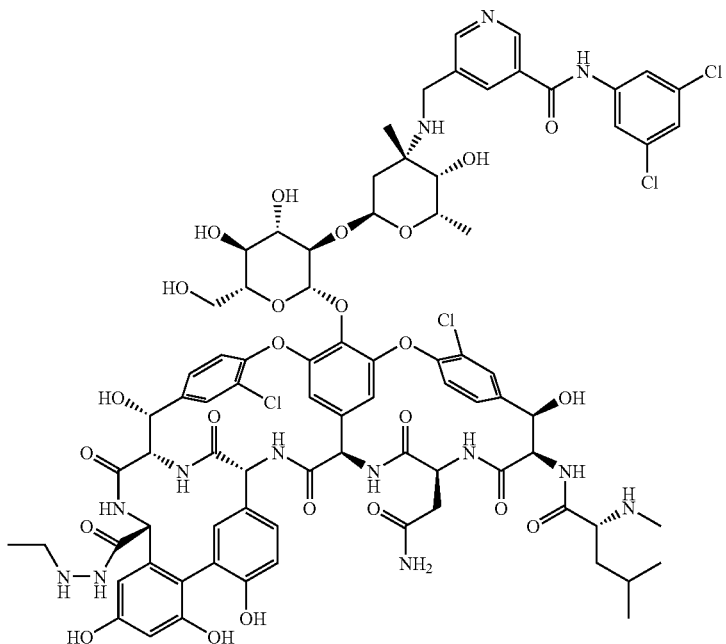
[Chemical Formula 165]

[M+H]⁺=1770
Anal calcd. for $C_{81}H_{89}Cl_4N_{13}O_{24} \cdot 11.9H_2O \cdot 2.4HCl$: C, 46.95%; H, 5.60%; N, 8.79%; Cl, 10.95%. Found: C, 46.92%; H, 5.49%; N, 8.86%; Cl, 11%.
Compound 127
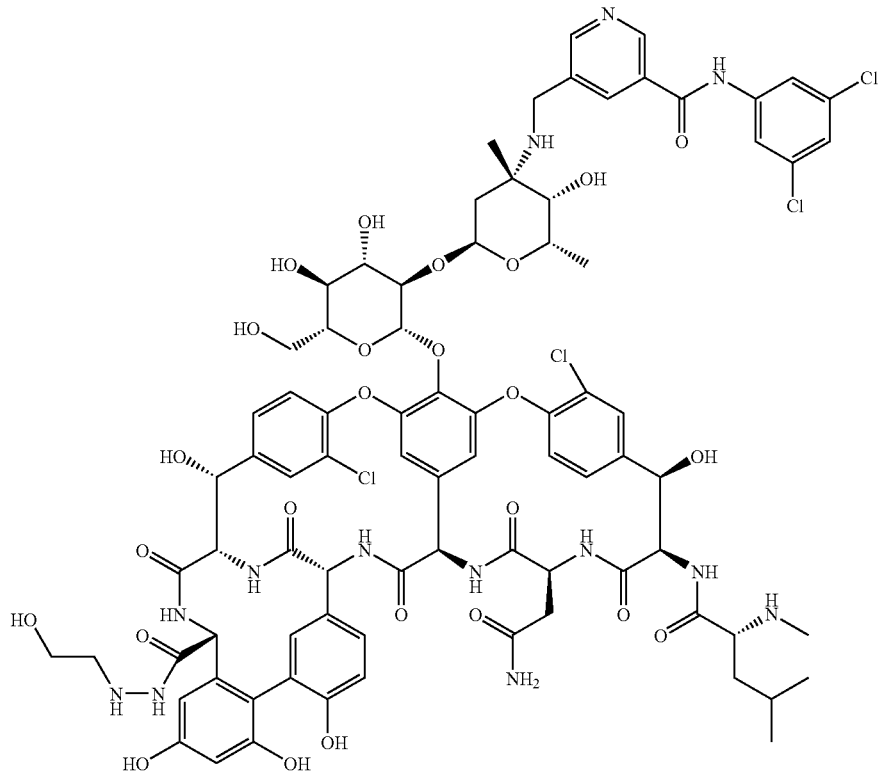
[Chemical Formula 166]

[M+H]⁺=1786
Anal calcd. for $C_{81}H_{89}Cl_4N_{13}O_{25} \cdot 11.3H_2O \cdot 2.1HCl$: C, 47.08%; H, 5.55%; N, 8.81%; Cl, 10.46%. Found: C, 47.03%; H, 5.52%; N, 8.98%; Cl, 10.40%.
Compound 128
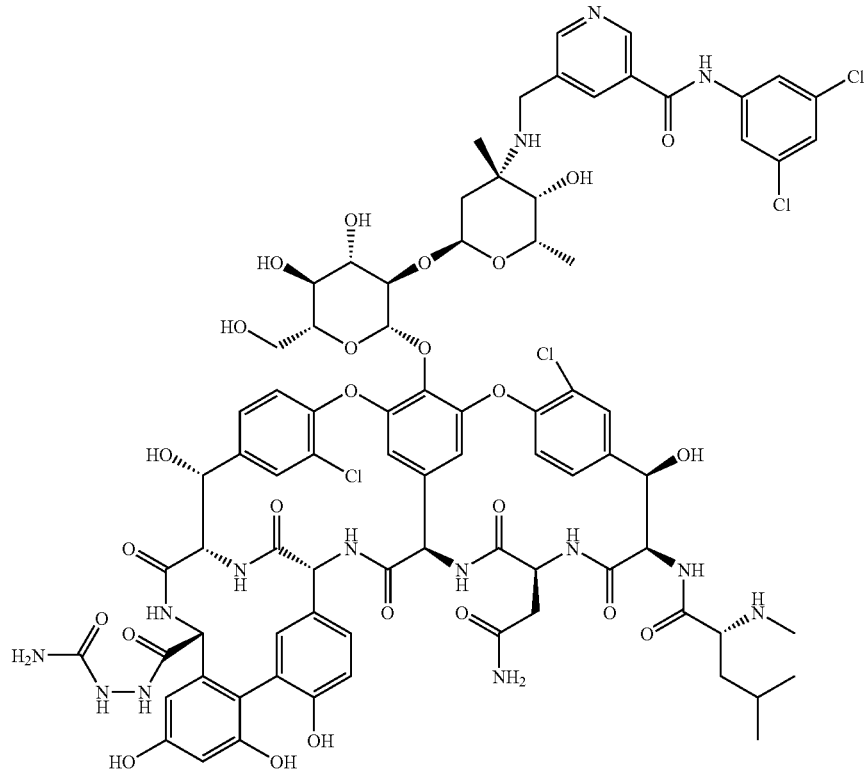
[Chemical Formula 167]

[M+H]⁺=1785
Anal calcd. for $C_{80}H_{86}Cl_4N_{14}O_{25}\cdot 10.6H_2O\cdot 3.0HCl$: C, 46.07%; H, 5.33%; N, 9.40%; Cl, 11.90%. Found: C, 46.04%; H, 5.20%; N, 9.47%; Cl, 11.89%.
Compound 129
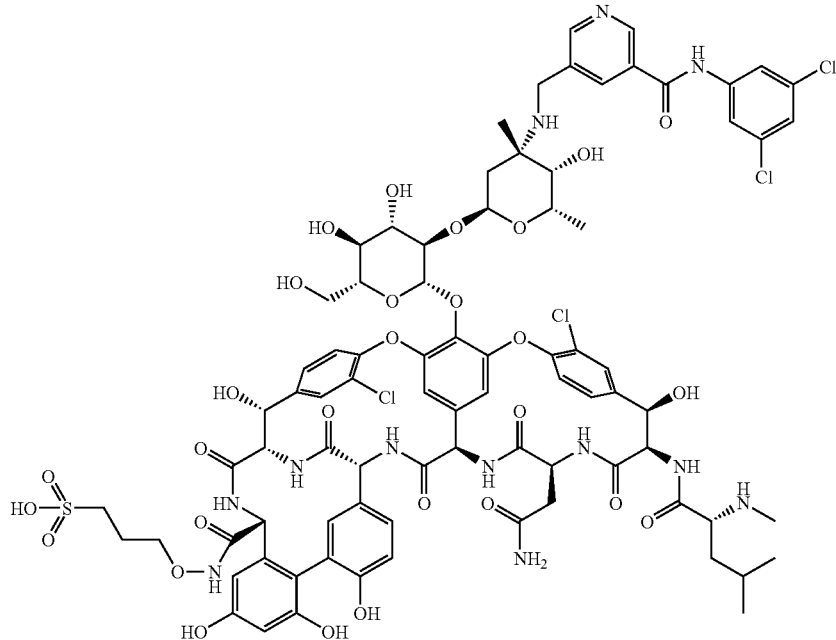
[Chemical Formula 168]
[M+H]⁺=1866
Anal calcd. for $C_{82}H_{90}Cl_4N_{12}O_{28}S_1\cdot 8.5H_2O\cdot 2.6HCl$: C, 46.60%; H, 5.23%; N, 7.95%; Cl, 11.07%; S, 1.52%. Found: C, 46.57%; H, 5.45%; N, 8.22%; Cl, 11.11%; S, 1.31%.
Compound 130
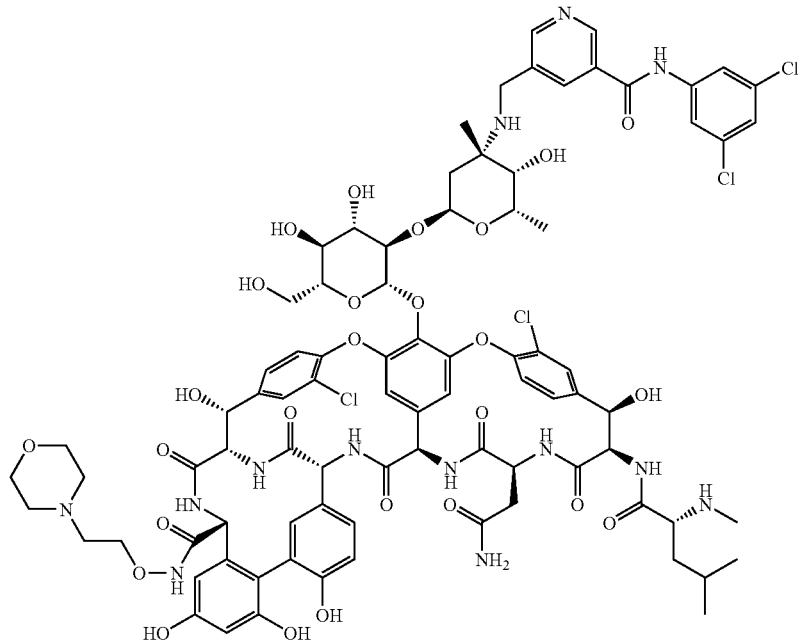
[Chemical Formula 169]

[M+H]$^+$=1856
Anal calcd. for $C_{85}H_{95}Cl_4N_{13}O_{26}\cdot13.4H_2O\cdot3.1HCl$: C, 46.17%; H, 5.69%; N, 8.24%; Cl, 11.38%. Found: C, 46.12%; H, 5.58%; N, 8.39%; Cl, 11.44%.
Compound 131
[Chemical Formula 170]
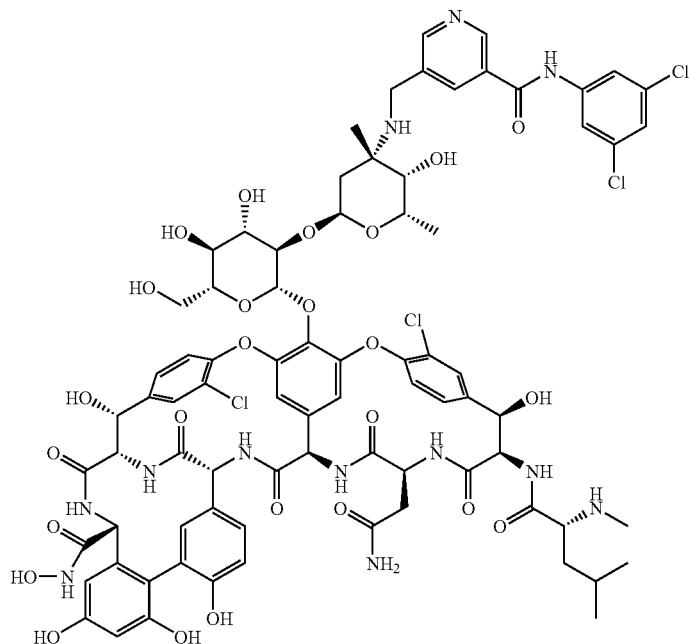

[M+H]$^+$=1743
Anal calcd. for $C_{79}H_{84}Cl_4N_{12}O_{25} \cdot 10.6H_2O \cdot 2.3HCl$: C, 47.01%; H, 5.37%; N, 8.33%; Cl, 11.07%. Found: C, 47.03%; H, 5.33%; N, 8.23%; Cl, 11.08%.
Compound 132
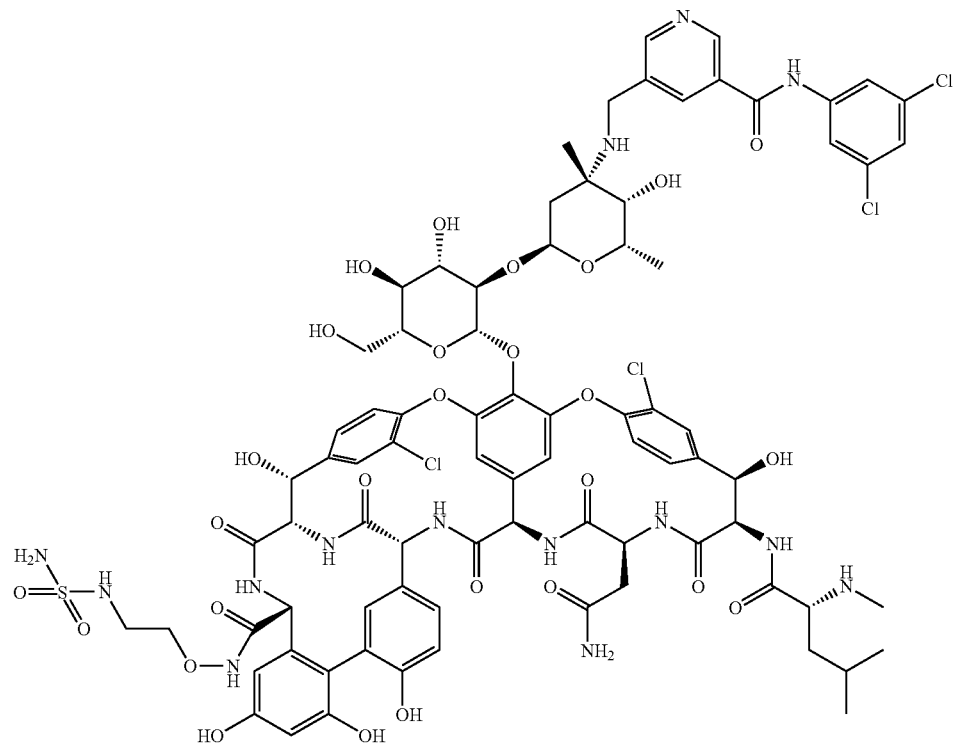
[Chemical Formula 171]

[M+H]⁺=1865
Anal calcd. for $C_{81}H_{90}Cl_4N_{14}O_{27}S_1 \cdot 9.5H_2O \cdot 2.3HCl$: C, 45.88%; H, 5.29%; N, 9.25%; Cl, 10.53%; S, 1.51%. Found: C, 45.93%; H, 5.27%; N, 9.12%; Cl, 10.46%; S, 1.33%.
Compound 133
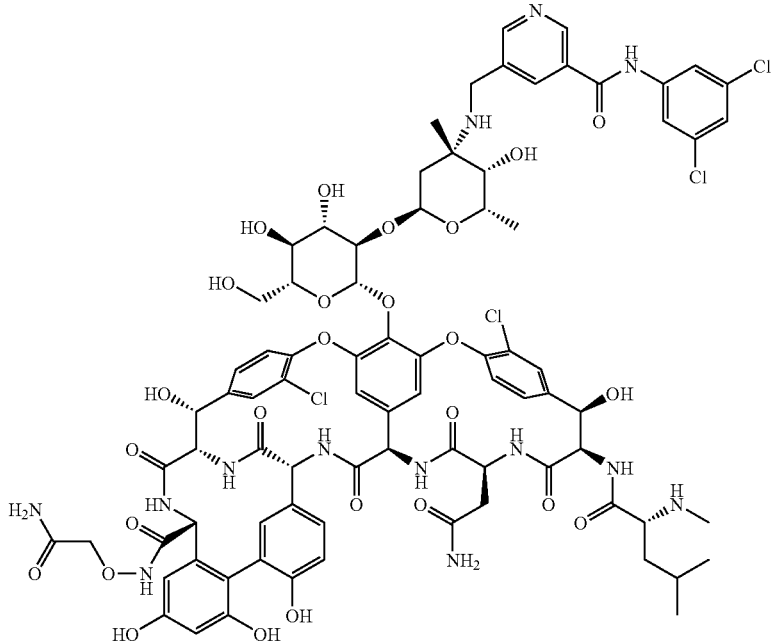
[Chemical Formula 172]
[M+H]⁺=1800
Anal calcd. for $C_{81}H_{87}Cl_4N_{13}O_{26} \cdot 10.9H_2O \cdot 2.4HCl$: C, 46.68%; H, 5.38%; N, 8.74%; Cl, 10.89%. Found: C, 46.67%; H, 5.41%; N, 8.81%; Cl, 10.92%.
Compound 134
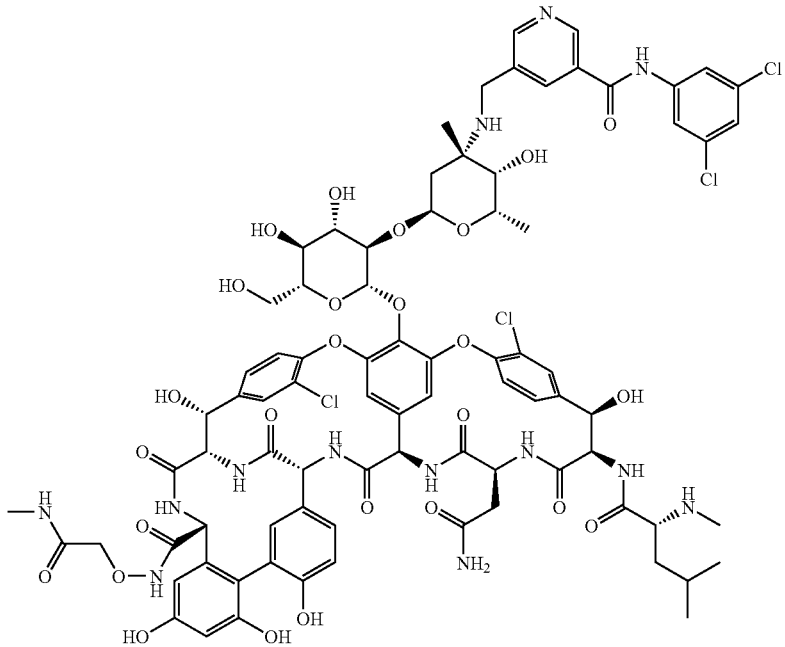
[Chemical Formula 173]

[M+H]⁺=1814
Anal calcd. for $C_{82}H_{89}Cl_4N_{13}O_{26}·10.2H_2O·2.3HCl$: C, 47.30%; H, 5.41%; N, 8.75%; Cl, 10.73%. Found: C, 47.26%; H, 5.34%; N, 8.87%; Cl, 10.75%.
Compound 135
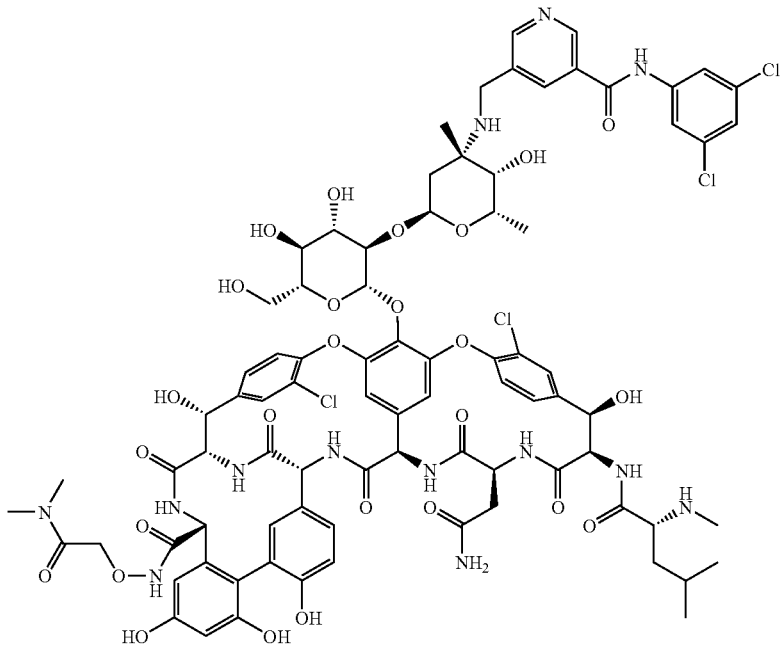
[Chemical Formula 174]
[M+H]⁺=1828
Anal calcd. for $C_{83}H_{91}Cl_4N_{13}O_{26}·10.8H_2O·2.4HCl$: C, 47.23%; H, 5.49%; N, 8.63%; Cl, 10.75%. Found: C, 47.26%; H, 5.34%; N, 8.87%; Cl, 10.75%.
Compound 136
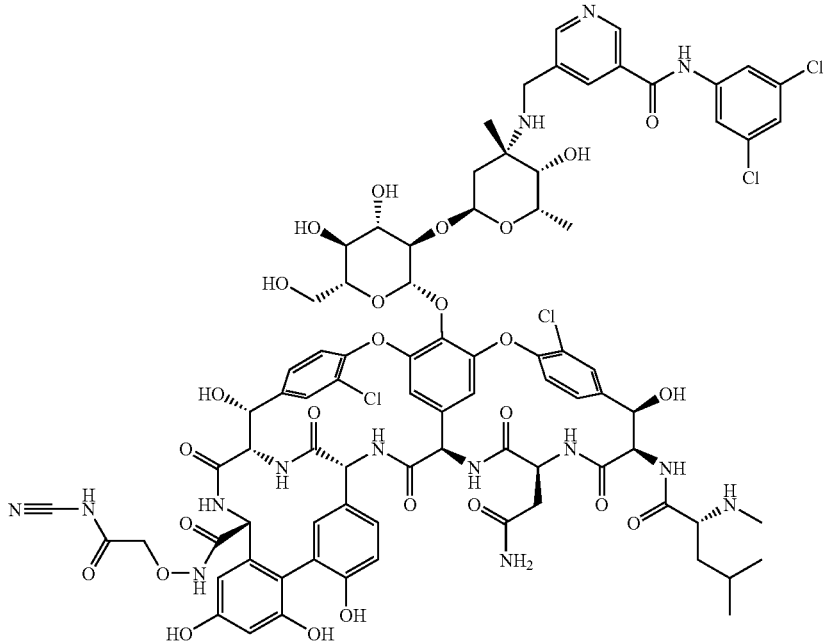
[Chemical Formula 175]

[M+H]+=1825
Anal calcd. for $C_{82}H_{86}Cl_4N_{14}O_{26} \cdot 10.6H_2O \cdot 2.3HCl$: C, 46.89%; H, 5.26%; N, 9.34%; Cl, 10.63%. Found: C, 46.91%; H, 5.27%; N, 9.38%; Cl, 10.59%.
Compound 137
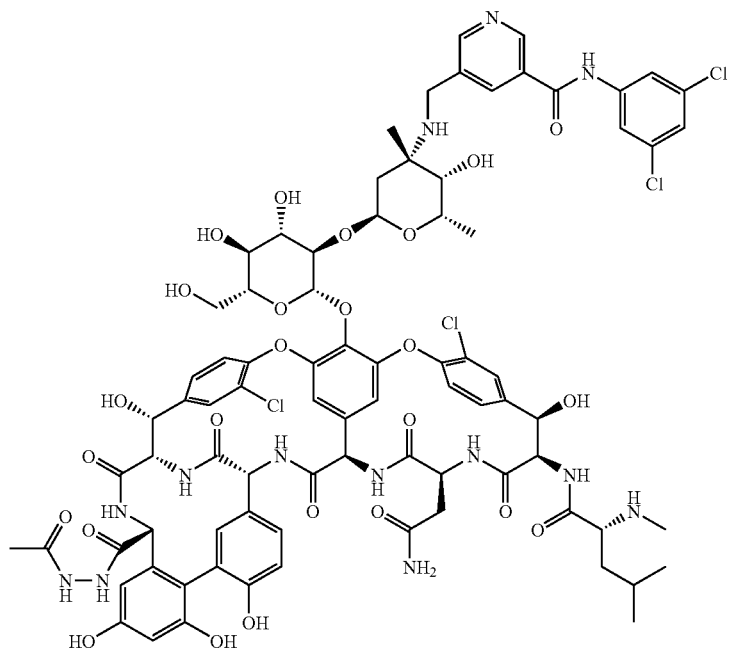
[Chemical Formula 176]
[M+H]+=1784
Anal calcd. for $C_{81}H_{87}Cl_4N_{13}O_{25} \cdot 11H_2O \cdot 2.2HCl$: C, 47.16%; H, 5.43%; N, 8.83%; Cl, 10.66%. Found: C, 47.13%; H, 5.39%; N, 8.99%; Cl, 10.68%.
Compound 138
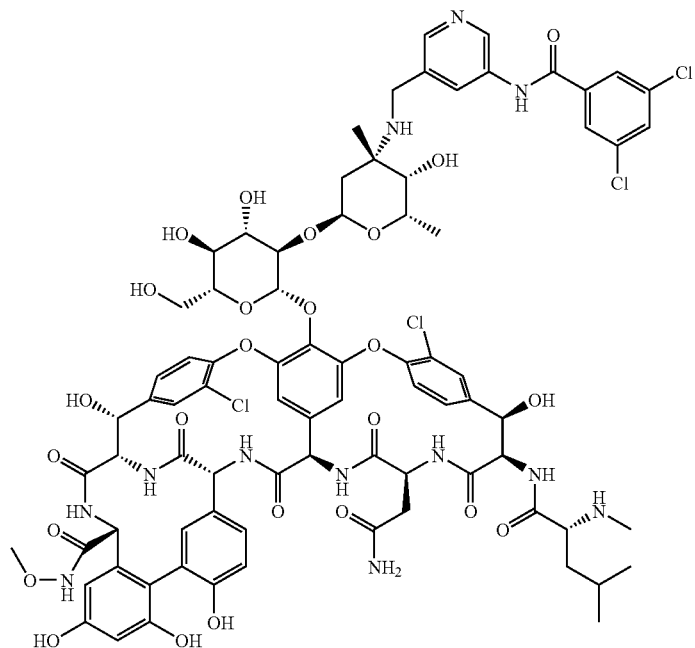
[Chemical Formula 177]

[M+H]⁺=1757
Anal. calcd. for $C_{80}H_{86}Cl_4N_{12}O_{25} \cdot 10.6H_2O \cdot 2.3HCl$: C, 47.28%; H, 5.43%; N, 8.27%; Cl, 10.99%. Found: C, 47.26%; H, 5.34%; N, 8.37%; Cl, 11.04%.
Compound 139
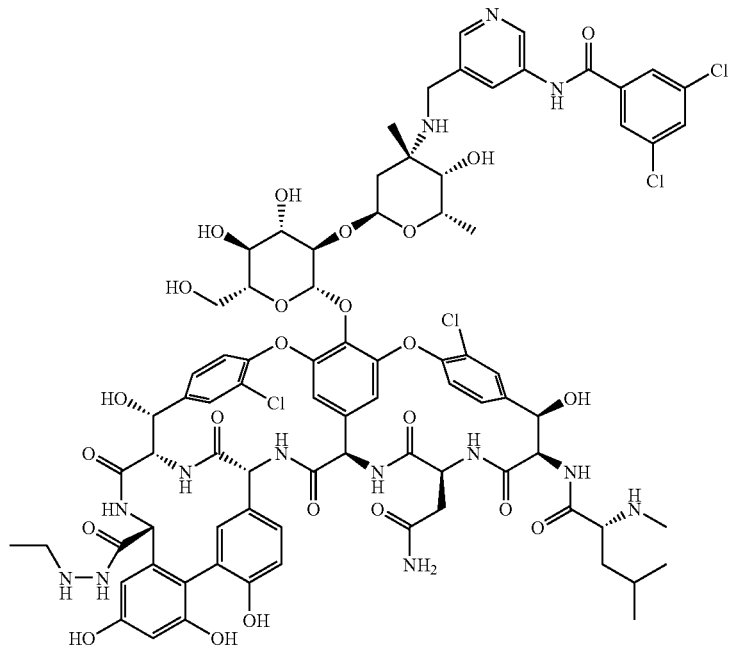
[Chemical Formula 178]
[M+H]⁺=1770
Anal. calcd. for $C_{81}H_{89}Cl_4N_{13}O_{24} \cdot 11.1H_2O \cdot 2.8HCl$: C, 46.94%; H, 5.54%; N, 8.79%; Cl, 11.63%. Found: C, 46.89%; H, 5.41%; N, 8.87%; Cl, 11.65%.
Compound 140
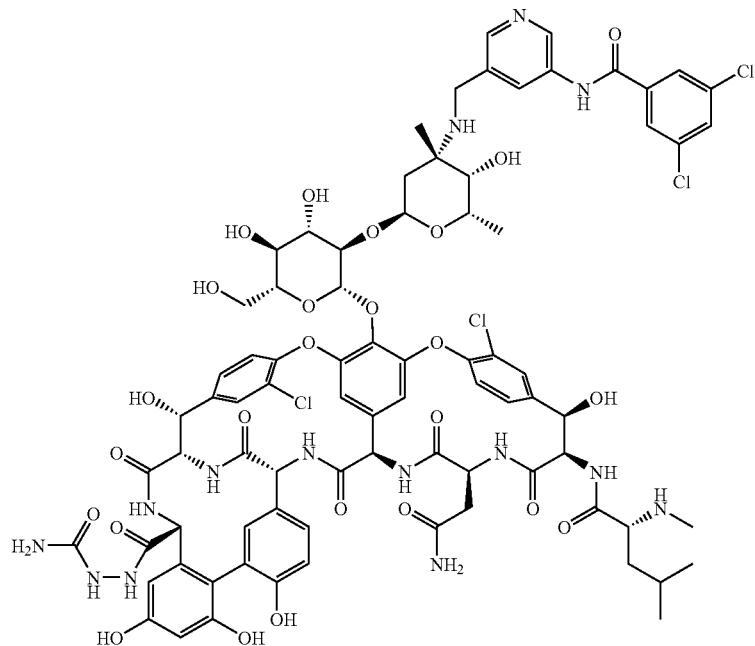
[Chemical Formula 179]

[M+H]⁺=1785
Anal calcd. for $C_{80}H_{86}Cl_4N_{14}O_{25} \cdot 11.8H_2O \cdot 2.8HCl$: C, 45.75%; H, 5.39%; N, 9.34%; Cl, 11.48%. Found: C, 45.72%; H, 5.26%; N, 9.43%; Cl, 11.45%.
Compound 141
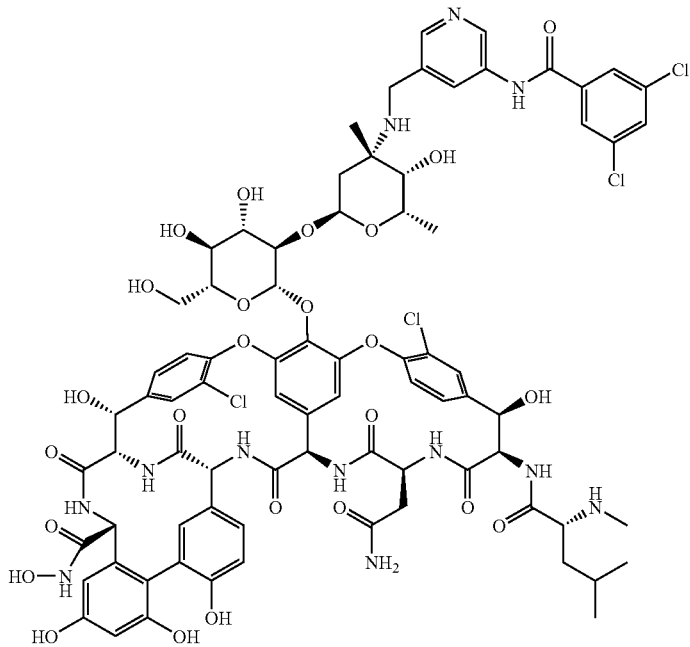
[Chemical Formula 180]
[M+H]⁺=1743
Anal calcd. for $C_{79}H_{84}Cl_4N_{12}O_{25} \cdot 11.2H_2O \cdot 2.3HCl$: C, 46.76%; H, 5.40%; N, 8.28%; Cl, 11.01%. Found: C, 46.73%; H, 5.32%; N, 8.37%; Cl, 11.06%.
Compound 142
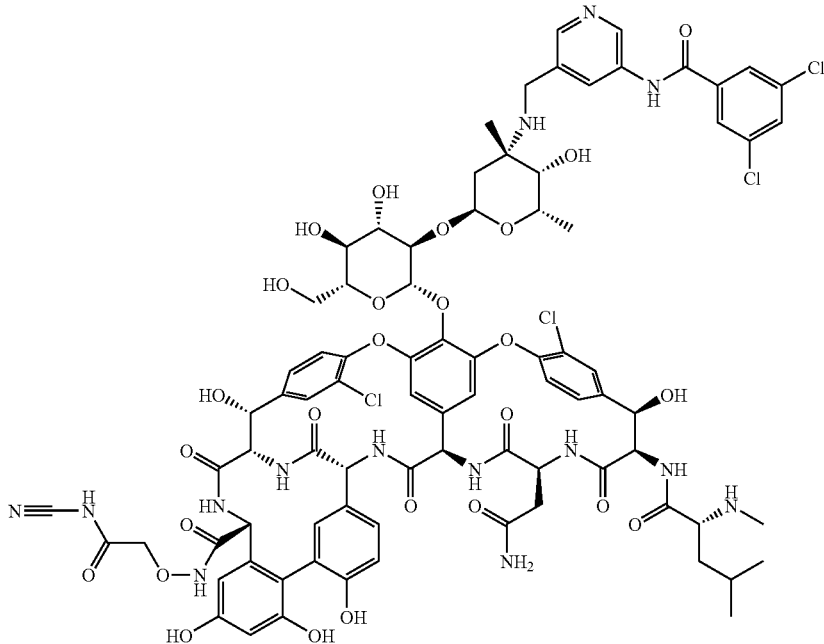
[Chemical Formula 181]

[M+H]$^+$=1825
Anal calcd. for $C_{82}H_{86}Cl_4N_{12}O_{26} \cdot 12.0H_2O \cdot 1.8HCl$: C, 46.74%; H, 5.35%; N, 9.31%; Cl, 9.76%. Found: C, 46.84%; H, 5.25%; N, 9.22%; Cl, 9.81%.
Compound 143
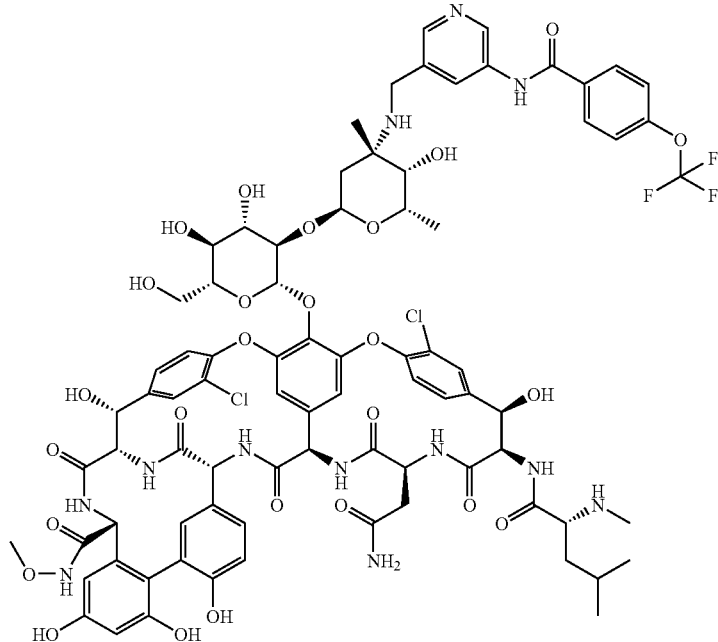
[Chemical Formula 182]
[M+H]$^+$=1772
Anal calcd. for $C_{81}H_{87}Cl_2F_3N_{12}O_{26} \cdot 11.6H_2O \cdot 2.0HCl$: C, 47.35%; H, 5.50%; N, 8.18%; Cl, 6.90%; F, 2.77%. Found: C, 47.29%; H, 5.32%; N, 8.38%; Cl, 6.91%; F, 2.66%.
Compound 144
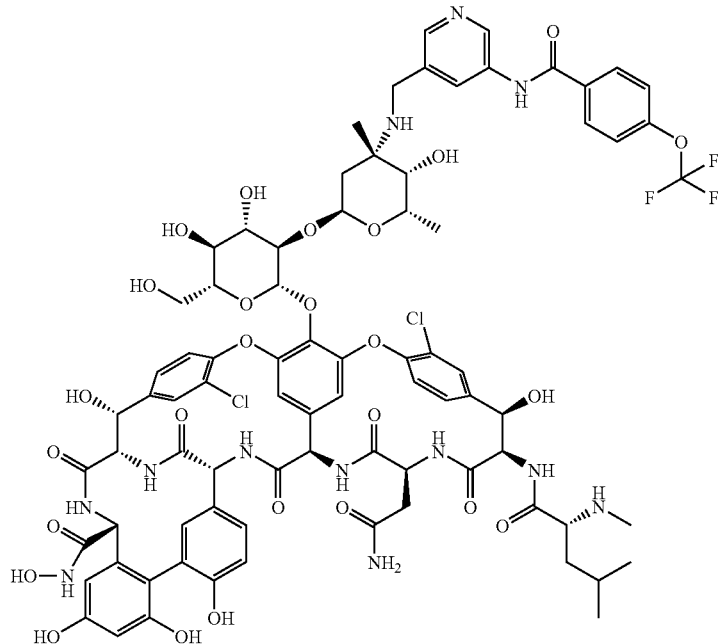
[Chemical Formula 183]

[M+H]⁺=1759
Anal calcd. for $C_{80}H_{85}Cl_2F_3N_{12}O_{26}\cdot11.0H_2O\cdot2.3HCl$: C, 47.09%; H, 5.40%; N, 8.24%; Cl, 7.47%; F, 2.79%. Found: C, 47.07%; H, 5.33%; N, 8.31%; Cl, 7.44%; F, 2.74%.
Compound 145
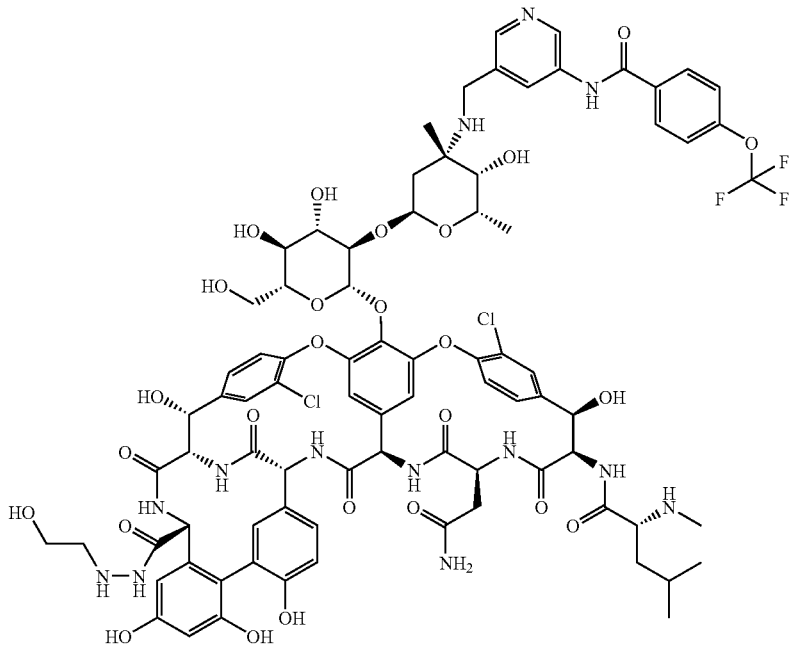
[Chemical Formula 184]
[M+H]⁺=1802
Anal calcd. for $C_{82}H_{90}Cl_2F_3N_{13}O_{26}\cdot11.7H_2O\cdot2.5HCl$: C, 46.82%; H, 5.55%; N, 8.66%; Cl, 7.58%; F, 2.71%. Found: C, 46.81%; H, 5.46%; N, 8.71%; Cl, 7.50%; F, 2.63%.
Compound 146
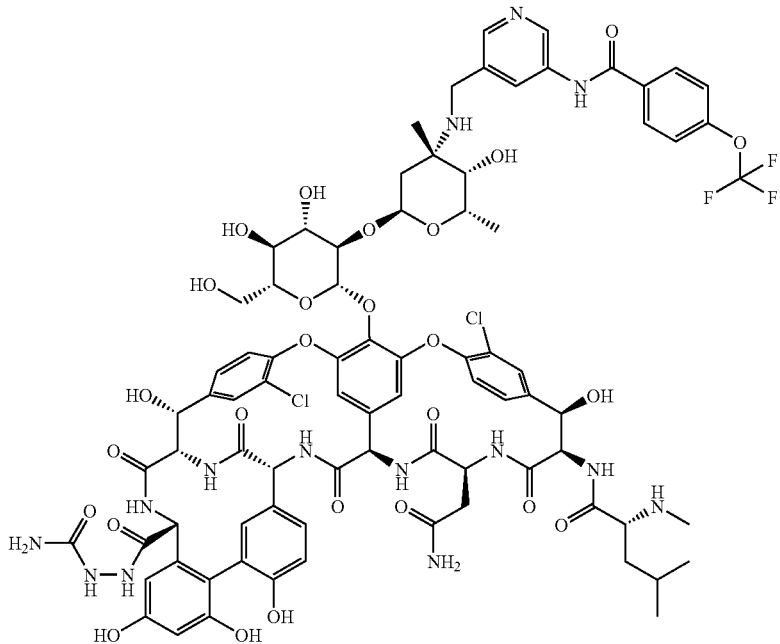
[Chemical Formula 185]

[M+H]⁺=1801
Anal calcd. for $C_{81}H_{87}Cl_2F_3N_{14}O_{26} \cdot 12.6H_2O \cdot 2.2HCl$: C, 46.16%; H, 5.47%; N, 9.30%; Cl, 7.06%; F, 2.70%. Found: C, 46.15%; H, 5.29%; N, 9.40%; Cl, 7.06%; F, 2.65%.
Compound 147
[Chemical Formula 186]
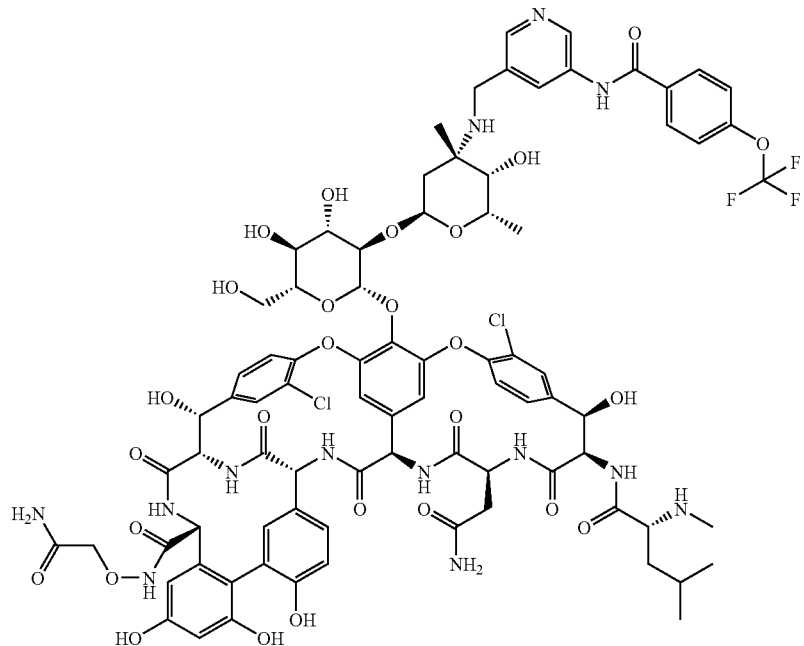
[M+H]⁺=1815
Anal calcd. for $C_{82}H_{88}Cl_2F_3N_{13}O_{27} \cdot 9.8H_2O \cdot 2.4HCl$: C, 47.36%; H, 5.33%; N, 8.76%; Cl, 7.50%; F, 2.74%. Found: C, 47.30%; H, 5.23%; N, 8.85%; Cl, 7.49%; F, 2.68%.
Compound 148
[Chemical Formula 187]
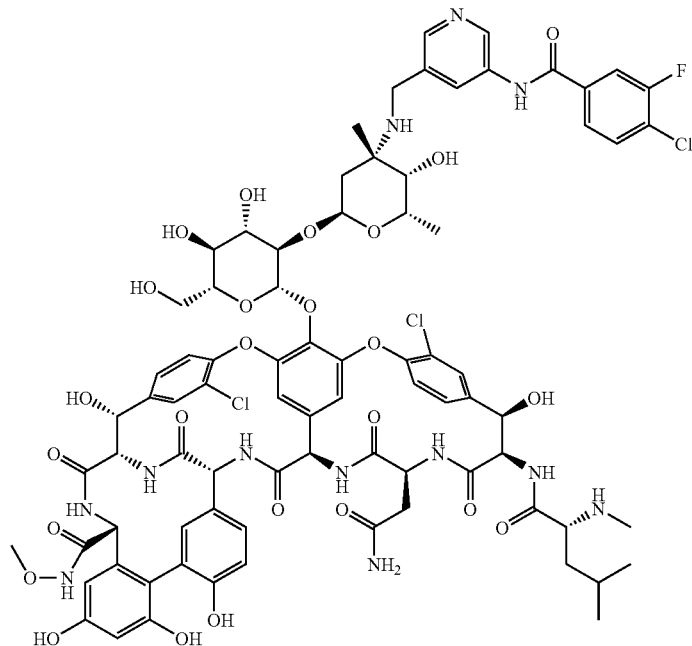

[M+H]⁺=1741
Anal calcd. for $C_{80}H_{86}Cl_3F_1N_{12}O_{25} \cdot 11.9H_2O \cdot 3.1HCl$: C, 46.45%; H, 5.50%; N, 8.13%; Cl, 10.46%; F, 0.92%. Found: C, 46.42%; H, 5.32%; N, 8.23%; Cl, 10.37%; F, 1.11%.
Compound 149
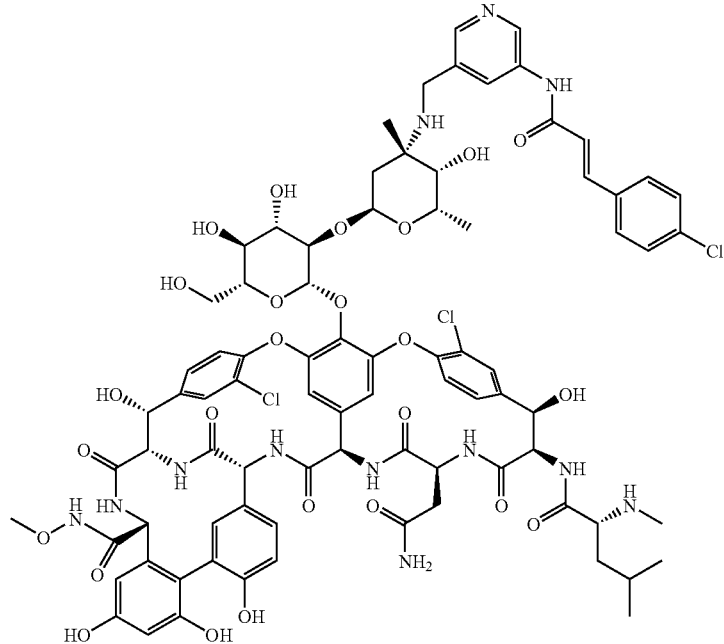
[Chemical Formula 188]
[M+H]⁺=1747
Anal calcd. for $C_{82}H_{89}Cl_3N_{12}O_{25} \cdot 12.0H_2O \cdot 2.3HCl$: C, 48.07%; H, 5.67%; N, 8.20%; Cl, 9.17%. Found: C, 48.04%; H, 5.54%; N, 8.27%; Cl, 9.23%.
Compound 150
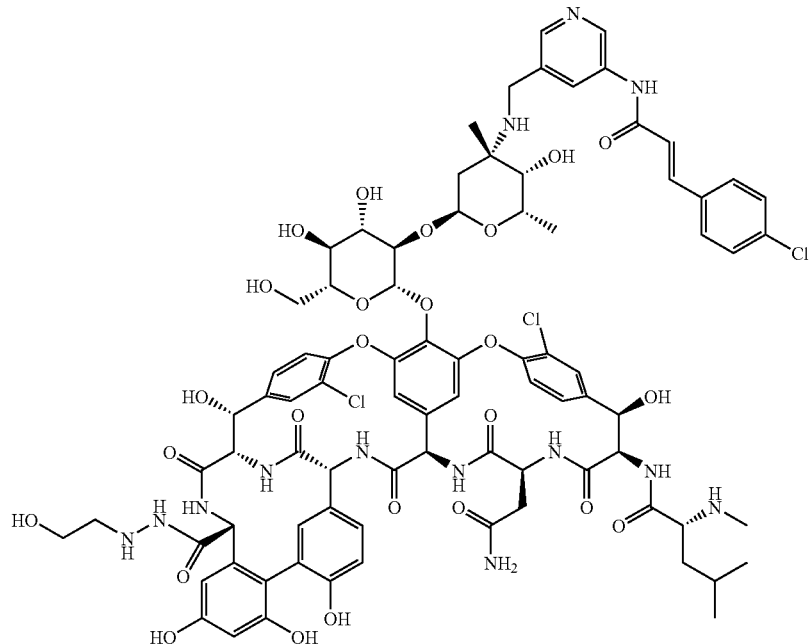
[Chemical Formula 189]

[M+H]$^+$=1776
Anal. calcd. for $C_{83}H_{92}Cl_3N_{13}O_{25} \cdot 11.3H_2O \cdot 2.5HCl$: C, 48.09%; H, 5.69%; N, 8.78%; Cl, 9.41%. Found: C, 48.08%; H, 5.66%; N, 8.97%; Cl, 9.33%.
Compound 151
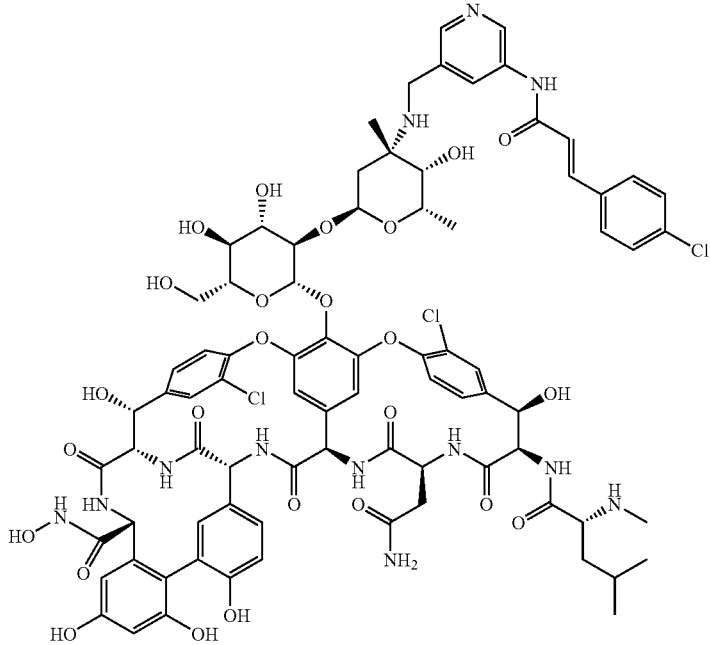
[Chemical Formula 190]
[M+H]$^+$=1733
Anal. calcd. for $C_{81}H_{87}Cl_3N_{12}O_{25} \cdot 12.0H_2O \cdot 2.3HCl$: C, 47.81%; H, 5.61%; N, 8.26%; Cl, 9.23%. Found: C, 47.78%; H, 5.56%; N, 8.31%; Cl, 9.18%.
Compound 152
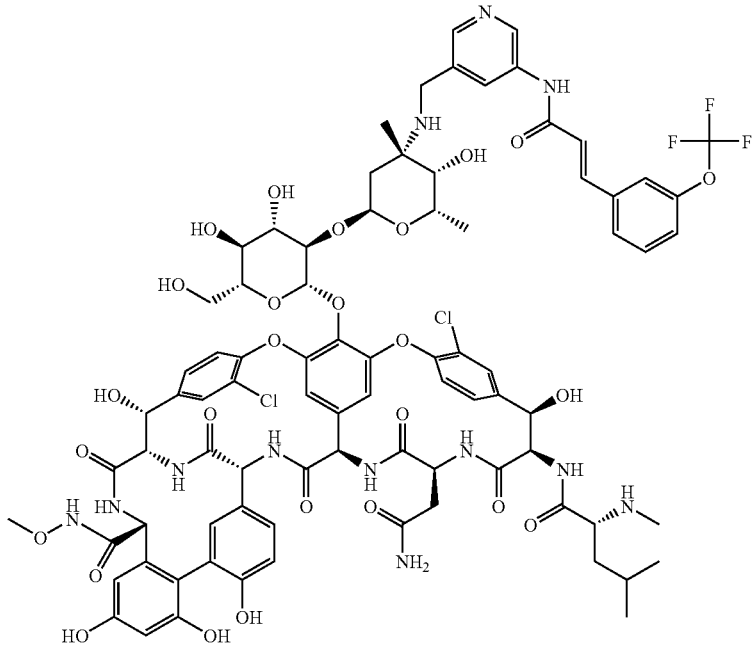
[Chemical Formula 191]

[M+H]⁺=1797
Anal calcd. for $C_{83}H_{89}Cl_2F_3N_{12}O_{26}\cdot 10.6H_2O\cdot 2.7HCl$: C, 47.74%; H, 5.45%; N, 8.05%; Cl, 7.98%; F, 2.73%. Found: C, 47.70%; H, 5.37%; N, 8.22%; Cl, 8.00%; F, 2.70%.
Compound 153
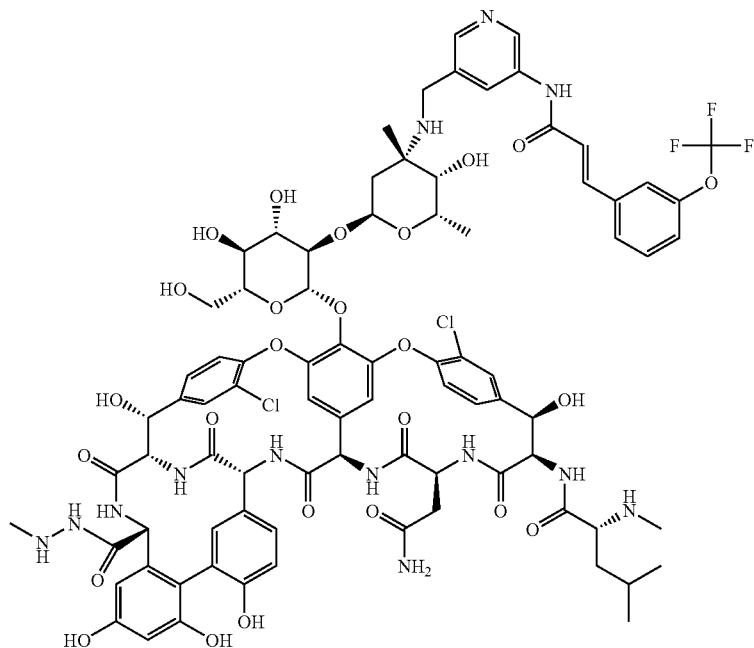
[Chemical Formula 192]
[M+H]⁺=1796
Anal calcd. for $C_{83}H_{90}Cl_2F_3N_{13}O_{25}\cdot 11.5H_2O\cdot 2.7HCl$: C, 47.40%; H, 5.54%; N, 8.66%; Cl, 7.92%; F, 2.71%. Found: C, 47.32%; H, 5.49%; N, 8.86%; Cl, 7.92%; F, 2.61%.
Compound 154
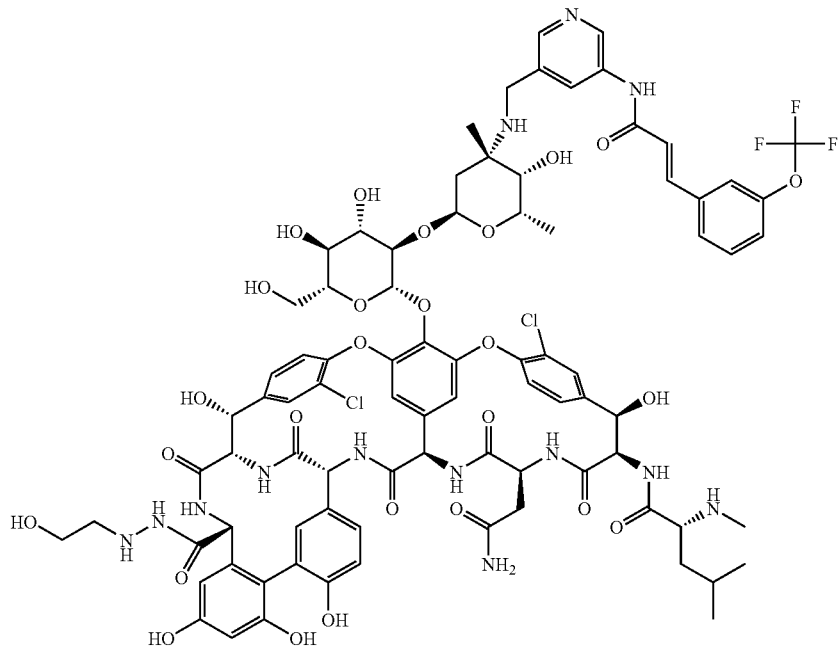
[Chemical Formula 193]

[M+H]⁺=1826
Anal calcd. for $C_{84}H_{92}Cl_2F_3N_{13}O_{26} \cdot 11.4H_2O \cdot 2.6HCl$: C, 47.42%; H, 5.56%; N, 8.56%; Cl, 7.66%; F, 2.68%. Found: C, 47.41%; H, 5.42%; N, 8.71%; Cl, 7.60%; F, 2.63%.
Compound 155
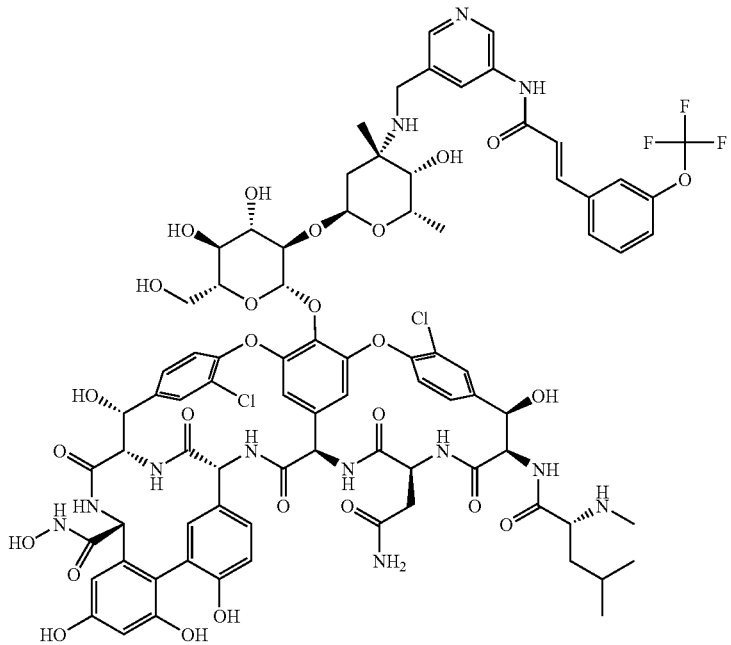
[Chemical Formula 194]
[M+H]⁺=1783
Anal calcd. for $C_{82}H_{87}Cl_2F_3N_{12}O_{26} \cdot 11.1H_2O \cdot 2.4HCl$: C, 47.53%; H, 5.43%; N, 8.11%; Cl, 7.53%; F, 2.75%. Found: C, 47.37%; H, 5.51%; N, 8.41%; Cl, 7.61%; F, 2.63%.
Compound 156
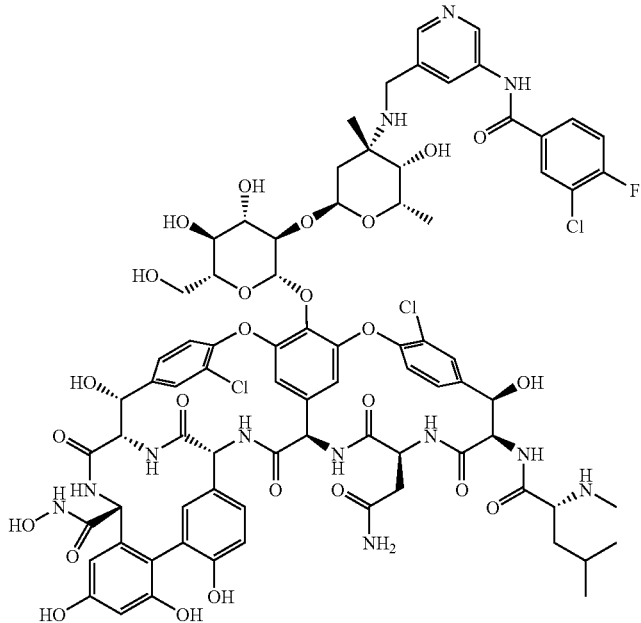
[Chemical Formula 195]

[M+H]$^+$=1725
Anal calcd. for $C_{79}H_{84}Cl_3FN_{12}O_{25} \cdot 10.4H_2O \cdot 2.2HCl$: C, 47.57%; H, 5.41%; N, 8.43%; Cl, 9.24%; F, 0.95%. Found: C, 47.51%; H, 5.40%; N, 8.73%; Cl, 9.16%; F, 1.00%.
Compound 157
[Chemical Formula 196]
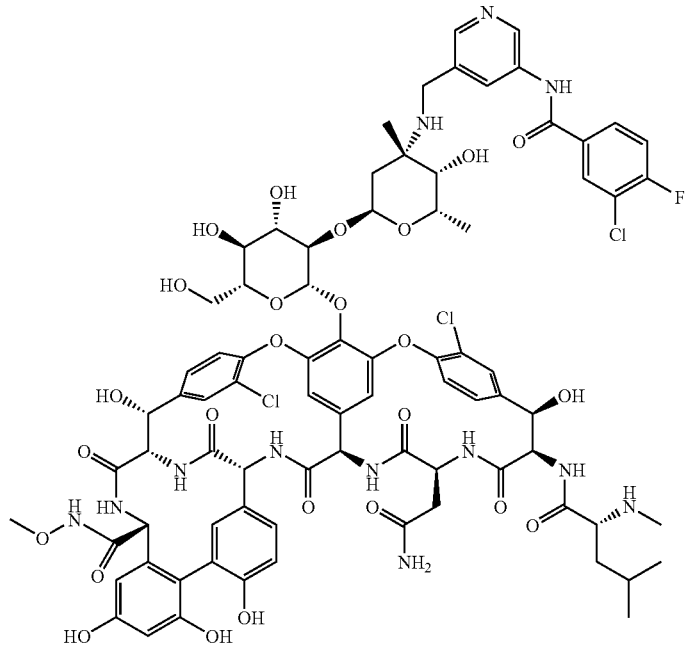
[M+H]$^+$=1739
Anal calcd. for $C_{80}H_{86}Cl_3FN_{12}O_{25} \cdot 9.2H_2O \cdot 2.2HCl$: C, 48.36%; H, 5.41%; N, 8.46%; Cl, 9.28%; F, 0.96%. Found: C, 48.30%; H, 5.67%; N, 8.72%; Cl, 9.37%; F, 0.97%.
Compound 158
[Chemical Formula 197]
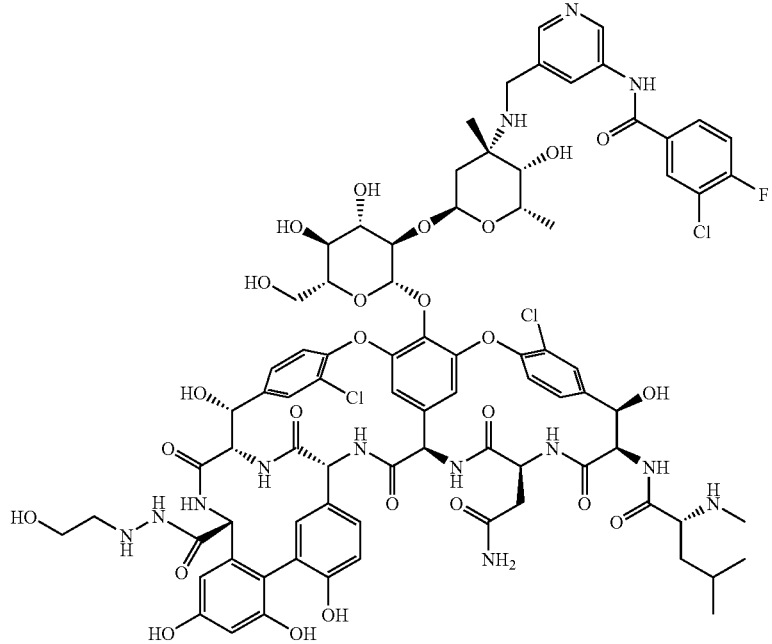

[M+H]⁺=1768
Anal calcd. for $C_{81}H_{89}Cl_3FN_{13}O_{25} \cdot 11.1H_2O \cdot 2.3HCl$: C, 47.37%; H, 5.57%; N, 8.87%; Cl, 9.15%; F, 0.93%. Found: C, 47.38%; H, 5.49%; N, 8.90%; Cl, 9.12%; F, 0.98%.
Compound 159
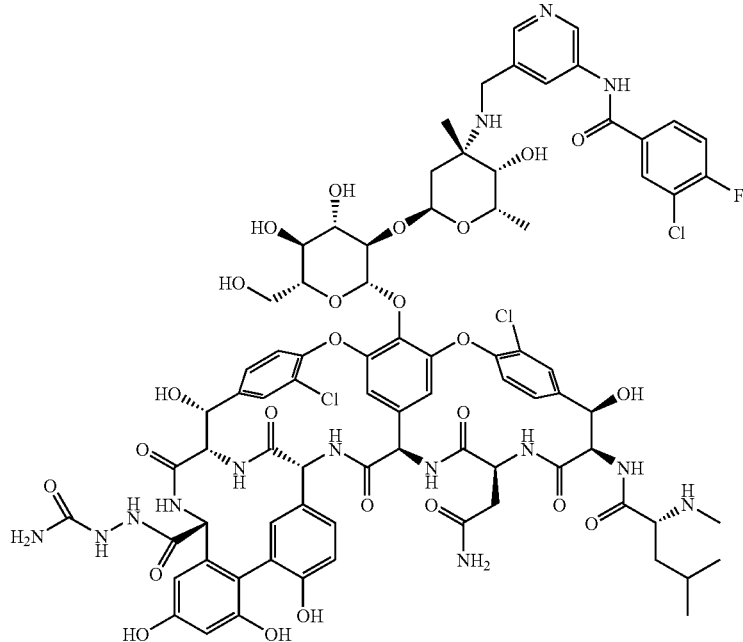
[Chemical Formula 198]
[M+H]⁺=1767
Anal calcd. for $C_{80}H_{86}Cl_3FN_{14}O_{25} \cdot 11.6H_2O \cdot 2.1HCl$: C, 46.77%; H, 5.46%; N, 9.54%; Cl, 8.80%; F, 0.92%. Found: C, 46.74%; H, 5.20%; N, 9.56%; Cl, 8.83%; F, 0.99%.
Compound 160
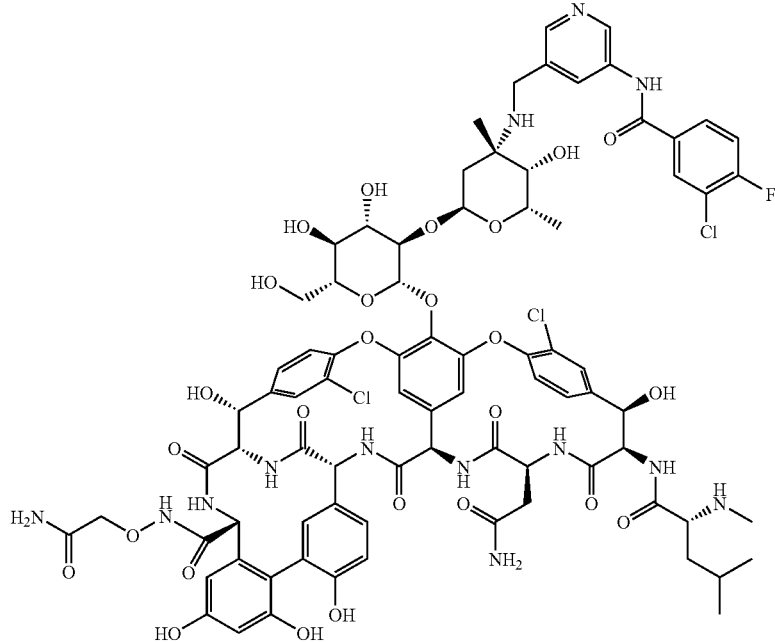
[Chemical Formula 199]

[M+H]⁺=1782
Anal calcd. for $C_{81}H_{87}Cl_3FN_{13}O_{26} \cdot 13.0H_2O \cdot 2.2HCl$: C, 46.36%; H, 5.53%; N, 8.68%; Cl, 8.79%; F, 0.91%. Found: C, 46.34%; H, 5.39%; N, 8.79%; Cl, 8.81%; F, 0.97%.
Compound 161
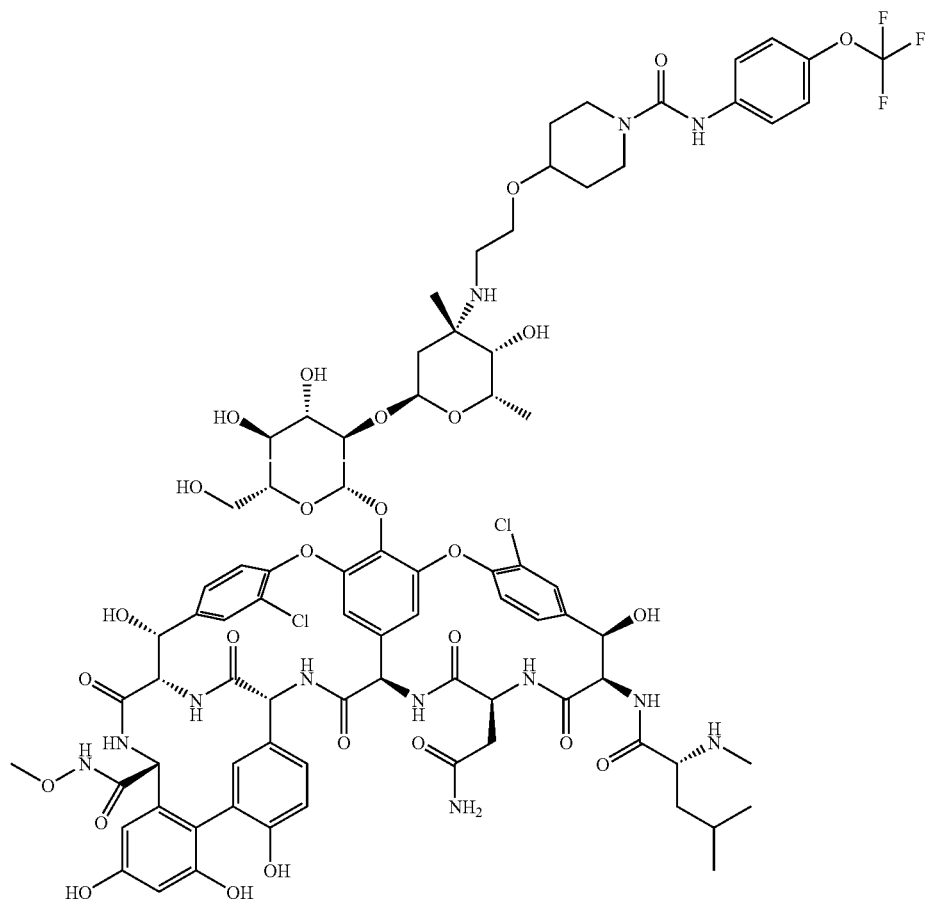
[Chemical Formula 200]

[M+H]⁺=1807
Anal calcd. for $C_{82}H_{95}Cl_2F_3N_{12}O_{27} \cdot 9.4H_2O \cdot 2.2HCl$: C, 47.85%; H, 5.68%; Cl, 7.23%; F, 2.77%; N, 8.17%. Found: C, 48.18%; H, 5.72%; Cl, 7.16%; F, 2.92%; N, 7.78%.
Compound 162
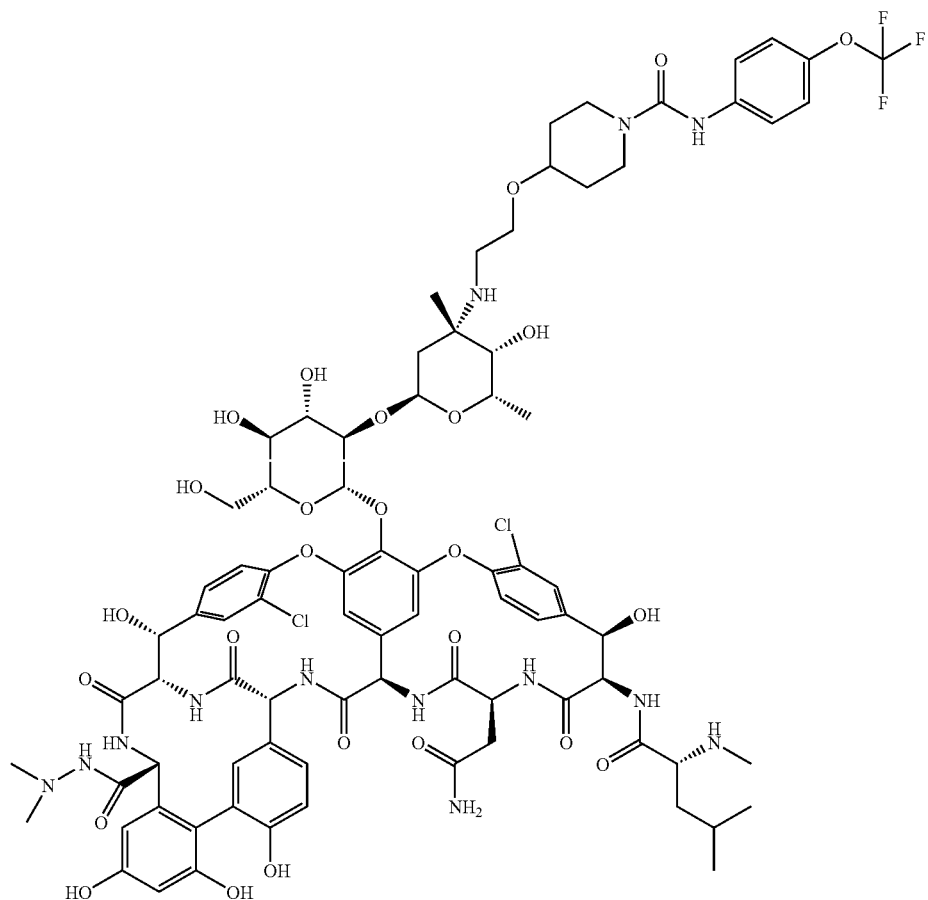
[Chemical Formula 201]

[M+H]⁺=1820
Anal calcd. for $C_{83}H_{98}Cl_2F_3N_{13}O_{26} \cdot 12.0H_2O \cdot 2.7HCl$: C, 46.66%; H, 5.88%; Cl, 7.80%; F, 2.67%; N, 8.52%. Found: C, 46.71%; H, 5.75%; Cl, 7.76%; F, 2.64%; N, 8.64%.
Compound 163
[Chemical Formula 202]
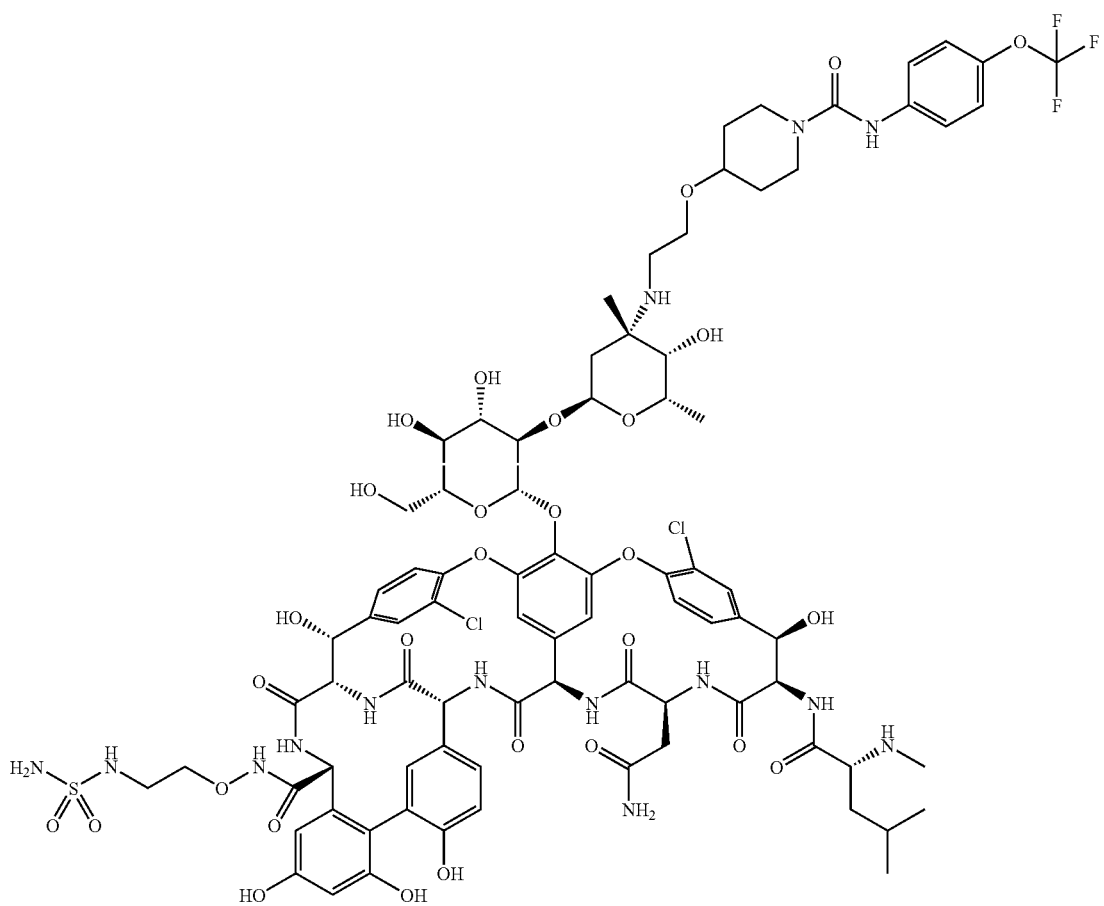

[M+H]⁺=1915
Anal calcd. for $C_{83}H_{99}Cl_2F_3N_{14}O_{29}S \cdot 9.2H_2O \cdot 2.1HCl$: C, 46.17%; H, 5.58%; Cl, 6.73%; F, 2.64%; N, 9.08%; S, 1.49%. Found: C, 46.11%; H, 5.64%; Cl, 6.73%; F, 2.52%; N, 9.23%; S, 1.29%.
Compound 164
[Chemical Formula 203]
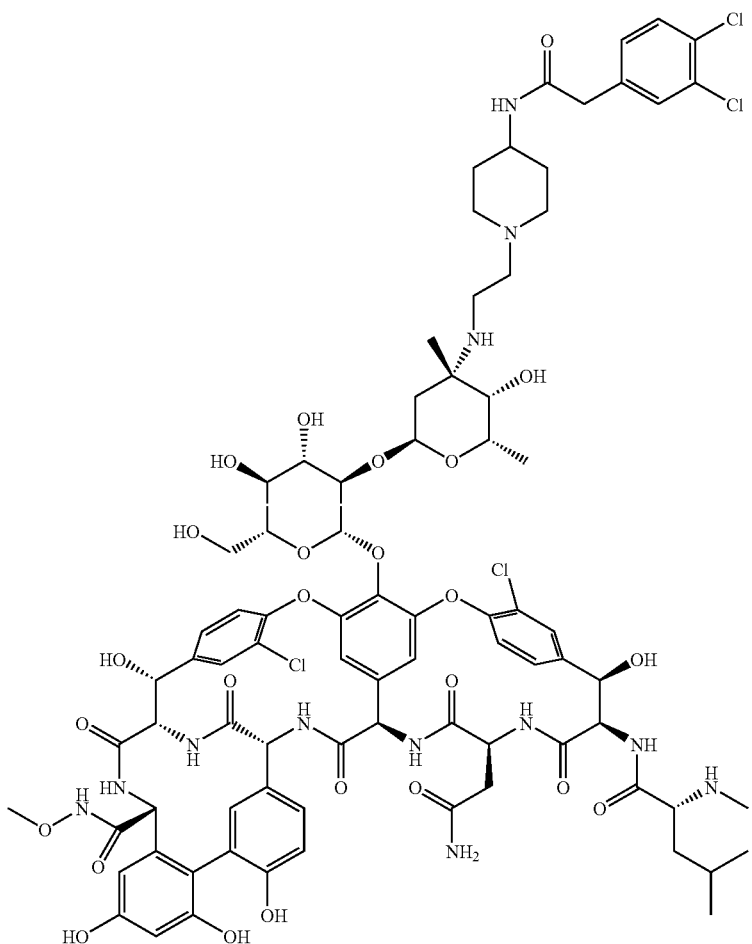

[M+H]⁺=1789
Anal calcd. for $C_{82}H_{96}Cl_4N_{12}O_{25}\cdot 11.5H_2O\cdot 2.9HCl$: C, 46.80%; H, 5.84%; Cl, 11.62%; N, 7.99%. Found: C, 46.84%; H, 5.81%; Cl, 11.65%; N, 8.21%.
Compound 165
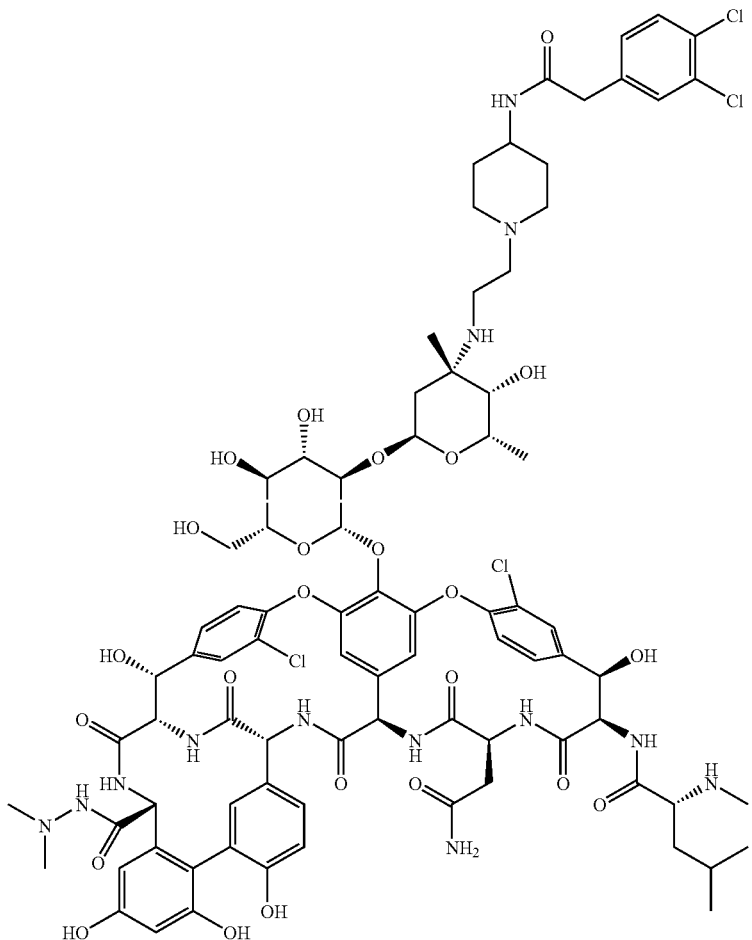
[Chemical Formula 204]

[M+H]⁺=1802
Anal calcd. for $C_{83}H_{99}Cl_4N_{13}O_{24} \cdot 11.5H_2O \cdot 3.6HCl$: C, 46.52%; H, 5.91%; Cl, 12.57%; N, 8.50%. Found: C, 46.54%; H, 5.80%; Cl, 12.55%; N, 8.61%.
Compound 166
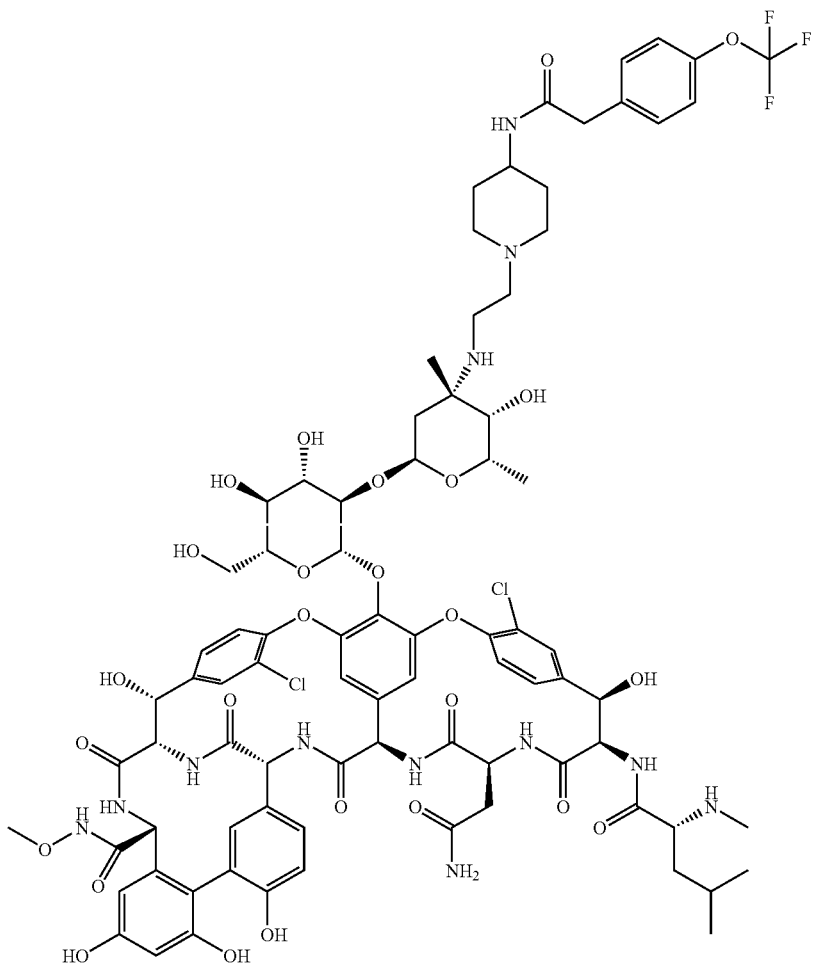
[Chemical Formula 205]

[M+H]⁺=1805
Anal calcd. for $C_{83}H_{97}Cl_2F_3N_{12}O_{26} \cdot 11.5H_2O \cdot 3.0HCl$: C, 46.95%; H, 5.84%; Cl, 8.35%; F, 2.68%; N, 7.92%. Found: C, 47.07%; H, 5.85%; Cl, 8.31%; F, 2.42%; N, 8.06%.
Compound 167
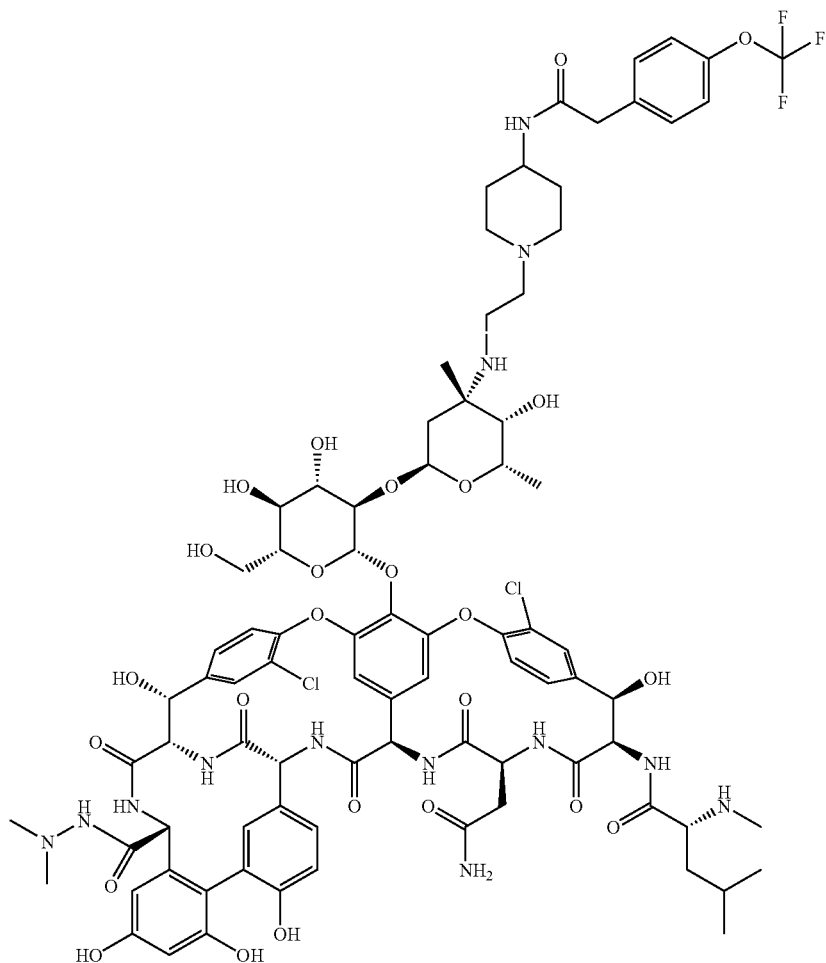
[Chemical Formula 206]

[M+H]⁺=1818
Anal calcd. for $C_{84}H_{100}Cl_2F_3N_{13}O_{25}\cdot 12.5H_2O\cdot 3.2HCl$: C, 46.68%; H, 5.98%; Cl, 8.53%; F, 2.64%; N, 8.42%. Found: C, 46.69%; H, 5.91%; Cl, 8.50%; F, 2.40%; N, 8.54%.
Compound 168
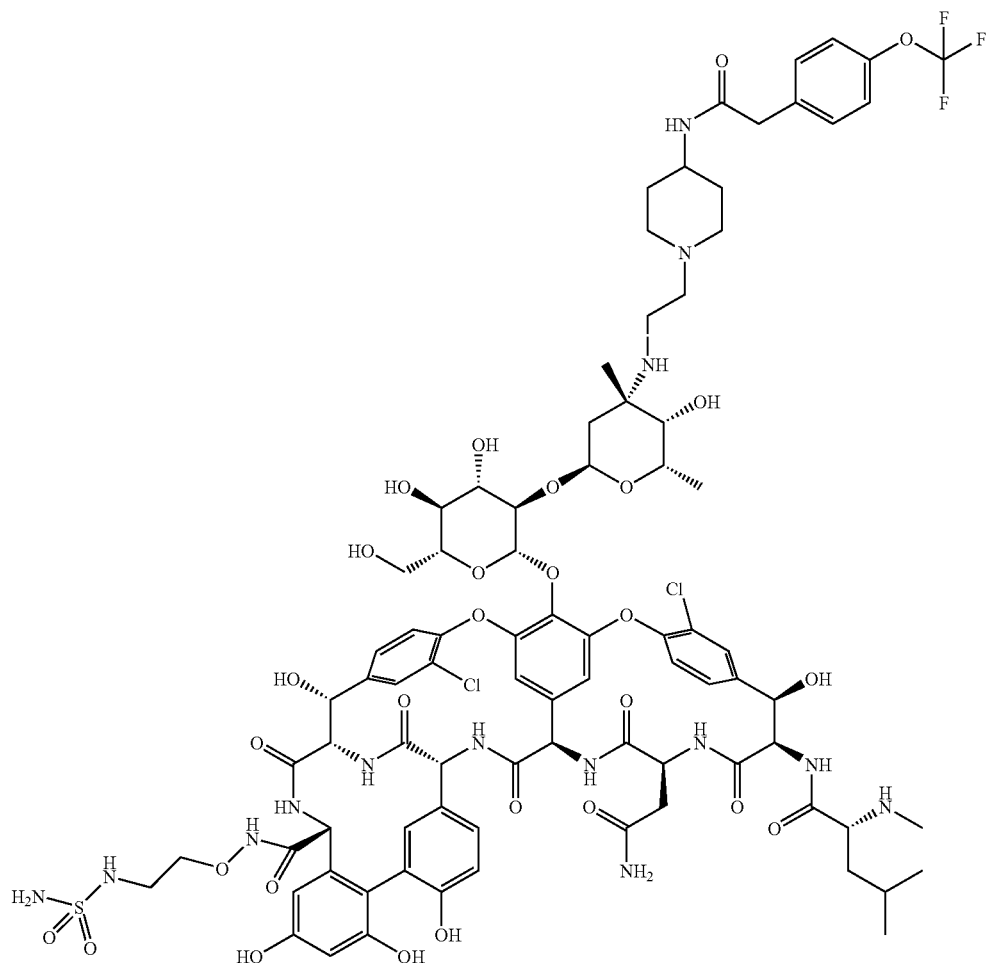
[Chemical Formula 207]

[M+H]⁺=1913
Anal calcd. for $C_{84}H_{101}Cl_2F_3N_{14}O_{28}S.11.7H_2O.2.9HCl$: C, 45.22%; H, 5.75%; Cl, 7.79%; F, 2.55%; N, 8.79%; S, 1.44%. Found: C, 45.19%; H, 5.64%; Cl, 7.84%; F, 2.32%; N, 8.94%; S, 1.42%.
Compound 169
[Chemical Formula 208]
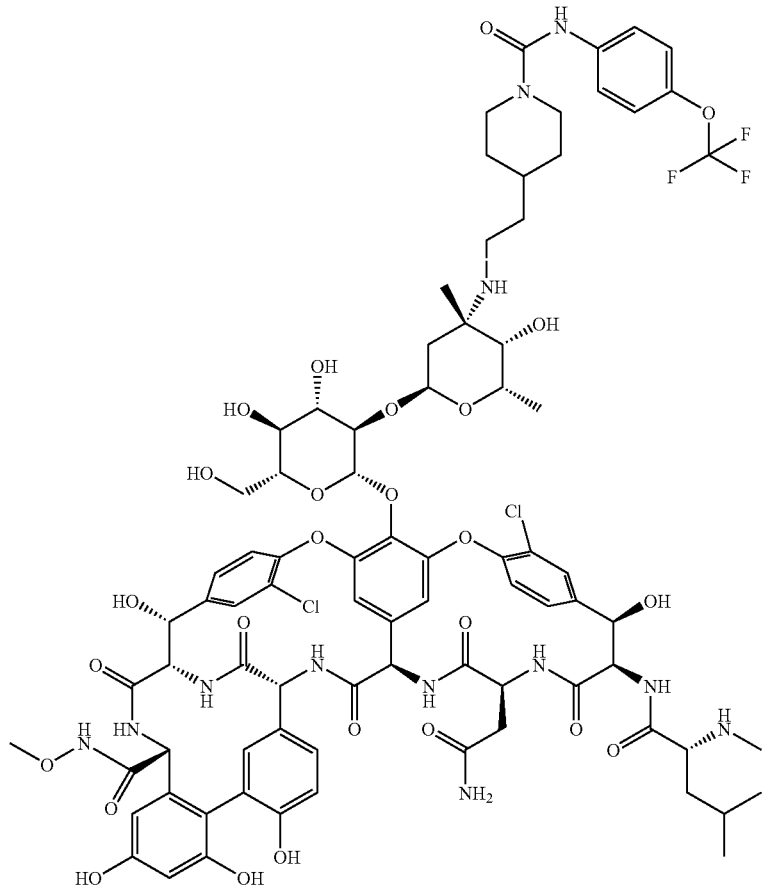

[M+H]⁺=1791
Anal calcd. for $C_{82}H_{95}Cl_2F_3N_{12}O_{26}\cdot 11.5H_2O\cdot 2.1HCl$: C, 47.43%; H, 5.83%; Cl, 7.00%; F, 2.74%; N, 8.10%. Found: C, 47.52%; H, 5.86%; Cl, 6.93%; F, 2.59%; N, 8.47%.
Compound 170
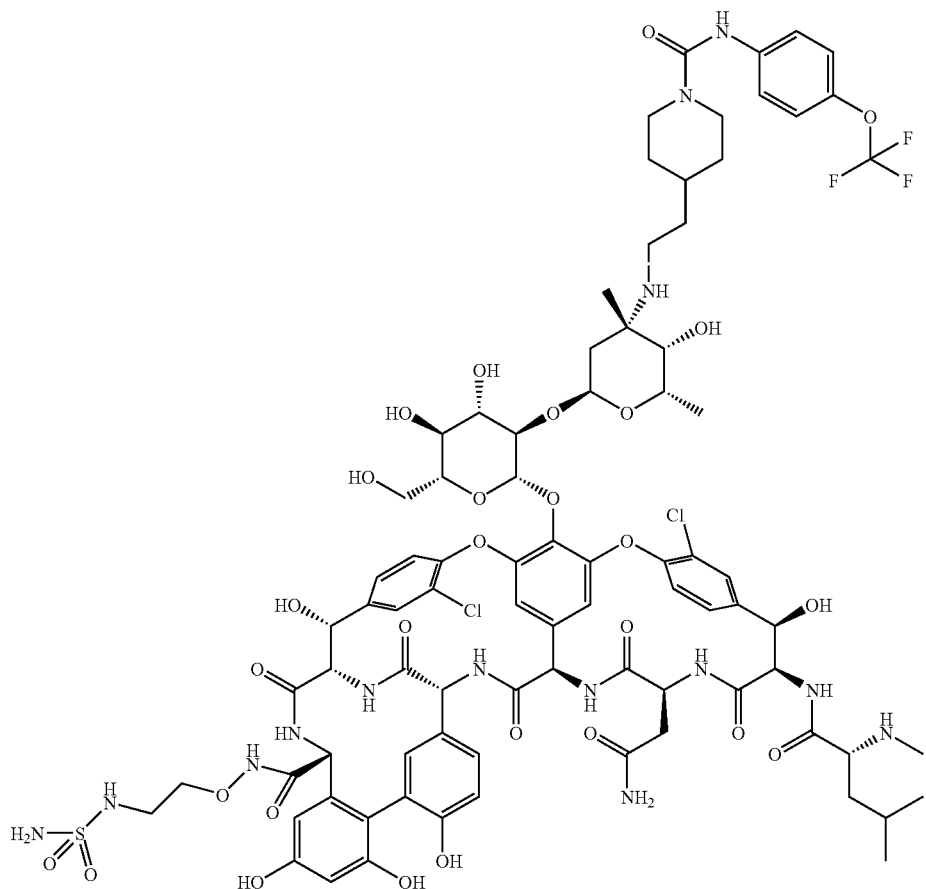
[Chemical Formula 209]

[M+H]⁺=1899
Anal calcd. for $C_{83}H_{99}Cl_2F_3N_{14}O_{28}S \cdot 10.0H_2O \cdot 2.0HCl$: C, 46.29%; H, 5.66%; Cl, 6.58%; F, 2.65%; N, 9.10%; S, 1.49%. Found: C, 46.12%; H, 5.72%; Cl, 6.65%; F, 2.46%; N, 9.10%; S, 1.40%.
Compound 171
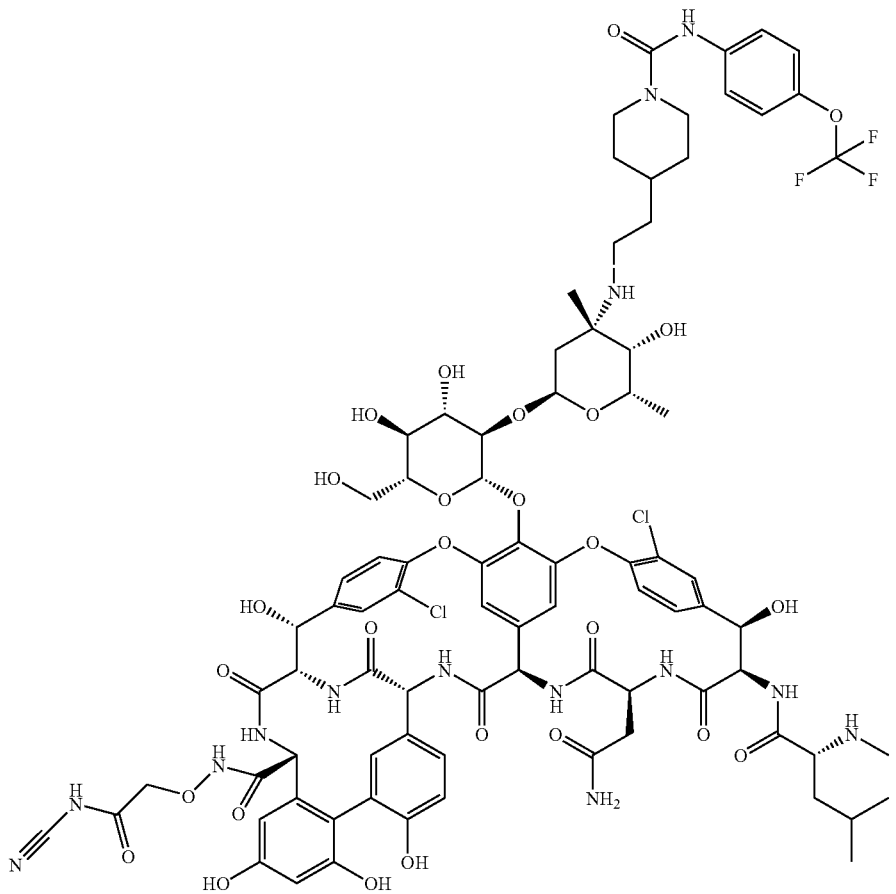
[Chemical Formula 210]

[M+H]$^+$=1859
Anal calcd. for $C_{84}H_{95}Cl_2F_3N_{14}O_{27} \cdot 11.0H_2O \cdot 2.1HCl$: C, 47.25%; H, 5.62%; Cl, 6.81%; F, 2.67%; N, 9.18%. Found: C, 47.07%; H, 5.65%; Cl, 6.87%; F, 2.50%; N, 9.47%.
Compound 172
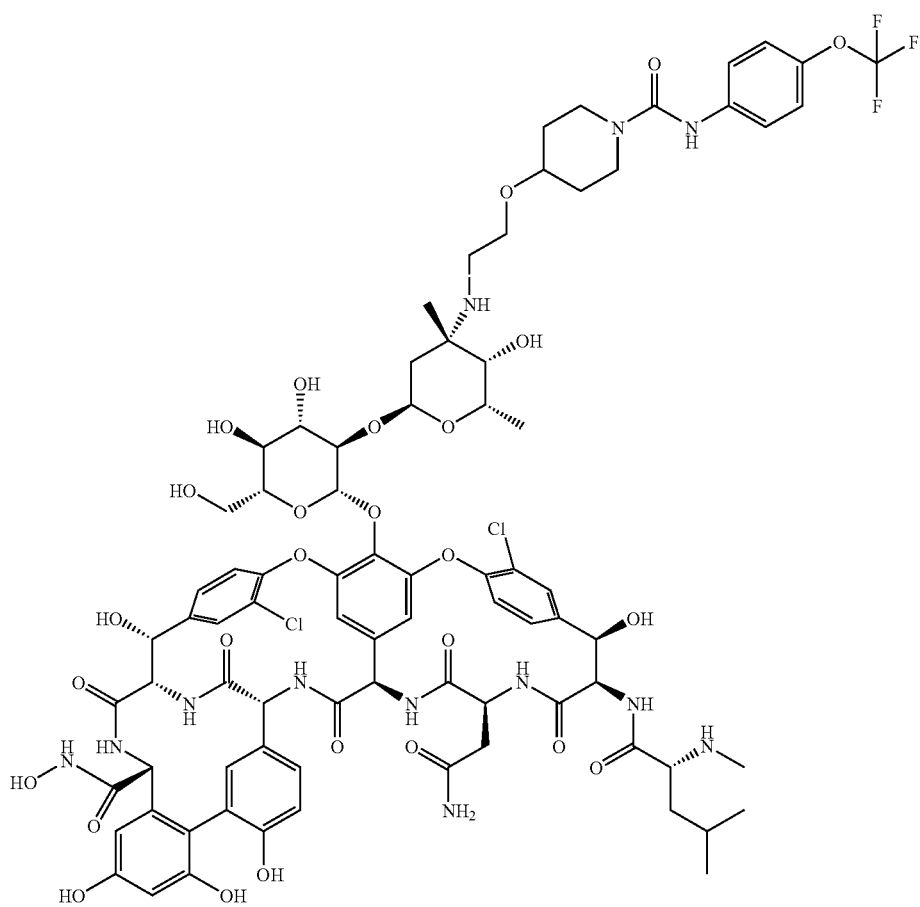
[Chemical Formula 211]

[M+H]⁺=1793
Anal calcd. for $C_{81}H_{93}Cl_2F_3N_{12}O_{27} \cdot 11.3H_2O \cdot 2.1HCl$: C, 46.89%; H, 5.72%; Cl, 7.01%; F, 2.75%; N, 8.10%. Found: C, 46.96%; H, 5.71%; Cl, 6.91%; F, 2.70%; N, 8.06%.
Compound 173
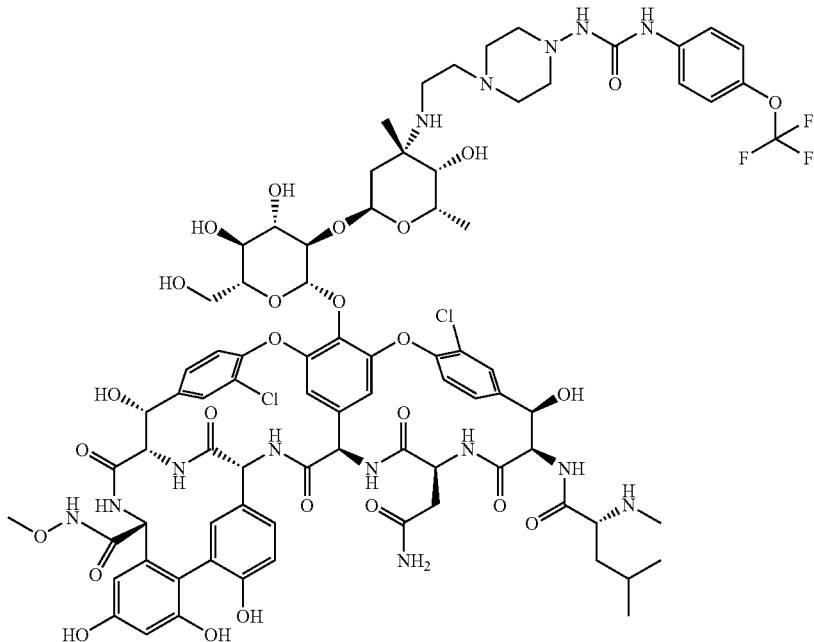
[Chemical Formula 212]
[M+H]⁺=1807
Anal calcd. for $C_{81}H_{95}F_3Cl_2N_{14}O_{26} \cdot 3.1HCl \cdot 10H_2O$: C, 46.29%; H, 5.66%; N, 9.33%; Cl, 8.60%; F, 2.71%. Found: C, 46.18%; H, 5.64%; N, 9.34%; F, 2.71%; Cl, 8.56%.
Compound 174
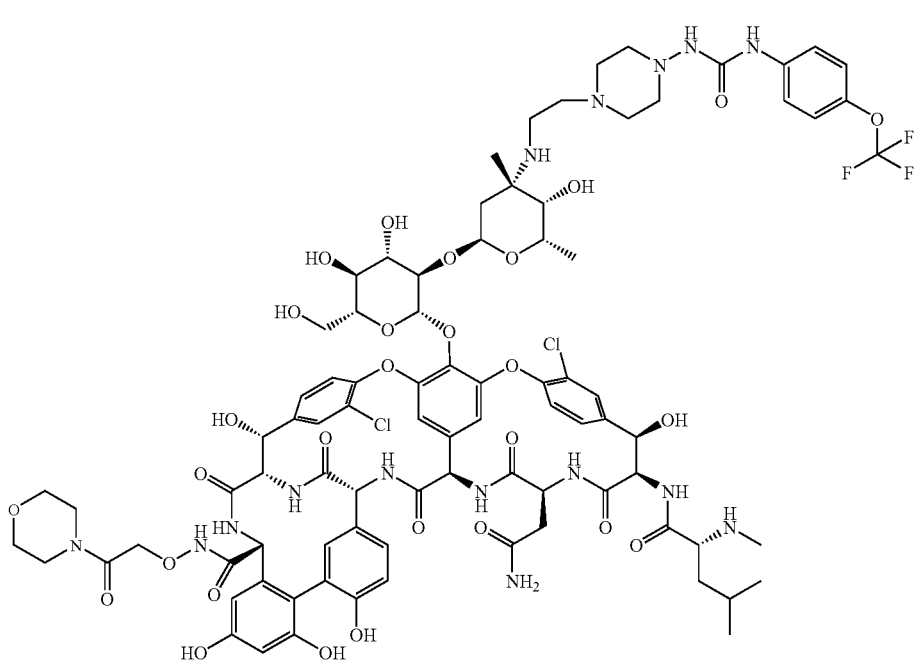
[Chemical Formula 213]

[M+H]⁺=1920
Anal calcd. for $C_{86}H_{102}F_3Cl_2N_{15}O_{28}\cdot 3.2HCl\cdot 10H_2O$: C, 46.56%; H, 5.69%; N, 9.47%; Cl, 8.31%; F, 2.57%. Found: C, 46.45%; H, 5.70%; N, 9.36%; F, 2.67%; Cl, 8.34%.
Compound 175
[Chemical Formula 214]
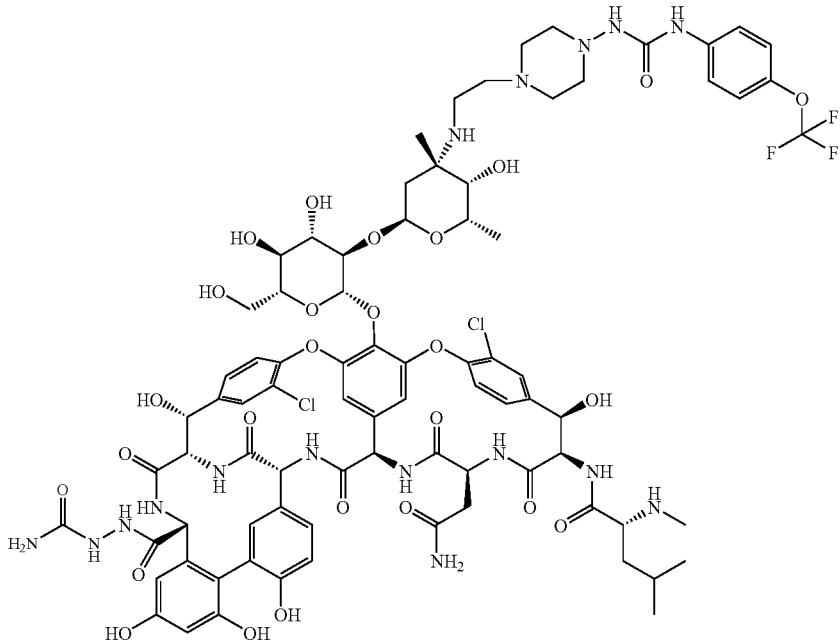
[M+H]⁺=1835
Anal calcd. for $C_{81}H_{95}F_3Cl_2N_{16}O_{26}\cdot 3.0HCl\cdot 13H_2O$: C, 44.62%; H, 5.73%; N, 10.28%; Cl, 8.13%; F, 2.61%. Found: C, 44.79%; H, 5.63%; N, 10.38%; F, 2.57%; Cl, 8.19%.
Compound 176
[Chemical Formula 215]
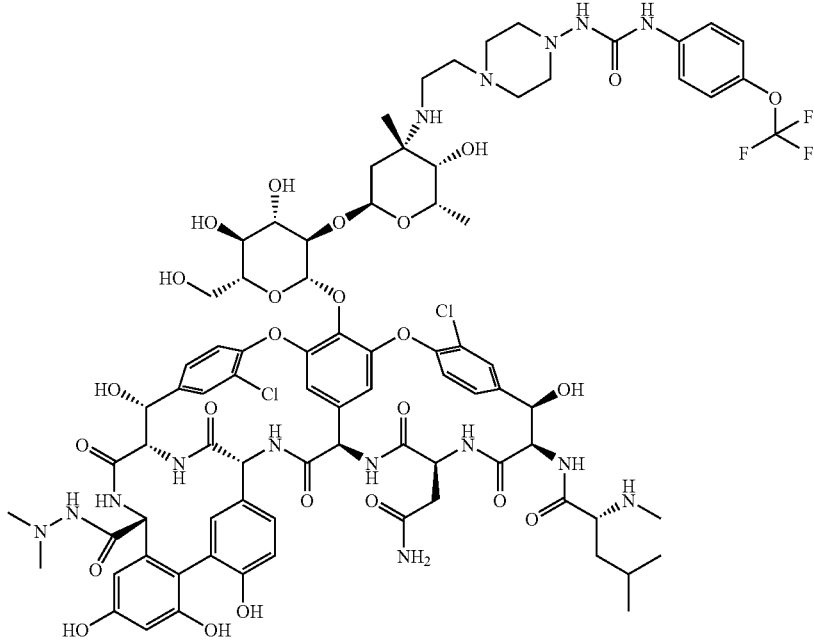

[M+H]⁺=1820
Anal calcd. for $C_{82}H_{98}F_3Cl_2N_{15}O_{25}\cdot 2.2HCl\cdot 12H_2O$: C, 46.50%; H, 5.91%; N, 9.92%; Cl, 7.03%; F, 2.69%. Found: C, 46.33%; H, 5.72%; N, 9.91%; F, 11.51%; Cl, 7.11%.
Compound 177
[Chemical Formula 216]
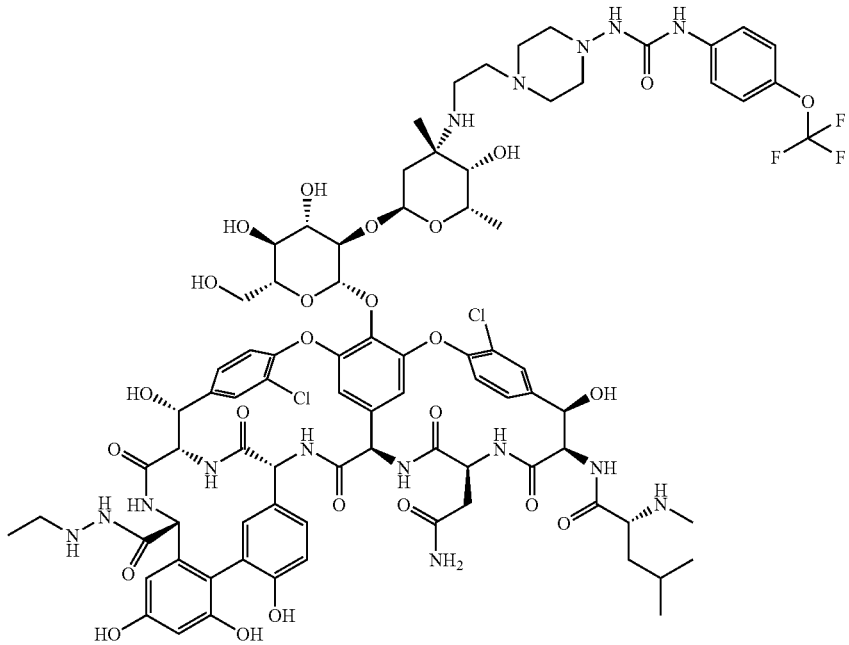
[M+H]⁺=1820
Anal calcd. for $C_{82}H_{98}F_3Cl_2N_{15}O_{25}\cdot 4HCl\cdot 11H_2O$: C, 45.48%; H, 5.77%; N, 9.70%; Cl, 9.82%; F, 2.63%. Found: C, 45.46%; H, 5.76%; N, 9.80%; F, 2.64%; Cl, 9.74%.
Compound 178
[Chemical Formula 217]
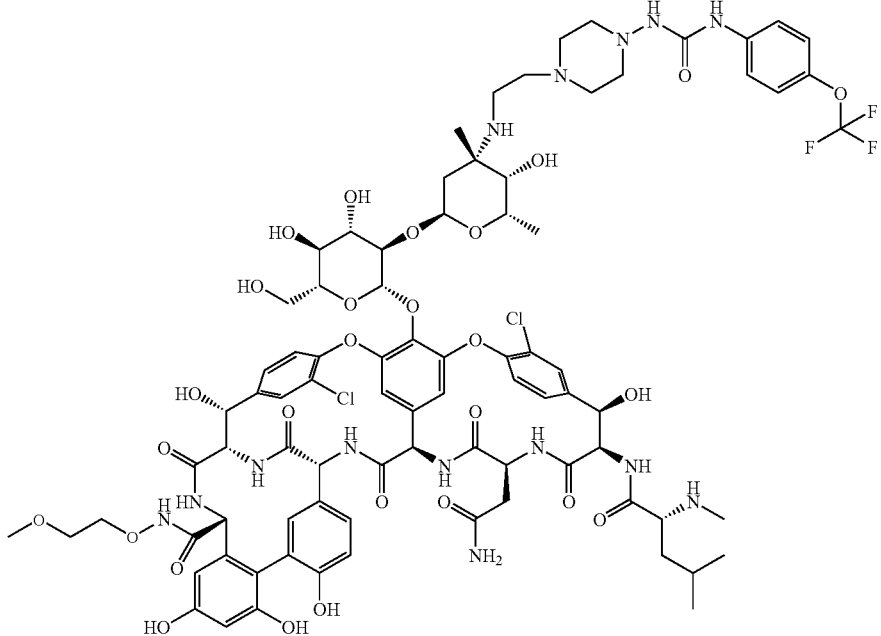

[M+H]$^+$=1851
Anal calcd. for $C_{83}H_{99}F_3Cl_2N_{14}O_{27}\cdot 3HCl\cdot 11H_2O$: C, 46.15%; H, 5.79%; N, 9.08%; Cl, 8.21%; F, 2.64%. Found: C, 46.13%; H, 5.76%; N, 9.22%; F, 2.59%; Cl, 8.28%.
Compound 179
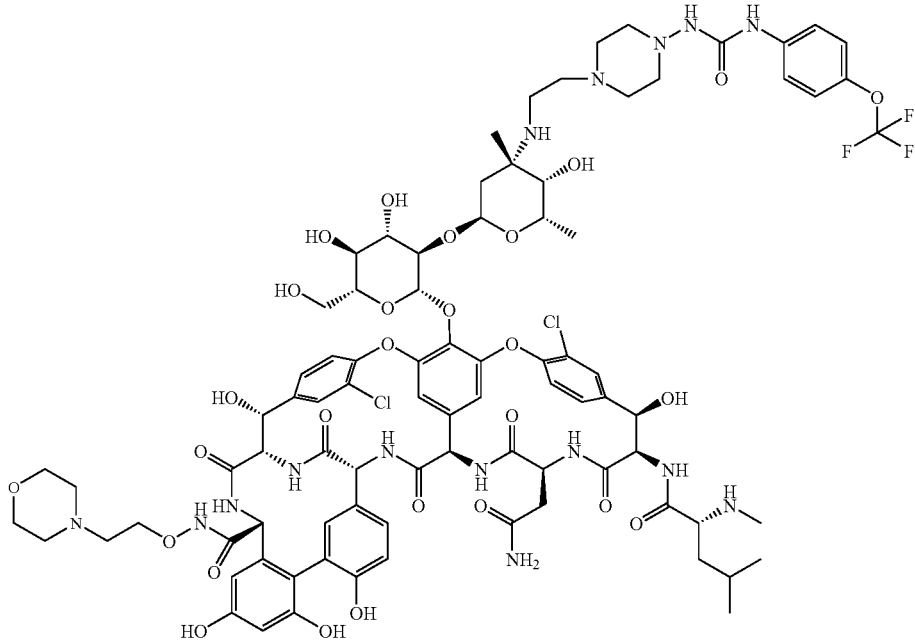
[Chemical Formula 218]
[M+H]$^+$=1906
Anal calcd. for $C_{86}H_{104}F_3Cl_2N_{15}O_{27}\cdot 4HCl\cdot 12H_2O$: C, 45.51%; H, 5.86%; N, 9.26%; Cl, 9.37%; F, 2.51%. Found: C, 45.60%; H, 5.90%; N, 9.41%; F, 2.59%; Cl, 9.55%.
Compound 180
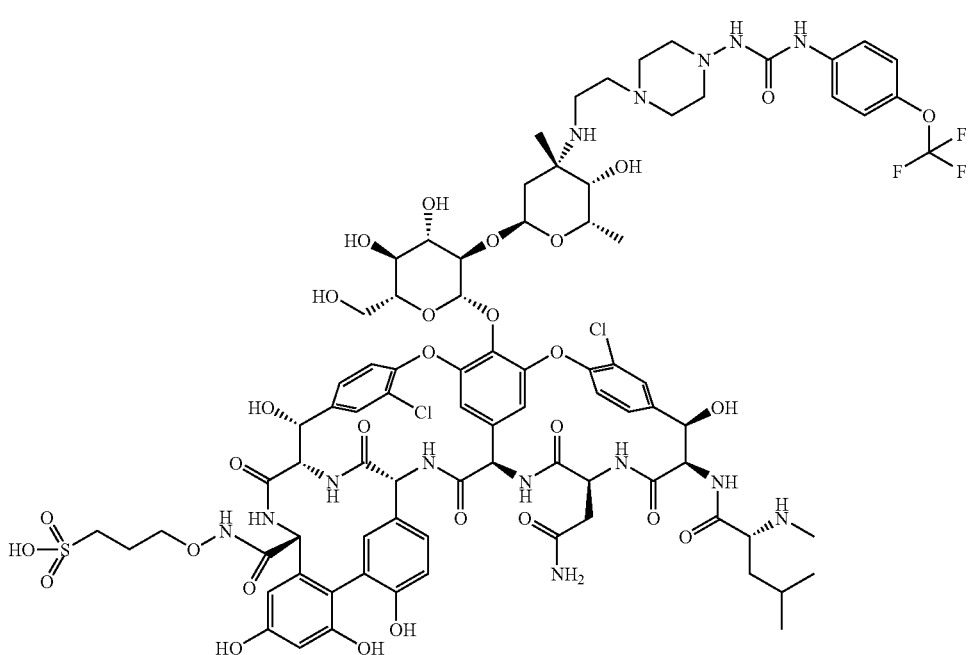
[Chemical Formula 219]

[M+H]⁺=1915
Anal calcd. for $C_{83}H_{99}F_3Cl_2N_{14}O_{29}S \cdot 2.2HCl \cdot 11.5H_2O$: C, 45.23%; H, 5.68%; N, 8.90%; Cl, 6.76%; F, 2.59%; S, 1.45%. Found: C, 45.21%; H, 5.72%; N, 8.84%; F, 2.78%; Cl, 6.75%; S, 1.46%.
Compound 181
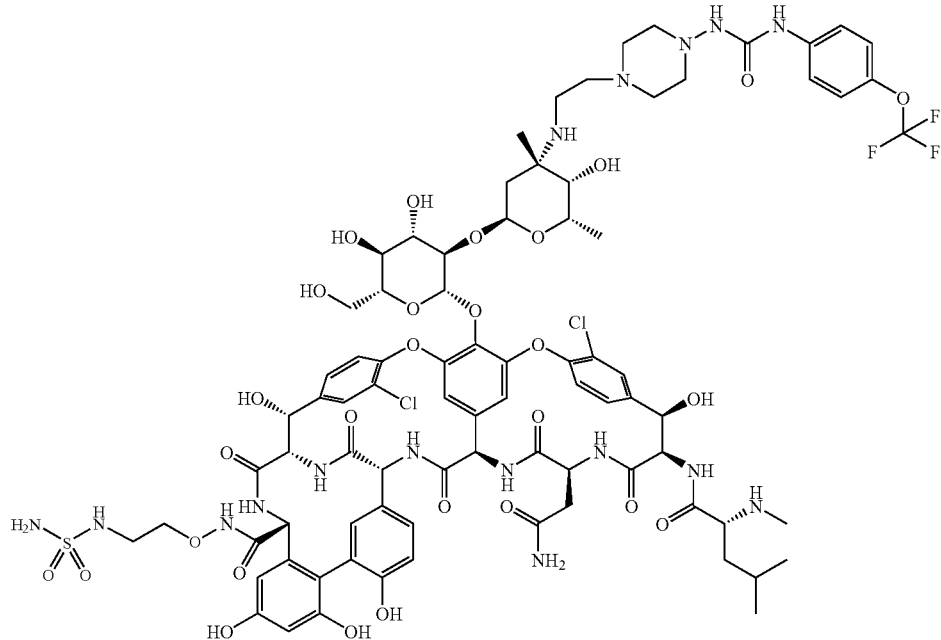
[Chemical Formula 220]

[M+H]⁺=1915
Anal calcd. for $C_{82}H_{99}F_3Cl_2N_{16}O_{28}S \cdot 3.2HCl \cdot 10H_2O$: C, 44.49%; H, 5.56%; N, 10.12%; Cl, 8.33%; F, 2.57%; S, 1.45%. Found: C, 44.61%; H, 5.54%; N, 10.01%; F, 2.70%; Cl, 8.24%; S, 1.47%.
Compound 182
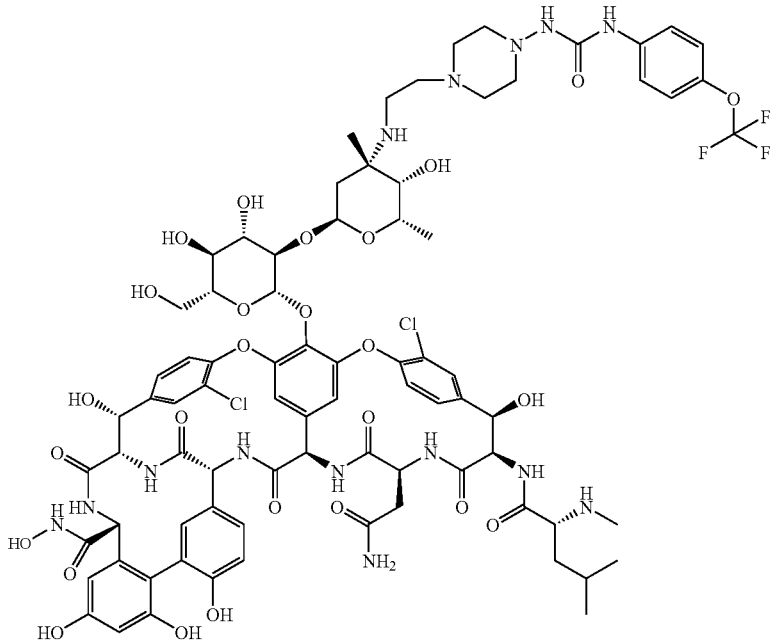
[Chemical Formula 221]
[M+H]⁺=1793
Anal calcd. for $C_{80}H_{93}F_3Cl_2N_{14}O_{26} \cdot 3HCl \cdot 11.8H_2O$: C, 45.40%; H, 5.70%; N, 9.26%; Cl, 8.38%; F, 2.69%. Found: C, 45.30%; H, 5.67%; N, 9.14%; F, 2.60%; Cl, 8.28%.
Compound 183
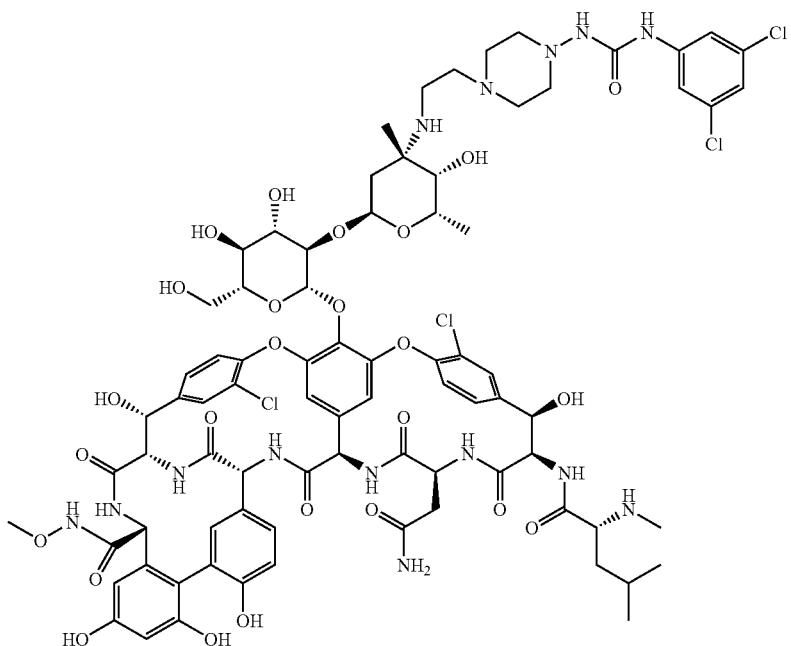
[Chemical Formula 222]

[M+H]$^+$=1791
Anal calcd. for $C_{80}H_{94}Cl_4N_{14}O_{25} \cdot 2.4HCl \cdot 10.5H_2O$: C, 46.41%; H, 5.72%; N, 9.47%; Cl, 10.96%. Found: C, 46.24%; H, 5.72%; N, 9.32%; Cl, 10.96%.
Compound 184
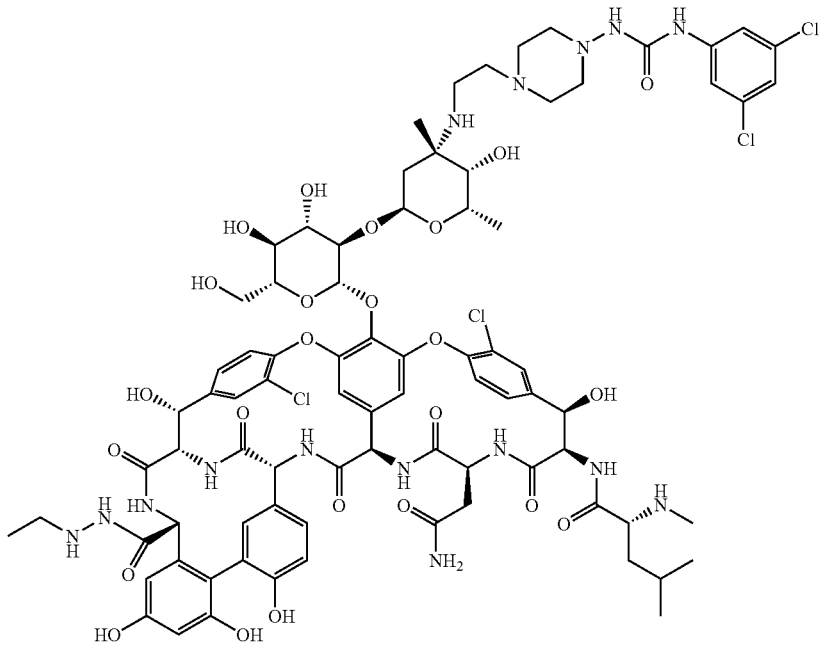
[Chemical Formula 223]
[M+H]$^+$=1804
Anal calcd. for $C_{81}H_{97}Cl_4N_{15}O_{24} \cdot 2.7HCl \cdot 11H_2O$: C, 46.26%; H, 5.83%; N, 9.99%; Cl, 11.29%. Found: C, 46.19%; H, 5.77%; N, 9.94%; Cl, 11.31%.
Compound 185
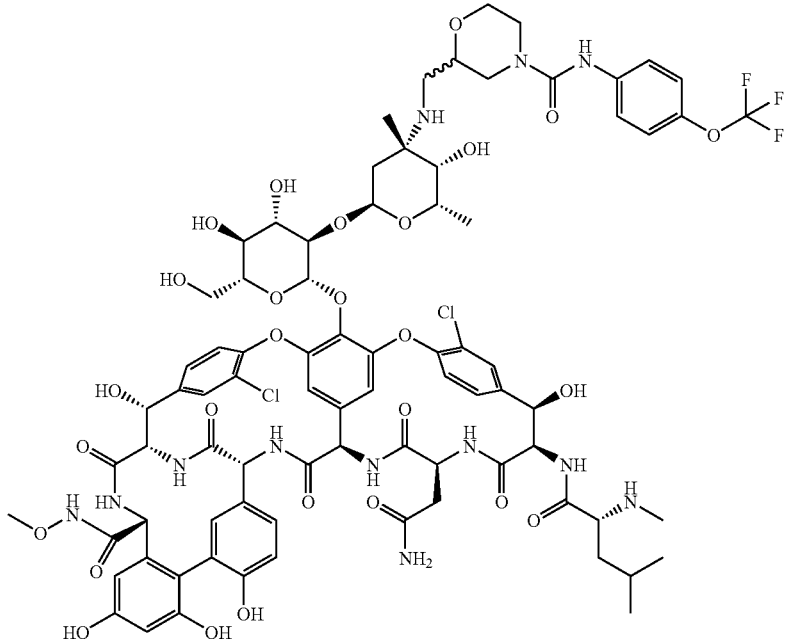
[Chemical Formula 224]

[M+H]$^+$=1779
Anal calcd. for $C_{80}H_{91}F_3Cl_2N_{12}O_{27}\cdot 2.1HCl\cdot 11.3H_2O$: C, 46.63%; H, 5.66%; N, 8.16%; Cl, 7.05%; F, 2.77%. Found: C, 46.83%; H, 5.52%; N, 8.51%; F, 2.70%; Cl, 7.03%.
Compound 186
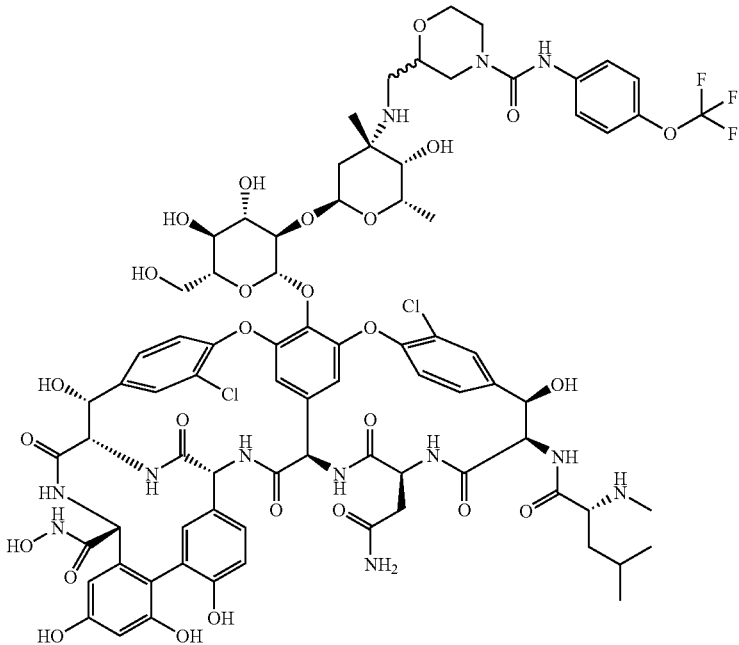
[Chemical Formula 225]
[M+H]$^+$=1765
Anal calcd. for $C_{79}H_{89}F_3Cl_2N_{12}O_{27}\cdot 2HCl\cdot 11H_2O$: C, 46.57%; H, 5.59%; N, 8.25%; Cl, 6.96%; F, 2.80%. Found: C, 46.41%; H, 5.57%; N, 8.30%; F, 2.90%; Cl, 6.94%.
Compound 187
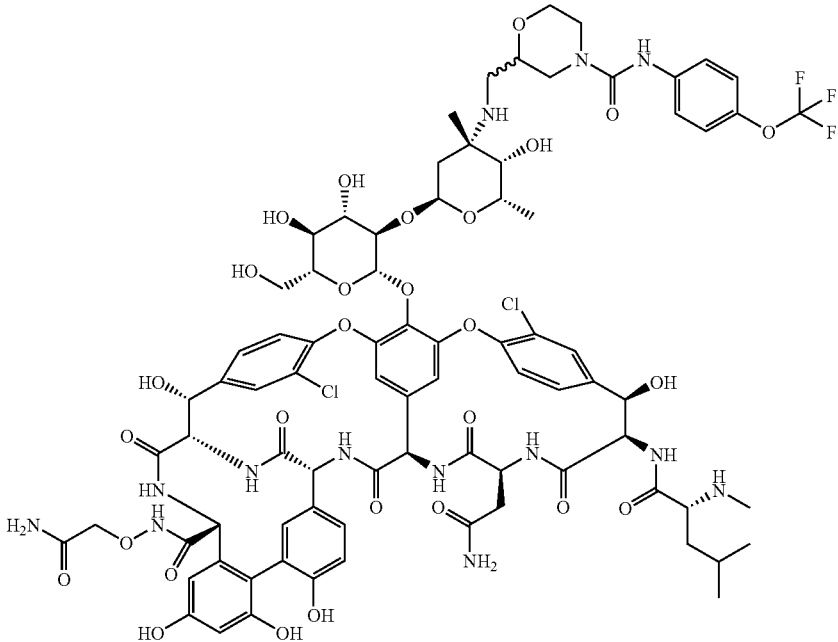
[Chemical Formula 226]

[M+H]$^+$=1822
Anal calcd. for $C_{81}H_{92}F_3Cl_2N_{13}O_{28} \cdot 2.1HCl \cdot 11H_2O$: C, 46.36%; H, 5.58%; N, 8.68%; Cl, 6.93%; F, 2.72%. Found: C, 46.59%; H, 5.46%; N, 8.91%; F, 2.67%; Cl, 7.01%.
Compound 188
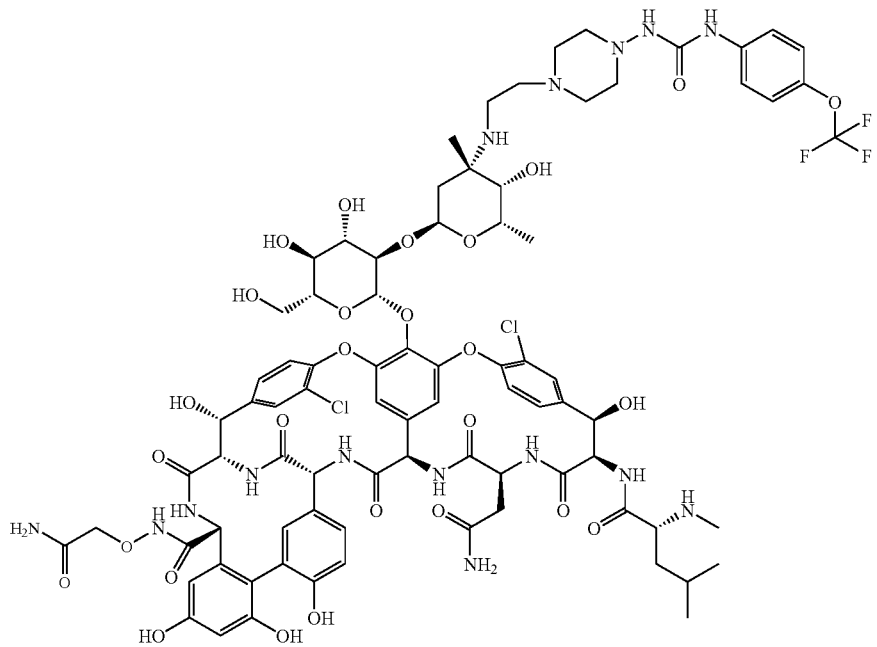
[Chemical Formula 227]
[M+H]$^+$=1850
Anal calcd. for $C_{82}H_{96}F_3Cl_2N_{15}O_{28} \cdot 3.1HCl \cdot 12H_2O$: C, 44.83%; H, 5.65%; N, 9.56%; Cl, 8.23%; F, 2.59%. Found: C, 44.92%; H, 5.47%; N, 9.81%; F, 2.55%; Cl, 8.27%.
Compound 189
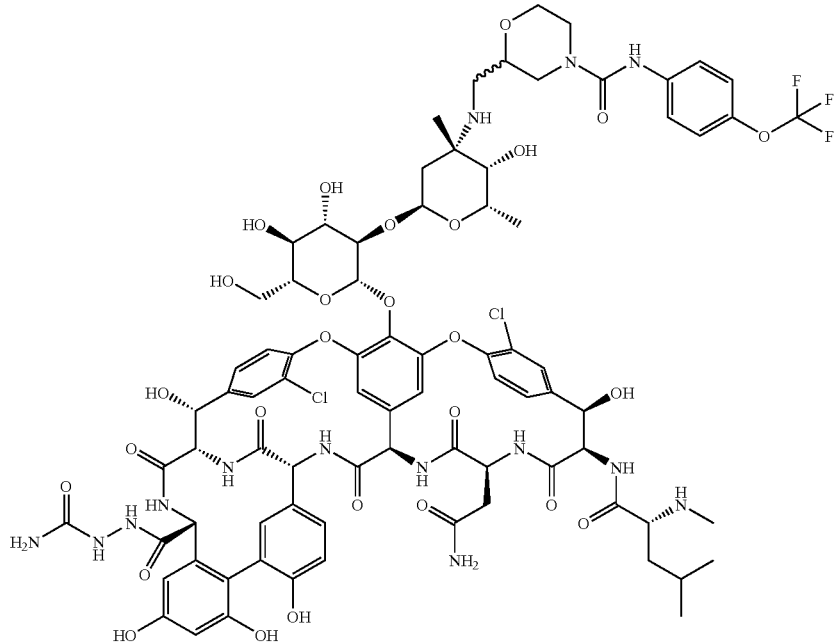
[Chemical Formula 228]

[M+H]⁺=1807
Anal calcd. for $C_{80}H_{91}F_3Cl_2N_{14}O_{27} \cdot 2.1HCl \cdot 11.5H_2O$: C, 45.92%; H, 5.59%; N, 9.37%; Cl, 6.95%; F, 2.72%. Found: C, 45.95%; H, 5.57%; N, 9.51%; F, 2.71%; Cl, 6.97%.
Compound 190
[Chemical Formula 229]
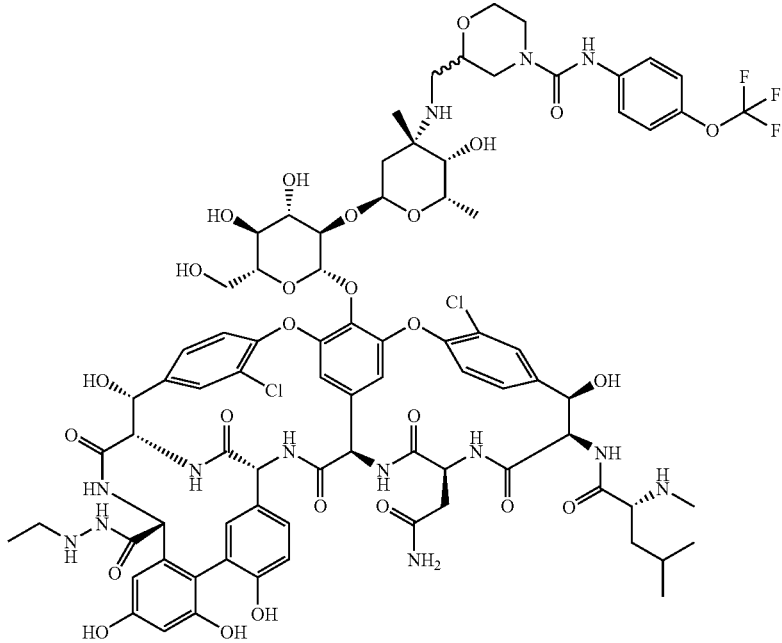
[M+H]⁺=1792
Anal calcd. for $C_{81}H_{94}F_3Cl_2N_{13}O_{26} \cdot 3HCl \cdot 11H_2O$: C, 46.30%; H, 5.71%; N, 8.67%; Cl, 8.44%; F, 2.71%. Found: C, 46.28%; H, 5.73%; N, 8.76%; F, 2.67%; Cl, 8.30%.
Compound 191
[Chemical Formula 230]
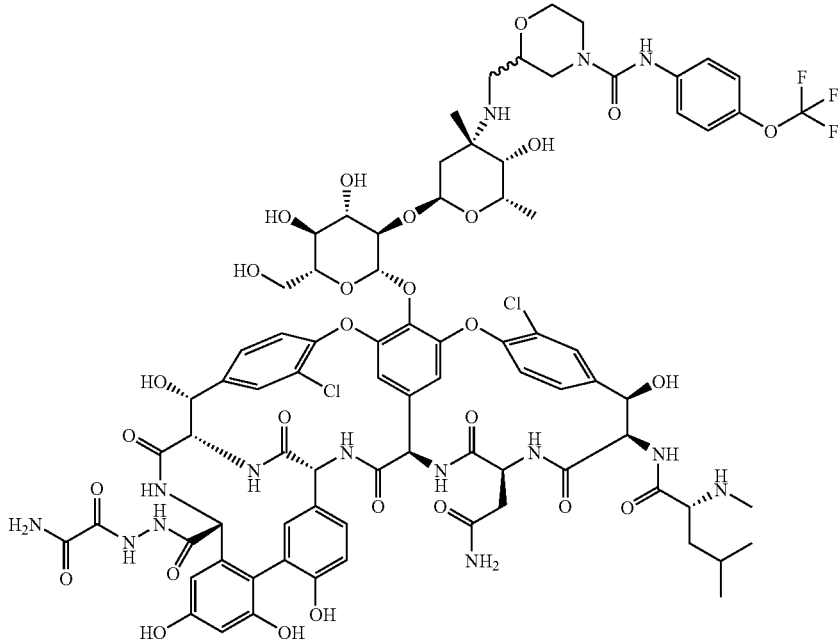

[M+H]$^+$=1835
Anal calcd. for $C_{81}H_{91}F_3Cl_2N_{14}O_{28}\cdot 2HCl\cdot 11.5H_2O$: C, 45.96%; H, 5.52%; N, 9.26%; Cl, 6.70%; F, 2.69%. Found: C, 45.92%; H, 5.43%; N, 9.42%; F, 2.68%; Cl, 6.78%.
Compound 192
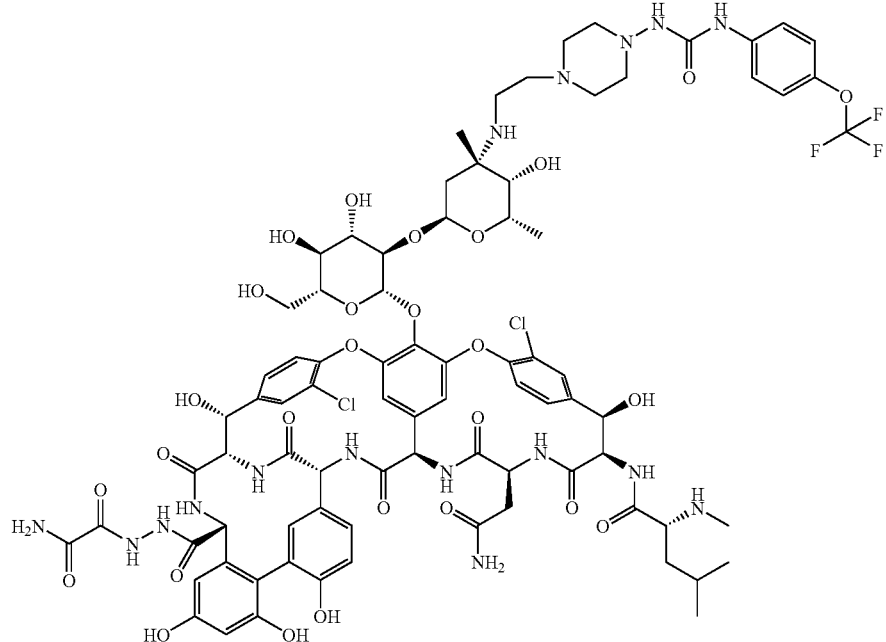
[Chemical Formula 231]
[M+H]$^+$=1863
Anal calcd. for $C_{82}H_{95}F_3Cl_2N_{16}O_{27}\cdot 3HCl\cdot 12.5H_2O$: C, 44.78%; H, 5.64%; N, 10.19%; Cl, 8.06%; F, 2.59%. Found: C, 44.80%; H, 5.58%; N, 10.24%; F, 2.45%; Cl, 8.07%.
Compound 193
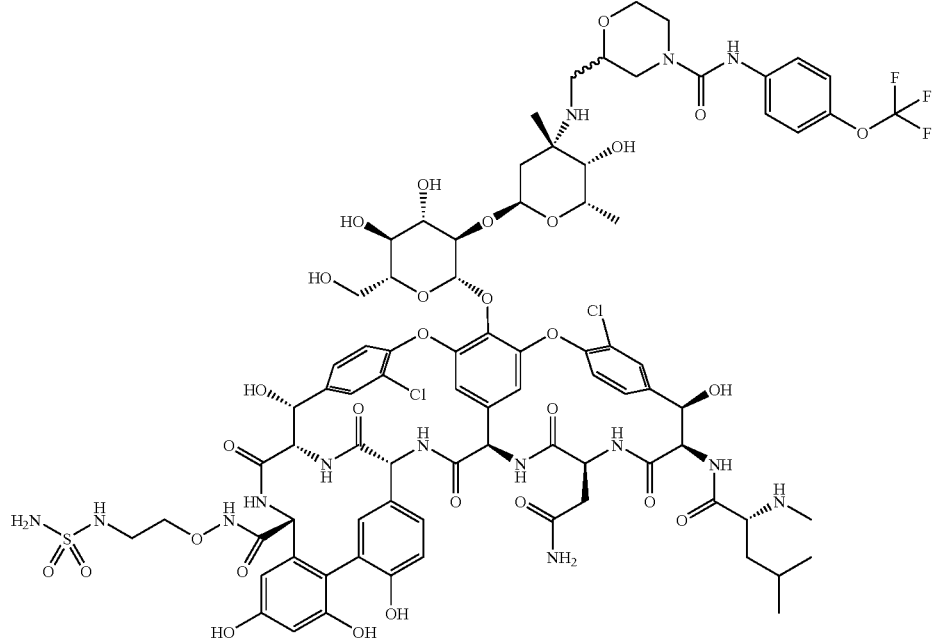
[Chemical Formula 232]

[M+H]⁺=1887
Anal calcd. for $C_{81}H_{95}F_3Cl_2N_{14}O_{29}S \cdot 2HCl \cdot 10H_2O$: C, 45.42%; H, 5.51%; N, 9.16%; Cl, 9.62%; F, 2.66%. Found: C, 45.33%; H, 5.50%; N, 9.19%; F, 2.64%; Cl, 6.62%.
Compound 194
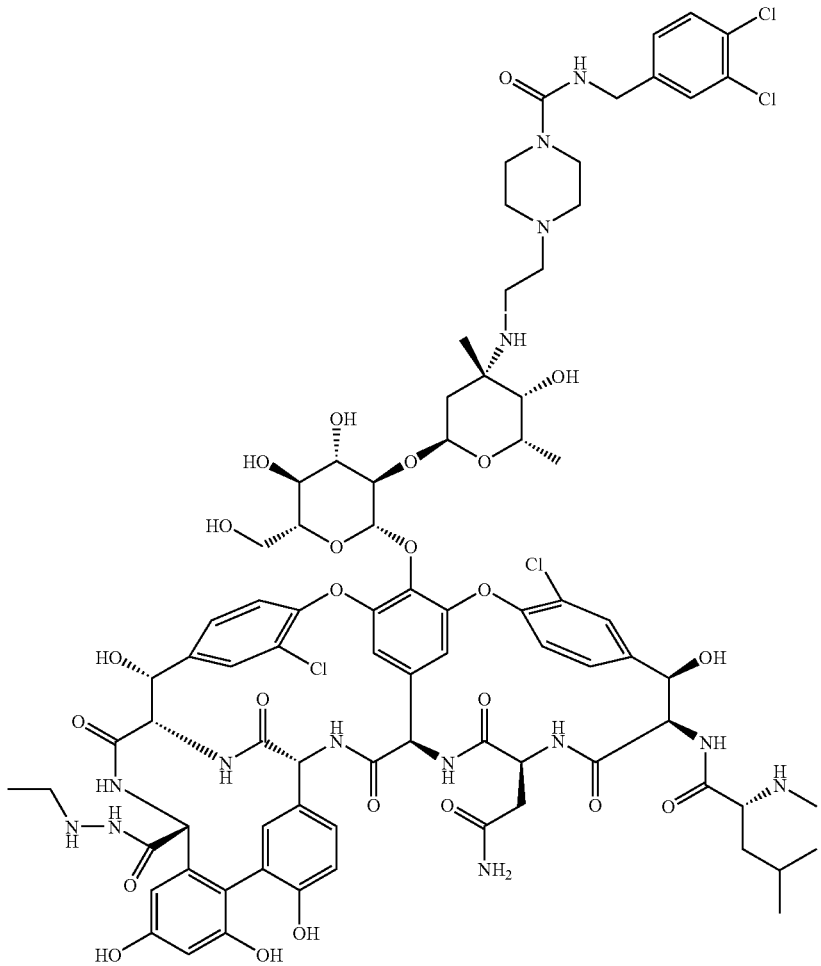
[Chemical Formula 233]

[M+H]⁺=1803
Anal calcd. for $C_{82}H_{98}Cl_4N_{14}O_{24} \cdot 11.6H_2O \cdot 2.8HCl$: C, 46.53%; H, 5.90%; N, 9.26%; Cl, 11.39%. Found: C, 46.50%; H, 5.68%; N, 9.27%; Cl, 11.29%.
Compound 195
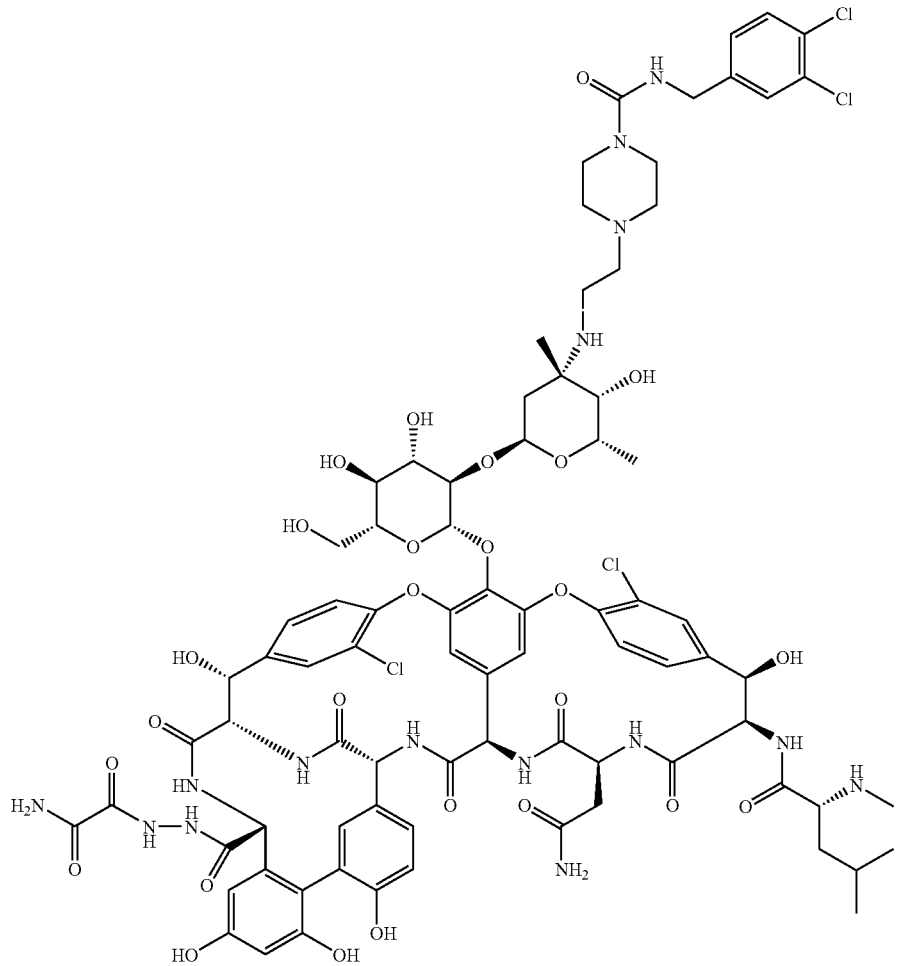
[Chemical Formula 234]

[M+H]+=1846
Anal calcd. for $C_{82}H_{95}Cl_4N_{15}O_{26}$·12.3$H_2O$·2.9HCl: C, 45.26%; H, 5.67%; N, 9.66%; Cl, 11.24%. Found: C, 45.26%; H, 5.37%; N, 9.72%; Cl, 11.17%.
Compound 196
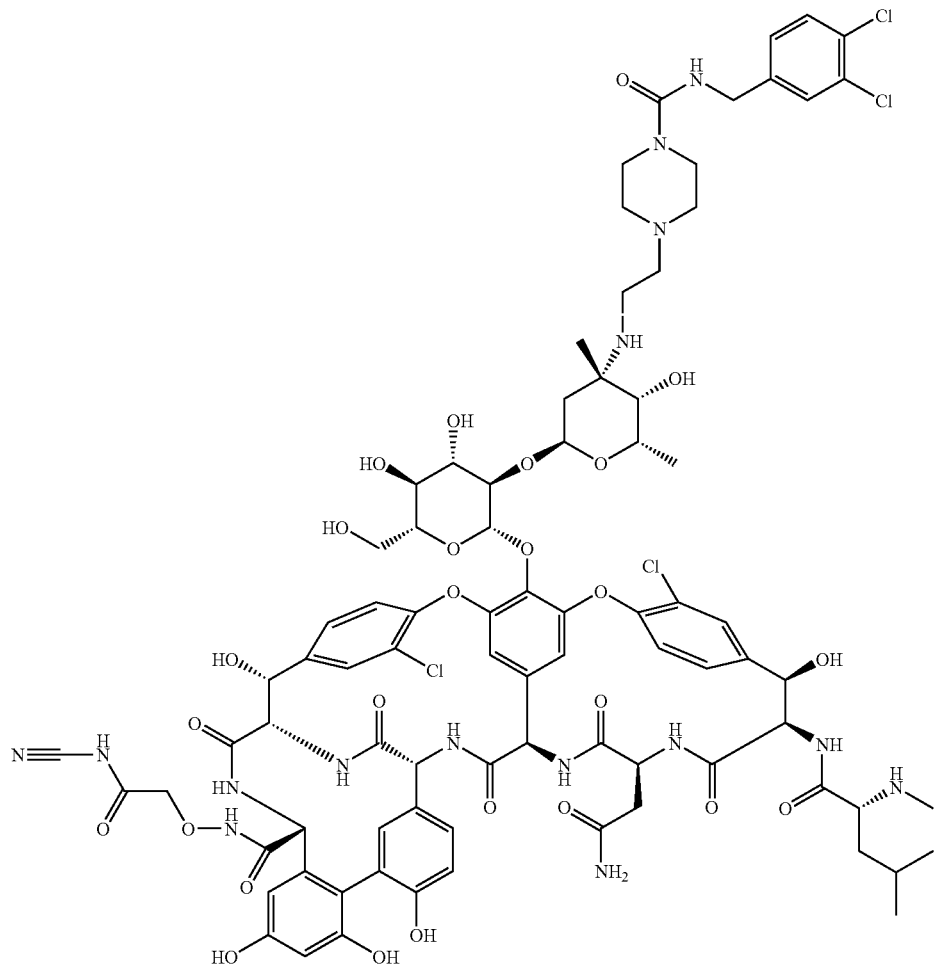
[Chemical Formula 235]

[M+H]⁺=1858
Anal calcd. for $C_{83}H_{95}Cl_4N_{15}O_{26}\cdot 10.8H_2O\cdot 1.5HCl$: C, 47.25%; H, 5.64%; N, 9.96%; Cl, 9.24%. Found: C, 47.136; H, 5.34%; N, 9.94%; Cl, 9.19%.
Compound 197
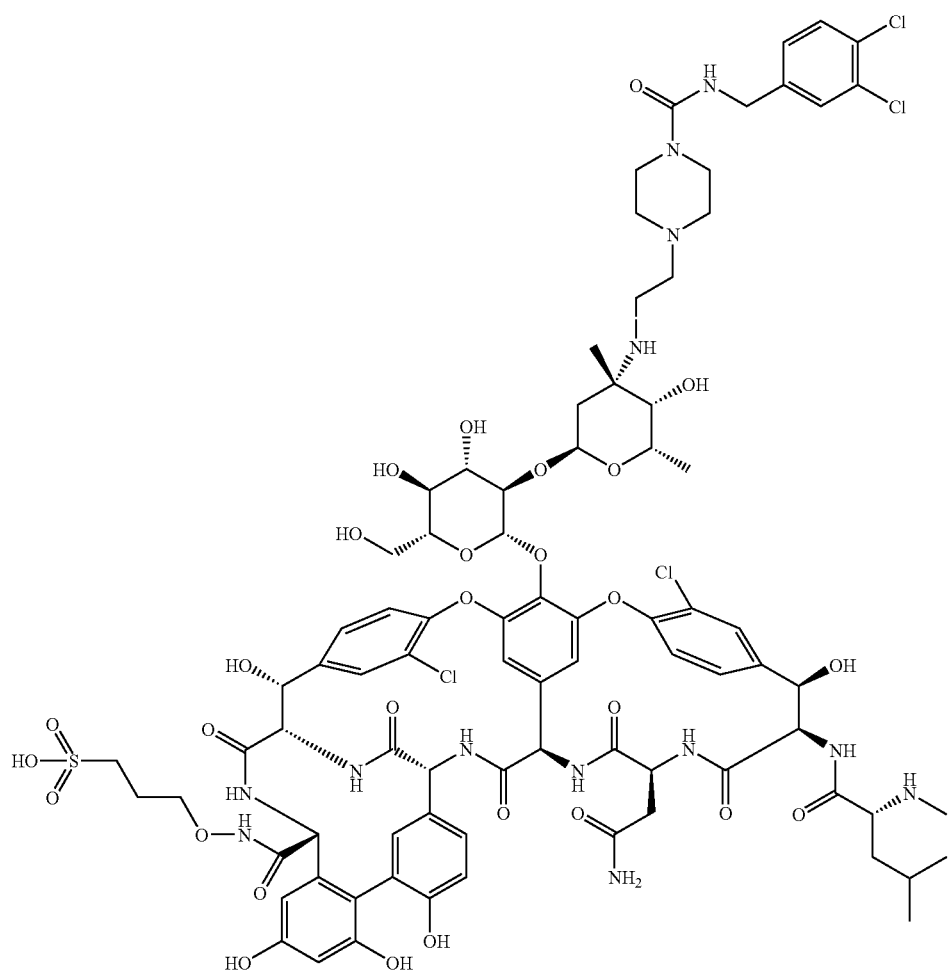
[Chemical Formula 236]

[M+H]$^+$=1898
Anal calcd. for $C_{83}H_{99}Cl_4N_{13}O_{28}S \cdot 16.2H_2O \cdot 1.7HCl$: C, 44.18%; H, 5.95%; N, 8.07%; Cl, 8.96%; S, 1.42%. Found: C, 44.20%; H, 5.88%; N, 8.14%; Cl, 8.92%; S, 1.33%.
Compound 198
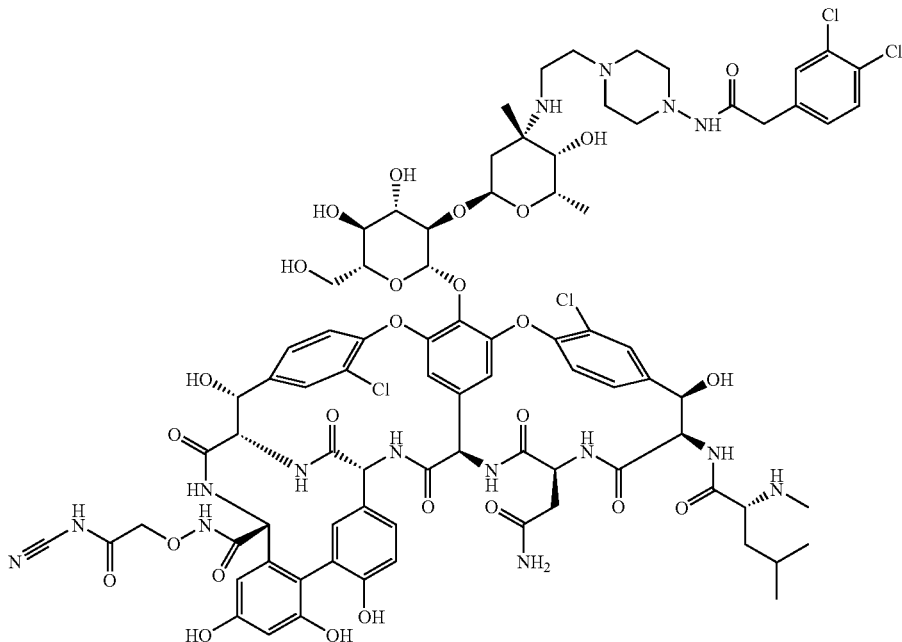
[Chemical Formula 237]
[M+H]$^+$=1858
Anal calcd. for $C_{83}H_{95}Cl_4N_{15}O_{26} \cdot 9.9H_2O \cdot 2.1HCl$: C, 47.12%; H, 5.57%; N, 9.93%; Cl, 10.22%. Found: C, 47.13%; H, 5.55%; N, 9.91%; Cl, 10.21%.
Compound 199
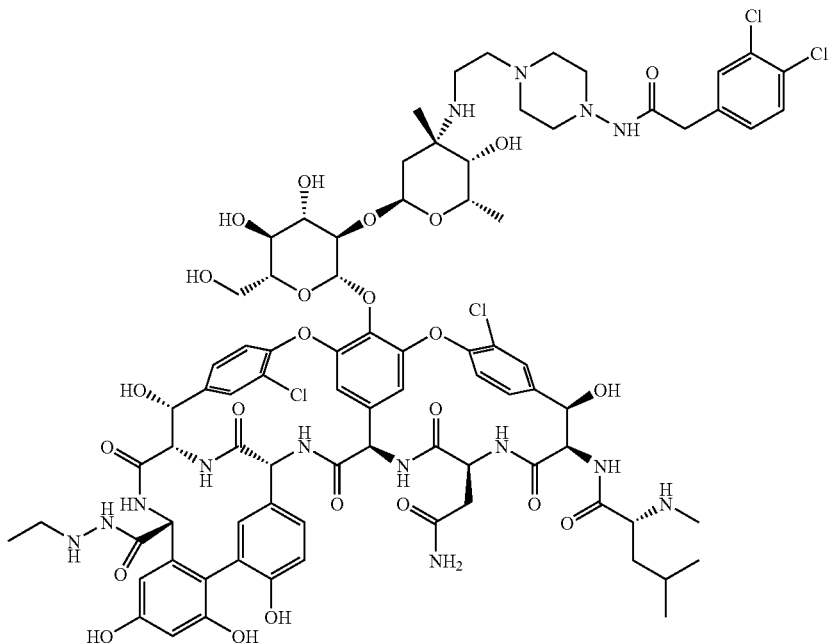
[Chemical Formula 238]

[M+H]⁺=1803
Anal calcd. for $C_{82}H_{98}Cl_4N_{14}O_{24}\cdot11.3H_2O\cdot3.7HCl$: C, 45.94%; H, 5.84%; N, 9.15%; Cl, 12.73%. Found: C, 45.85%; H, 5.74%; N, 9.32%; Cl, 12.78%.
Compound 200
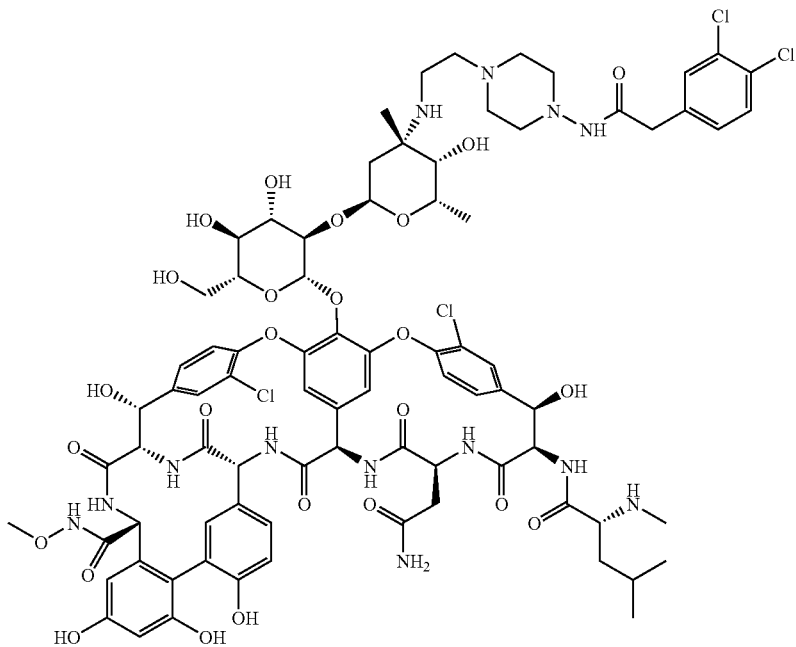
[Chemical Formula 239]
[M+H]⁺=1790
Anal calcd. for $C_{81}H_{95}Cl_4N_{13}O_{25}\cdot10.4H_2O\cdot2.7HCl$: C, 46.81%; H, 5.75%; N, 8.76%; Cl, 11.43%. Found: C, 46.86%; H, 5.82%; N, 8.57%; Cl, 11.50%.
Compound 201
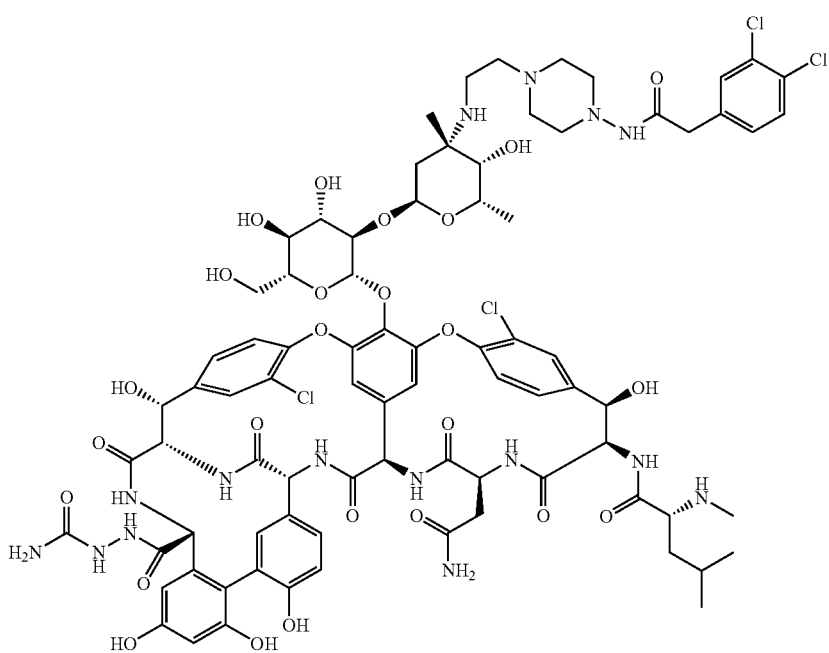
[Chemical Formula 240]

[M+H]$^+$=1818
Anal calcd. for $C_{81}H_{95}Cl_4N_{15}O_{25} \cdot 11H_2O \cdot 3HCl$: C, 45.72%; H, 5.68%; N, 9.87%; Cl, 11.66%. Found: C, 45.74%; H, 5.62%; N, 9.96%; Cl, 11.69%.
Compound 202
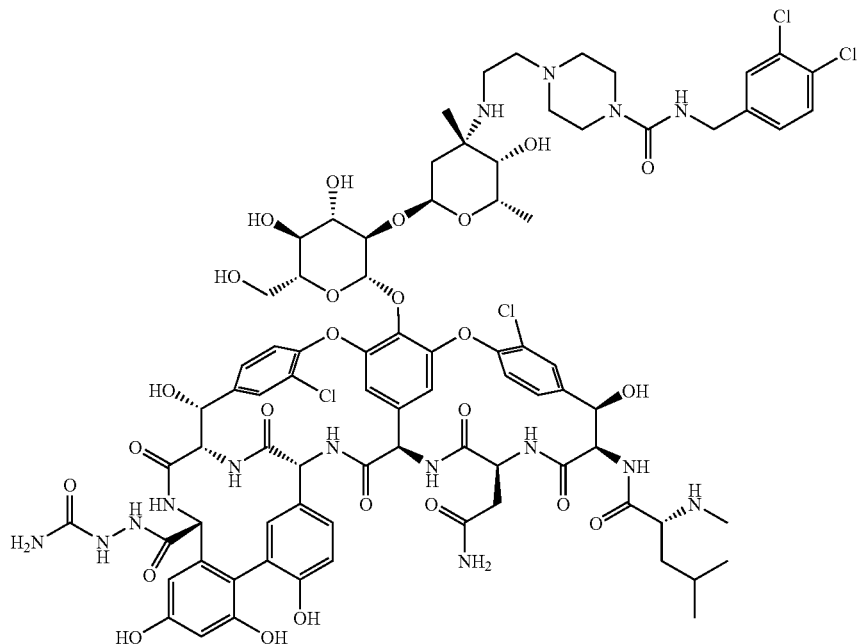
[Chemical Formula 241]
[M+H]$^+$=1818
Anal calcd. for $C_{81}H_{95}Cl_4N_{15}O_{25} \cdot 10.7H_2O \cdot 2.8HCl$: C, 45.99%; H, 5.68%; N, 9.93%; Cl, 11.4%. Found: C, 45.98%; H, 5.6%; N, 9.95%; Cl, 11.33%.
Compound 203
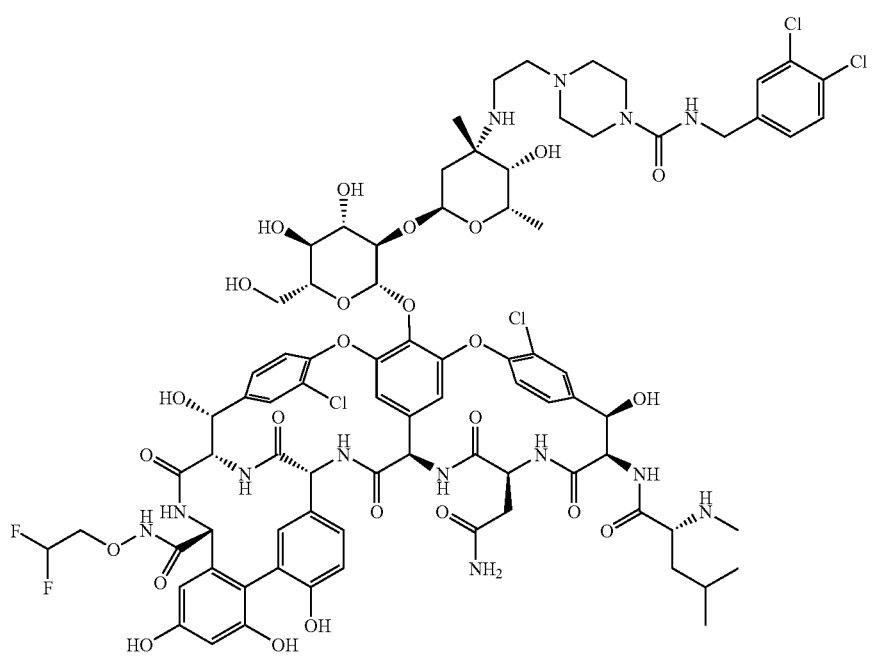
[Chemical Formula 242]

[M+H]$^+$=1840
Anal calcd. for $C_{82}H_{95}Cl_4F_2N_{13}O_{25}$·9.2H$_2$O·2.7HCl: C, 46.75%; H, 5.55%; N, 8.64%; Cl, 11.28%; F, 1.80%. Found: C, 46.83%; H, 5.61%; N, 8.60%; Cl, 11.29%; F, 1.23%.
Compound 204
[Chemical Formula 243]
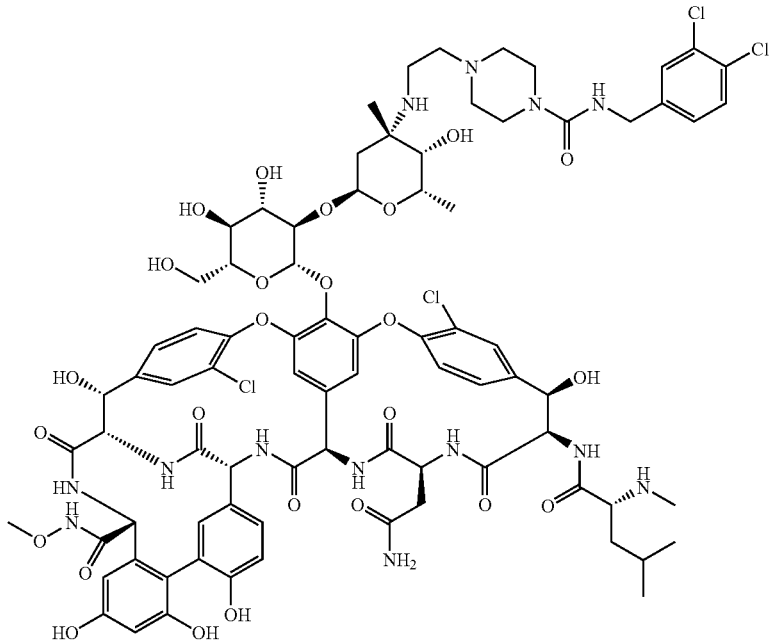
[M+H]$^+$=1790
Anal calcd. for $C_{81}H_{95}Cl_4N_{13}O_{25}$·18.6H$_2$O·3.1HCl: C, 43.42%; H, 6.09%; N, 8.13%; Cl, 11.23%. Found: C, 43.30%; H, 6.03%; N, 8.71%; Cl, 11.17%.
Compound 205
[Chemical Formula 244]
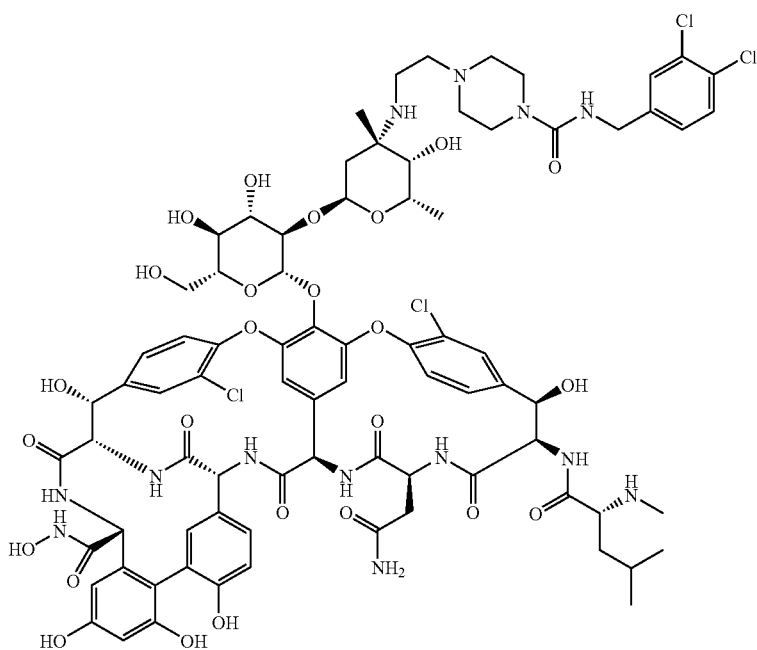

[M+H]⁺=1776
Anal calcd. for $C_{80}H_{93}Cl_4N_{13}O_{25}\cdot10.2H_2O\cdot2.9HCl$: C, 46.46%; H, 5.67%; N, 8.81%; Cl, 11.83%. Found: C, 46.41%; H, 5.68%; N, 8.97%; Cl, 11.90%.
Compound 206
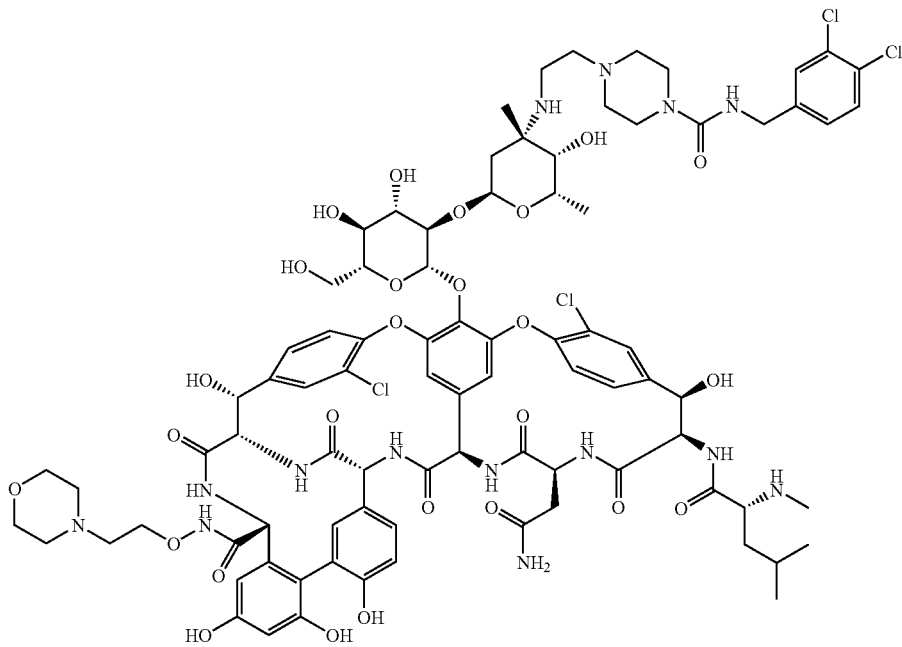
[Chemical Formula 245]
[M+H]⁺=1889
Anal calcd. for $C_{86}H_{104}Cl_4N_{14}O_{26}\cdot10.7H_2O\cdot3.9HCl$: C, 46.39%; H, 5.85%; N, 8.81%; Cl, 12.58%. Found: C, 46.28%; H, 5.83%; N, 9.42%; Cl, 12.60%.
Compound 207
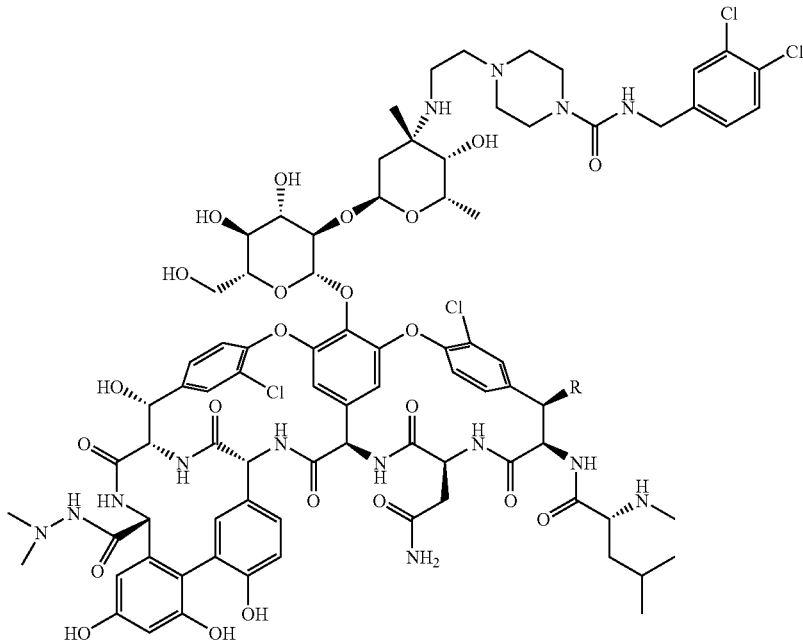
[Chemical Formula 246]

[M+H]⁺=1803
Anal calcd. for $C_{82}H_{98}Cl_4N_{14}O_{24} \cdot 12.1H_2O \cdot 3.6HCl$: C, 45.71%; H, 5.88%; N, 9.10%; Cl, 12.50%. Found: C, 45.67%; H, 5.78%; N, 9.14%; Cl, 12.50%.
Compound 208
[Chemical Formula 247]
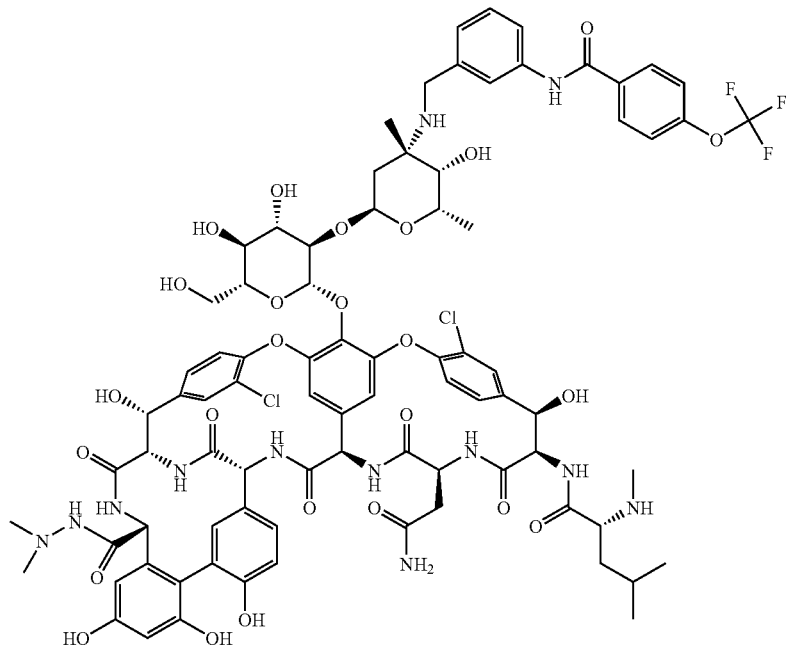
[M+H]⁺=1783
Anal calcd. for $C_{83}H_{91}Cl_2F_3N_{12}O_{25} \cdot 11H_2O \cdot 2.7HCl$: C, 47.90%; H, 5.60%; N, 8.08%; Cl, 8.01%; F, 2.74%. Found: C, 48.00%; H, 5.51%; N, 8.13%; Cl, 8.05%; F, 2.74%.
Compound 209
[Chemical Formula 248]
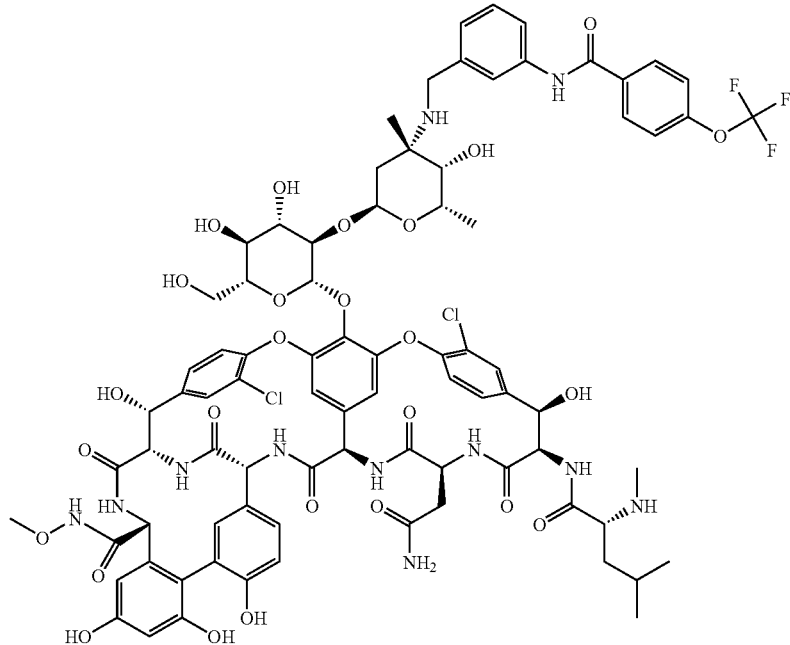

[M+H]⁺=1770
Anal calcd. for $C_{82}H_{88}Cl_2F_3N_{11}O_{26} \cdot 9H_2O \cdot 2HCl$: C, 49.08%; H, 5.42%; N, 7.68%; Cl, 7.07%; F, 2.84%. Found: C, 49.02%; H, 5.39%; N, 7.79%; Cl, 7.00%; F, 2.83%.
Compound 210
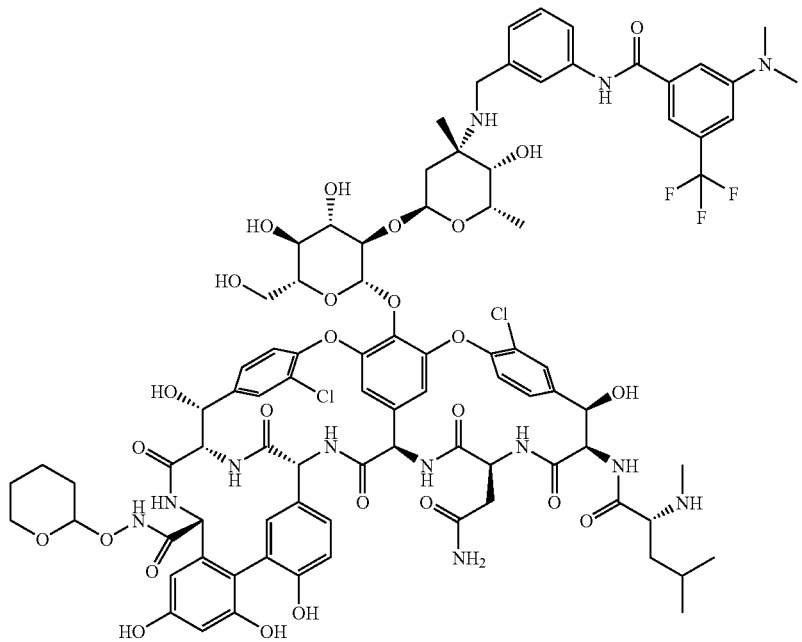
[Chemical Formula 249]
[M+H]⁺=1867
Anal calcd. for $C_{88}H_{99}Cl_2F_3N_{12}O_{26} \cdot 9H_2O \cdot 2.9HCl$: C, 49.47%; H, 5.66%; N, 7.87%; Cl, 8.13%; F, 2.67%. Found: C, 49.54%; H, 5.67%; N, 7.95%; Cl, 8.16%; F, 2.92%.
Compound 211
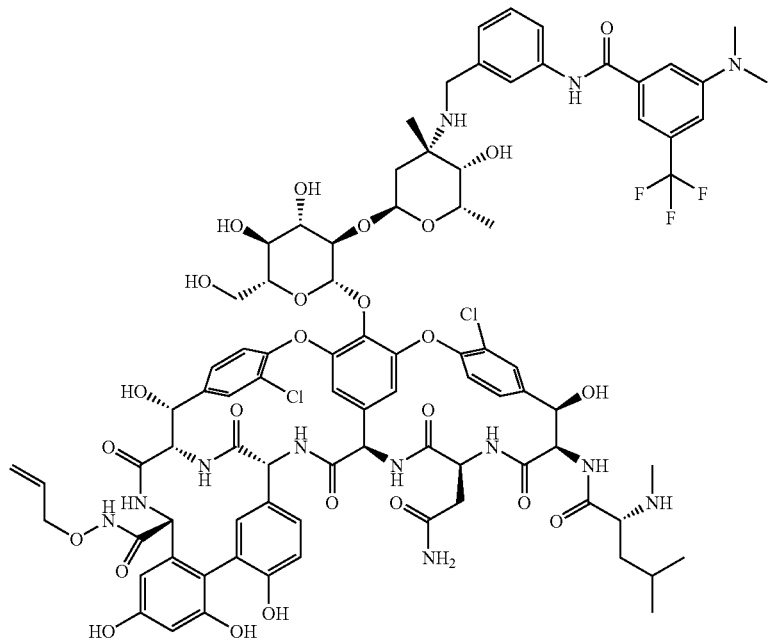
[Chemical Formula 250]

[M+H]+=1823
Anal calcd. for $C_{86}H_{95}Cl_2F_3N_{12}O_{26} \cdot 10H_2O \cdot 2.6HCl$: C, 49.20%; H, 5.65%; N, 8.01%; Cl, 7.77%; F, 2.71%. Found: C, 49.33%; H, 5.60%; N, 8.08%; Cl, 7.86%; F, 2.67%.
Compound 212
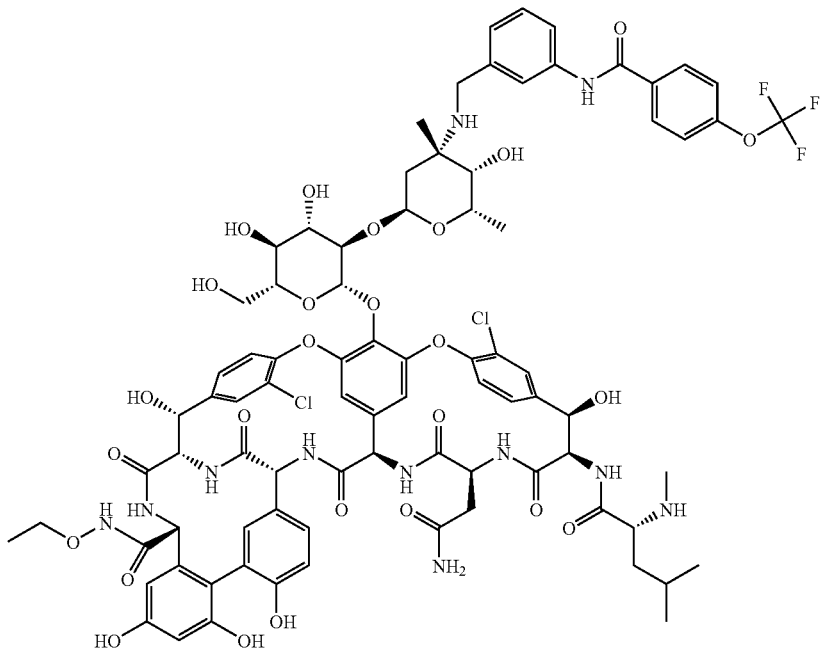
[Chemical Formula 251]
[M+H]+=1784
Anal calcd. for $C_{83}H_{90}Cl_2F_3N_{11}O_{26} \cdot 9H_2O \cdot 2.0HCl$: C, 49.34%; H, 5.49%; N, 7.63%; Cl, 7.02%; F, 2.82%. Found: C, 49.19%; H, 5.42%; N, 7.65%; Cl, 7.07%; F, 2.88%.
Compound 213
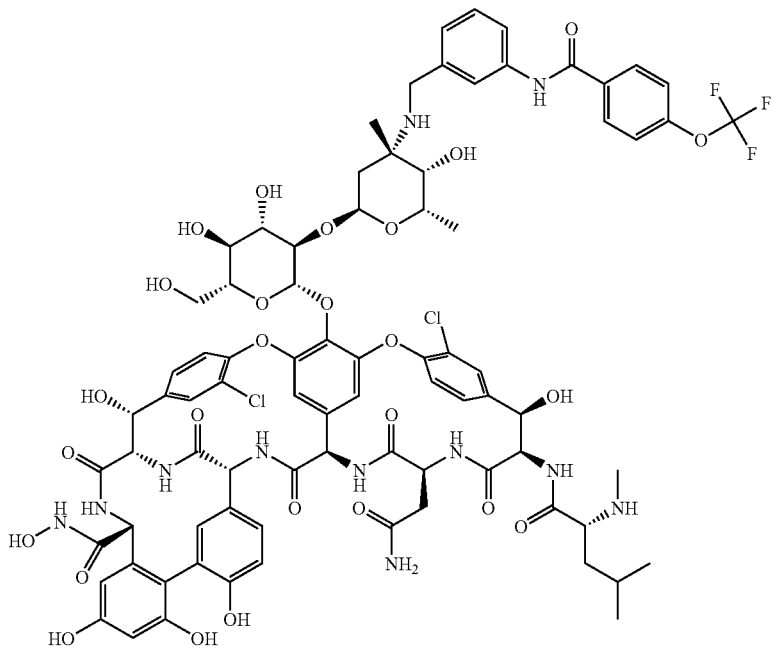
[Chemical Formula 252]

[M+H]⁺=1756
Anal calcd. for $C_{81}H_{86}Cl_2F_3N_{11}O_{26}\cdot 5H_2O\cdot 2HCl$: C, 50.66%; H, 5.14%; N, 8.02%; Cl, 7.38%; F, 2.97%. Found: C, 50.63%; H, 5.19%; N, 8.20%; Cl, 7.40%; F, 2.88%.
Compound 214
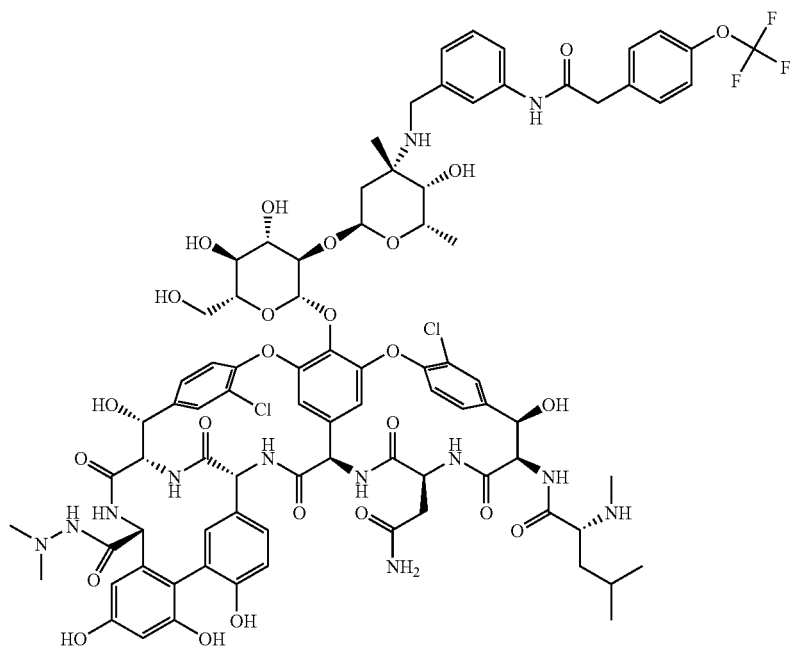
[Chemical Formula 253]
[M+H]⁺=1797
Anal calcd. for $C_{84}H_{93}Cl_2F_3N_{12}O_{25}\cdot 10H_2O\cdot 2.4HCl$: C, 48.83%; H, 5.63%; N, 8.13%; Cl, 7.55%; F, 2.76%. Found: C, 48.99%; H, 5.58%; N, 8.40%; Cl, 7.60%; F, 2.76%.
Compound 215
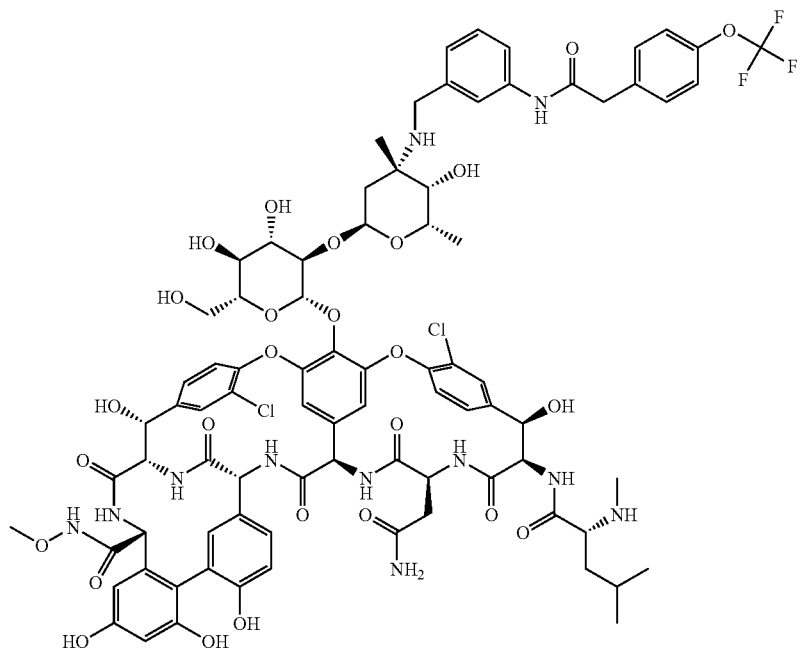
[Chemical Formula 254]

[M+H]$^+$=1784
Anal calcd. for $C_{83}H_{90}Cl_2F_3N_{11}O_{26} \cdot 9H_2O \cdot 2HCl$: C, 49.34%; H, 5.49%; N, 7.63%; Cl, 7.02%; F, 2.82%. Found: C, 49.13%; H, 5.53%; N, 7.68%; Cl, 7.06%; F, 2.76%.
Compound 216
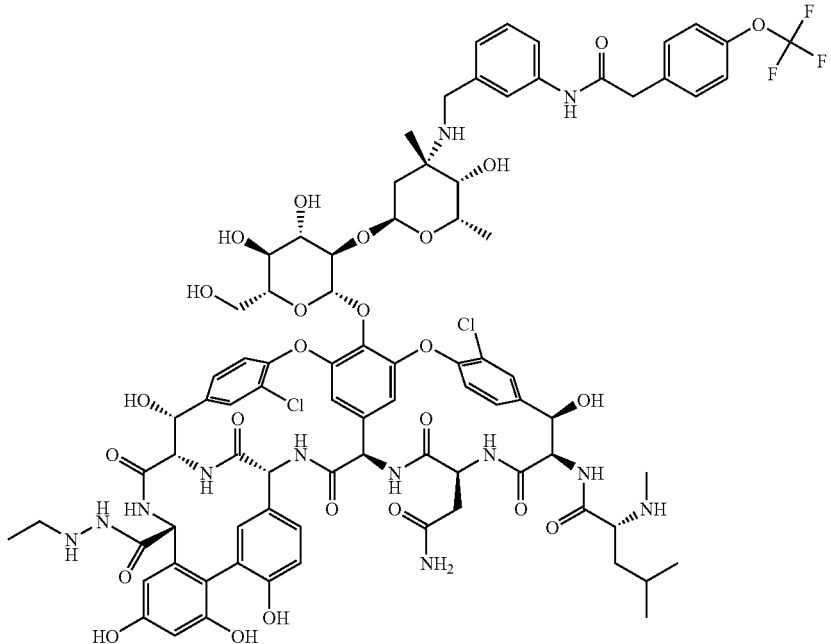
[Chemical Formula 255]
[M+H]$^+$=1797
Anal calcd. for $C_{84}H_{93}Cl_2F_3N_{12}O_{25} \cdot 10H_2O \cdot 2.5HCl$: C, 48.74%; H, 5.62%; N, 8.12%; Cl, 7.71%; F, 2.75%. Found: C, 48.78%; H, 5.60%; N, 8.33%; Cl, 7.78%; F, 2.68%.
Compound 217
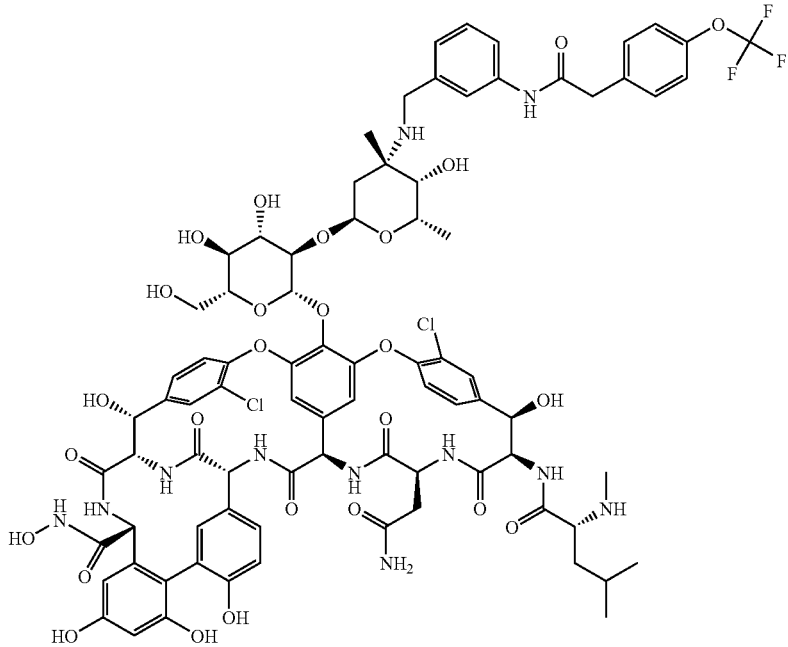
[Chemical Formula 256]

[M+H]$^+$=1770
Anal calcd. for $C_{82}H_{88}Cl_2F_3N_{11}O_{26} \cdot 10H_2O \cdot 2HCl$: C, 48.65%; H, 5.48%; N, 7.61%; Cl, 7.00%; F, 2.82%. Found: C, 48.68%; H, 5.40%; N, 7.73%; Cl, 7.06%; F, 2.71%.
Compound 218
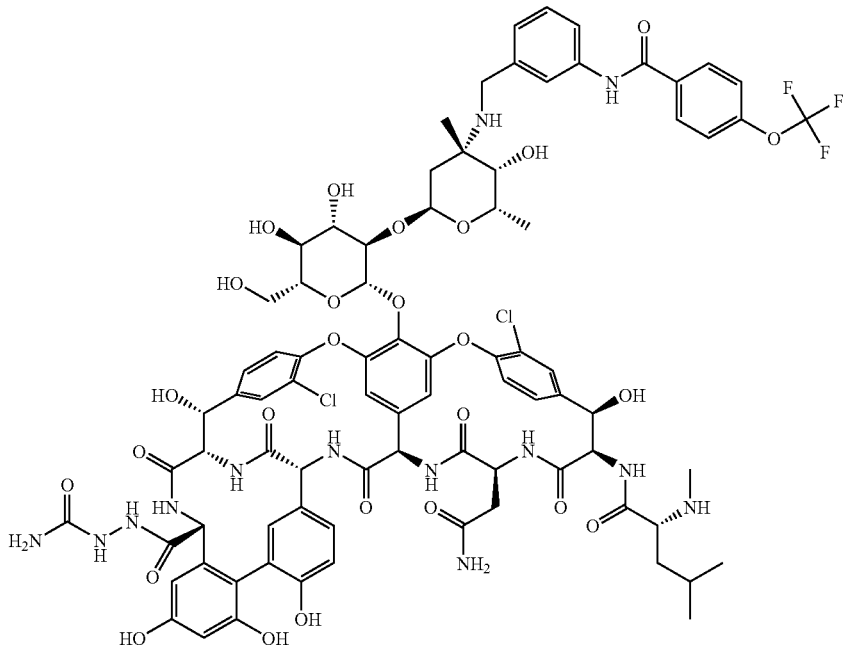
[Chemical Formula 257]
[M+H]$^+$=1798
Anal calcd. for $C_{82}H_{88}Cl_2F_3N_{13}O_{26} \cdot 10H_2O \cdot 2.1HCl$: C, 47.90%; H, 5.40%; N, 8.86%; Cl, 7.07%; F, 2.77%. Found: C, 47.95%; H, 5.37%; N, 9.10%; Cl, 7.17%; F, 2.72%.
Compound 219
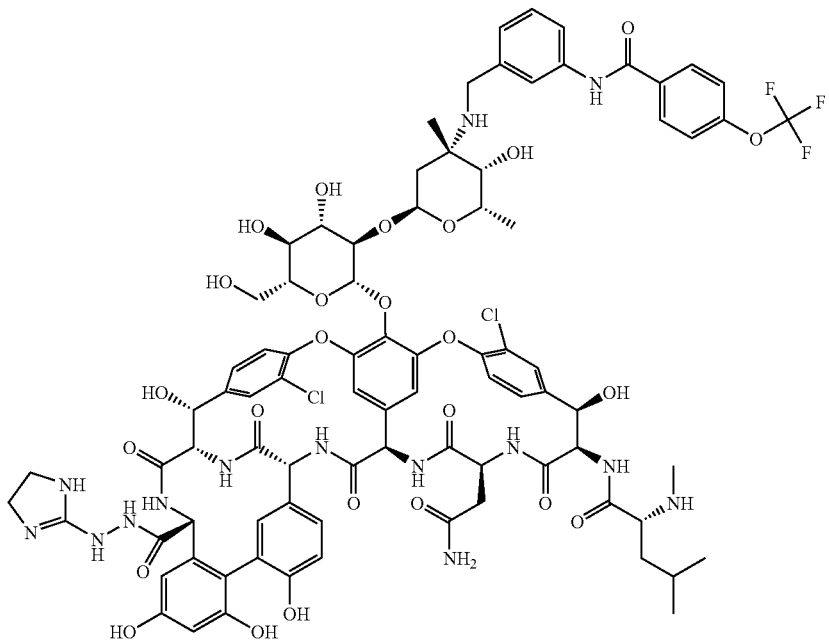
[Chemical Formula 258]

$[M+H]^+=1823$
Anal calcd. for $C_{84}H_{91}Cl_2F_3N_{14}O_{25} \cdot 10H_2O \cdot 3HCl$: C, 47.72%; H, 5.44%; N, 9.28%; Cl, 8.38%; F, 2.70%. Found: C, 47.54%; H, 5.49%; N, 9.45%; Cl, 8.39%; F, 2.55%.
Compound 220
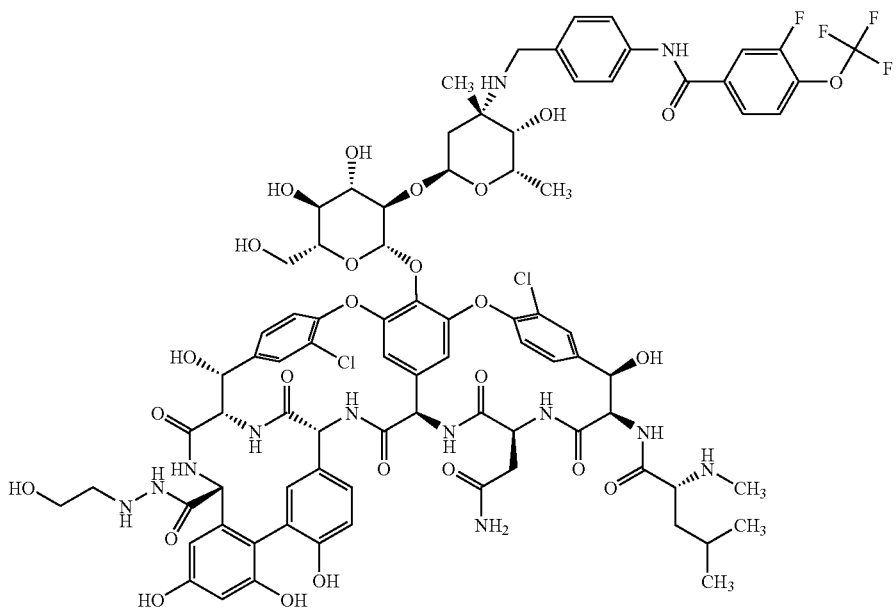
$[M+H]^+=1817$
Anal calcd. for $C_{83}H_{90}Cl_2F_4N_{12}O_{26} \cdot 12.0H_2O \cdot 2.7HCl$: C, 46.73%; H, 5.51%; N, 7.88%; Cl, 7.81%; F, 3.56%. Found: C, 46.70%; H, 5.53%; N, 7.92%; Cl, 7.88%; F, 3.48%.
Compound 221
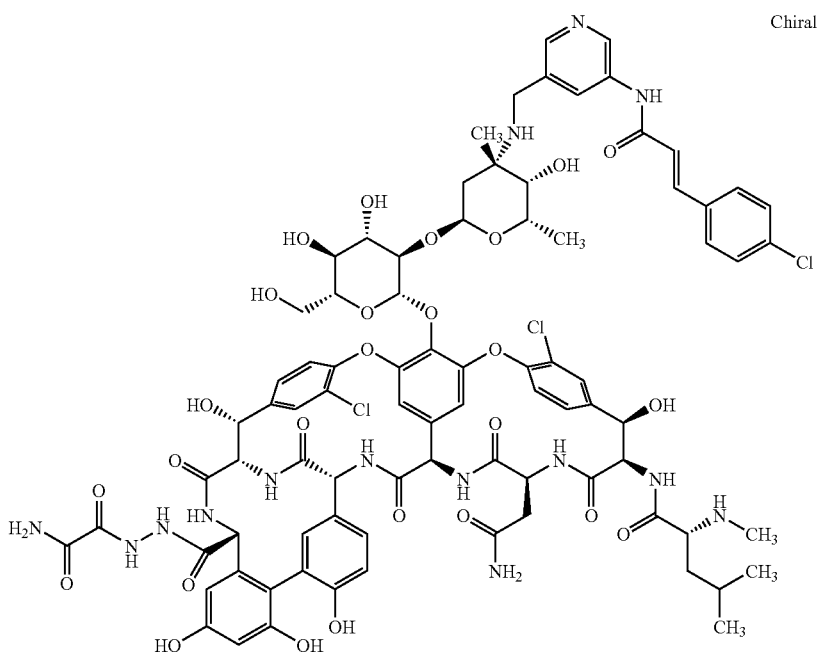

[M+H]$^+$=1803
Anal calcd. for $C_{83}H_{89}Cl_3N_{14}O_{26} \cdot 15.9H_2O \cdot 2.5HCl$: C, 45.67%; H, 5.69%; N, 8.98%; Cl, 8.93%. Found: C, 45.71%; H, 5.51%; N, 8.87%; Cl, 8.96%.
Compound 222
[Chemical Formula 261]
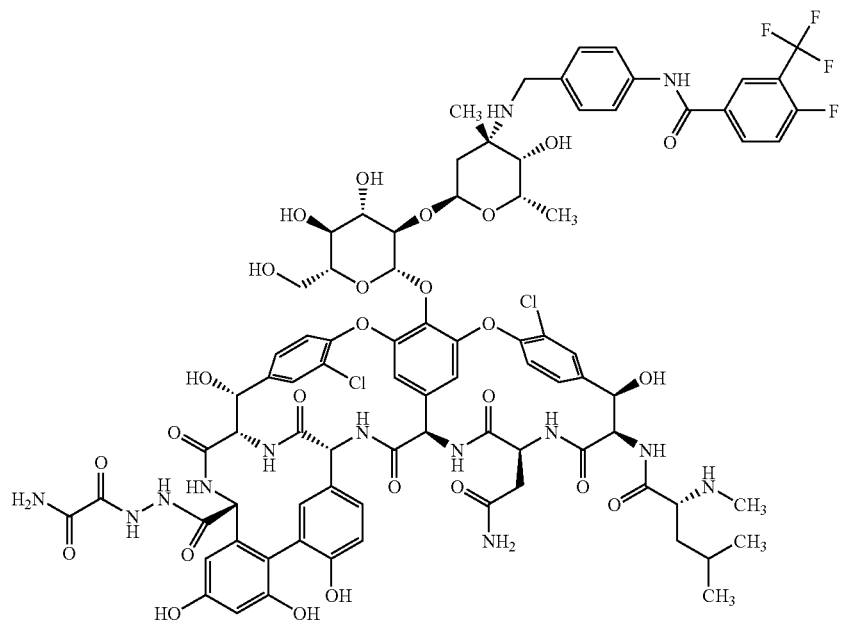
[M+H]$^+$=1828
Anal calcd. for $C_{83}H_{87}Cl_2F_4N_{13}O_{26} \cdot 18.0H_2O \cdot 3.2HCl$: C, 43.91%; H, 5.60%; N, 8.02%; Cl, 8.12%; F, 3.35%. Found: C, 43.87%; H, 5.15%; N, 8.01%; Cl, 8.03%; F, 3.24%.
Compound 223
[Chemical Formula 262]
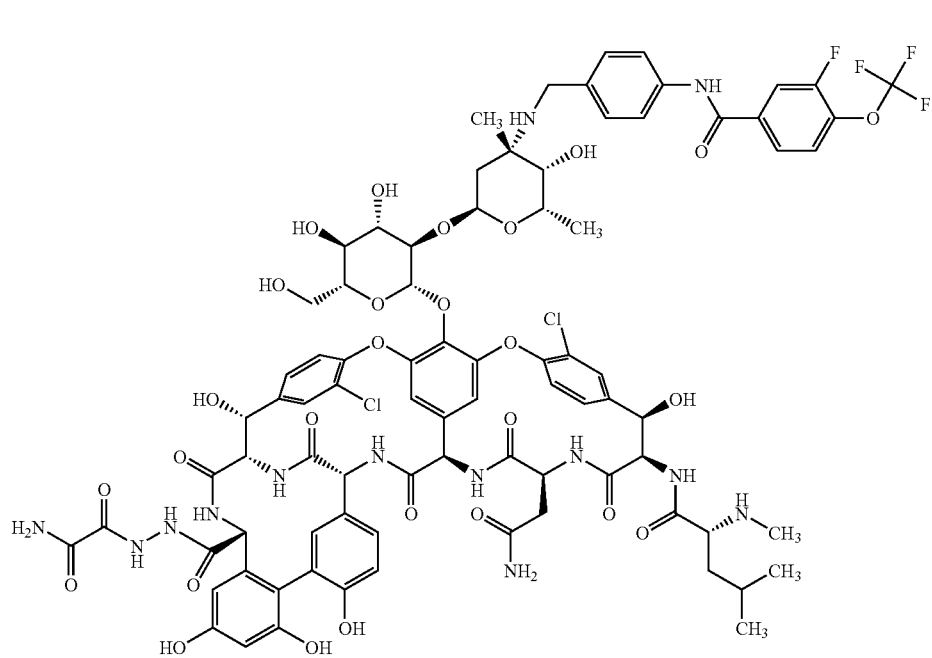

[M+H]⁺=1844
Anal calcd. for $C_{83}H_{87}Cl_2F_4N_{13}O_{27}\cdot13.0H_2O\cdot2.1HCl$: C, 46.23%; H, 5.38%; N, 8.44%; Cl, 6.74%; F, 3.52%. Found: C, 46.19%; H, 5.20%; N, 8.44%; Cl, 6.73%; F, 3.52%.
Compound 224
[Chemical Formula 263]
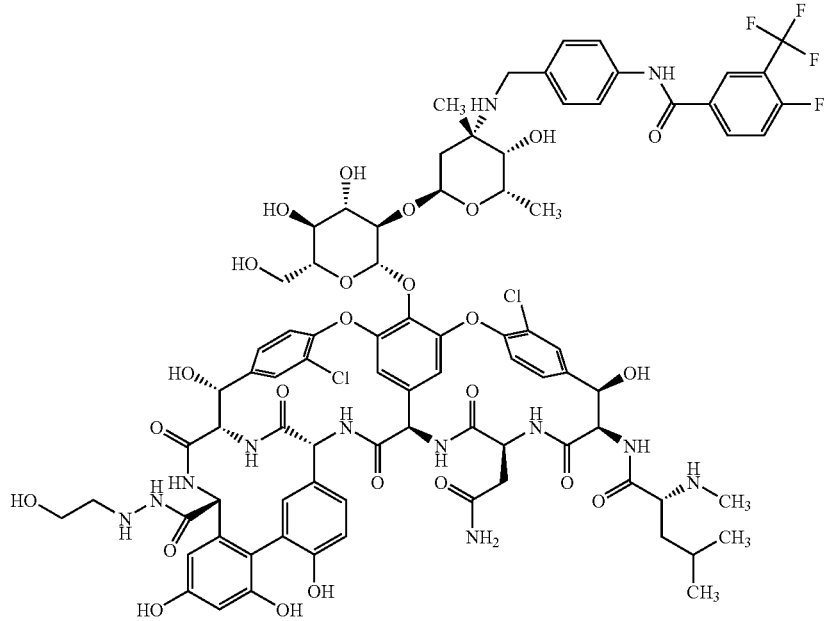
[M+H]⁺=1801
Anal calcd. for $C_{83}H_{90}Cl_2F_4N_{12}O_{25}\cdot12.6H_2O\cdot2.3HCl$: C, 47.17%; H, 5.60%; N, 7.95%; Cl, 7.21%; F, 3.60%. Found: C, 47.16%; H, 5.44%; N, 7.91%; Cl, 7.21%; F, 3.48%.
Compound 225
[Chemical Formula 264]
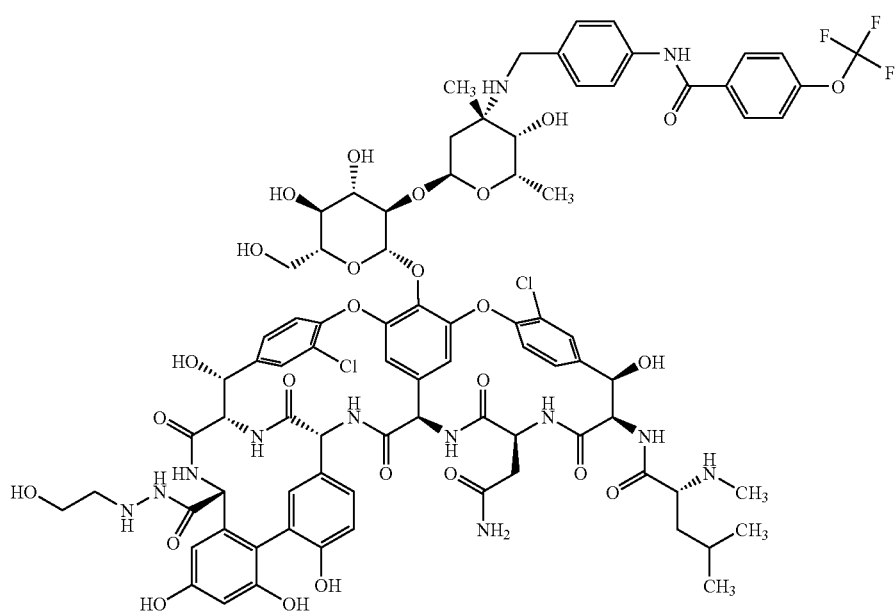

[M+H]⁺=1799
Anal calcd. for $C_{83}H_{91}Cl_2F_3N_{12}O_{26}\cdot11.1H_2O\cdot2.3HCl$: C, 47.83%; H, 5.59%; N, 8.06%; Cl, 7.31%; F, 2.73%. Found: C, 47.87%; H, 5.64%; N, 8.03%; Cl, 7.36%; F, 2.69%.
Compound 226
[Chemical Formula 265]
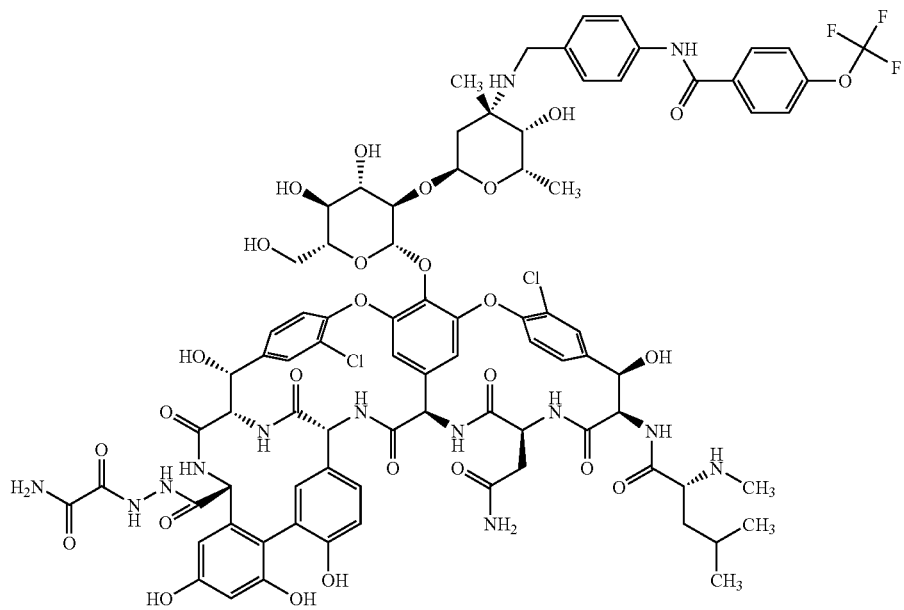
[M+H]⁺=1826
Anal calcd. for $C_{83}H_{88}Cl_2F_3N_{13}O_{27}\cdot10.3H_2O\cdot2.2HCl$: C, 47.62%; H, 5.34%; N, 8.70%; Cl, 7.11%; F, 2.72%. Found: C, 47.69%; H, 5.46%; N, 8.66%; Cl, 7.06%; F, 2.58%.
Compound 227
[Chemical Formula 266]
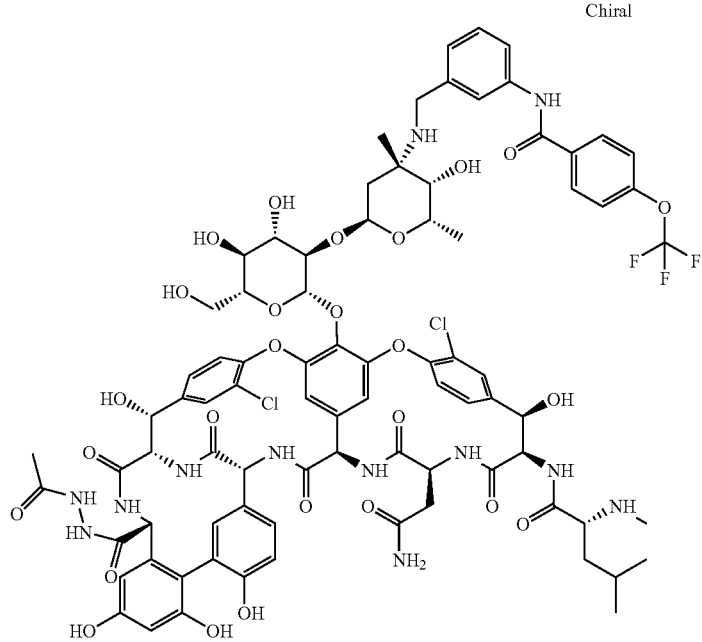

[M+H]⁺=1797
Anal calcd. for $C_{83}H_{89}Cl_2F_3N_{12}O_{26} \cdot 11.1H_2O \cdot 1.8HCl$: C, 48.30%; H, 5.52%; N, 8.14%; Cl, 6.53%; F, 2.76%. Found: C, 48.41%; H, 5.55%; N, 7.62%; Cl, 6.53%; F, 2.53%.
Compound 228
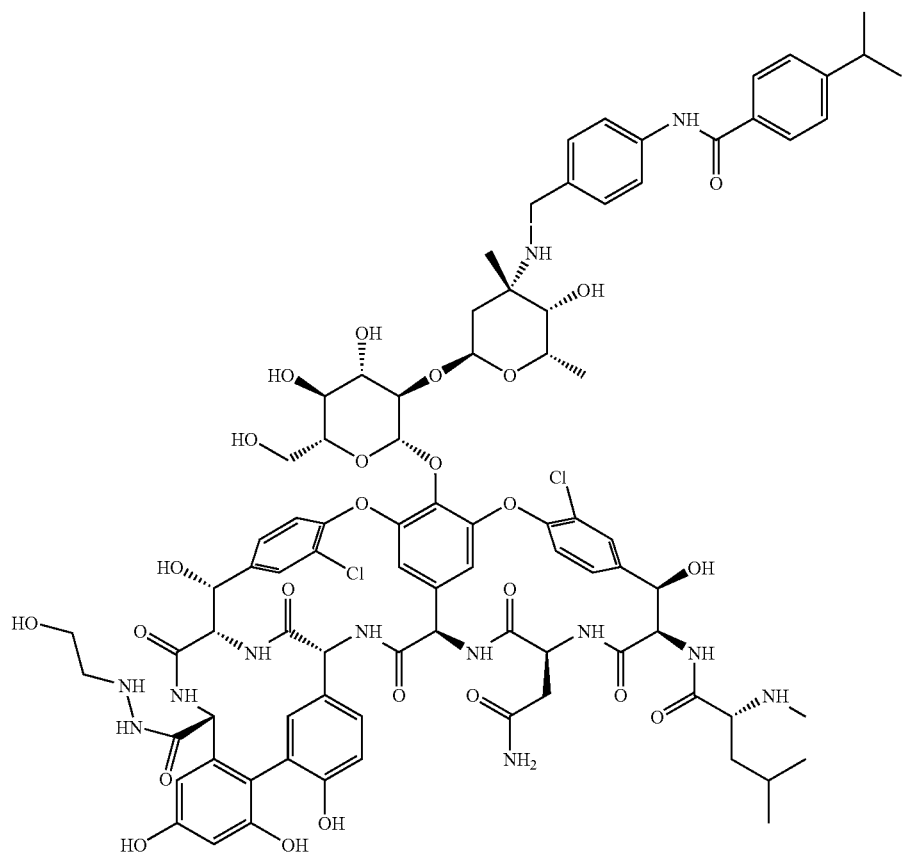
[Chemical Formula 267]

[M+H]⁺=1757
Anal calcd. for $C_{85}H_{98}Cl_2N_{12}O_{25}\cdot11.2H_2O\cdot2.2HCl$: C, 50.03%; H, 6.06%; N, 8.24%; Cl, 7.30%. Found: C, 49.98%; H, 6.00%; N, 8.39%; Cl, 7.32%.
Compound 229
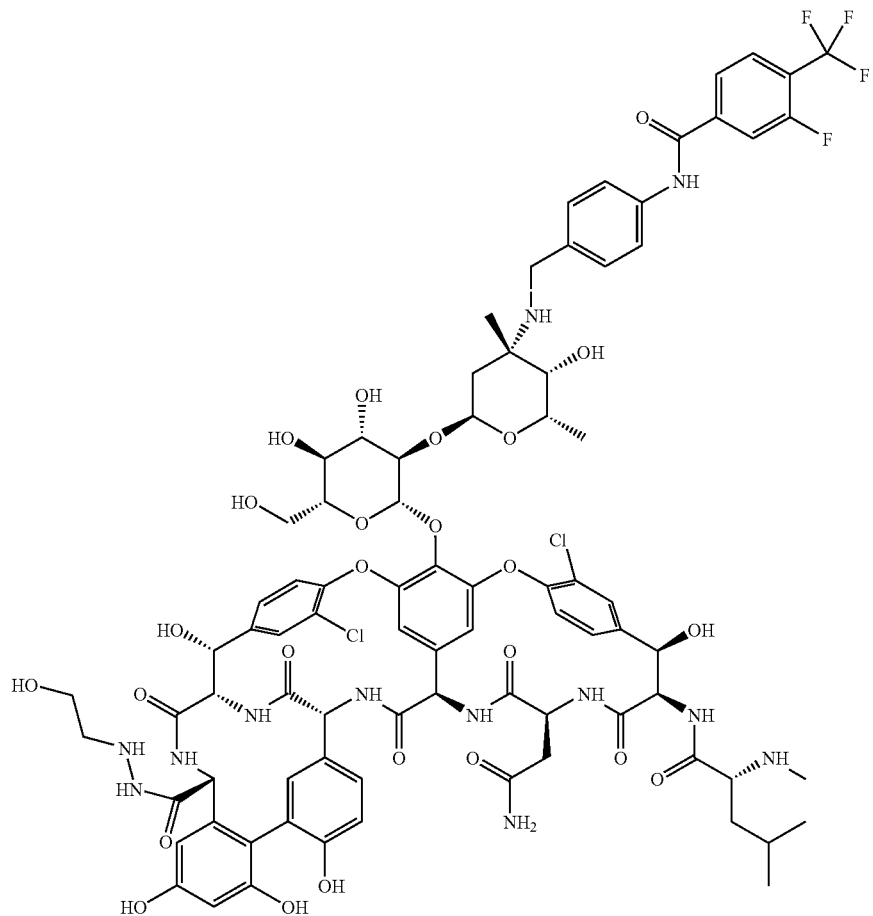
[Chemical Formula 268]

[M+H]+=1801
Anal calcd. for $C_{83}H_{90}Cl_2F_4N_{12}O_{25}\cdot 11.9H_2O\cdot 3.0HCl$: C, 46.88%; H, 5.54%; N, 7.90%; Cl, 8.34%; F, 3.57%. Found: C, 46.93%; H, 5.49%; N, 7.68%; Cl, 8.40%; F, 3.34%.
Compound 230
[Chemical Formula 269]
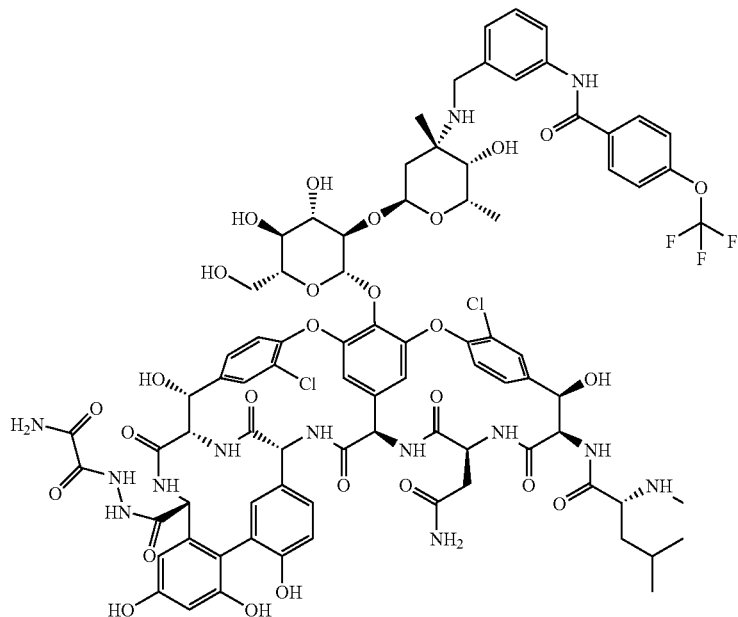
[M+H]+=1826
Anal calcd. for $C_{83}H_{88}Cl_2F_3N_{13}O_{27}\cdot 10.0H_2O\cdot 2.2HCl$: C, 47.75%; H, 5.32%; N, 8.72%; Cl, 7.13%; F, 2.73%. Found: C, 47.72%; H, 5.32%; N, 8.92%; Cl, 7.06%; F, 2.71%.
Compound 231
[Chemical Formula 270]
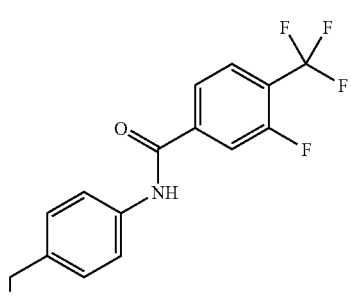

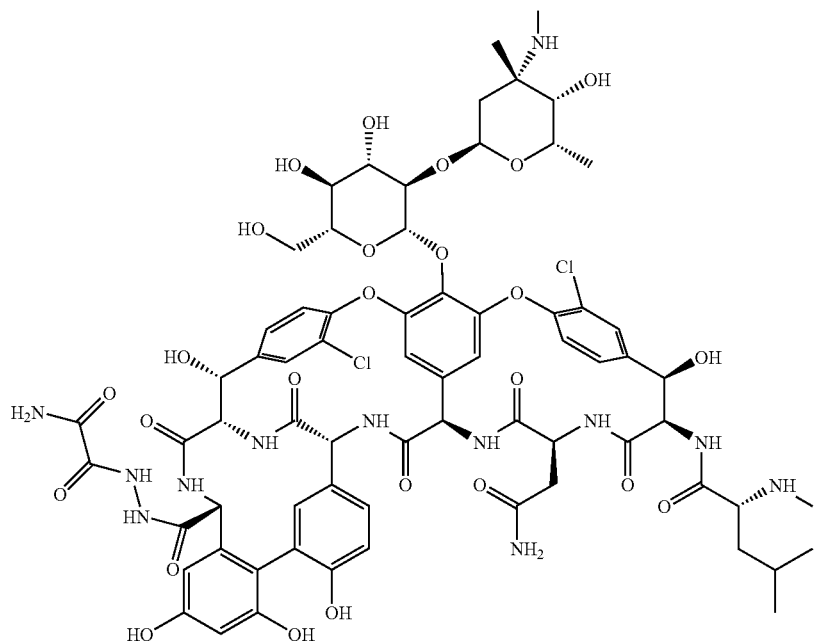
$[M+H]^+=1828$
Anal calcd. for $C_{83}H_{87}Cl_2F_4N_{13}O_{26} \cdot 10.2H_2O \cdot 1.7HCl$: C; 48.04%; H, 5.30%; N, 8.77%; Cl, 6.32%; F, 3.66%. Found: C, 48.33%; H, 5.44%; N, 7.83%; Cl, 6.37%; F, 3.22%.
Compound 232
[Chemical Formula 271]
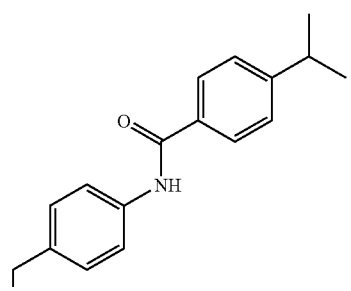

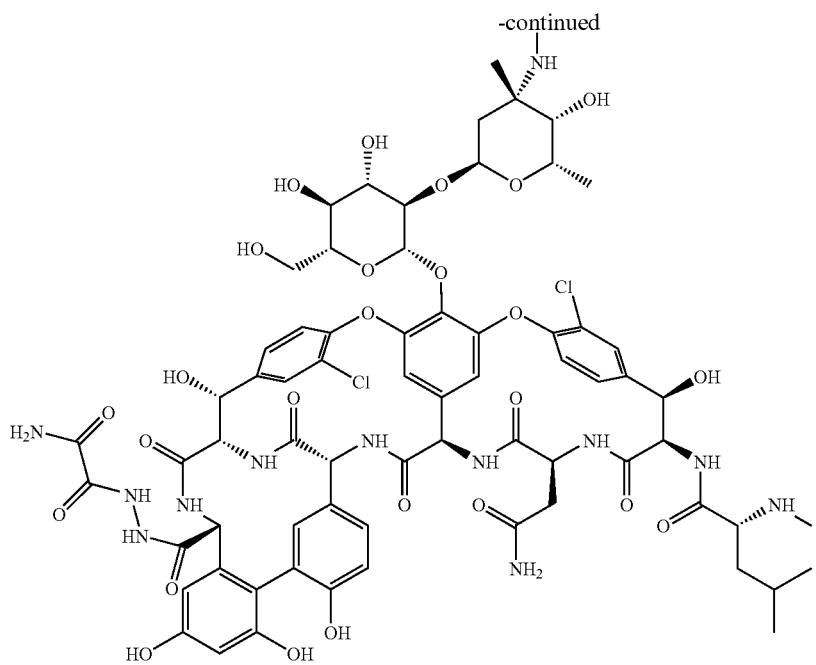
-continued

[M+H]⁺=1784
Anal calcd. for $C_{85}H_{95}Cl_2N_{13}O_{26} \cdot 10.8H_2O \cdot 1.9HCl$: C, 49.81%; H, 5.83%; N, 8.88%; Cl, 6.75%. Found: C, 49.91%; H, 5.75%; N, 8.39%; Cl, 6.79%.

Test Example 1

In Vitro Assay of Antimicrobial Activity
Method

For several compounds of the invention, minimal inhibitory concentration (MIC) was determined by the microdilution method using cation adjusted Mueller-Hinton broth well known in the art.

Results

The compounds of the invention showed a strong antimicrobial activity against various bacteria, including vancomycin-resistant strains. In particular, the compound of Example 4 showed MIC=4 μg/mL against vancomycin-resistant *enterococcus E. faecalis* SR7914 (VanA), and MIC=0.5 μg/mL against methicillin-resistant *Staphylococcus aureus S. aureus* SR3637 (H-MRSA).

Test Example 2

The compounds of the invention were tested for water solubility and toxicity.

The compounds of the invention showed good water solubility. Also, in a single-dose intravenous toxicity screening test in mouse (dosage: 30 mg/kg), the compound of the invention (e.g., the compound of Example 2 (Compound 2) etc.) showed good histological findings in kidney etc., as compared with its corresponding compound having —COOH at the C-terminal.

Formulations

It is to be noted that the following Formulations 1 to 8 are mere illustration, but not intended to limit the scope of the invention. The term "active ingredient" means the compounds of the invention, a tautomer, a prodrug, a pharmaceutically acceptable salt or a solvate thereof.

Formulation 1
Hard gelatin capsules are prepared using of the following ingredients:

|  | Dose (mg/capsule) |
|---|---|
| Active ingredient | 250 |
| Starch, dried | 200 |
| Magnesium stearate | 10 |
| Total | 460 mg |

Formulation 2
A tablet is prepared using of the following ingredients:

|  | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

|  | Weight |
|---|---|
| Active ingredient | 0.25 |
| Ethanol | 25.75 |
| Propellant (chlorodifluoromethane) | 22 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation 4

Tablets, each containing 60 mg of active ingredient, are made as follows.

| | |
|---|---|
| Active ingredient | 60 mg |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| Active ingredient | 80 mg |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppository, each containing 225 mg of active ingredient, are made as follows:

| | |
|---|---|
| Active ingredient | 225 mg |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1000 mL |

The solution of the above ingredients generally is administered intravenously to a subject at a rate of 1 mL per minute.

Industrial Applicability

The glycopeptide derivatives of the invention, pharmaceutically acceptable salts and solvates thereof are useful in the medical treatment and show a biological activity, including antimicrobial activity. Accordingly, the present invention provides a method for the treatment of infections diseases, particularly diseases caused by gram-positive microbial in animal, and the compounds of the invention is particularly useful in the treatment of infections with methicillin resistant *staphylococcus*. The compound is also useful for the treatment of infections with *enterococcus* including vancomycin-resistant *enterococcus* (VRE). Example of such disease includes severe infections with *staphylococcus* such as staphylococcal endocarditis and staphylococcal sepsis.

What is claimed is:

1. A compound of the formula:

[Chemical Formula 1]

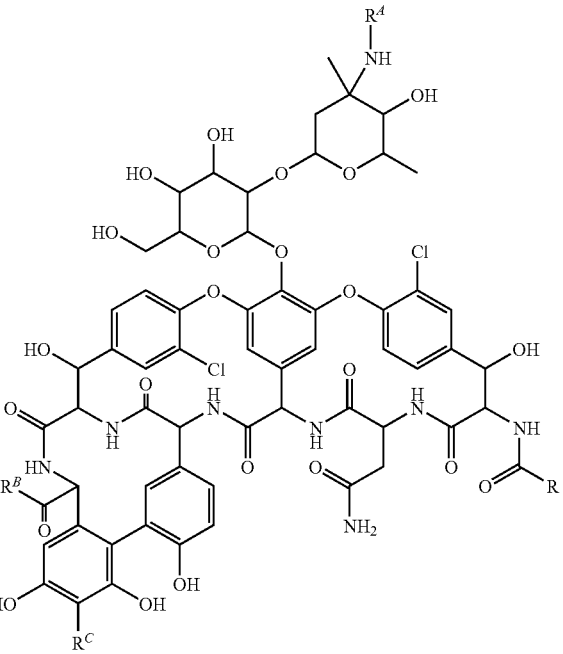

or a pharmaceutically acceptable salt thereof, wherein $R^A$ is

—$X^1$—$Ar^1$—$X^2$—Y—$X^3$—$Ar^2$ wherein
$X^1$ is $C_1$-$C_3$ alkylene;
$X^2$ is a single bond;
$X^3$ is a single bond;
Y is —$NR^2CO$— or —$CONR^2$-wherein $R^2$ is hydrogen or lower alkyl; and
$Ar^1$ is a carbocycle or heterocycle, each of which is optionally substituted and may have at least one unsaturated bond;

$Ar^2$ is optionally substituted aryl;
$R^B$ is —$NHNR^xR^Y$
wherein
$R^x$ is hydrogen or lower alkyl;
$R^Y$ is selected from the group consisting of optionally substituted lower alkyl, and optionally substituted carbamoyl;
$R^c$ is hydrogen; and
R is —$CH(NHR^D)CH_2CH(CH_3)_2$ wherein $R^D$ is hydrogen or lower alkyl;
with the proviso that the compound is not the following compounds:

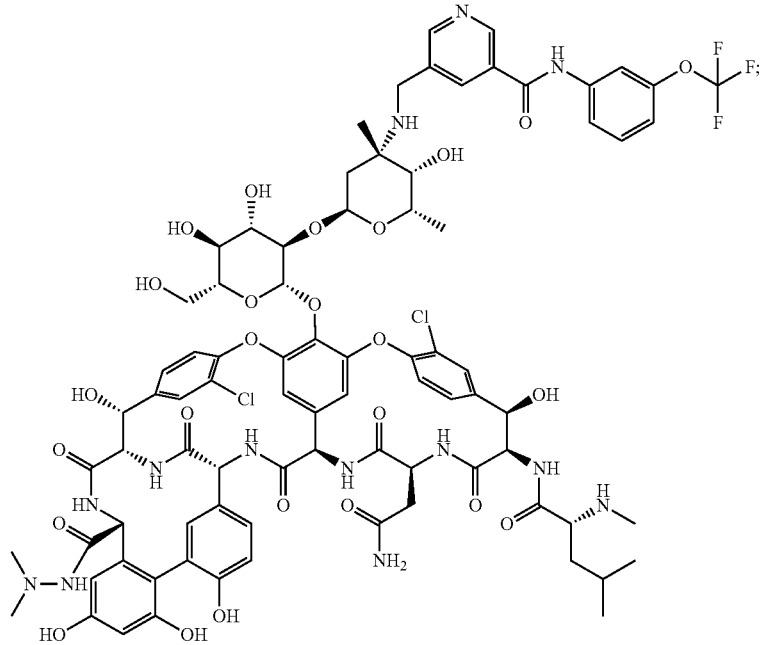

[Chemical Formula 3]

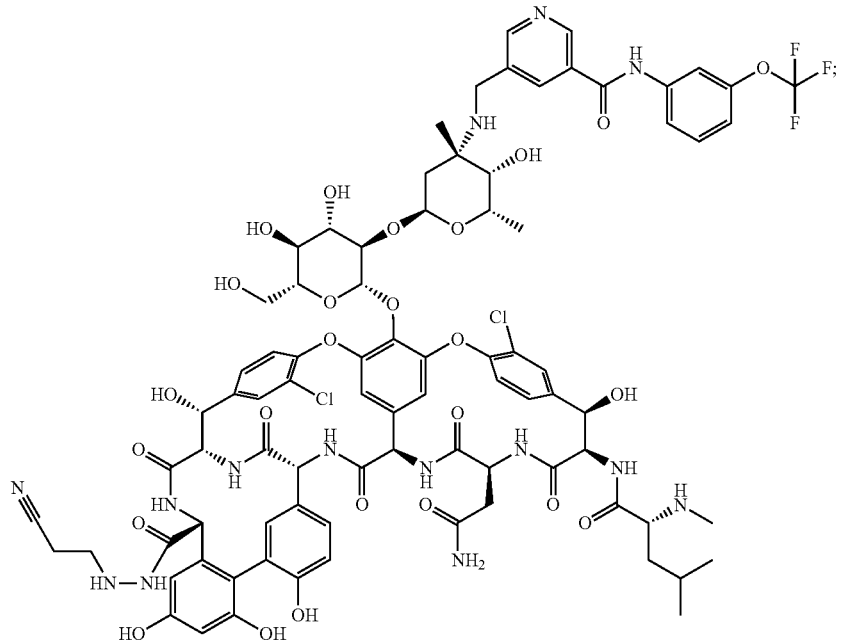

[Chemcial Formula 4]

-continued

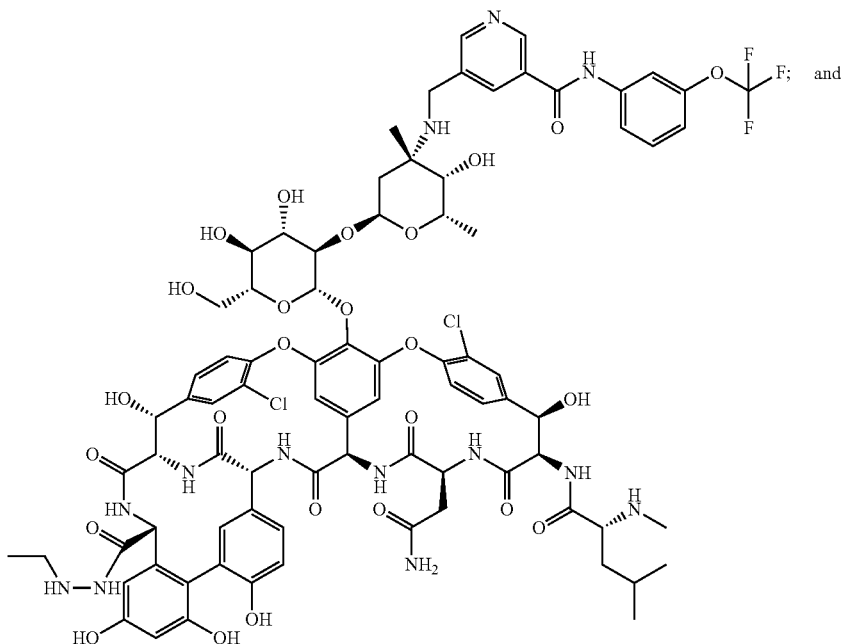

[Chemical Formula 5]

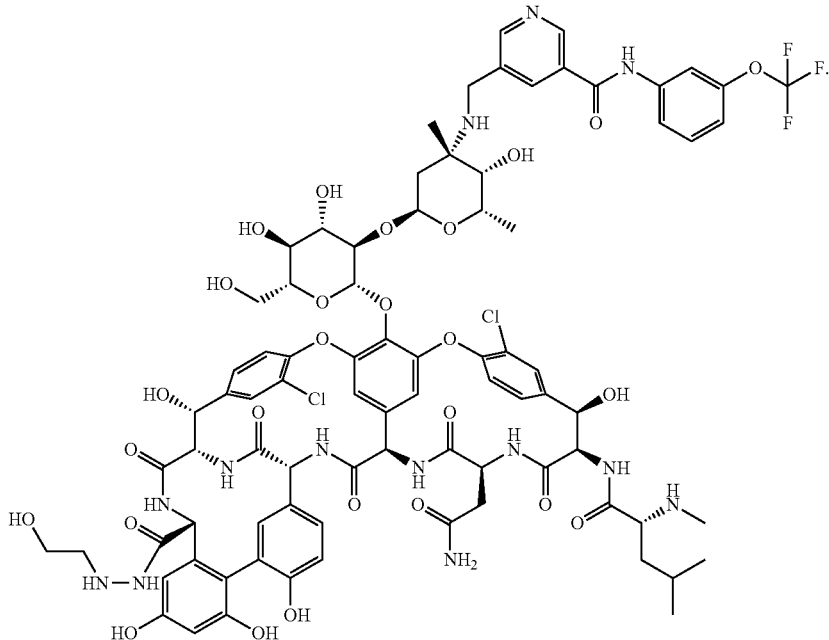

[Chemical Formula 6]

2. The compound according to claim 1, or a pharmaceutically acceptable salt thereof, wherein $R^Y$ is optionally substituted lower alkyl.

3. The compound according to claim 1, or a pharmaceutically acceptable salt thereof, wherein $Ar^1$ is optionally substituted phenyl or optionally substituted five- to seven-membered nitrogen atom-containing heterocyclic group.

4. The compound according to claim 1, or a pharmaceutically acceptable salt thereof, wherein $Ar^2$ is optionally substituted phenyl.

5. The compound according to claim 1, or a pharmaceutically acceptable salt thereof, wherein $Ar^2$ is phenyl optionally substituted with the same or different one or two substituents selected from the group consisting of halogen, halogenated lower alkyl, halogenated lower alkoxy, and halogenated lower alkylthio.

6. The compound according to claim 1, or a pharmaceutically acceptable salt thereof, wherein $Ar^2$ is phenyl substituted with the same or different one or two substituents selected from the group consisting of halogen and halogenated lower alkoxy.

7. The compound according to claim 1, or a pharmaceutically acceptable salt thereof, wherein $Ar^2$ is

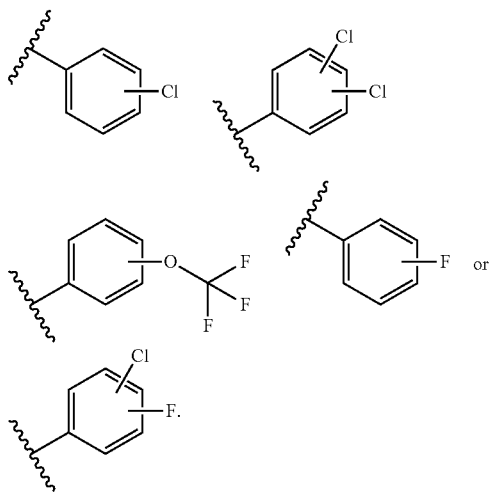

8. The compound according to claim 1, or a pharmaceutically acceptable salt thereof,
wherein
$R^B$ is —NHNR$^X$R$^Y$
wherein
$R^X$ is hydrogen; and
$R^Y$ is lower alkyl substituted with OH, =O or lower alkoxy.

9. The compound according to claim 1, or a pharmaceutically acceptable salt thereof,
wherein
$R^B$ is —NHNR$^X$R$^Y$
wherein
$R^X$ is hydrogen;
$R^Y$ is selected from the group consisting of optionally substituted lower alkyl and optionally substituted carbamoyl;
Y is —NR$^2$CO— or —CONR$^2$-wherein R$^2$ is hydrogen or lower alkyl;
$Ar^1$ is optionally substituted phenyl or optionally substituted five-to seven-membered nitrogen atom-containing heterocyclic group;
$Ar^2$ is optionally substituted phenyl;
$X^1$ is $C_1$-$C_3$ alkylene;
$X^2$ is a single bond;
$X^3$ is a single bond;
$R^C$ is hydrogen; and
R is —CH(NHR$^D$)CH$_2$CH(CH$_3$)$_2$ wherein R$^D$ is hydrogen or lower alkyl.

10. The compound according to claim 1, or a pharmaceutically acceptable salt thereof, wherein
$R^B$ is —NHNR$^X$R$^Y$
wherein
$R^X$ is hydrogen;
$R^Y$ is selected from the group consisting of optionally substituted lower alkyl and optionally substituted carbamoyl;
Y is —NR$^2$CO— or —CONR$^2$-wherein R$^2$ is hydrogen or lower alkyl;
$Ar^1$ is phenyl or five-to seven-membered nitrogen atom-containing heterocyclic group optionally substituted with oxo;
$Ar^2$ is phenyl substituted with the same or different one or two substituents selected from the group consisting of halogen, halogenated lower alkyl, halogenated lower alkoxy, and halogenated lower alkylthio;
$X^1$ is $C_1$-$C_3$ alkylene;
$X^2$ is a single bond;
$X^3$ is a single bond;
$R^c$ is hydrogen; and
R is —CH(NHR$^D$)CH$_2$CH(CH$_3$)$_2$ wherein R$^D$ is hydrogen or lower alkyl.

11. The compound according to claim 1, or a pharmaceutically acceptable salt thereof, wherein
$R^B$ is —NHNR$^X$R$^Y$
wherein
$R^X$ is hydrogen;
$R^Y$ is selected from the group consisting of lower alkyl substituted with OH, =O or lower alkoxy and carbamoyl substituted with lower alkyl;
Y is —NHCO— or —CONH—;
$Ar^1$ is

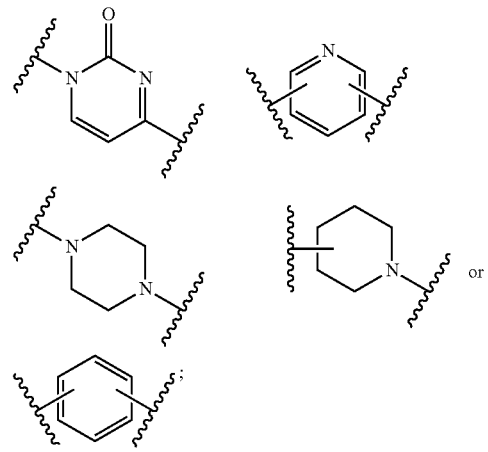

$Ar^2$ is

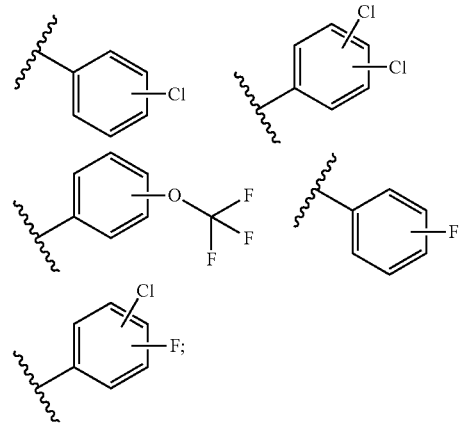

$X^1$ is $C_1$-$C_3$ alkylene;
$X^2$ is a single bond;
$X^3$ is a single bond;
$R^C$ is hydrogen; and
R is —CH(NHR$^D$)CH$_2$CH(CH$_3$)$_2$ wherein R$^D$ is hydrogen or lower alkyl.

12. A pharmaceutical composition comprising the compound according to claim 1 or a pharmaceutically acceptable salt thereof, and a pharmaceutically acceptable carrier or diluent.

* * * * *